(12) United States Patent
Huigens, III et al.

(10) Patent No.: US 11,419,335 B2
(45) Date of Patent: Aug. 23, 2022

(54) N-ARYLATED ANALOGUES AND USES THEREOF

(71) Applicant: University of Florida Research Foundation, Incorporated, Gainesville, FL (US)

(72) Inventors: Robert William Huigens, III, Williston, FL (US); Yasmeen Abouelhassan, Gainesville, FL (US); Akash Basak, South Bend, IN (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 0 days.

(21) Appl. No.: 16/467,461

(22) PCT Filed: Dec. 7, 2017

(86) PCT No.: PCT/US2017/065121
§ 371 (c)(1),
(2) Date: Jun. 6, 2019

(87) PCT Pub. No.: WO2018/106922
PCT Pub. Date: Jun. 14, 2018

(65) Prior Publication Data
US 2019/0373890 A1    Dec. 12, 2019

Related U.S. Application Data

(60) Provisional application No. 62/431,353, filed on Dec. 7, 2016.

(51) Int. Cl.
| | |
|---|---|
| *A01N 43/50* | (2006.01) |
| *A61K 31/4174* | (2006.01) |
| *A61K 31/4184* | (2006.01) |
| *A61K 31/4164* | (2006.01) |
| *C07D 233/58* | (2006.01) |
| *C07D 235/08* | (2006.01) |
| *C07D 249/04* | (2006.01) |

(52) U.S. Cl.
CPC .......... *A01N 43/50* (2013.01); *C07D 233/58* (2013.01); *C07D 235/08* (2013.01); *C07D 249/04* (2013.01)

(58) Field of Classification Search
CPC ............... A01N 43/50; A61K 31/4174; A61K 31/4184; A61K 31/4164; C07D 233/58; C07D 235/08
USPC ......... 514/396, 394; 548/343.5, 346.1, 304.4
See application file for complete search history.

(56) References Cited

U.S. PATENT DOCUMENTS

| | | | |
|---|---|---|---|
| 7,097,888 B2 | 8/2006 | Shukla et al. | |
| 2014/0142307 A1 | 5/2014 | Youngs et al. | |

FOREIGN PATENT DOCUMENTS

| | | | | | |
|---|---|---|---|---|---|
| JP | 2009215200 A | * | 9/2009 | | |
| JP | 2009286780 A | * | 12/2009 | ............ | A01N 43/50 |
| WO | WO 2009/133923 A1 | | 11/2009 | | |
| WO | WO-2010009279 A1 | * | 1/2010 | ............ | A61K 31/24 |

OTHER PUBLICATIONS

Ex parte Cao, Decision rendered by the Board of Appeals and Interferences in U.S. Appl. No. 10/696,862 on Sep. 21, 2011. (Year: 2011).*
English (machine) translation of the Japanese Patent Publication JP-2009286780-A. (Year: 2021).*
De Waelheyns, E., K. Segers, M. Frantzeskos, J. Anne, G. Nicolaes and A. Economou, "Identification of small-molecule inhibitors against SecA by structure-based virtual ligand screening" The Journal of Antibiotics (2015) 68, pp. 666-673. (Year: 2015).*
De Waelheyns et al. "Identification of small-molecule inhibitors against SecA by structure-based virtual ligand screening" The Journal of Antibiotics (2015) 68, pp. 666-673 (Supplementary Information: pp. 1-21). (Year: 2015).*
English translation of the claims of Japanese Patent Publication JP2009215200A. (Year: 2022).*
English translation of the description of Japanese Patent Publication JP2009215200A. (Year: 2022).*
Radic, B., R. Roncevic, M. Mesic, A. Fajdetic and Z. Binenfeld, Imidazole derivatives. Bis-imidazolium and imidazolium-pyridinium oximes: reaction, inhibition and protective action on soman phosph. human erythrocyte acetylcholinesterase. VII, Acta Pharmaceutica (1994), 44(3), pp. 251-255 (Abstract). (Year: 1994).*

(Continued)

*Primary Examiner* — Joseph R Kosack
*Assistant Examiner* — Sagar Patel
(74) *Attorney, Agent, or Firm* — Wolf, Greenfield & Sacks, P.C.

(57) ABSTRACT

The present invention provides novel compounds of Formula (I') and (I), and pharmaceutically acceptable salts, solvates, hydrates, polymorphs, co-crystals, tautomers, stereoisomers, isotopically labeled derivatives, prodrugs, and compositions thereof. Also provided are methods and kits involving the inventive compounds or compositions for killing a microorganism (e.g., bacteria, fungi, viruses, protozoa, or multicellular parasites), the prevention and/or treatment of infectious diseases (e.g., infections by microorganisms, bacterial infection, cystic fibrosis infection, foreign body infection, urinary tract infection (UTI), or infections leading to biofilms), controlling and/or eradicating biofilms (e.g., bacterial biofilms), preventing biofilm formation, sterilizing a surface, and/or eradicating persister cells (e.g., in a subject in need thereof or in a subject involving a biofilm).

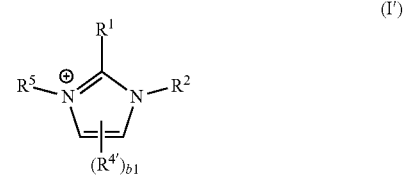

(I')

45 Claims, 80 Drawing Sheets

(56) References Cited

OTHER PUBLICATIONS

International Search Report and Written Opinion, dated Feb. 26, 2019, in connection with Application No. PCT/US2017/065121.
Abouelhassan et al., Identification of N-Arylated NH125 Analogues as Rapid Eradicating Agents against MRSA Persister Cells and Potent Biofilm Killers of Gram-Positive Pathogens. Chembiochem. Feb. 16, 2017;18(4):352-357. doi: 10.1002/cbic.201600622. Epub Jan. 16, 2017.
Basak et al., Antimicrobial peptide-inspired NH125 analogues: bacterial and fungal biofilmeradicating agents and rapid killers of MRSA persisters. Org Biomol Chem. Jul. 5, 2017;15(26):5503-5512. doi: 10.1039/c7ob01028a.
Basak et al., Synthetically Tuning the 2-Position of Halogenated Quinolines: Optimizing antibacterial and Biofilm Eradication Activities via Alkylation and Reductive Amination Pathways. Chem. Eur. J. 2016;22:9181-9189. doi: 10.1002/chem.201600926.
Bender et al., NH125 Reduces the Level of CPEB3, an RNA Binding Protein, to promote Synaptic GluA2 Expression. Neuropharmacol. 2016;101:531-537. doi: 10.1016/j.neuropharm.2015.03.017. Author Manuscript.
Böttcher et al., Synthesis and activity of biomimetic biofilm disruptors. J Am Chem Soc. Feb. 27, 2013;135(8):2927-30. doi: 10.1021/ja3120955. Epub Feb. 13, 2013.
Cano et al., Transition-Metal-Free O-, S-, and N-Arylation of Alcohols, Thiols, Amides, Amines, and Related Heterocycles. J Org. Chem. 2011;76(2):654-660. doi: 10.1021/jo1022052.
Dorjnamjin et al., Synthesis of silver nanoparticles using hydroxyl functionalized ionic liquids and their antimicrobial activity. Int J Mol Sci. May 2008;9(5):807-20. doi: 10.3390/ijms9050807. Epub May 20, 2008.
Garrison et al., Halogenated Phenazines that Potently Eradicate Biofilms, MRSA Persister Cells in Non-Biofilm Cultures, and *Mycobacterium tuberculosis*. Angew Chem Int Ed Engl. Dec. 1, 2015;54(49):14819-23. doi:10.1002/anie.201508155. Epub Oct. 20, 2015.
Garrison et al., Structure-Activity Relationships of a Diverse Class of Halogenated Phenazines That Targets Persistent, Antibiotic-Tolerant Bacterial Biofilms and *Mycobacterium tuberculosis*. J Med Chem. Apr. 28, 2016;59(8):3808-25. doi:10.1021/acs.jmedchem.5b02004. Epub Apr. 6, 2016.
Keren et al., Persister cells and tolerance to antimicrobials. FEMS Microbiol Lett. Jan. 15, 2004;230(1):13-8. Erratum in: FEMS Microbiol Lett. May 1, 2004;234(1):187.
Roveta et al., Activity of daptomycin on biofilms produced on a plastic support by *Staphylococcus* spp. Int J Antimicrob Agents. Apr. 2008;31(4):321-8. doi: 10.1016/j.ijantimicag.2007.11.012. Epub Feb. 21, 2008.
Trunz et al., 1-Aryl-4-nitro-1H-imidazoles, a new promising series for the treatment of human African trypanosomiasis. Eur J Med Chem. May 2011;46(5):1524-35. doi: 10.1016/j.ejmech.2011.01.071. Epub Feb. 26, 2011.
Worthington et al., Small molecule control of bacterial biofilms. Org Biomol Chem. Oct. 7, 2012;10(37):7457-74. doi: 10.1039/c2ob25835h. Author Manuscript.
Yamamoto et al., Identification and characterization of a potent antibacterial agent, NH125 against drug-resistant bacteria. Biosci Biotechnol Biochem. Apr. 2000;64(4):919-23.
International Preliminary Report on Patentability dated Jun. 20, 2019, in connection with International Application No. PCT/US2017/065121.
PCT/US2017/065121, Feb. 26, 2018, International Search Report and Written Opinion.
Abouelhassan et al., Rapid kill assessment of an N-arylated NH125 analogue against drug-resistant microorganisms. Medchemcomm. Jan. 29, 2019;10(5):712-716. doi: 10.1039/c8md00613j.
Kim et al., Identification of an Antimicrobial Agent Effective against Methicillin-Resistant *Staphylococcus aureus* Persisters Using a Fluorescence-Based Screening Strategy. PLoS One. Jun. 3, 2015;10(6):e0127640. doi: 10.1371/journal.pone.0127640.
Kim et al., NH125 kills methicillin-resistant *Staphylococcus aureus* persisters by lipid bilayer disruption. Future Med Chem. 2016;8(3):257-69. doi: 10.4155/fmc.15.189. Epub Feb. 24, 2016.

\* cited by examiner

A.) Chemical Structures of Membrane-Active Antibacterial Agents Used During This Study B.) Synthesis of N-Arylated NH125 analogues 1 and 2

N-ARYLATED ANALOGUES AND USES THEREOF

RELATED APPLICATIONS

This application is a national stage filing under 35 U.S.C. § 371 of international PCT application, PCT/US2017/065121, filed Dec. 7, 2017, which claims priority under 35 U.S.C. § 119(e) to U.S. Provisional Application, U.S. Ser. No. 62/431,353, filed Dec. 7, 2016, each of which is incorporated herein by reference.

BACKGROUND OF THE INVENTION

Bacterial biofilms are ubiquitous, surface-attached communities of slow- or non-replicating bacteria (e.g., persister cells) housed within a protective extracellular matrix of biomolecules and display high levels of tolerance to biocides, antibiotics, and other chemical insults (i.e., host immune response during infection).[1-5] Although biofilm-associated infections have received much attention over the past two decades, it should be no surprise that biofilms affect multiple sectors in society (e.g., medical[1-7], industrial[8,9] and agricultural[10,11]). Numerous applications exist for small molecule biofilm-control strategies, a few of which include disinfectants, therapeutic agents, crop protection agents.[12,13]

Individual, free-swimming planktonic bacteria use organic signaling molecules to communicate with each other in a process called quorum sensing to monitor their population density and coordinate group behavior, including the simultaneous surface attachment, colonization, and development into a mature biofilm.[14] Biofilms disperse some bacterial cells back into their surrounding environment in a process called biofilm dispersion, which enables bacteria to establish biofilms in new locations (See FIG. 1).[2] Over the last several years, small molecules have been identified that inhibit biofilm formation and disperse established biofilms through various mechanisms, including the modulation of quorum sensing.[12,13] Alternatively, a much smaller collection of compounds have been identified that eradicate biofilm cells, including non-dividing persister cells.[5,7,15,16]

Antimicrobial peptides (AMPs) are produced by an extensive variety of organisms to defend themselves against bacterial infection and operate through various membrane-destroying mechanisms.[17] A diverse array of AMP-inspired, membrane-active amphiphilic compounds have been reported to demonstrate potent antibacterial and anti-biofilm activities while evading the development of bacterial resistance (i.e., quaternary ammonium cations, QAC).[16-23] Membrane-targeting compounds often are challenging to develop for human therapeutic use due to membrane selectivity issues[19]; however, such agents have diverse biomedical applications and can be highly effective as disinfectants. For instance, a lack of sterilized hospital environments, including surfaces and instruments, is a major problem that leads to life-threatening hospital-acquired infections (HAI).[24,25]

Therefore, there remains a need to develop new compounds for treating and/or preventing infectious diseases (e.g., bacterial infection, cystic fibrosis infection, foreign body infection, or urinary tract infection (UTI)), and for controlling and eradicating biofilms.

SUMMARY OF THE INVENTION

The present invention provides compounds of Formula (I') or (I), and pharmaceutically acceptable salts, solvates, hydrates, polymorphs, co-crystals, tautomers, stereoisomers, isotopically labeled derivatives, and prodrugs, and compositions thereof. The present invention further provides methods of using the inventive compounds, and pharmaceutically acceptable salts, solvates, hydrates, polymorphs, co-crystals, tautomers, stereoisomers, isotopically labeled derivatives, and prodrugs, and compositions thereof, as therapeutics for the prevention and/or treatment of infectious diseases. In certain embodiments, the inventive compounds are used for killing a microorganism (e.g., bacteria, fungi, viruses, protozoa, or multicellular parasites), the prevention and/or treatment of infectious diseases (e.g., infections by microorganisms, bacterial infection, cystic fibrosis infection, foreign body infection, urinary tract infection (UTI), or infections leading to biofilms), controlling and/or eradicating biofilms (e.g., bacterial biofilms), preventing biofilm formation, sterilizing a surface, killing persister cells, and/or eradicating persister cells (e.g., in a subject in need thereof, or in a subject involving a biofilm).

In one aspect, the present disclosure provides compounds of Formula (I'):

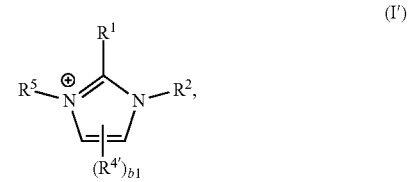

and pharmaceutically acceptable salts, solvates, hydrates, polymorphs, co-crystals, tautomers, stereoisomers, isotopically labeled derivatives, and prodrugs thereof, wherein $R^1$, $R^2$, $R^4$, $R^5$, and b are as defined herein.

In certain embodiments, the compound of Formula (I') is of Formula (I). In one aspect, the present disclosure provides compounds of Formula (I):

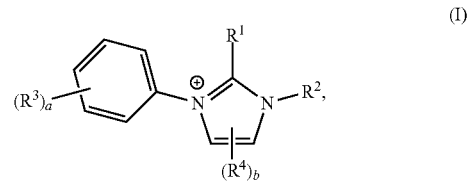

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, $R^4$, a, and b are as defined herein.

Exemplary compounds of Formula (I') and (I) include, but are not limited to:

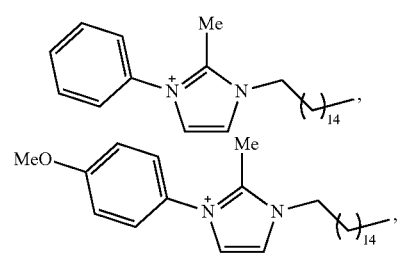

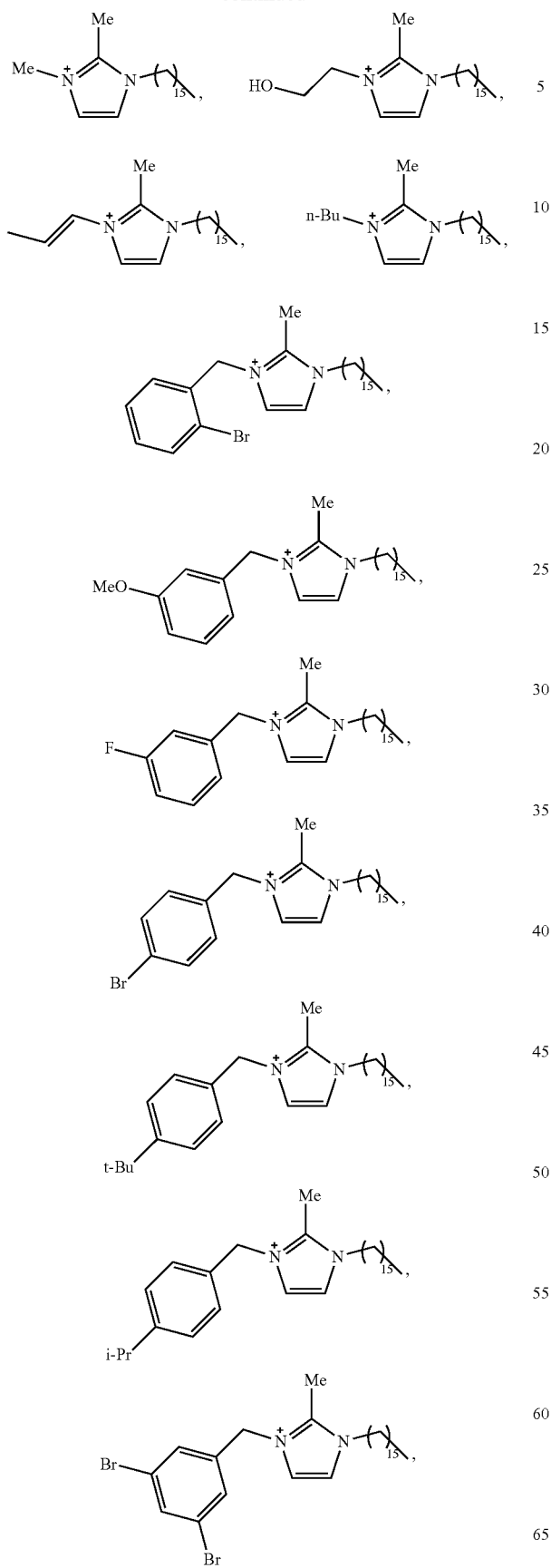
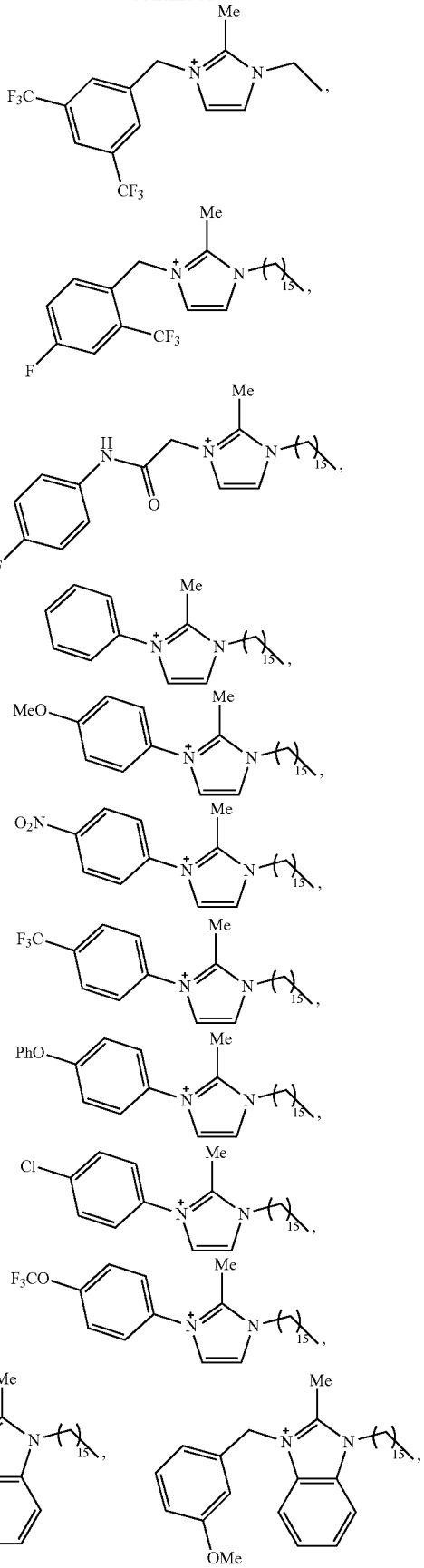

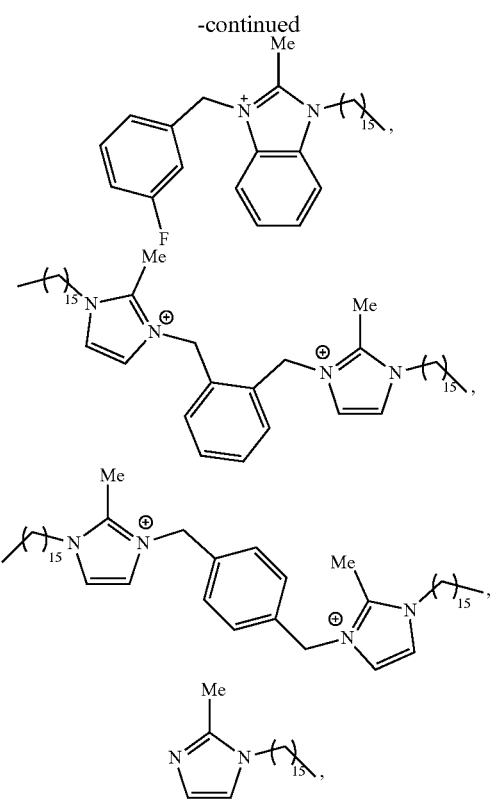

and pharmaceutically acceptable salts, solvates, hydrates, polymorphs, co-crystals, tautomers, stereoisomers, isotopically labeled derivatives, and prodrugs thereof.

In another aspect, the present disclosure provides pharmaceutical compositions including a compound described herein, and optionally a pharmaceutically acceptable excipient. In another aspect, the present disclosure provides compounds described herein, and pharmaceutically acceptable salts thereof. In certain embodiments, the pharmaceutical compositions described herein include a therapeutically or prophylactically effective amount of a compound described herein. The pharmaceutical composition may be useful for killing a microorganism (e.g., bacteria, fungi, viruses, protozoa, or multicellular parasites), treating and/or preventing an infectious disease (e.g., infections by microorganisms, bacterial infection, cystic fibrosis infection, foreign body infection, urinary tract infection (UTI), or infections leading to biofilms) in a subject in need thereof, controlling and/or eradicating biofilms (e.g., bacterial biofilms), preventing biofilm formation, sterilizing a surface, killing persister cells, and/or eradicating persister cells (e.g., in a subject in need thereof, or in a subject involving a biofilm). In certain embodiments, the infectious disease is a bacterial infection (e.g., an infection with a Gram-positive bacterium).

In another aspect, the present invention provides methods for killing a microorganism (e.g., bacteria, fungi, viruses, protozoa, or multicellular parasites), the prevention and/or treatment of infectious diseases (e.g., infections by microorganisms, bacterial infection, cystic fibrosis infection, foreign body infection, urinary tract infection (UTI), or infections leading to biofilms), controlling and/or eradicating biofilms (e.g., bacterial biofilms), preventing biofilm formation, sterilizing a surface, killing persister cells, and/or eradicating persister cells (e.g., in a subject in need thereof, or in a subject involving a biofilm).

The present invention provides methods for administering to a subject in need thereof an effective amount of a compound, or pharmaceutical composition thereof, as described herein. Also described are methods for killing microorganisms (e.g., bacteria, fungi, viruses, protozoa, or multicellular parasites) with an effective amount of a compound, or pharmaceutical composition thereof, as described herein. In certain embodiments, a method described herein further includes administering to the subject an additional pharmaceutical agent. In certain embodiments, a method described herein further includes killing microorganisms (e.g., bacteria, fungi, viruses, protozoa, or multicellular parasites) with an additional pharmaceutical agent (e.g., an anti-infectious disease agent or anti-microbial agent). In certain embodiments, the additional pharmaceutical agent is an antibacterial agent, antifungal agent, antiviral agent, an agent for killing protozoa, or an anti-parasitic agent.

In yet another aspect, the present invention provides compounds of Formula (I') or (I), and pharmaceutically acceptable salts, solvates, hydrates, polymorphs, co-crystals, tautomers, stereoisomers, isotopically labeled derivatives, prodrugs, and compositions thereof, for use in the treatment of a disease (e.g., an infectious disease (e.g., bacterial infection, cystic fibrosis infection, foreign body infection, urinary tract infection (UTI), or infections leading to biofilms)), controlling and/or eradicating biofilms (e.g., bacterial biofilms), preventing biofilm formation, sterilizing a surface, killing persister cells, and/or eradicating persister cells (e.g., in a subject in need thereof, or in a subject involving a biofilm). The present invention also provides uses of a compound described herein, e.g., a compound of Formula (I') or (I), or a pharmaceutically acceptable salt, solvate, hydrate, polymorph, co-crystal, tautomer, stereoisomer, isotopically labeled derivative, or prodrug thereof, and a pharmaceutically acceptable excipient, in killing a microorganism (e.g., bacteria, fungi, viruses, protozoa, or multicellular parasites), the prevention and/or treatment of infectious diseases (e.g., infections by microorganisms, bacterial infection, cystic fibrosis infection, foreign body infection, urinary tract infection (UTI), or infections leading to biofilms), controlling and/or eradicating biofilms (e.g., bacterial biofilms), preventing biofilm formation, sterilizing a surface, killing persister cells, and/or eradicating persister cells (e.g., in a subject in need thereof, or in a subject involving a biofilm).

Another aspect of the present disclosure relates to kits comprising a container with a compound, or pharmaceutical composition thereof, as described herein. The kits described herein may include a single dose or multiple doses (e.g., a full course of antibiotics for treating an infection (e.g., 7 days of antibiotics, or 10 days of antibiotics)) of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency, such as the U.S. Food and Drug Administration (FDA).

The details of one or more embodiments of the invention are set forth herein. Other features, objects, and advantages of the invention will be apparent from the Detailed Description, Examples, Figures, and Claims.

Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —C$^A$H(C$^B$H$_2$C$^C$H$_3$)— includes only one carbon unit C$^A$. The term "C$_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —CH(C$_2$H$_5$)— is a $C_1$ hydrocarbon chain, and

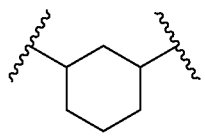 [SMILES: *C1CCCC(*)C1]

is a $C_3$ hydrocarbon chain. When a range of values is used, e.g., a $C_1$-6 hydrocarbon chain, the meaning of the range is as described herein. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

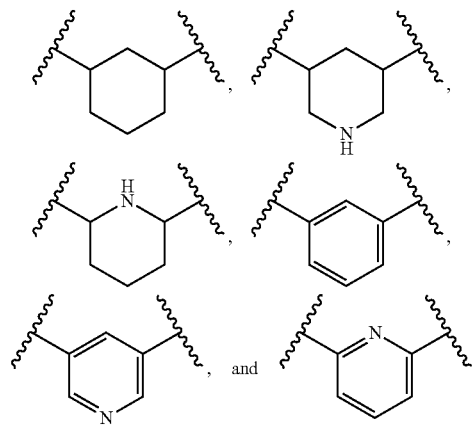

are all examples of a hydrocarbon chain. In contrast, in certain embodiments

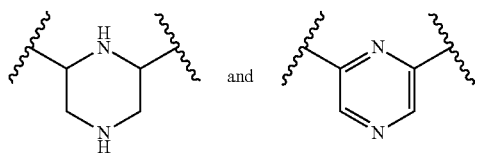 [SMILES: *C1CNCC(*)N1 ; *c1cncc(*)n1]

are not within the scope of the hydrocarbon chains described herein.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CF_2Cl_2$, —$CF_2Cl$, and the like.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-4}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 8 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 $\pi$ electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic, tricyclic) 4n+2 aromatic ring system (e.g., having 6, 10, or 14 □ electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{aa}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC —C(=O)N($R^{bb}$)$_2$, —N$R^{bb}$C(=O)$R^{aa}$, —N$R^{bb}$CO$_2R^{aa}$, —N$R^{bb}$C(=O)N($R^{bb}$)$_2$, —C(=N$R^{bb}$)$R^{aa}$, —C(=N$R^{bb}$)O$R^{aa}$, —OC(=N$R^{bb}$)$R^{aa}$, —OC(=N$R^{bb}$)O$R^{aa}$, —C(=N$R^{bb}$)N($R^{bb}$)$_2$, —OC(=N$R^{bb}$)N($R^{bb}$)$_2$, —N$R^{bb}$C(=N$R^{bb}$)N($R^{bb}$)$_2$, —C(=O)N$R^{bb}$SO$_2R^{aa}$, —N$R^{bb}$SO$_2R^{aa}$, —SO$_2$N($R^{bb}$)$_2$, —SO$_2R^{aa}$, —SO$_2$O$R^{aa}$, —OSO$_2R^{aa}$, —S(=O)$R^{aa}$, —OS(=O)$R^{aa}$, —Si($R^{aa}$)$_3$, —OSi($R^{aa}$)$_3$ —C(=S)N($R^{bb}$)$_2$, —C(=O)S$R^{aa}$, —C(=S)S$R^{aa}$, —SC(=S)S$R^{aa}$, —SC(=O)S$R^{aa}$, —OC(=O)S$R^{aa}$, —SC(=O)O$R^{aa}$, —SC(=O)$R^{aa}$, $C_{1-10}$ alkyl, $C_{1-10}$ haloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2R^{aa}$, =N$R^{bb}$, or =NO$R^{cc}$;

each instance of $R^{aa}$ is, independently, selected from $C_{1-10}$ alkyl, $C_{1-10}$ haloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl, $C_{1-10}$ haloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ haloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$X$^-$, —N(O$R^{ee}$)$R^{ff}$, —SH, —S$R^{ee}$, —SS$R^{ee}$, —C(=O)$R^{ee}$, —CO$_2$H, —CO$_2R^{ee}$, —OC(=O)$R^{ee}$, —OCO$_2R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2R^{ee}$, —SO$_2$N($R^{ff}$)$_2$, —SO$_2R^{ee}$, —SO$_2$O$R^{ee}$, —OSO$_2R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, $C_{1-6}$ alkyl, $C_{1-6}$ haloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ haloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ haloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3$$^+$X$^-$, —NH($C_{1-6}$ alkyl)$_2$$^+$X$^-$, —NH$_2$($C_{1-6}$ alkyl)$^+$X$^-$, —NH$_3$$^+$X$^-$, —N(O$C_{1-6}$ alkyl)($C_{1-6}$ alkyl), —N(OH)($C_{1-6}$ alkyl), —NH (OH), —SH, —S$C_{1-6}$ alkyl, —SS($C_{1-6}$ alkyl), —C(=O) ($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N ($C_{1-6}$ alkyl)$_2$, —OC(=O)NH($C_{1-6}$ alkyl), —NHC(=O) ($C_{1-6}$ alkyl), —N($C_{1-6}$ alkyl)C(=O)($C_{1-6}$ alkyl), —NHCO$_2$ ($C_{1-6}$ alkyl), —NHC(=O)N($C_{1-6}$ alkyl)$_2$, —NHC(=O)NH ($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N(C-s alkyl)$_2$, —C(=NH)NH($C_{1-6}$ alkyl), —C(=NH)NH$_2$, —OC(=NH)N($C_{1-6}$ alkyl)$_2$, —OC(NH) NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2C_{1-6}$ alkyl, —SO$_2$O$C_{1-6}$ alkyl, —OSO$_2C_{1-6}$ alkyl, —SO$C_{1-6}$ alkyl, —Si($C_{1-6}$ alkyl)$_3$, —OSi($C_{1-6}$ alkyl)$_3$ —C(=S)N($C_{3-6}$ alkyl)$_2$, C(=S)NH($C_{1-6}$ alkyl), C(=S) NH$_2$, —C(=O)S($C_{1-6}$ alkyl), —C(=S)S$C_{1-6}$ alkyl, —SC (=S)S$C_{1-6}$ alkyl, $C_{1-6}$ alkyl, $C_{1-6}$ haloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HCO$_3$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}MesBr_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

In certain embodiments, the carbon atom substituent includes, but is not limited to, halogen, —CN, —NO$_2$, —N$_3$, —SO$_2$H, —SO$_3$H, —OH, —OR$^{aa}$, —N(R$^{bb}$)$_2$, —SH, —SR$^{aa}$, —C(=O)R$^{aa}$, —CO$_2$H, —CHO, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —S(=O)R$^{aa}$, —Si(R$^{aa}$)$_3$, C$_{1-10}$ alkyl, C$_{1-10}$ haloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups.

As used herein, the term "halo" or "halogen" refers to fluorine (fluoro, —F), chlorine (chloro, —Cl), bromine (bromo, —Br), or iodine (iodo, —I).

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). "Alkoxy" or "alkoxyl" refers to a radical of the formula: —O— alkyl.

As used herein, a "counterion" is a negatively charged group associated with a positively charged quaternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{aa}$)$_2$, —CN, —C(=O)R$^{aa}$, —C(=O)N(R$^{aa}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, C$_{1-10}$ haloalkyl, C$_{2-10}$ alkenyl, C$_{2-10}$ alkynyl, heteroC$_{1-10}$alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{aa})_2$, $-P(OR^{aa})_3{}^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl) methyl, 3-(imidazol-1-yl)bis(4',4"-dimethoxyphenyl) methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})R^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{aa})_2$, —$P(OR)_3{}^+X^-$, —$P(=O)(R^{aa})_2$, —$P(=O)(OR^{aa})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

As used herein, a "leaving group" (LG) is an art-understood term referring to a molecular fragment that departs with a pair of electrons in a heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —$OC(=O)SR^{aa}$, —$OC(=O)R^{aa}$, —$OCO_2R^{aa}$, —$OC(=O)N(R^{bb})_2$, —$OC(=NR^{bb})R^{aa}$, —$OC(=NR^{bb})OR^{aa}$, —$OC(=NR^{bb})N(R^{bb})_2$, —$OS(=O)R^{aa}$, —$OSO_2R^{aa}$, —$OP(R^{aa})_2$, —$OP(R^{aa})_3$, —$OP(=O)_2R^{aa}$, —$OP(=O)(R^{aa})_2$, —$OP(=O)(OR^{cc})_2$, —$OP(=O)_2N(R^{bb})_2$, and —$OP(=O)(NR^{bb})_2$, wherein $R^{aa}$, $R^{bb}$, and $R^{cc}$ are as defined herein). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, amines, ammonia, alcohols, ether moieties, sulfur-containing moieties, thioether moieties, zinc halides, magnesium moieties, diazonium salts, and copper moieties.

As used herein, the term "salt" refers to any and all salts, and encompasses pharmaceutically acceptable salts. The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "surface" refers to any living or inert surface. In certain embodiments, surface refers to a surface in an aqueous environment.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I') or (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2 H$_2$O) and hexahydrates (R·6 H$_2$O)).

As used herein, the term "tautomer" includes two or more interconvertible forms resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and/or solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I') or (I), which have cleavable groups and become by solvolysis or under physiological conditions the compounds of Formula (I') or (I) which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formula (I') or (I) may be preferred in certain instances.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals, such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In certain embodiments, the animal is fish. A "patient" refers to a human subject in need of treatment of a disease.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound of Formula (I') or (I) refers to an amount sufficient to elicit a desired biological response, i.e., treating the condition. As will be appreciated by those of ordinary skill in this art, the effective amount of a compound of Formula (I') or (I) may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound of Formula (I') or (I) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (I') or (I) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "independently" is used herein to indicate that the groups can be identical or different.

The terms "labeled", "labeled with a detectable agent", and "labeled with a detectable moiety" are used herein interchangeably. "Label" and "detectable moiety" are also used interchangeably herein. When used in reference to a probe compound, these terms specify that the probe compound can be detected or visualized. In certain embodiments, a label is selected such that it generates a signal which can be measured and whose intensity is related to the amount of probe compound bound to a protein (e.g., in a sample). A label may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Labels suitable for use in the present invention may be detectable by any of a variety of means including, but not limited to, spectroscopic, photochemical, biochemical, immunochemical, electrical, optical or chemical means. Labels suitable for use in the present invention may be detectable by any of a variety of means including, but not limited to, spectroscopic, photochemical, biochemical, immunochemical, electrical, optical, or chemical means. Suitable labels include, but are not limited to, affinity tags, radionuclides (such as, for example, $^{32}P$, $^{35}S$, $^{3}H$, $^{14}C$, $^{125}I$, $^{131}I$, and the like), fluorescent dyes, phosphorescent dyes, chemiluminescent agents (such as, for example, acridinium esters, stabilized dioxetanes, and the like), spectrally resolvable inorganic fluorescent semiconductor nanocrystals (i.e., quantum dots), metal nanoparticles (e.g., gold, silver, copper, and platinum) or nanoclusters (such as, for example, those used in an ELISA, i.e., horseradish peroxidase, beta-galactosidase, luciferase, alkaline phosphatase), colorimetric labels (such as, for example, dyes, colloidal gold, and the like), magnetic labels (such as, for example, Dynabeads™), and haptens. Labels may include labels capable of providing a detectable signal, either directly or indirectly. Exemplary labels include radioisotopes, fluorescent molecules, isotopes (e.g., radioactive isotopes), biotin, and the like.

In certain embodiments, the label comprises a fluorescent moiety. Numerous known fluorescent labeling moieties of a wide variety of chemical structures and physical characteristics are suitable for use in the practice of the present invention. Suitable fluorescent dyes include, but are not limited to, fluorescein and fluorescein dyes (e.g., fluorescein isothiocyanine (FITC), naphthofluorescein, 4',5'-dichloro-2',7'-dimethoxy-fluorescein, 6-carboxyfluorescein or FAM), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), Oregon Green Dyes (e.g., Oregon Green 488, Oregon Green 500, Oregon Green 514), Texas Red, Texas Red-X, Spectrum Red™, Spectrum Green™, cyanine dyes (e.g. Cy-3™, Cy-5™, Cy-3.5™, Cy-5.5™), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDyes (e.g., IRD40, IRD 700, IRD 800), and the like. For more examples of suitable fluorescent dyes and methods for coupling fluorescent dyes to other chemical entities see, for example, *The Handbook of Fluorescent Probes and Research Products*, 9th Ed., Molecular Probes, Inc., Eugene, Oreg.

The term "luminescence" or "luminescent" means any process of light emission including fluorescence, phosphorescence, scintillation, chemiluminescence, and bioluminescence.

The term "chemiluminescence," "chemiluminescent," or "chemiluminescent substrate" refers to a chemical that produces light as a result of a chemical reaction. Commonly used chemiluminescent substrates include, but are not limited to, luminol (5-amino-2,3-dihydro-1, 4-phthalazinedione), lophine (2, 4, 5-triphenylimidazole), lucigenin (bis-N-methylacridinium), other acridinium esters, luciferin-luciferase, and thioxene derivatives. For example, in the art-recognized ECL™ detection system of Amersham, an acridinium substrate is oxidized by horse radish peroxidase to produce acridinium esters, which react with excess peroxide at an alkaline pH to produce visible chemiluminescence at 430 nm.

In certain embodiments, the label comprises an affinity tag. The term "affinity tag" includes any moiety that takes part in an interaction (e.g., antigen and antibody, enzyme and substrate, receptor and ligand) that facilitates capture and/or purification of the molecule. Examples of such affinity moieties include small chemical compounds (such as biotin and derivatives thereof), short amino acid sequences (e.g., 2 to 20 amino acids in length, 4 to 12 amino acids in length), such as the $(His)_6$ tag, $(Leu)_3$ tag, or FLAG tag. The affinity moiety may also be a fluorous tag, which is a fluorinated alkyl group (e.g., perfluoroalkyl) that allows for recovery of the molecule via its interaction with a fluorous phase (e.g., a fluorous liquid phase, a fluorous solid phase). Other affinity moieties are well known in the art.

In certain embodiments, the affinity moiety is selected from the group consisting of $(His)_6$ tag, $(His)_4$ tag, $(His)_3$ tag, $(His)_2$ tag, $(Leu)_4$ tag, $(Leu)_3$ tag, $(Leu)_2$ tag, HA tag, FLAG tag, VSV-G tag, HSV tag, V5 tag, biotin and derivatives thereof, carbohydrates, and glycans. In certain embodiments, the affinity moiety is $C_4$-$C_{20}$ perfluoroalkyl (e.g., $C_6$-$C_{12}$ perfluoroalkyl, $C_6$-$C_8$ perfluoroalkyl, $C_4$ perfluoroalkyl, $C_5$ perfluoroalkyl, $C_6$ perfluoroalkyl, $C_7$ perfluoroalkyl, $C_8$ perfluoroalkyl, $C_9$ perfluoroalkyl, $C_{10}$ perfluoroalkyl, $C_{11}$ perfluoroalkyl, $C_{12}$ perfluoroalkyl, $C_{13}$ perfluoroalkyl, $C_{14}$ perfluoroalkyl, $C_{15}$ perfluoroalkyl, $C_{16}$ perfluoroalkyl, $C_{17}$ perfluoroalkyl, $C_{18}$ perfluoroalkyl, $C_{19}$ perfluoroalkyl, or $C_{20}$ perfluoroalkyl). In certain embodiments, the affinity moiety is biotin. In certain embodiments, the affinity moiety is $C_8$ perfluoroalkyl.

The term "*Staphylococcus* species" refers to Gram-positive bacteria, which appear as grape-like clusters when viewed through a microscope and as large, round, golden-yellow colonies, often with beta-hemolysis, when grown on blood agar plates. An exemplary species of *Staphylococcus* is *Staphylococcus aureus*. An exemplary species of *Staphylococcus* is methicillin-resistant *Staphylococcus aureus* (MRSA). In certain embodiments, *Staphylococcus aureus* refers to antibiotic-resistant strains (e.g., MRSA), resistant to certain antibiotics (e.g., methicillin, penicillin, oxacillin, nafcillin, cephalosporins, tetracyclines, or vancomycin).

The term "*Streptococcus* species" refers to a genus of spherical, Gram-positive bacteria, and a member of the phylum *Firmicutes*. Streptococci are *lactobacillales* or lactic acid bacteria. *Streptococcus* species include *S. hemolyticus*, *S. mitis*, *S. salivarius*, and *S. pneumoniae*. *Streptococcus* species are responsible for infectious diseases such as meningitis, bacterial pneumonia, endocarditis, erysipelas, and necrotizing fasciitis ("flesh-eating" microbial infections).

The term "*Enterococcus* species" refers to a genus of *lactobacillales* or lactic acid bacteria of the *phylum Firmicutes*. They are Gram-positive cocci which often occur in pairs (Diplococci, for example, Diplococcus pneumoniae). *Enterococci* are facultative anaerobic organisms.

The term "*Bacillus* species" refers to a large number of diverse, rod-shaped Gram-positive bacteria that are motile by peritrichous flagella and are aerobic, such as *B. anthracis* and *B. subtilis* or anaerobic such as *Clostridium* spp., for example, *C. difficile*. These bacilli belong to division *Firmicutes*.

As used herein, the term "infectious disease" refers to an illness caused by a pathogenic biological agent that results from transmission from an infected person, animal, or reservoir to a susceptible host, either directly or indirectly, through an intermediate plant or animal host, vector, or inanimate environment. Last J M. ed. A dictionary of epidemiology. 4th ed. New York: Oxford University Press, 1988. Infectious disease is also known as transmissible disease or communicable disease. In certain embodiments, infectious diseases may be asymptomatic for much or even all of their course in a given host. Infectious pathogens or microorganisms include some viruses, bacteria, fungi, protozoa, multicellular parasites, and aberrant proteins known as prions.

BRIEF DESCRIPTION OF THE DRAWINGS

The accompanying drawings, which constitute a part of this specification, illustrate several embodiments of the invention and together with the description, serve to explain the principles of the invention.

DETAILED DESCRIPTION OF THE INVENTION

Figure 1:
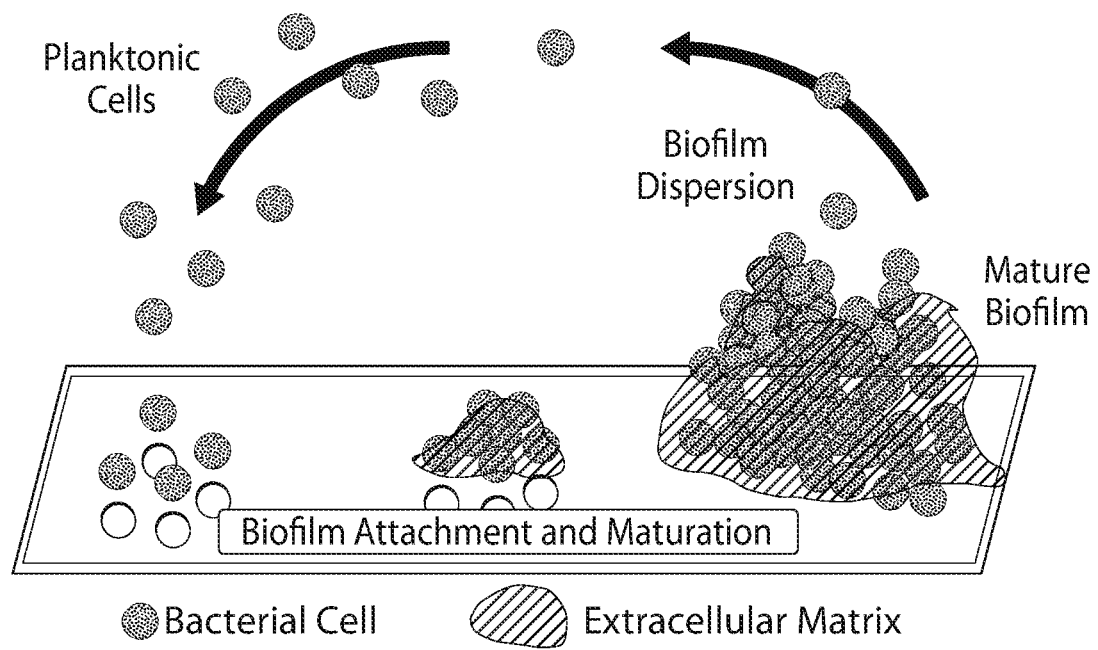
FIG. 1. The process of biofilm formation, maturation and dispersion.

Recently, NH 125 (depicted in FIG. 2A) was reported to eradicate methicillin-resistant *Staphylococcus aureus* (MRSA) biofilms and persister cells in stationary cultures through the depolarization of the outer membrane,[26] then later lipid bilayer destruction.[27] This is interesting as NH 125 also has reported anticancer[28,29] and neuromodulatory[30,31] activities in vitro and in vivo. The charged nitrogen atom of the imidazole heterocycle along with the long aliphatic tail led us to believe that NH 125 elicits its antibacterial activities through the destruction and lysis of bacterial membranes, similar to other quaternary ammonium cations.[16,18,32] In addition, new synthetic analogues of NH125 could be rapidly synthesized and lead to the identification of more effective persister- and biofilm-killing agents against drug-resistant and tolerant pathogenic bacteria.

Bacterial biofilms housing dormant persister cells are innately tolerant to antibiotics and disinfectants, yet several membrane-active agents are known to eradicate tolerant bacterial cells. NH 125, a membrane-active persister-killer and starting point for development, led to the identification of N-arylated analogues 1 and 2 (see FIG. 2A) and displayed improved biofilm-killing potencies and rapid persister-killing activities in stationary cultures of methicillin-resistant *Staphylococcus aureus* (MRSA). Compounds 1 and 2 were found to be good membrane-active agents in biofilm eradication assays with 1 demonstrating minimum biofilm eradication concentrations (MBEC) of 23.5, 11.7, and 2.35 µM against MRSA, methicillin-resistant *S. epidermidis* (MRSE), and vancomycin-resistant *Enterococcus faecium* (VRE) biofilms, respectively. The panel of membrane-active agents was tested against MRSA stationary cultures, and 1 was found to rapidly eradicate MRSA stationary cells by 4-logs (99.99%) in 30 minutes. The potent biofilm eradication and rapid persister cell killing exhibited by N-arylated analogues of NH 125 could have significant impact addressing biofilm-associated problems and as antibacterial agents. The compounds of Formula (I') or (I) (e.g., compounds 1 and 2) may also be useful in other therapeutic areas.

The present invention provides compounds for killing a microorganism (e.g., bacteria, fungi, viruses, protozoa, or multicellular parasites), treating and/or preventing infectious diseases (e.g., infections by microorganisms, bacterial infections, cystic fibrosis infection, foreign body infection, urinary tract infection (UTI), or infections leading to biofilms), controlling and/or eradicating biofilms (e.g., bacterial biofilms), preventing biofilm formation, sterilizing a surface, killing persister cells, and/or eradicating persister cells (e.g., in a subject). Also provided by the present disclosure are pharmaceutical compositions, kits, methods, and uses including a compound of Formula (I') or (I) as described herein.

Compounds

Aspects of the present disclosure relate to the compounds described herein. The compounds described herein may be useful in killing a microorganism (e.g., bacteria, fungi, viruses, protozoa, or multicellular parasites), treating and/or preventing infectious diseases (e.g., infections by microorganisms, bacterial infections, cystic fibrosis infection, foreign body infection, urinary tract infection (UTI), or infections leading to biofilms), controlling and/or eradicating biofilms (e.g., bacterial biofilms), preventing biofilm formation, sterilizing a surface, killing persister cells, and/or eradicating persister cells (e.g., in a subject in need thereof or in a subject involving a biofilm). In certain embodiments, a compound described herein is a compound of any one of Formula (I') or (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I') or (I), or a pharmaceutically acceptable salt thereof.

In certain embodiments, a compound described herein is of Formula (I'):

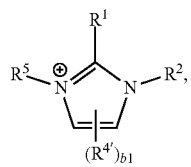

or a pharmaceutically acceptable salt, solvate, hydrate, tautomer, or stereoisomer thereof, wherein:
$R^1$ is hydrogen or optionally substituted alkyl;
$R^2$ is optionally substituted $C_5$-$C_{24}$ alkyl;
$R^5$ is absent, or independently hydrogen, optionally substituted alkyl, optionally substituted acyl, optionally substituted alkenyl, or optionally substituted aryl;
each instance of $R^{4'}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, sulfonyl, —OR$^a$, —N(R$^b$)$_2$, —SR$^a$ or optionally two instances of $R^{4'}$ are joined together with the intervening atoms to form optionally substituted aryl;
each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; and
each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^b$ are joined together with the intervening atoms to form optionally substituted heterocyclyl or optionally substituted heteroaryl; and
b1 is 0, 1, or 2.

In certain embodiments, the compound of Formula (I') is of Formula (I).

In certain embodiments, a compound described herein is of Formula (I):

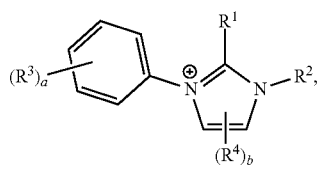

or a pharmaceutically acceptable salt, solvate, hydrate, tautomer, or stereoisomer thereof, wherein:
$R^1$ is hydrogen or optionally substituted alkyl,
$R^2$ is optionally substituted $C_5$-$C_{24}$ alkyl;
each instance of $R^3$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, sulfonyl, —OR$^a$, —N(R$^b$)$_2$, or —SR$^a$;
each instance of $R^4$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, sulfonyl, —OR$^a$, —N(R$^b$)$_2$, or —SR$^a$;
each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; and
each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl;
a is 0, 1, 2, 3, 4, or 5; and
b is 0, 1, or 2.

Formulae (I') and (I) include substituent $R^1$. In certain embodiments, $R^1$ is hydrogen. In certain embodiments, $R^1$ is optionally substituted alkyl (e.g., substituted or unsubstituted $C_{1-6}$ alkyl). In certain embodiments, $R^1$ is substituted or unsubstituted methyl. In certain embodiments, $R^1$ is substituted methyl. In certain embodiments, $R^1$ is unsubstituted methyl. In certain embodiments, $R^1$ is substituted or unsubstituted ethyl. In certain embodiments, $R^1$ is substituted or unsubstituted propyl.

Formulae (I') and (I) include substituent $R^2$. In certain embodiments, $R^2$ is optionally substituted $C_5$-$C_{24}$ alkyl. In certain embodiments, $R^2$ is optionally substituted $C_{10}$-$C_{20}$ alkyl. In certain embodiments, $R^2$ is optionally substituted $C_{12}$-$C_{20}$ alkyl. In certain embodiments, $R^2$ is optionally substituted $C_{12}$-$C_{16}$ alkyl. In certain embodiments, $R^2$ is optionally substituted $C_{10}$, $C_{11}$, $C_{12}$, $C_{13}$, $C_{14}$, $C_{15}$, or $C_{16}$ alkyl. In certain embodiments, $R^2$ is optionally substituted $C_{14}$ alkyl. In certain embodiments, $R^2$ is unsubstituted $C_{14}$ alkyl. In certain embodiments, $R^2$ is optionally substituted $C_{16}$ alkyl. In certain embodiments, $R^2$ is unsubstituted $C_{16}$ alkyl. In certain embodiments, $R^2$ is optionally substituted alkenyl (e.g., substituted or unsubstituted $C_{2-6}$ alkenyl). In certain embodiments, $R^2$ is optionally substituted alkynyl (e.g., substituted or unsubstituted $C_{2-6}$ alkynyl). Formula (I) includes zero or more instances of $R^3$. In certain embodiments, a is 0. In certain embodiments, a is 1. In certain embodiments, a is 2. In certain embodiments, a is 3. In certain embodiments, a is 4. In certain embodiments, a is 5. In certain embodiments, at least one instance of $R^3$ is hydrogen. In certain embodiments, at least one instance of $R^3$ is substituted or unsubstituted acyl (e.g., —C(═O)Me). In certain embodiments, at least one instance of $R^3$ is halogen (e.g., F, Cl, Br, or I). In certain embodiments, at least one instance of $R^3$ is F. In certain embodiments, at least one instance of $R^3$ is Cl. In certain embodiments, at least one instance of $R^3$ is Br. In certain embodiments, at least one instance of $R^3$ is I.

In certain embodiments, at least one instance of $R^3$ is —CN. In certain embodiments, at least one instance of $R^3$ is —SCN. In certain embodiments, at least one instance of $R^3$ is —NO$_2$. In certain embodiments, at least one instance of $R^3$ is —N$_3$. In certain embodiments, at least one instance of $R^3$ is substituted or unsubstituted alkyl (e.g., substituted or unsubstituted $C_{1-6}$ alkyl). In certain embodiments, at least one instance of $R^3$ is optionally substituted $C_1$-$C_6$ alkyl. In certain embodiments, at least one instance of $R^3$ is substituted or unsubstituted methyl. In certain embodiments, at least one instance of $R^3$ is substituted methyl. In certain embodiments, at least one instance of $R^3$ is —CF$_3$. In certain embodiments, at least one instance of $R^3$ is unsubstituted methyl. In certain embodiments, at least one instance of $R^3$ is substituted or unsubstituted ethyl. In certain embodiments, at least one instance of $R^3$ is substituted or unsubstituted propyl. In certain embodiments, at least one instance of $R^3$ is substituted or unsubstituted alkenyl (e.g., substituted or unsubstituted $C_{2-6}$ alkenyl). In certain embodiments, at least one instance of $R^3$ is substituted or unsubstituted alkynyl (e.g., substituted or unsubstituted $C_{2-6}$ alkynyl). In certain embodiments, at least one instance of $R^3$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^3$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^3$ is substituted or unsubstituted aryl (e.g., substituted or unsubstituted, 6- to 10-membered aryl). In certain embodiments, at least one instance of $R^3$ is substituted or unsubstituted benzyl. In certain embodiments, at least one instance of $R^3$ is substituted benzyl. In certain embodiments, at least one instance of $R^3$ is unsubstituted benzyl. In certain embodiments, at least one instance of $R^3$ is substituted or unsubstituted phenyl. In certain embodiments, at least one instance of $R^3$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur, or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^3$ is —OR$^a$ (e.g., —OH or —OMe). In certain embodiments, at least one instance of $R^3$ is —OR$^a$, wherein $R^a$ is optionally substituted $C_1$-$C_6$ alkyl or optionally substituted aryl. In certain embodiments, at least one instance of $R^3$ is —OMe. In certain embodiments, at least one instance of $R^3$ is —OCF$_3$. In certain embodiments, at least one instance of $R^3$ is —OEt. In certain embodiments, at least one instance of $R^3$ is —O(n-Pr). In certain embodiments, at least one instance of $R^3$ is —O(n-Bu). In certain embodiments, at least one instance of $R^3$ is —O(t-Bu). In certain embodiments, at least one instance of $R^3$ is —Oph. In certain embodiments, at least one instance of $R^3$ is hydrogen, halogen, or —OR$^a$, wherein $R^a$ is optionally substituted $C_1$-$C_6$ alkyl or optionally substituted aryl. In certain embodiments, at least one instance of $R^3$ is —N(R$^b$)$_2$ (e.g., —NMe$_2$). In certain embodiments, at least one instance of $R^3$ is sulfonyl. In certain embodiments, at least one instance of $R^3$ is —SR$^a$ (e.g., —SMe).

In certain embodiments, $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom. In certain embodiments, $R^a$ is hydrogen. In certain embodiments, $R^a$ is optionally substituted acyl. In certain embodiments, $R^a$ is optionally substituted alkyl (e.g., substituted or unsubstituted $C_{1-6}$ alkyl). In certain embodiments, $R^a$ is optionally substituted alkenyl (e.g., substituted or unsubstituted $C_{2-6}$ alkenyl). In certain embodiments, $R^a$ is substituted or unsubstituted alkynyl (e.g., substituted or unsubstituted $C_{2-6}$ alkynyl). In certain embodiments, $R^a$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^a$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^a$ is substituted or unsubstituted aryl (e.g., substituted or unsubstituted, 6- to 10-membered aryl). In certain embodiments, $R^a$ is substituted or unsubstituted benzyl. In certain embodiments, $R^a$ is substituted or unsubstituted phenyl. In certain embodiments, $R^a$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^a$ is an oxygen protecting group when attached to an oxygen atom. In certain embodiments, $R^a$ is a sulfur protecting group when attached to a sulfur atom.

In certain embodiments, $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^b$ are joined together with the intervening atoms to form optionally substituted heterocyclyl or optionally substituted heteroaryl. In certain embodiments, $R^b$ is hydrogen. In certain embodiments, $R^b$ is optionally substituted acyl. In certain embodiments, $R^b$ is optionally substituted alkyl (e.g., substituted or unsubstituted $C_{1-6}$ alkyl). In certain embodiments, $R^b$ is optionally substituted alkenyl (e.g., substituted or unsubstituted $C_{2-6}$ alkenyl). In certain embodiments, $R^b$ is substituted or unsubstituted alkynyl (e.g., substituted or unsubstituted $C_{2-6}$ alkynyl). In certain embodiments, $R^b$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^b$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^b$ is substituted or unsubstituted aryl (e.g., substituted or unsubstituted, 6- to 10-membered aryl). In certain embodiments, $R^b$ is substituted or unsubstituted benzyl. In certain embodiments, $R^b$ is substituted or unsubstituted phenyl. In certain embodiments, $R^b$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^b$ is an nitrogen protecting group when attached to an nitrogen atom. In certain embodiments, two instances of $R^b$ are joined together with the intervening atoms to form optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur) or optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (I) includes zero or more instances of $R^4$. In certain embodiments, b is 0. In certain embodiments, b is 1. In certain embodiments, b is 2. In certain embodiments, at least one instance of $R^4$ is hydrogen. In certain embodiments, both instances of $R^4$ are hydrogen. In certain embodiments, at least one instance of $R^4$ is substituted or unsubstituted acyl (e.g., —C(=O)Me). In certain embodiments, at least one instance of $R^4$ is halogen (e.g., F, Cl, Br, or I). In certain embodiments, at least one instance of $R^4$ is —CN. In certain embodiments, at least one instance of $R^4$ is —SCN. In certain embodiments, at least one instance of $R^4$ is —NO$_2$. In certain embodiments, at least one instance of $R^4$ is —N$_3$. In certain embodiments, at least one instance of $R^4$ is substituted or unsubstituted alkyl (e.g., substituted or unsubstituted $C_{1-6}$ alkyl). In certain embodiments, at least one instance of $R^4$ is optionally substituted $C_1$-$C_6$ alkyl. In certain embodiments, at least one instance of $R^4$ is substituted or unsubstituted methyl. In certain embodiments, at least one instance of $R^4$ is substituted or unsubstituted ethyl. In certain embodiments, at least one instance of $R^4$ is substituted or unsubstituted propyl. In certain embodiments, at least one instance of $R^4$ is substituted or unsubstituted alkenyl (e.g., substituted or unsubstituted $C_{2-6}$ alkenyl). In certain embodiments, at least one instance of $R^4$ is substituted or unsubstituted alkynyl (e.g., substituted or unsubstituted $C_{2-6}$ alkynyl). In certain embodiments, at least one instance of $R^4$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^4$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^4$ is substituted or unsubstituted aryl (e.g., substituted or unsubstituted, 6- to 10-membered aryl). In certain embodiments, at least one instance of $R^4$ is substituted or unsubstituted benzyl. In certain embodiments, at least one instance of $R^4$ is substituted benzyl. In certain embodiments, at least one instance of $R^4$ is unsubstituted benzyl. In certain embodiments, at least one instance of $R^4$ is substituted or unsubstituted phenyl. In certain embodiments, at least one instance of $R^4$ is substituted phenyl. In certain embodiments, at least one instance of $R^4$ is unsubstituted phenyl. In certain embodiments, at least one instance of $R^4$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^4$ is sulfonyl. In certain embodiments, at least one instance of $R^4$ is —OR$^a$ (e.g., —OH or —OMe). In certain embodiments, at least one instance of $R^4$ is —OR$^a$, wherein $R^a$ is optionally substituted $C_1$-$C_6$ alkyl. In certain embodiments, at least one instance of $R^4$ is —OMe. In certain embodiments, at least one instance of $R^4$ is —OEt. In certain embodiments, at least one instance of $R^4$ is —O(n-Pr). In certain embodiments, at least one instance of $R^4$ is —O(n-Bu). In certain embodiments, at least one instance of $R^4$ is —O(t-Bu). In certain embodiments, at least one instance of $R^4$ is hydrogen or —OR$^a$, wherein $R^a$ is optionally substituted $C_1$-$C_6$ alkyl. In certain embodiments, at least one instance of $R^4$ is —N(R$^b$)$_2$ (e.g., —NMe$_2$). In certain embodiments, at least one instance of $R^4$ is —SR$^a$ (e.g., —SMe).

Formula (I') includes zero or more instances of $R^{4'}$. In certain embodiments, b1 is 0. In certain embodiments, b1 is 1. In certain embodiments, b1 is 2. In certain embodiments, at least one instance of $R^{4'}$ is $R^4$. In certain embodiments, at least one instance of $R^{4'}$ is hydrogen. In certain embodiments, at least one instance of $R^{4'}$ is substituted or unsubstituted acyl (e.g., —C(=O)Me). In certain embodiments, at least one instance of $R^{4'}$ is halogen (e.g., F, Cl, Br, or I). In certain embodiments, at least one instance of $R^{4'}$ is —CN. In certain embodiments, at least one instance of $R^{4'}$ is —SCN. In certain embodiments, at least one instance of $R^{4'}$ is —NO$_2$. In certain embodiments, at least one instance of $R^{4'}$ is —N$_3$. In certain embodiments, at least one instance of $R^{4'}$ is substituted or unsubstituted alkyl (e.g., substituted or unsubstituted $C_{1-6}$ alkyl). In certain embodiments, at least one instance of $R^{4'}$ is optionally substituted $C_1$-$C_6$ alkyl. In certain embodiments, at least one instance of $R^{4'}$ is substituted or unsubstituted methyl. In certain embodiments, at least one instance of $R^{4'}$ is substituted or unsubstituted ethyl. In certain embodiments, at least one instance of $R^{4'}$ is substituted or unsubstituted propyl. In certain embodiments, at least one instance of $R^{4'}$ is substituted or unsubstituted alkenyl (e.g., substituted or unsubstituted $C_{2-6}$ alkenyl). In certain embodiments, at least one instance of $R^{4'}$ is substituted or unsubstituted alkynyl (e.g., substituted or unsubstituted $C_{2-6}$ alkynyl). In certain embodiments, at least one instance of $R^{4'}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{4'}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{4'}$ is substituted or unsubstituted aryl (e.g., substituted or unsubstituted, 6- to 10-membered aryl). In certain embodiments, at least one instance of $R^{4'}$ is substituted or unsubstituted benzyl. In certain embodiments, at least one instance of $R^{4'}$ is substituted benzyl. In certain embodiments, at least one instance of $R^{4'}$ is unsubstituted benzyl. In certain embodiments, at least one instance of $R^{4'}$ is substituted or unsubstituted phenyl. In certain embodiments, at least one instance of $R^{4'}$ is substituted phenyl. In certain embodiments, at least one instance of $R^{4'}$ is unsubstituted phenyl. In certain embodiments, at least one instance of $R^{4'}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{4'}$ is sulfonyl. In certain embodiments, at least one instance of $R^{4'}$ is —$OR^a$ (e.g., —OH or —OMe). In certain embodiments, at least one instance of $R^{4'}$ is —$OR^a$, wherein $R^a$ is optionally substituted $C_1$-$C_6$ alkyl. In certain embodiments, at least one instance of $R^{4'}$ is —OMe. In certain embodiments, at least one instance of $R^{4'}$ is —OEt. In certain embodiments, at least one instance of $R^{4'}$ is —O(n-Pr). In certain embodiments, at least one instance of $R^{4'}$ is —O(n-Bu). In certain embodiments, at least one instance of $R^{4'}$ is —O(t-Bu). In certain embodiments, at least one instance of $R^{4'}$ is hydrogen or —$OR^a$, wherein $R^a$ is optionally substituted $C_1$-$C_6$ alkyl. In certain embodiments, at least one instance of $R^{4'}$ is —$N(R^b)_2$ (e.g., —$NMe_2$). In certain embodiments, at least one instance of $R^{4'}$ is —$SR^a$ (e.g., —SMe).

In certain embodiments, two instances of $R^{4'}$ are joined together with the intervening atoms to form optionally substituted aryl. In certain embodiments, the compound of Formula (I') is of formula:

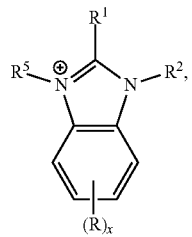

wherein each instance of R is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; and x is 0, 1, 2, 3, or 4. In certain embodiments, the compound of Formula (I') is of formula:

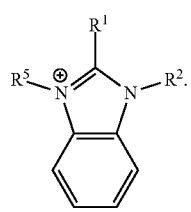

Formula (I') includes $R^5$. In certain embodiments, $R^5$ is hydrogen. In certain embodiments, $R^5$ is optionally substituted alkyl (e.g., substituted or unsubstituted $C_{1-6}$ alkyl). In certain embodiments, $R^5$ is optionally substituted $C_1$-$C_6$ alkyl. In certain embodiments, $R^5$ is substituted or unsubstituted methyl. In certain embodiments, $R^5$ is unsubstituted methyl. In certain embodiments, $R^5$ is substituted methyl. In certain embodiments, $R^5$ is of the formula

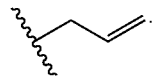

In certain embodiments, $R^5$ is of the formula:

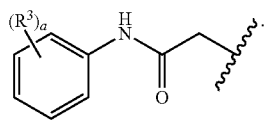

In certain embodiments, $R^5$ is of the formula:

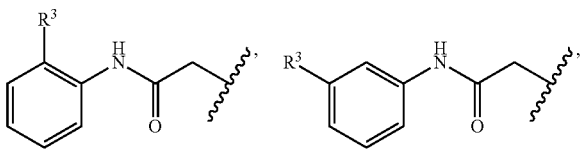

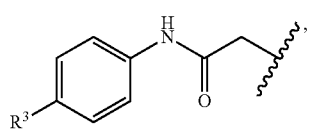

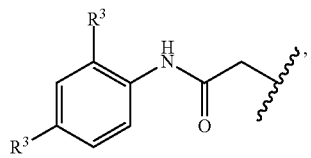

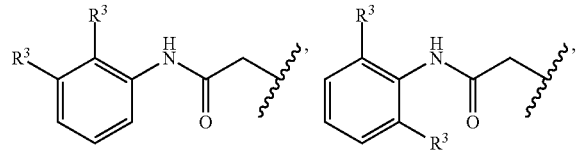

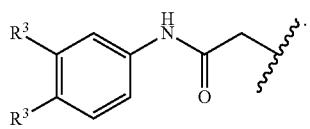

or

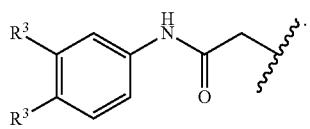

In certain embodiments, $R^5$ is of the formula

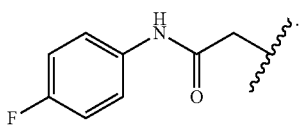 [SMILES: *CC(=O)Nc1ccc(F)cc1]

In certain embodiments, $R^5$ is substituted or unsubstituted ethyl. In certain embodiments, $R^5$ is substituted ethyl. In certain embodiments, $R^5$ is of the formula:

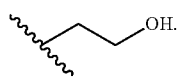

In certain embodiments, $R^5$ is substituted or unsubstituted propyl. In certain embodiments, $R^5$ is n-butyl. In certain embodiments, $R^5$ is t-butyl.

In certain embodiments, $R^5$ is substituted or unsubstituted alkenyl (e.g., substituted or unsubstituted $C_{2-6}$ alkenyl). In certain embodiments, $R^5$ is optionally substituted alkynyl (e.g., substituted or unsubstituted $C_{2-6}$ alkynyl). In certain embodiments, $R^5$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^5$ is optionally substituted acyl (e.g., —C(=O)Me). In certain embodiments, $R^5$ is optionally substituted aryl (e.g., substituted or unsubstituted, 6- to 10-membered aryl). In certain embodiments, $R^5$ is substituted or unsubstituted benzyl. In certain embodiments, $R^5$ is unsubstituted benzyl. In certain embodiments, $R^5$ is substituted benzyl. In certain embodiments, $R^5$ is of the formula:

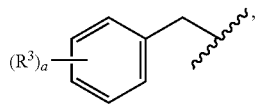

wherein: $R^3$ is optionally substituted $C_1$-$C_6$ alkyl, halogen, —$NO_2$, —$OR^a$, or optionally substituted aryl; each instance of $R^a$ is independently hydrogen or optionally substituted $C_1$-$C_6$ alkyl; a is 0, 1, 2, or 3. In certain embodiments, $R^5$ is of the formula:

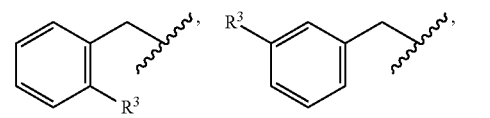

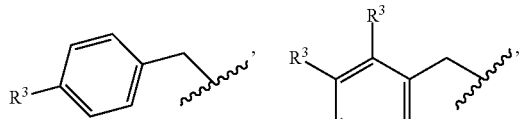

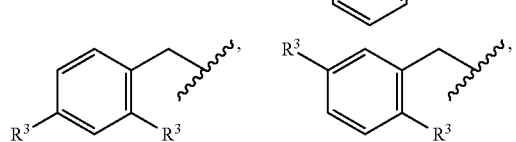

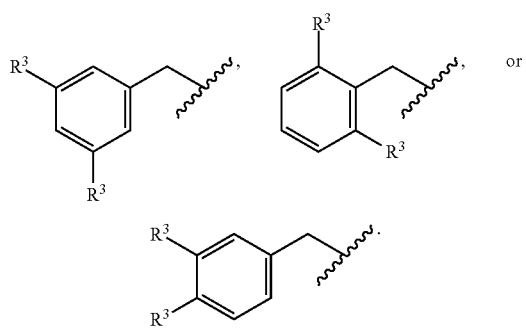

In certain embodiments, $R^5$ is of the formula:

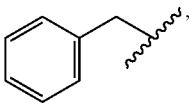
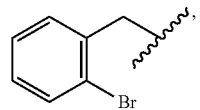
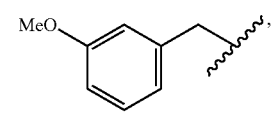
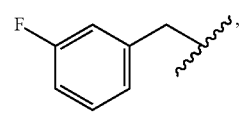
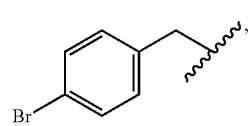
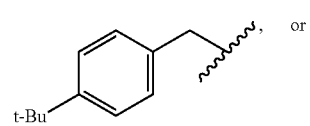
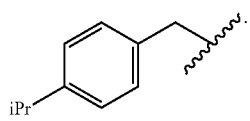

In certain embodiments, $R^5$ is of the formula:

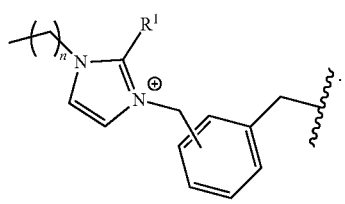

In certain embodiments, $R^5$ is of the formula:

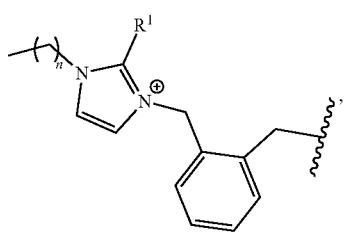

-continued

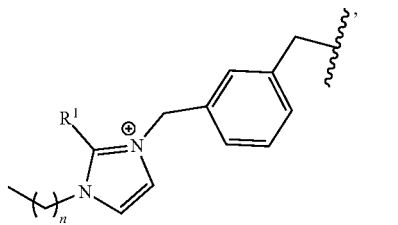, or

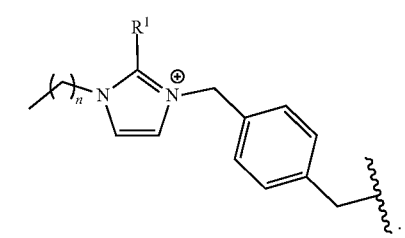.

In certain embodiments, $R^5$ is of the formula:

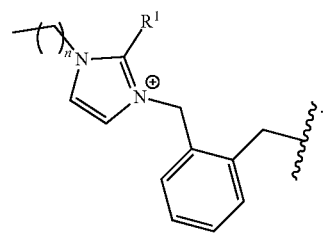

In certain embodiments, $R^5$ is of the formula:

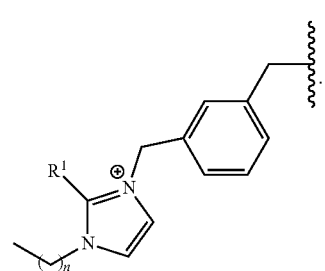

In certain embodiments, $R^5$ is of the formula:

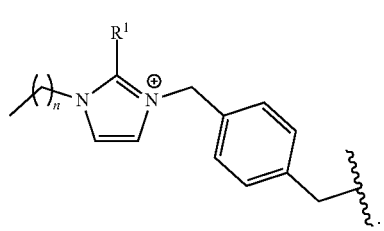.

In certain embodiments, $R^5$ is of the formula:

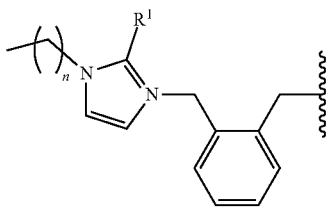

or

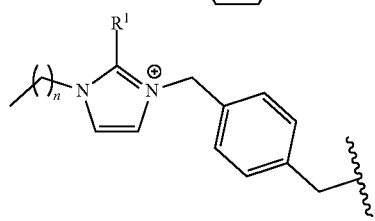.

In certain embodiments, $R^5$ is of the formula:

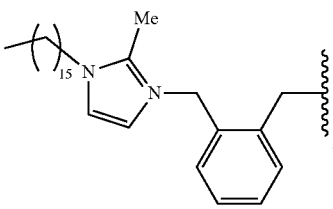, or

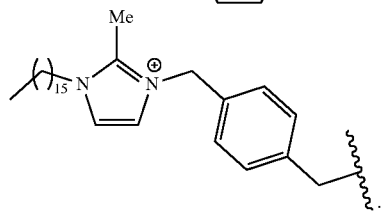.

In certain embodiments, $R^5$ is substituted or unsubstituted phenyl. In certain embodiments, $R^5$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, $R^5$ is absent, or independently hydrogen, optionally substituted alkyl, optionally substituted acyl, optionally substituted alkenyl, or optionally substituted aryl.

In certain embodiments, in a compound of Formula (I'), $R^1$ is hydrogen or optionally substituted alkyl, $R^2$ is optionally substituted $C_5$-$C_{24}$ alkyl; each instance of $R^3$ is independently hydrogen, halogen, or —$OR^a$, wherein $R^a$ is optionally substituted alkyl; each instance of $R^{4'}$ is independently hydrogen, halogen, optionally substituted alkyl; $R^5$ is optionally substituted alkyl or optionally substituted aryl, or optionally two instances of $R^{4'}$ are joined together with the intervening atoms to form optionally substituted aryl; a is 0, 1, 2, 3, 4, or 5; and b is 0, 1, or 2.

In certain embodiments, in a compound of Formula (I), $R^1$ is hydrogen or optionally substituted alkyl, $R^2$ is optionally substituted $C_5$-$C_{24}$ alkyl; each instance of $R^3$ is independently hydrogen, halogen, or —$OR^a$, wherein $R^a$ is optionally substituted alkyl; each instance of $R^4$ is independently hydrogen, halogen, optionally substituted alkyl; a is 0, 1, 2, 3, 4, or 5; and b is 0, 1, or 2.

In certain embodiments, the compound of Formula (I') is of the formula:

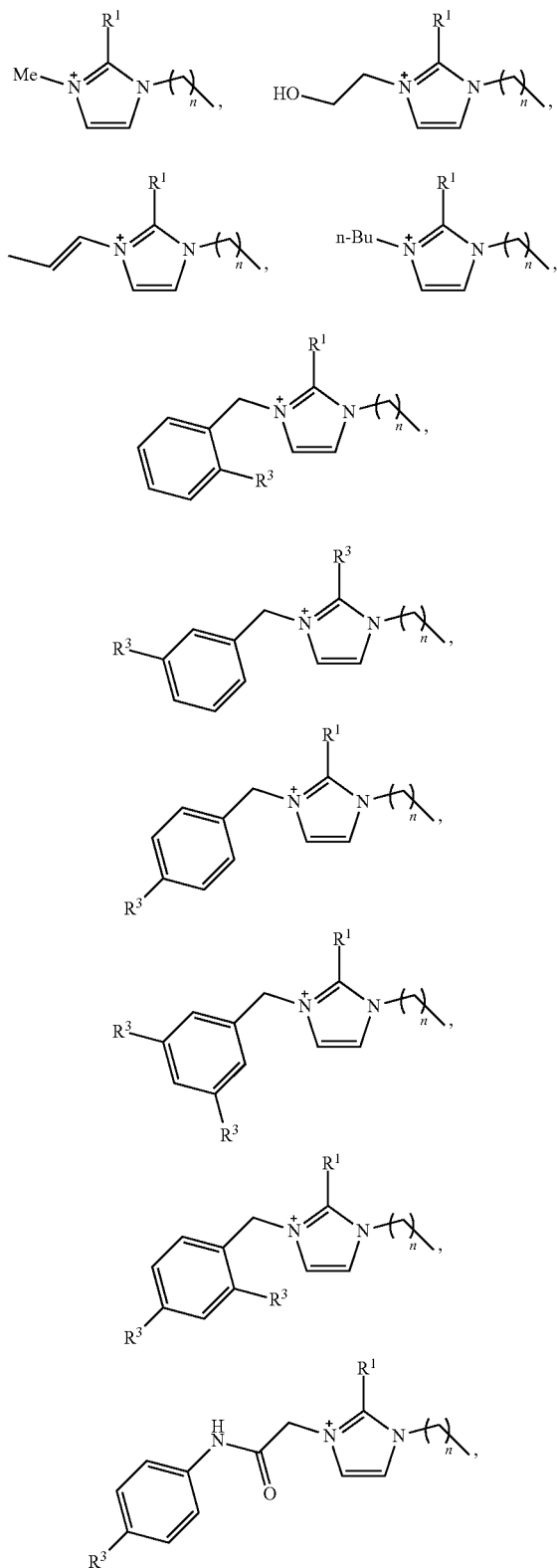

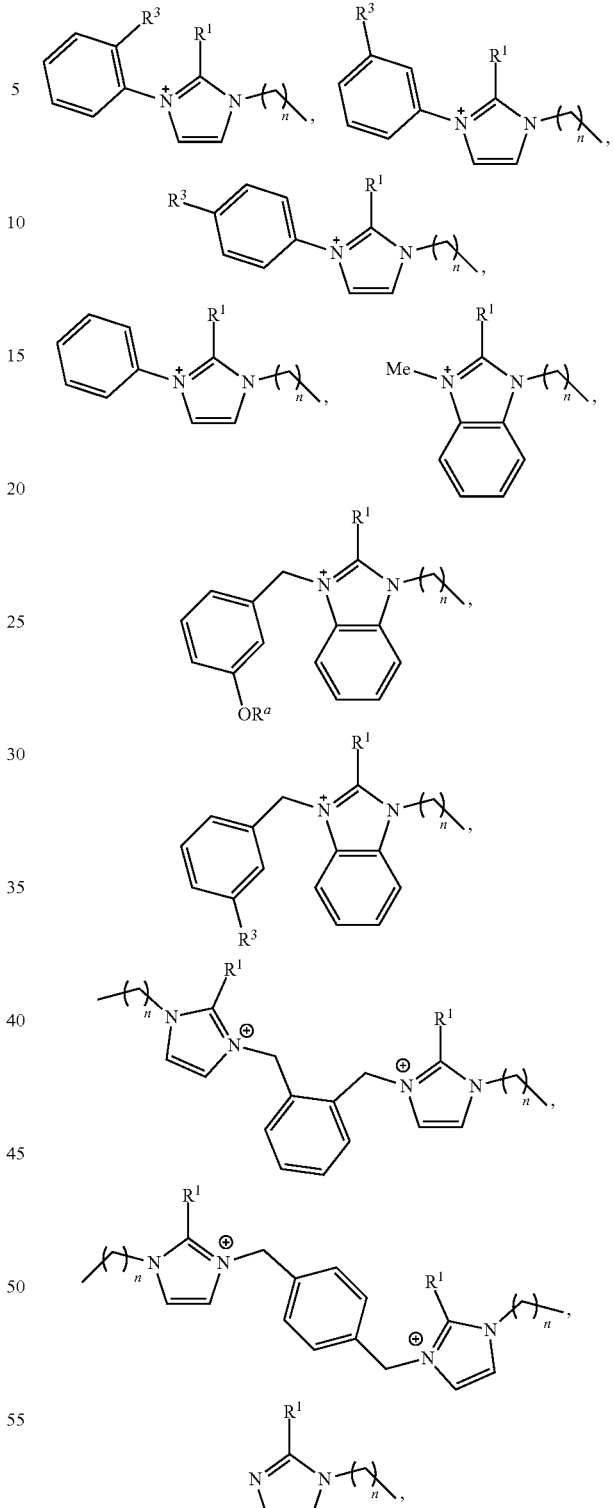

or a pharmaceutically acceptable salt, solvate, hydrate, polymorph, co-crystal, tautomer, stereoisomer, isotopically labeled derivative, or prodrug thereof, wherein n is 11, 12, 13, 14, or 15.

In certain embodiments, the compound of Formula (I') is of the formula:

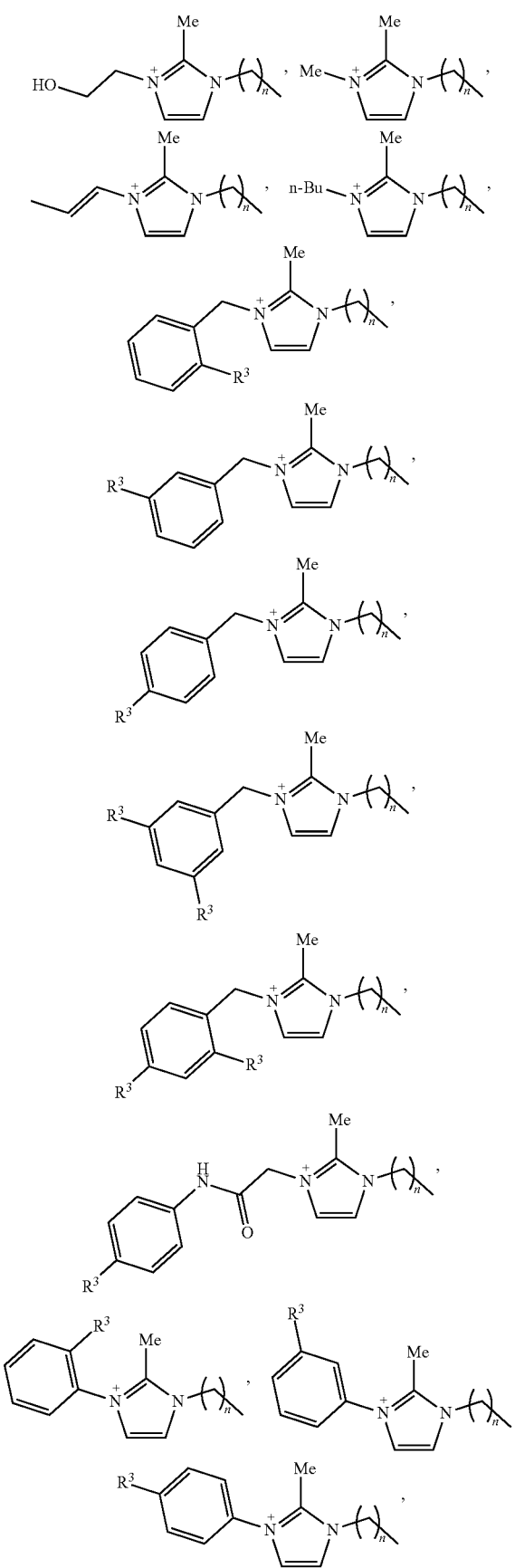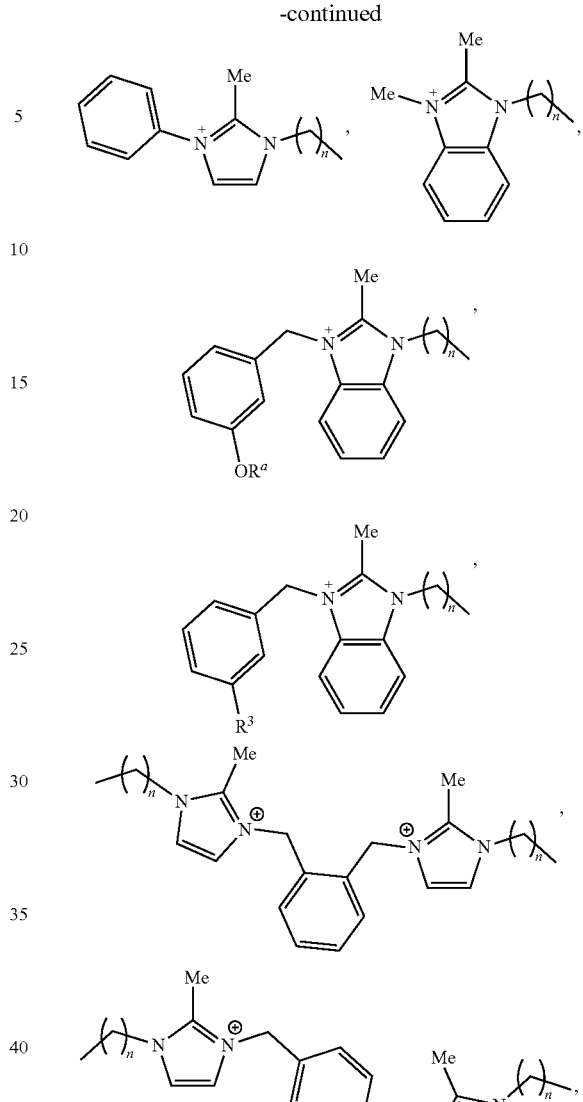
or a pharmaceutically acceptable salt, solvate, hydrate, polymorph, co-crystal, tautomer, stereoisomer, isotopically labeled derivative, or prodrug thereof,
wherein n is 11, 12, 13, 14, or 15.
In certain embodiments, the compound of Formula (I') is of the formula:
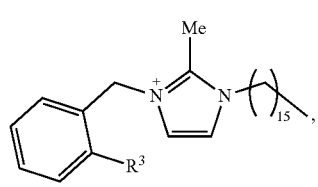

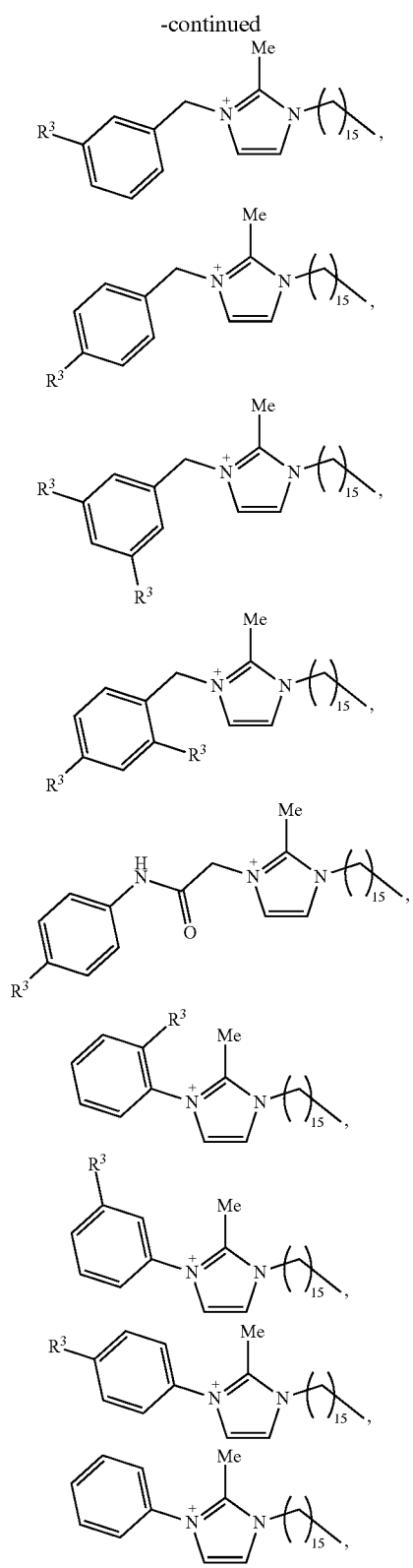
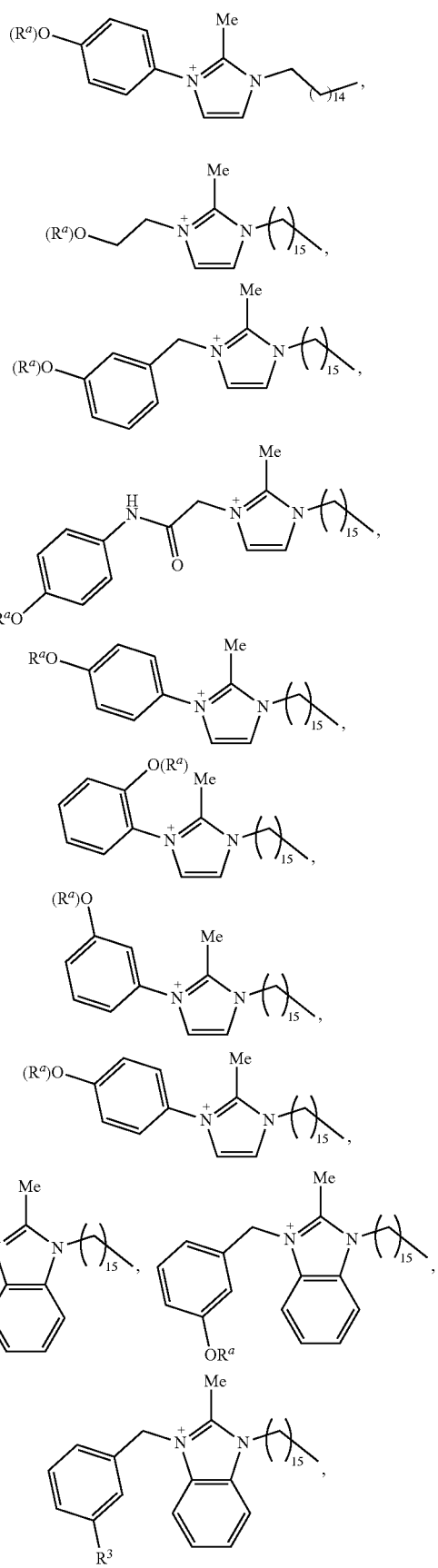
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:

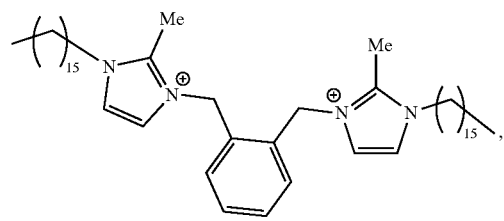
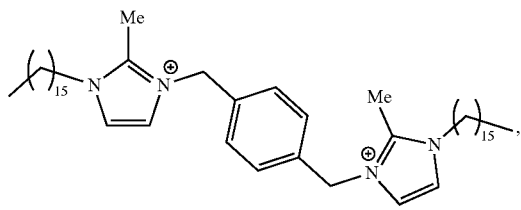
or a pharmaceutically acceptable salt, solvate, hydrate, polymorph, co-crystal, tautomer, stereoisomer, isotopically labeled derivative, or prodrug thereof.
In certain embodiments, the compound of Formula (I') is of the formula:
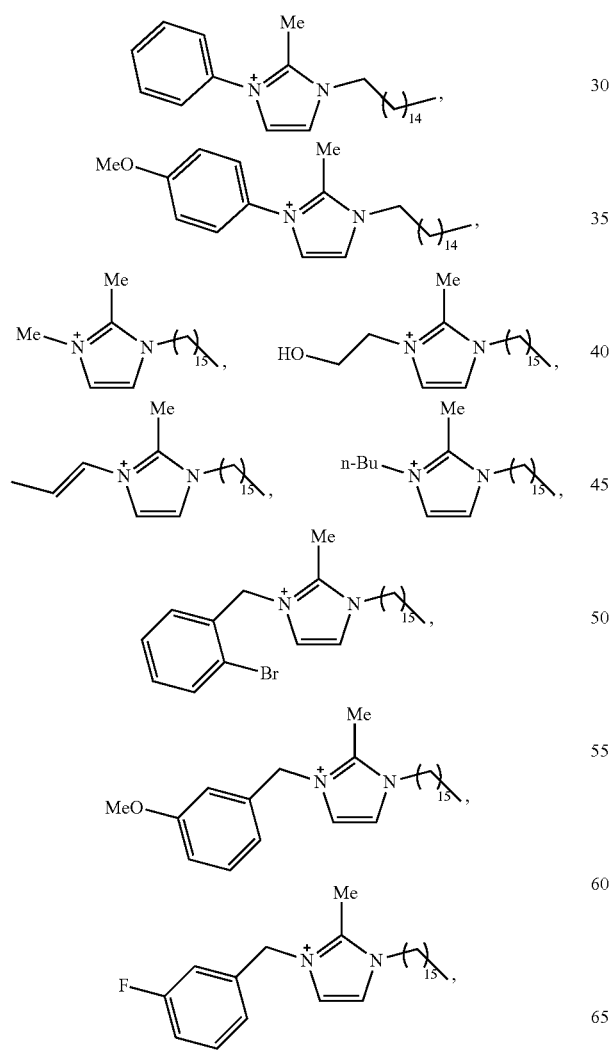
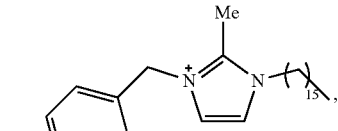
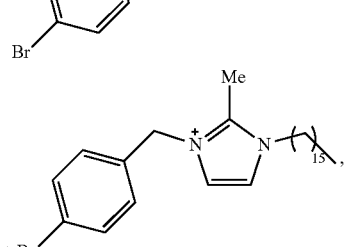
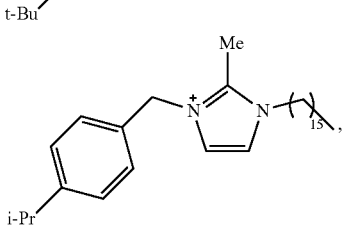
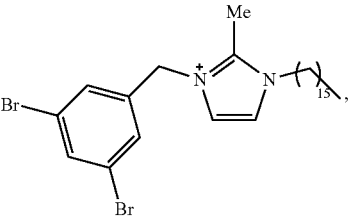
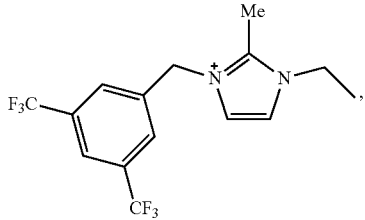
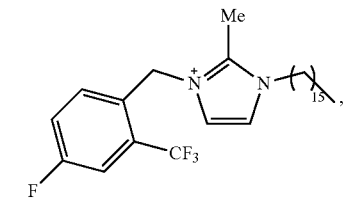
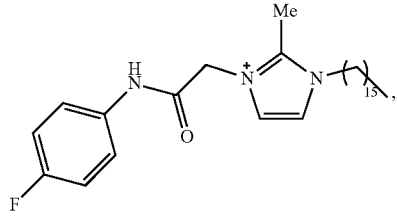
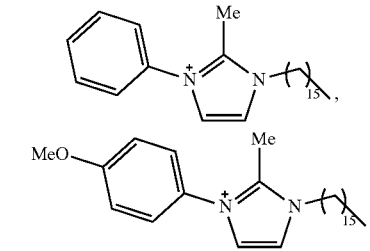

53
-continued
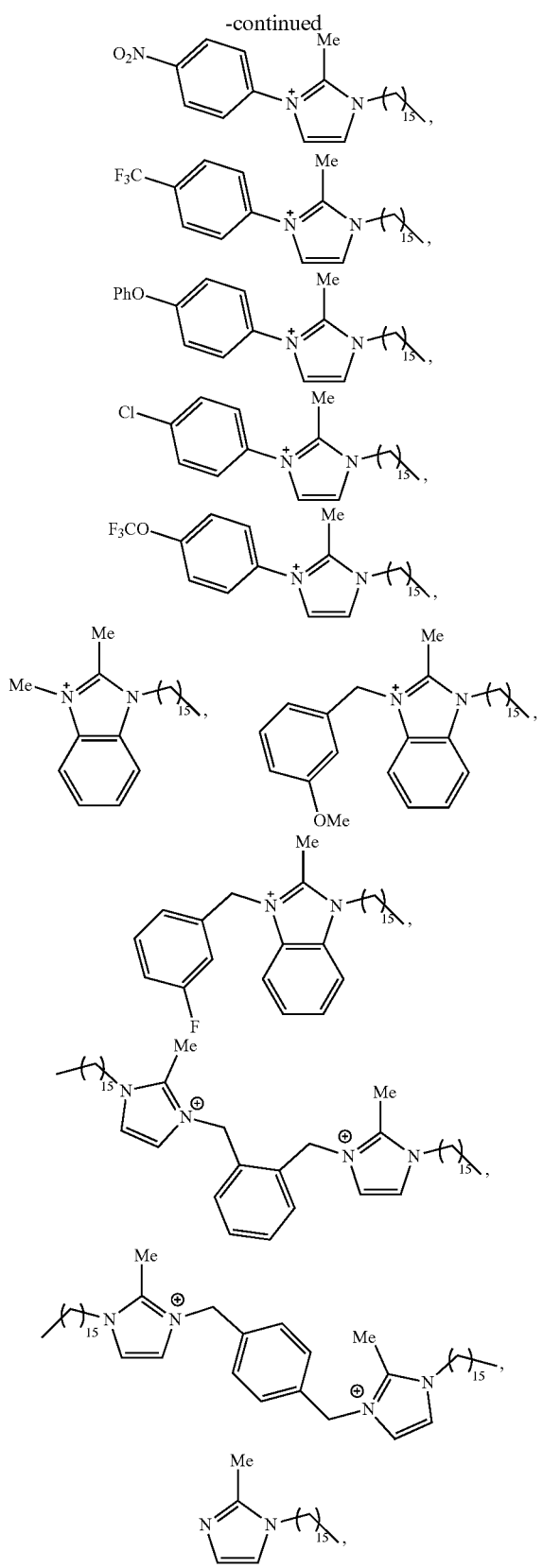
or a pharmaceutically acceptable salt, solvate, hydrate, polymorph, co-crystal, tautomer, stereoisomer, isotopically labeled derivative, or prodrug thereof.
54
In certain embodiments, the compound of Formula (I') is of the formula:
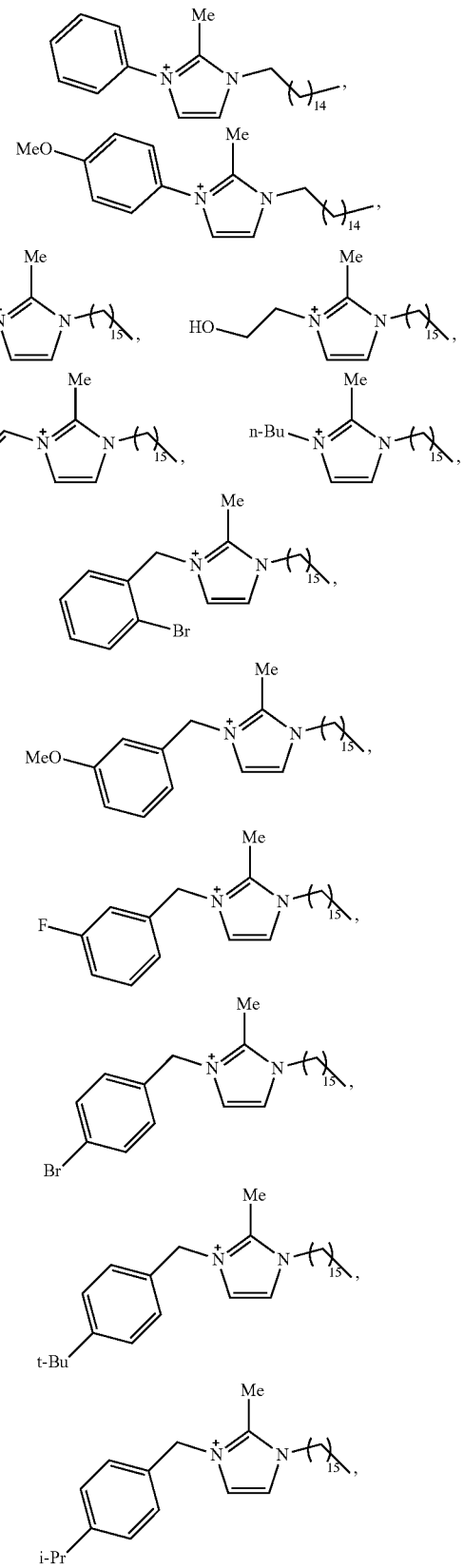

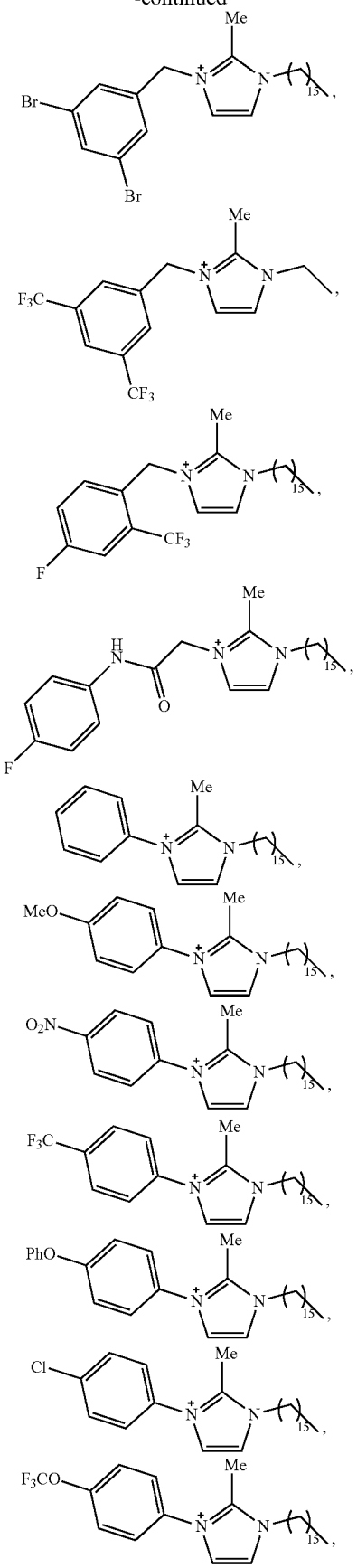

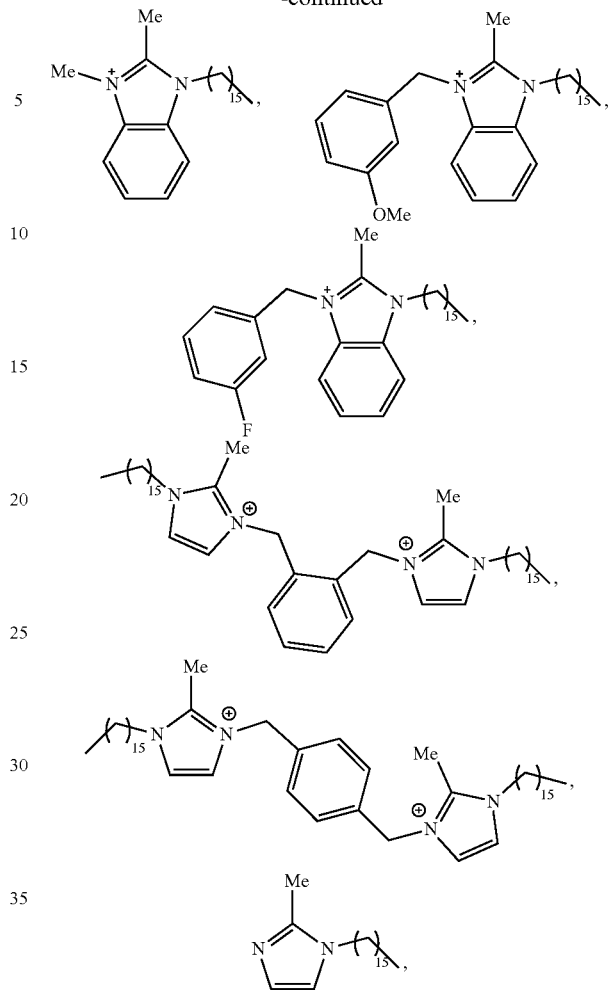

or a pharmaceutically acceptable salt thereof.

In certain embodiments, the compound of Formula (I') is of the formula:

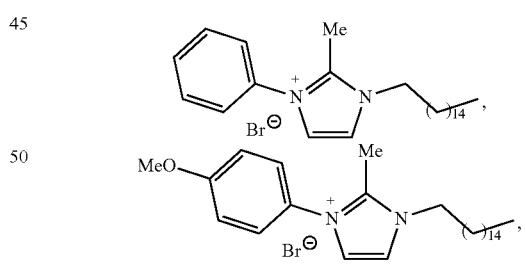

or a pharmaceutically acceptable solvate, hydrate, polymorph, co-crystal, tautomer, stereoisomer, isotopically labeled derivative, or prodrug thereof.

In certain embodiments, provided is the compound of Formula (I') or (I), or halide salts thereof. In certain embodiments, provided is the compound of Formula (I') or (I), or bromide salts thereof. In certain embodiments, provided is the compound of Formula (I') or (I), or chloride salts thereof. In certain embodiments, provided is the compound of Formula (I') or (I), or fluoride salts thereof. In certain embodiments, provided is the compound of Formula (I') or (I), or iodide salts thereof.

In certain embodiments, a compound described herein is a compound of Formula (I') or (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I'), or a pharmaceutically acceptable salt thereof. In certain embodiments, a compound described herein is a compound of Table A. In certain embodiments, a compound described herein is a compound of Formula (I'), of Table A, or a pharmaceutically acceptable salt thereof. In certain embodiments, a compound described herein is a compound of Table B. In certain embodiments, a compound described herein is a compound of Table A or Table B.

Pharmaceutical Compositions, Kits, and Administration

The present invention provides pharmaceutical compositions comprising a compound described herein, e.g., a compound of Formula (I') or (I), or a pharmaceutically acceptable form thereof, as described herein, and a pharmaceutically acceptable excipient. The present invention also provides pharmaceutical compositions for use killing a microorganism (e.g., bacteria, fungi, viruses, protozoa, or multicellular parasites), the prevention and/or treatment of infectious diseases (e.g., infections by microorganisms, bacterial infection, cystic fibrosis infection, foreign body infection, urinary tract infection (UTI), or infections leading to biofilms), controlling and/or eradicating biofilms (e.g., bacterial biofilms), preventing biofilm formation, sterilizing a surface, killing persister cells, and/or eradicating persister cells (e.g., in a subject in need thereof, or in a subject involving a biofilm) comprising a compound described herein, e.g., a compound of Formula (I') or (I), or a pharmaceutically acceptable salt, solvate, hydrate, polymorph, co-crystal, tautomer, stereoisomer, isotopically labeled derivative, or prodrug thereof, and a pharmaceutically acceptable excipient. In certain embodiments, a provided composition comprises two or more compounds described herein. In certain embodiments, a compound described herein, or a pharmaceutically acceptable salt, solvate, hydrate, polymorph, co-crystal, tautomer, stereoisomer, isotopically labeled derivative, or prodrug thereof, is provided in an effective amount in the pharmaceutical composition. In certain embodiments, the effective amount is a therapeutically effective amount. In certain embodiments, the effective amount is an amount effective for inhibiting bacterial growth. In certain embodiments, the effective amount is an amount effective for killing microorganisms. In certain embodiments, the effective amount is an amount effective for killing fungi. In certain embodiments, the effective amount is an amount effective for killing viruses. In certain embodiments, the effective amount is an amount effective for killing protozoa. In certain embodiments, the effective amount is an amount effective for killing multicellular parasites. In certain embodiments, the effective amount is an amount effective for killing bacteria. In certain embodiments, the effective amount is an amount effective for killing persister cells. In certain embodiments, the effective amount is an amount effective for killing persister cells in bacteria biofilms. In certain embodiments, the effective amount is an amount effective for controlling and/or eradicating biofilms (e.g., bacterial biofilms). In certain embodiments, the effective amount is an amount effective for preventing biofilm formation. In certain embodiments, the effective amount is an amount effective for sterilizing a surface.

In certain embodiments, the bacterium which is the causative agent of the infection is a Gram-negative bacterium. In certain embodiments, the Gram-negative bacterium is selected from the group consisting of *Escherichia, Citrobacter, Enterobacter, Klebsiella, Proteus, Serratia, Shigella, Salmonella, Morganella, Providencia, Edwardsiella, Erwinia, Hafnia, Yersinia, Acinetobacter, Vibrio, Aeromonas, Pseudomonas, Haemophilus, Pasteurella, Campylobacter, Helicobacter, Branhamella, Moraxella, Neisseria, Veillonella, Fusobacterium, Bacteroides, Actinobacillus, Aggregatibacter, Agrobacterium, Porphyromonas, Prevotella, Ruminobacter, Roseburia, Caulobacter, Francisella, Borrelia, Treponema, Brucella*, and *Rickettsia*. In certain embodiments, the Gram-negative bacterium is selected from the group consisting of *Escherichia coli, Morganella morganii, Branhamella catarrhalis, Veillonella parvula, Actinobacillus actinomycetemcomitans, Aggregatibacter actinomycetemcomitans, Caulobacter crescentus*, and *Treponema pallidum*. In certain embodiments, the Gram-negative bacterium is selected from the group consisting of *Escherichia coli, Citrobacter* spp, *Enterobacter* spp, *Klebsiella* spp, *Proteus* spp, *Serratia* spp, *Shigella* spp, *Salmonella* spp, *Morganella morganii, Providencia* spp, *Edwardsiella* spp, *Erwinia* spp, Hafnia spp, *Yersinia* spp, *Acinetobacter* spp, *Vibrio* spp, *Aeromonas* spp, *Pseudomonas* spp, *Haemophilus* spp, *Pasteurella* spp, *Campylobacter* spp, *Helicobacter* spp, *Branhamella catarrhalis, Moraxella* spp, *Neisseria* spp, *Veillonella parvula, Fusobacterium* spp, *Bacteroides* spp, *Actinobacillus actinomycetemcomitans, Aggregatibacter actinomycetemcomitans, Agrobacterium* spp, *Porphyromonas* spp, *Prevotella* spp, Ruminobacter spp, *Roseburia* spp, *Caulobacter crescentus, Francisella* spp, *Borrelia* spp, *Treponema pallidum, Brucella* spp, and *Rickettsia*.

In certain embodiments, the bacterium is a Gram-positive bacterium. In certain embodiments, the bacterium is at least one selected from the group consisting of *Staphylococcus* sp., *Enterococcus* sp., *Escherichia coli, Bacillus* sp., *Salmonella* sp., and *Mycobacterium* sp. In certain embodiments, the Gram-positive bacterium is selected from the group consisting of *Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium, Corynebacterium, Capnocytophaga, Bifidobacterium*, and *Gardnerella*. In certain embodiments, the Gram-positive bacterium is selected from the group consisting of *Staphylococcus* spp, *Streptococcus* spp, *Micrococcus* spp, Peptococcus spp, *Peptostreptococcus* spp, *Enterococcus* spp, *Bacillus* spp, *Clostridium* spp, *Lactobacillus* spp, *Listeria* spp, Erysipelothrix spp, *Propionibacterium* spp, *Eubacterium* spp, *Corynebacterium* spp, Capnocytophaga spp, *Bifidobacterium* spp, and *Gardnerella* spp.

In certain embodiments, the bacterium is a drug-resistant bacterium. In certain embodiments the bacterium is selected from the group consisting of methicillin-resistant *Staphylococcus aureus* (MRSA), methicillin-resistant *Staphylococcus epidermidis* (MRSE), penicillin-resistant *Streptococcus pneumonia*, quinolone-resistant *Staphylococcus aureus* (QRSA), vancomycin-resistant *Staphylococcus aureus* (VRSA), vancomycin-resistant *Enterococci* (VRE), or multi-drug resistant *Mycobacterium tuberculosis* (MDR-TB). In certain embodiments, the Gram-positive bacterium is methicillin resistant *Staphylococcus aureus* (MRSA), methicillin-resistant *Staphylococcus epidermidis* (MRSE), or vancomycin resistant *Enterococcus faecium* (VRE).

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit. In some embodiments, the pharmaceutical composition or compound includes a full course of antibiotics for treating an infection (e.g., 7 days of antibiotics, or 10 days of antibiotics)).

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U. S. P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Jet injection devices which deliver liquid vaccines to the dermis via a liquid jet injector and/or via a needle which pierces the stratum corneum and produces a jet which reaches the dermis are suitable. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inhibiting the activity of a protein kinase (e.g., IRAK) in a subject, biological sample, tissue, or cell), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., an infectious disease). In certain embodiments, the additional pharmaceutical agent is an antibacterial agent, antifungal agent, antiviral agent, an agent for killing protozoa, or an anti-parasitic agent. In certain embodiments, the additional pharmaceutical agent is an antimicrobial agent In certain embodiments, the additional pharmaceutical agent is a pharmaceutical agent useful for treating and/or preventing a proliferative disease, inflammatory disease, autoimmune disease, genetic disease, hematological disease, neurological disease, painful condition, psychiatric disorder, or metabolic disorder. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins, and a combination thereof.

Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutically agent is an antibiotic. Exemplary antibiotics include, but are not limited to, penicillins (e.g., penicillin, amoxicillin), cephalosporins (e.g., cephalexin), macrolides (e.g., erythromycin, clarithromycin, azithromycin, troleandomycin), fluoroquinolones (e.g., ciprofloxacin, levofloxacin, ofloxacin), sulfonamides (e.g., co-trimoxazole, trimethoprim), tetracyclines (e.g., tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline)), aminoglycosides (e.g., gentamicin, tobramycin, paromomycin), aminocyclitol (e.g., spectinomycin), chloramphenicol, sparsomycin, or quinupristin/dalfopristin (Syndercid™).

Also encompassed by the invention are kits (e.g., pharmaceutical packs) for killing a microorganism (e.g., bacteria, fungi, viruses, protozoa, or multicellular parasites), the prevention and/or treatment of infectious diseases (e.g., infections by microorganisms, bacterial infection, cystic fibrosis infection, foreign body infection, urinary tract infection (UTI), or infections leading to biofilms), controlling and/or eradicating biofilms (e.g., bacterial biofilms), preventing biofilm formation, sterilizing a surface, killing persister cells, and/or eradicating persister cells (e.g., in a subject, or in a subject involving a biofilm). The kits provided may comprise an inventive pharmaceutical composition or compound and a container (e.g., a vial, ampule, bottle, syringe, and/or dispenser package, or other suitable container). The kits provided may comprise an additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins, etc. In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form. In some embodiments, the inventive pharmaceutical composition or compound provided includes multiple doses. In some embodiments, the inventive pharmaceutical composition or compound includes a full course of antibiotics for treating an infection (e.g., 7 days of antibiotics, or 10 days of antibiotics)).

Methods of Use and Treatment

The present invention provides compounds and pharmaceutical compositions useful for inhibiting microorganism growth. The present invention provides compounds and pharmaceutical compositions useful for inhibiting bacterial growth. The present invention provides compounds and pharmaceutical compositions useful for killing microorganisms (e.g., bacteria, fungi, viruses, protozoa, or multicellular parasites). The present invention provides compounds and pharmaceutical compositions useful for killing bacteria. In one aspect, the present invention provides methods for inhibiting bacterial growth or killing bacteria comprising administering an effective amount of a compound described herein (e.g., a compound of Formula (I') or (I)), or a pharmaceutically acceptable salt, solvate, hydrate, polymorph, co-crystal, tautomer, stereoisomer, isotopically labeled derivative, or prodrug thereof), to a subject in need of treatment. In another aspect, the present invention provides methods for treating or preventing an infection (e.g., an infection by a microorganism, a bacterial infection, cystic fibrosis infection, foreign body infection, urinary tract infection (UTI), or infections leading to biofilms), controlling and/or eradicating biofilms (e.g., bacterial biofilms), preventing biofilm formation, sterilizing a surface, killing persister cells, and/or eradicating persister cells (e.g., in a subject) comprising administering an effective amount of a compound described herein (e.g., a compound of Formula (I') or (I)), or a pharmaceutically acceptable salt, solvate, hydrate, polymorph, co-crystal, tautomer, stereoisomer, isotopically labeled derivative, or prodrug thereof), to a subject in need of treatment.

In certain embodiments, the effective amount is a therapeutically effective amount. In certain embodiments, the effective amount is a prophylactically effective amount. In certain embodiments, the subject is suffering from an infection (e.g., an infection by a microorganism, a cystic fibrosis infection, foreign body infection, urinary tract infection (UTI), or infections leading to biofilms). In certain embodiments, the subject is suffering from a bacterial infection. In certain embodiments, the subject is susceptible to having a bacterial infection. In certain embodiments, the subject has been exposed or is at risk of being exposed to a pathogenic microorganism. The infection may be prevented or at least the chances of infection may be reduced by the administration of a prophylactic amount of a compound described herein.

In yet another aspect, provided is a method of treating or preventing an infection caused by microorganisms that are resistant to other treatments. In another aspect, provided is a method of treating or preventing a bacterial infection caused by bacteria that are resistant to other treatments. In certain embodiments, provided is a method of treating or preventing a bacterial infection caused by bacteria that are drug resistant or drug tolerant. In certain embodiments, the bacteria are drug resistant (e.g., the bacteria are not killed and/or the bacterial growth is not stopped) to the effects of drugs to which they were formerly sensitive. In certain embodiments, the bacteria are drug tolerant, where certain bacterial cells that undergo antimicrobial drug treatment are dormant (e.g., metabolically inactive) persister cells that survive antimicrobial drug treatment that kills the majority of the other bacterial cells. In certain embodiments, provided is a method of treating or preventing a bacterial infection caused by bacteria that are multi-drug tolerant. In certain embodiments, provided is a method of treating or preventing a bacterial infection caused by bacteria that are multi-drug resistant. In certain embodiments, provided is a method of treating or preventing a bacterial infection caused by bacteria that neither grow nor die in the presence of other antimicrobial drug treatments. In certain embodiments, provided methods can be conducted in vivo (i.e., by administration to a subject). For example, in certain embodiments, provided is a method of treating and/or preventing a bacterial infection comprising administering an effective amount of a compound of the present invention, e.g., a compound of Formula (I') or (I), or a pharmaceutically acceptable salt, solvate, hydrate, polymorph, co-crystal, tautomer, stereoisomer, isotopically labeled derivative, or prodrug thereof, to a subject with a bacterial infection or at risk of developing a bacterial infection.

For example, in certain embodiments, provided is a method of treating a microbial infection comprising contacting a microorganism with an effective amount of the compound of the present invention. In certain embodiments, provided is an in vitro method of treating microbial infection comprising contacting a microorganism in a cell culture with an effective amount of the compound of the present invention. In certain embodiments, provided is an in vivo method of treating microbial infection comprising administering an effective amount of the compound of the present invention to a subject with a microbial infection. In certain embodiments, the microorganism is a bacterium. In certain embodiments, the microorganism is a fungus. In certain embodiments, the microorganism is a virus. In certain embodiments, the microorganism is a protozoa. In certain embodiments, the microorganism is a multicellular parasites.

In another aspect, the present invention provides a method of killing microorganisms (e.g., bacteria, fungi, viruses, protozoa, or multicellular parasites). In certain embodiments, provided is a method of killing bacteria. In certain embodiments, provided is a method of killing fungi. In certain embodiments, provided is a method of killing viruses. In certain embodiments, provided is a method of killing protozoa. In certain embodiments, provided is a method of killing multicellular parasites. In another aspect, the present invention provides a method of killing bacteria in a subject comprising administering an effective amount of a compound described herein, or a pharmaceutically acceptable salt, solvate, hydrate, polymorph, co-crystal, tautomer, stereoisomer, isotopically labeled derivative, or prodrug thereof.

In another aspect, the present invention provides a method of preventing and/or treating infectious diseases (e.g., infections caused by microorganisms, bacterial infection, cystic fibrosis infection, foreign body infection, urinary tract infection (UTI), or infections leading to biofilms). In certain embodiments, provided is a method of method of preventing and/or treating infections caused by microorganisms. In certain embodiments, provided is a method of method of preventing and/or treating bacterial infection. In certain embodiments, provided is a method of method of preventing and/or treating cystic fibrosis infection. In certain embodiments, provided is a method of method of preventing and/or treating foreign body infection. In certain embodiments, provided is a method of method of preventing and/or treating urinary tract infection (UTI). In certain embodiments, provided is a method of method of preventing and/or treating infections leading to biofilms.

In another aspect, the present invention provides a method of controlling and/or eradicating biofilms (e.g., bacterial biofilms). In certain embodiments, provided is a method of controlling biofilms. In certain embodiments, provided is a method of eradicating biofilms. In certain embodiments, the biofilms are bacterial biofilms. In certain embodiments, the compounds described herein treat biofilm. In certain embodiments, the compounds described herein prevent biofilm formation. In certain embodiments, the compounds described herein treat bacterial biofilm. In certain embodiments, the compounds described herein kill persister cells. In certain embodiments, the compounds described herein eradicate persister cells. In certain embodiments, the compounds described herein eradicate persister cells in a subject. In certain embodiments, the compounds described herein treat bacterial biofilm and kill persister cells. In certain embodiments, the compounds described herein treat bacterial biofilm and eradicate persister cells. In certain embodiments, the compounds described herein sterilize a surface. In certain embodiments, provided is a method of killing bacterial biofilms and persister cells. In certain embodiments, provided is a method of killing bacterial biofilms and persister cells by depolarizing the outer membrane of bacterial cells and destroying the lipid bilayer of bacterial cells. In certain embodiments, provided is a method of depolarizing the outer membrane of bacterial cells. In certain embodiments, provided is a method of destroying the lipid bilayer of bacterial cells. In certain embodiments, provided is a method of treating a proliferative disease (e.g., cancer) in a subject in need thereof. In certain embodiments, provided is a method of inducing neuromodulatory activity in a in a subject in need thereof.

The present invention provides use of a compound of the present invention, e.g., a compound of Formula (I') or (I), or a pharmaceutically acceptable salt, solvate, hydrate, polymorph, co-crystal, tautomer, stereoisomer, isotopically labeled derivative, or prodrug thereof, for the manufacture of a medicament for use in treating and/or preventing an infection (e.g., a bacterial infection, cystic fibrosis infection, foreign body infection, urinary tract infection (UTI), or infections leading to biofilms) in a subject in need thereof. In certain embodiments, the present invention provides a compound of the present invention, e.g., a compound of Formula (I') or (I), or a pharmaceutically acceptable salt, solvate, hydrate, polymorph, co-crystal, tautomer, stereoisomer, isotopically labeled derivative, or prodrug thereof, for use in killing a microorganism (e.g., bacteria, fungi, viruses, protozoa, or multicellular parasites), treating and/or preventing infectious diseases (e.g., infections by microorganisms, bacterial infection, cystic fibrosis infection, foreign body infection, urinary tract infection (UTI), or infections leading to biofilms), controlling and/or eradicating biofilms (e.g., bacterial biofilms), preventing biofilm formation, sterilizing a surface, killing persister cells, and/or eradicating persister cells (e.g., in a subject, or in a subject involving a biofilm).

In certain embodiments, the bacterial infection being treated or prevented is an infection with a Gram-positive bacteria. Exemplary Gram-positive bacteria include, but are not limited to, *Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium, Corynebacterium, Capnocytophaga, Bifidobacterium,* and *Gardnerella*. Exemplary Gram-positive bacteria include, but are not limited to, *Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium,* and *Corynebacterium*. In certain embodiments, the Gram-positive bacteria is selected from the group consisting of *Staphylococcus* spp, *Streptococcus* spp, *Micrococcus* spp, Peptococcus spp, *Peptostreptococcus* spp, *Enterococcus* spp, *Bacillus* spp, *Clostridium* spp, *Lactobacillus* spp, *Listeria* spp, Erysipelothrix spp, *Propionibacterium* spp, *Eubacterium* spp, *Corynebacterium* spp, Capnocytophaga spp, *Bifidobacterium* spp, and *Gardnerella* spp. In certain embodiments, the Gram-positive bacterium is methicillin resistant *Staphylococcus aureus* (MRSA), methicillin-resistant *Staphylococcus epidermidis* (MRSE), or vancomycin resistant *Enterococcus faecium* (VRE). In certain embodiments, the Gram-positive bacteria is a bacteria of the phylum *Firmicutes*. In certain embodiments, the bacteria is a member of the phylum *Firmicutes* and the genus *Enterococcus*, i.e., the bacterial infection is an *Enterococcus* infection. Exemplary *Enterococci* bacteria include, but are not limited to, *E. avium, E. durans, E. faecalis, E. faecium, E. gallinarum, E. solitarius, E. casseliflavus,* and *E. raffinosus*. In certain embodiments, the *Enterococcus* infection is an *E. faecalis* infection. In certain embodiments, the *Enterococcus* infection is an *E. faecium* infection. In certain embodiments, the bacteria is a member of the phylum *Firmicutes* and the genus *Staphylococcus*, i.e., the bacterial infection is a *Staphylococcus* infection. Exemplary Staphylococci bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. pseudointermedius, S. pseudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri,* and *S. xylosus*. In certain embodiments, the *Staphylococcus* infection is an *S. aureus* infection. In certain embodiments, the *Staphylococcus* infection is an *S. epidermis* infection.

In certain embodiments, the bacterial infection being treated or prevented is an infection with a Gram-negative bacteria. Exemplary Gram-negative bacteria include, but are not limited to, *Escherichia, Citrobacter, Enterobacter, Klebsiella, Proteus, Serratia, Shigella, Salmonella, Morganella, Providencia, Edwardsiella, Erwinia, Hafnia, Yersinia, Acinetobacter, Vibrio, Aeromonas, Pseudomonas, Haemophilus, Pasteurella, Campylobacter, Helicobacter, Branhamella, Moraxella, Neisseria, Veillonella, Fusobacterium, Bacteroides, Actinobacillus, Aggregatibacter, Agrobacterium, Porphyromonas, Prevotella, Ruminobacter, Roseburia, Caulobacter, Francisella, Borrelia, Treponema, Brucella,* and *Rickettsia*. In certain embodiments, the bacterium is selected from the group consisting of *Escherichia coli, Morganella morganii, Branhamella catarrhalis, Veillonella parvula, Actinobacillus actinomycetemcomitans, Aggregatibacter actinomycetemcomitans, Caulobacter crescentus,* and *Treponema pallidum*. Exemplary Gram-negative bacteria include, but are not limited to, *Escherichia coli, Caulobacter crescentus, Pseudomonas aeruginosa, Agrobacterium tumefaciens, Branhamella catarrhalis, Citrobacter diversus, Enterobacter aerogenes, Klebsiella pneumoniae, Proteus mirabilis, Salmonella typhimurium, Neisseria meningitidis, Serratia marcescens, Shigella sonnei, Neisseria gonorrhoeae, Acinetobacter baumannii, Salmonella enteritidis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Morganella morganii, Edwardsiella tarda, Acinetobacter baumannii* and *Haemophilus influenzae*. In certain embodiments, the Gram-negative bacterium is selected from the group consisting of *Escherichia coli, Citrobacter* spp, *Enterobacter* spp, *Klebsiella* spp, *Proteus* spp, *Serratia* spp, *Shigella* spp, *Salmonella* spp, *Morganella morganii, Providencia* spp, *Edwardsiella* spp, *Erwinia* spp, Hafnia spp, *Yersinia* spp, *Acinetobacter* spp, *Vibrio* spp, *Aeromonas* spp, *Pseudomonas* spp, *Haemophilus* spp, *Pasteurella* spp, *Campylobacter* spp, *Helicobacter* spp, *Branhamella catarrhalis, Moraxella* spp, *Neisseria* spp, *Veillonella parvula, Fusobacterium* spp, *Bacteroides* spp, *Actinobacillus actinomycetemcomitans, Aggregatibacter actinomycetemcomitans, Agrobacterium* spp, *Porphyromonas* spp, *Prevotella* spp, Ruminobacter spp, *Roseburia* spp, *Caulobacter* crescentus, Francisella spp, Borrelia spp, Treponema pallidum, Brucella spp, and Rickettsia. In certain embodiments, the Gram-negative bacteria is Acinetobacter baumannii, Pseudomonas aeruginosa, or Klebsiella pneumoniae. In certain embodiments, the Gram-negative bacteria species is Escherichia coli, Bacillus sp., Salmonella sp., and Mycobacterium sp.

In certain embodiments, the bacterial infection is resistant to other antibiotic therapy. For example, in certain embodiments, the bacterial infection is vancomycin resistant (VR). In certain embodiments, the bacterial infection is a vancomycin-resistant E. faecalis infection. In certain embodiments, the bacterial infection is a vancomycin-resistant E. faecium infection. In certain embodiments, the bacterial infection is a vancomycin-resistant Staphylococcus aureus (VRSA) infection. In certain embodiments, the bacterial infection is a vancomycin-resistant Enterococci (VRE) infection. In certain embodiments, the bacterial infection is methicillin-resistant (MR). In certain embodiments, the bacterial infection is a methicillin-resistant S. aureus (MRSA) infection. In certain embodiments, the bacterial infection is methicillin-resistant Staphylococcus epidermidis (MRSE) infection. In certain embodiments, the bacterial infection is a penicillin-resistant Streptococcus pneumonia infection. In certain embodiments, the bacterial infection is a quinolone-resistant Staphylococcus aureus (QRSA) infection. In certain embodiments, the bacterial infection is multi-drug resistant Mycobacterium tuberculosis infection. Staphylococcus aureus refers to antibiotic-resistant strains (e.g., MRSA), In certain embodiments, the bacterial infection is resistant to certain antibiotics (e.g., methicillin, penicillin, oxacillin, nafcillin, cephalosporins, tetracyclines, or vancomycin).

In certain embodiments, the infection leads to biofilms. In certain embodiments, the infection is a cystic fibrosis infection. In certain embodiments, the infection is a foreign body infection. In certain embodiments, the infection is a urinary tract infection (UTI).

Examples

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Chemical Syntheses

All synthetic reactions were carried out under an inert atmosphere of argon unless otherwise specified. All reagents for chemical synthesis were purchased from commercial sources and used without further purification. Reagents were purchased at ≥95% purity and commercially available controls were used in our biological investigations without further purification. Analytical thin layer chromatography (TLC) was performed using 250 μm Silica Gel 60 F254 pre-coated plates (EMD Chemicals Inc.). Flash column chromatography was performed using 230-400 Mesh 60 Å Silica Gel from Sorbent Technologies. All melting points were obtained, uncorrected, using a Mel-Temp capillary melting point apparatus from Laboratory Services Inc.

NMR experiments were recorded using broadband probes on a Varian Mercury-Plus-400 spectrometer via VNMR-J software (400 MHz for $^1$H and 100 MHz for $^{13}$C). All spectra are presented using MestReNova 8.1 (Mnova) software and are displayed without the use of the signal suppression function. Spectra were obtained in the following solvents (reference peaks also included for $^1$H and $^{13}$C NMRs): CDCl$_3$ ($^1$H NMR: 7.26 ppm; $^{13}$C NMR: 77.23 ppm), d$_6$-DMSO ($^1$H NMR: 2.50 ppm; $^{13}$C NMR: 39.52 ppm). All NMR experiments were performed at room temperature. Chemical shift values (δ) are reported in parts per million (ppm) for all $^1$H NMR and $^{13}$C NMR spectra. $^1$H NMR multiplicities are reported as: s=singlet, d=doublet, t=triplet, q=quartet, p=pentet, m=multiplet. High-Resolution Mass Spectrometry (HRMS) were obtained for all new compounds from the Chemistry Department at the University of Florida.

General C—N Coupling Procedure for the Synthesis of 5 and 6.

To a stirring solution of 2-methyl-1H-imidazole 4 (800 mg, 9.74 mmol) in 6 mL anhydrous dimethyl sulfoxide under argon was added iodobenzene (1.09 mL, 9.74 mmol), then copper (I) iodide (185 mg, 0.97 mmol) and finally anhydrous potassium carbonate (2.69 g, 19.49 mmol). The reaction mixture was allowed to stir at 130° C. for 48 hours in a sealed tube. After the completion of the reaction, the contents of the reaction mixture were transferred to a separatory funnel containing ethyl acetate (200 mL). The organic layer was washed with water (4×40 mL), then brine (2×30 mL) before the organic layers were collected, dried with anhydrous sodium sulfate, filtered, and concentrated in vacuo to give the crude product which was then purified via flash column chromatography using hexanes:ethyl acetate (1:1 to 1:4) to elute pure 2-methyl-1-phenyl-1H-imidazole 5 as a clear oil (730 mg, 47%).

General Alkylation Procedure for the Synthesis of 1 and 2.

To a stirring solution of 2-methyl-1-phenyl-1H-imidazole 5 (700 mg, 4.46 mmol) in 5 mL anhydrous acetonitrile in a glass tube at room temperature was added 1-bromohexadecane (1.42 mL, 4.87 mmol) and the mixture was sealed and heated at 110° C. for 24 hours. The reaction was then allowed to cool to room temperature before being concentrated via rotovap. The crude product was stirred in anhydrous ether under argon for 5 hours and the resulting white precipitate was filtered and washed with anhydrous ether and dried under vacuum to obtain 1 as a pure white solid (1.81 g, 85%).

Example 1. Synthetic Procedures and Characterization Data

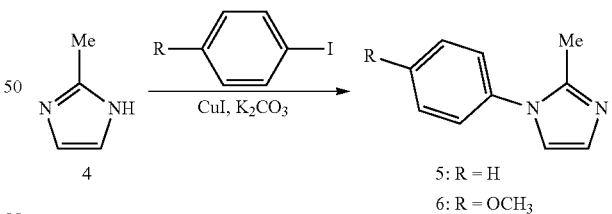

5: R = H
6: R = OCH$_3$

Synthesis of 2-methyl-1-aryl-1H-imidazole 5

To a stirring solution of 2-methyl-1H-imidazole 4 (800 mg, 9.74 mmol) in 6 mL anhydrous dimethyl sulfoxide under argon was added iodobenzene (1.09 mL, 9.74 mmol), copper(I) iodide (185 mg, 0.97 mmol) and anhydrous potassium carbonate (2.69 g, 19.49 mmol). The reaction mixture was then heated to 130° C. and allowed to stir for 48 hours in a sealed tube. Following completion of the reaction, the mixture was transferred to a separatory funnel containing ethyl acetate (200 mL) and the crude product was washed with water (4×40 mL) and brine (2×30 mL) before the organic layer was collected and dried with anhydrous sodium sulfate, filtered, and concentrated in vacuo. The product was purified via flash column chromatography using hexanes:ethyl acetate (1:1 to 1:4) to elute pure 2-methyl-1-phenyl-1H-imidazole 5 as a clear oil (730 mg, 47%).

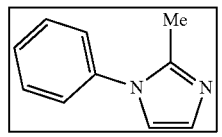

5

Yield: 47% yield; 730 mg of 5 was isolated as a clear oil. $^1$H NMR (400 MHz, CDCl$_3$): δ 7.51-7.37 (m, 3H), 7.30-7.22 (m, 2H), 6.98 (dd, J=9.7, 1.4 Hz, 2H), 2.35 (s, 3H). $^{13}$C NMR (100 MHz, CDCl$_3$): δ 144.8, 138.2, 129.6, 128.3, 127.8, 125.6, 120.8, 13.9. Note: NMR spectra match those previously reported.[1]

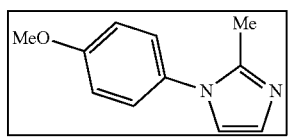

6

Yield: 45% yield; 260 mg of 6 was isolated as a clear oil. $^1$H NMR (400 MHz, CDCl$_3$): δ 7.21-7.14 (m, 2H), 7.02-6.91 (m, 4H), 3.83 (s, 3H), 2.29 (s, 3H). $^{13}$C NMR (100 MHz, CDCl$_3$): δ 159.5, 145.2, 131.0, 127.5, 127.0, 121.1, 114.7, 55.7, 13.7. Note: NMR spectra match those previously reported. (Cano, R.; Ramón, D. J.; Yus, M. *J. Org. Chem.* 2011, 76, 654-660).

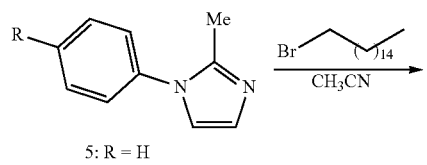

5: R = H
6: R = OCH$_3$

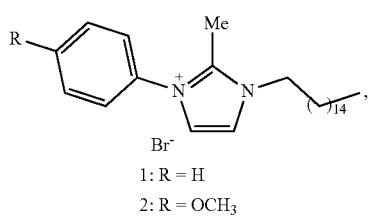

1: R = H
2: R = OCH$_3$

Synthesis of 2-methyl-3-aryl-1-hexadecyl-1H-imidazol-3-ium bromide 1

To a stirring solution of 2-methyl-1-phenyl-1H-imidazole 5 (700 mg, 4.46 mmol) in 5 mL anhydrous acetonitrile in a 10 mL glass tube was added 1-bromohexadecane (1.42 mL, 4.87 mmol) and the resulting mixture was heated to 110° C. in a sealed tube and allowed to stir for 24 hours. After the reaction was complete, the solution was allowed to cool to room temperature and acetonitrile was evaporated in vacuo. The crude product was then stirred in anhydrous ether under argon for 5 hours resulting in a white precipitate which was filtered under an argon environment. The resulting solid was washed with cold anhydrous ether and dried under vacuum to obtain 1 as a white solid (1.81 g, 85%).

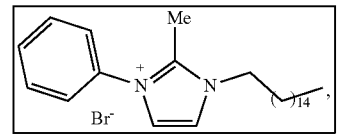

1

Yield: 85% yield; 1.81 g of 1 was isolated as a white solid. $^1$H NMR (400 MHz, DMSO-d$_6$): δ 7.95 (d, J=2.1 Hz, 1H), 7.94 (d, J=2.2 Hz, 1H), 7.71-7.60 (m, 5H), 4.19 (dd, J=7.5, 7.5 Hz, 2H), 2.53 (s, H), 1.80 (p, J=7.2 Hz, 2H), 1.44-1.17 (m, 26H), 0.85 (t, J=6.5 Hz, 3H). $^{13}$C NMR (100 MHz, DMSO-d$_6$): δ 144.3, 134.7, 130.3, 129.9, 125.9, 122.4, 121.6, 47.9, 31.2, 28.9, 28.9, 28.9, 28.8, 28.6, 28.5, 25.6, 22.0, 13.8, 10.2. Note: 19 of the 26 $^{13}$C NMR signals could be found, several signals buried at 29 ppm. HRMS (ESI): calc. for C$_{26}$H$_{43}$N$_2$[M]$^+$: 383.3421, found: 383.3425. MP: 84-85° C.

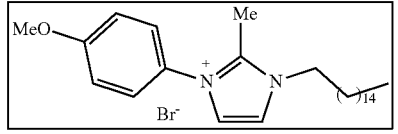

2

Yield: 84% yield; 310 mg of 2 was isolated as a white solid. $^1$H NMR (400 MHz, d$_6$-DMSO): δ 7.90 (dd, J=13.9, 2.1 Hz, 2H), 7.58-7.52 (m, 2H), 7.24-7.10 (m, 2H), 4.19 (t, J=7.5 Hz, 2H), 3.85 (s, 3H), 1.79 (p, J=8.0 Hz, 2H), 1.42-1.16 (m, 29H), 0.85 (t, J=6.7 Hz, 3H). $^{13}$C NMR (100 MHz, d$_6$-DMSO): δ 160.3, 144.5, 127.5, 127.4, 122.7, 121.5, 115.0, 55.7, 47.9, 31.3, 29.1, 29.0, 29.0, 28.9, 28.7, 28.6, 25.7, 22.1, 14.0, 10.2. Note: 20 of the 27 $^{13}$C NMR signals could be found, several signals buried at 29 ppm. HRMS (ESI): calc. for C$_{27}$H$_{45}$N$_2$O [M]$^+$: 413.3526, found: 413.3514. MP: 78-79° C.

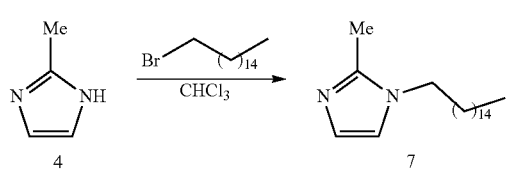

4       7

Synthesis of 1-hexadecyl-2-methyl-1H-imidazole 7

To a stirring solution of 2-methyl-1H-imidazole 4 (650 mg, 4.91 mmol) in 50 mL anhydrous chloroform was added 1-bromohexadecane (0.30 mL, 1.0 mmol). The reaction mixture was then refluxed for 16 hours. When the reaction was complete, the mixture was allowed to cool to room temperature and then chloroform was evaporated in vacuo. The crude mixture was then transferred to a separatory funnel in ethyl acetate (100 mL) and organic layer was washed using water (3×30 mL) and brine (2×30 mL) before the organic layer was collected and dried with anhydrous sodium sulfate, filtered, and concentrated in vacuo. The crude product was then purified via flash column chromatography using hexanes:ethyl acetate (1:1 to 1:9) to elute pure 1-hexadecyl-2-methyl-1H-imidazole 7 as a clear oil which turned into a white solid upon standing (210 mg, 70%). $^1$H NMR (400 MHz, CDCl$_3$): δ 6.88 (d, J=1.3 Hz, 1H), 6.78 (d, J=1.3 Hz, 1H), 3.79 (dd, J=7.2, 7.2 Hz, 2H), 2.35 (s, 3H), 1.69 (p, J=7.4 Hz, 2H), 1.34-1.17 (m, 26H), 0.86 (t, J=6.7 Hz, 3H). $^{13}$C NMR (100 MHz, CDCl$_3$): δ 144.5, 127.1, 119.2, 46.2, 32.1, 30.9, 29.9, 29.9, 29.8, 29.8, 29.8, 29.8, 29.7, 29.6, 29.5, 29.3, 26.8, 22.9, 14.3, 13.2.

MP: 39-40° C. Note: NMR spectra match those previously reported. (Langat, J.; Bellayer, S.; Hudrlik, P.; Hudrlik, A.; Maupin, P. H.; Gilman, J. W.; Raghavan, D. *Polymer* 2006, 47, 6698-6709).

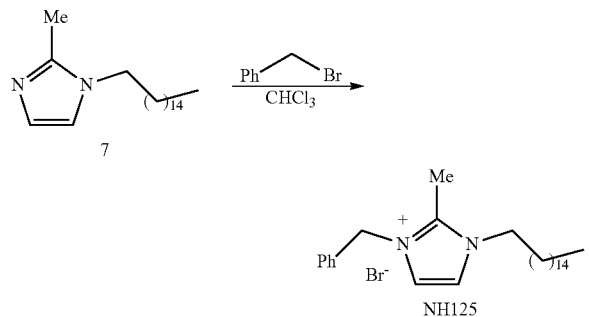

7

Synthesis of 3-benzyl-1-hexadecyl-2-methyl-1H-imidazol-3-ium bromide (NH125)

To a stirring solution of 1-hexadecyl-2-methyl-1H-imidazole 7 (200 mg, 0.65 mmol) in 5 mL anhydrous chloroform in a 10 mL glass tube at room temperature, benzyl bromide (0.10 mL, 0.81 mmol) was added and the mixture was sealed and heated at 90° C. for 24 hours. The solution was then allowed to cool to room temperature and chloroform was evaporated in vacuo. The crude product was stirred in anhydrous ether under argon for 3 hours and resulting white precipitate was filtered under an argon environment, precipitate was washed with anhydrous ether and dried under vacuum to obtain NH125 as a white solid (295 mg, 95%). $^1$H NMR (400 MHz, d$_6$-DMSO): δ 7.76 (s, 2H), 7.45-7.34 (m, 3H), 7.34-7.29 (m, 2H), 5.42 (s, 2H), 4.11 (t, J=7.4 Hz, 2H), 2.62 (s, 3H), 1.72 (p, J=7.3 Hz, 2H), 1.36-1.09 (m, 26H), 0.85 (t, J=6.7 Hz, 3H). $^{13}$C NMR (100 MHz, d$_6$-DMSO): δ 144.0, 134.6, 129.0, 128.5, 127.7, 121.7, 121.6, 50.6, 47.7, 31.3, 29.0, 29.0, 28.9, 28.9, 28.7, 28.5, 25.6, 22.1, 14.0, 9.5. Note: 20 of the 25 $^{13}$C NMR signals could be found, several signals buried at 29 ppm. MP: 72-74° C. Note: NMR spectra matches those previously reported. (Kitayama, T.; Koyanagi, T.; Omatsu, M.; Ogawa, M. *PCT Int. Appl.* 2009, WO2009133923 A1 20091105).

Compound 3 (known membrane-targeting agent) was synthesized following a literature protocol reported previously. (Hoque, J.; Konai, M. M.; Samaddar, S.; Gonuguntala, S.; Manjunath, G. B.; Ghosh, C.; Haldar, J. *Chem. Commun.* 2015, 51, 13670-13673)

$^1$H NMR (400 MHz, CDCl$_3$): δ 8.69 (t, J=5.7 Hz, 2H), 4.66 (s, 4H), 3.74-3.54 (m, 4H), 3.43 (s, 12H), 3.27 (q, J=6.0 Hz, 4H), 1.83-1.71 (m, 4H), 1.64-1.52 (m, 4H), 1.40-1.18 (m, 24H), 0.86 (t, J=6.8 Hz, 6H). $^{13}$C NMR (100 MHz, CDCl$_3$): δ 163.1, 66.1, 63.4, 52.2, 39.5, 31.8, 29.2, 29.2, 28.3, 26.7, 26.4, 23.1, 22.7, 14.2. MP: 177-178° C. Note: NMR spectra matches those previously reported. (Hoque, J.; Konai, M. M.; Samaddar, S.; Gonuguntala, S.; Manjunath, G. B.; Ghosh, C.; Haldar, J. *Chem. Commun.* 2015, 51, 13670-13673)

Exemplary Synthetic Route to 2-Methyl Imidazole Analogues

Exemplary Method 1:

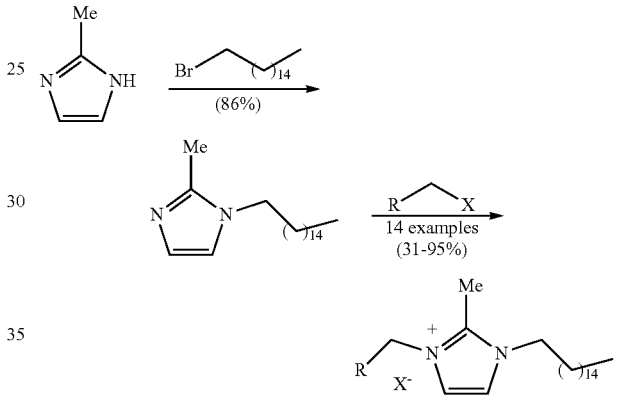

Exemplary Method 2:

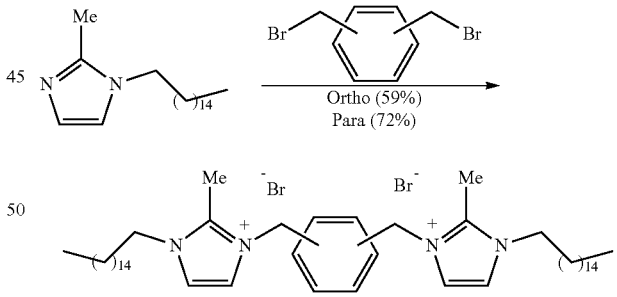

Exemplary Synthetic Route to 2-Methyl Benzimidazole Analogues

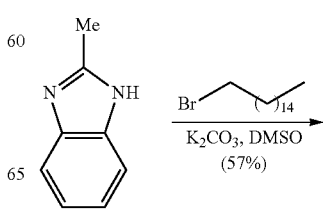

3

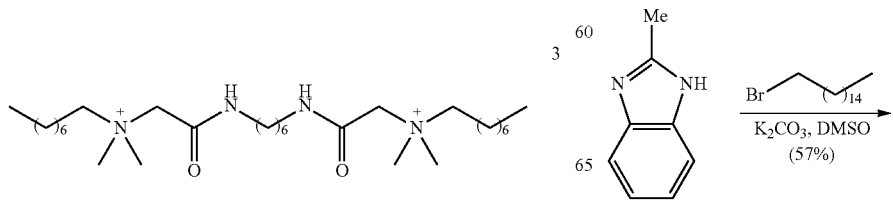

79

-continued

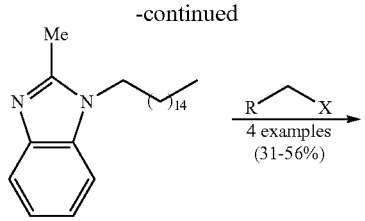

4 examples
(31-56%)

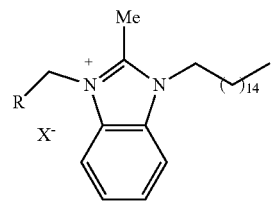

Exemplary Synthetic Route to Aryl Imidazole Analogues
Exemplary Method 1:

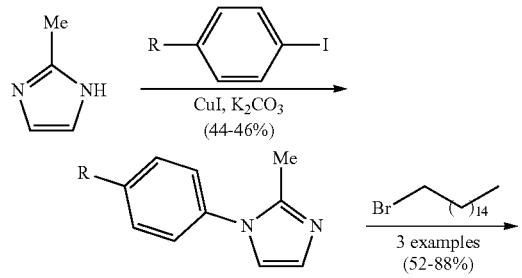

80

-continued

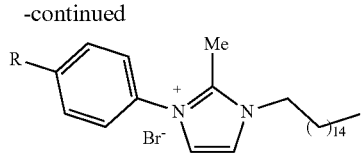

Exemplary Method 2:

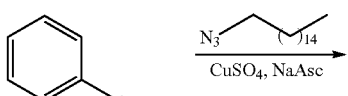

$\xrightarrow{\text{CuSO}_4, \text{NaAsc}}$

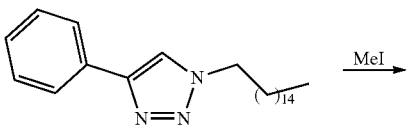

$\xrightarrow{\text{MeI}}$

TABLE A

Exemplary NH-125 Analogues

| Compound number | Generic Formula | Definition of R (and % yield) | Structure |
|---|---|---|---|
| NH125 | | | Me, benzyl-N+-imidazole-N-(CH2)14-chain |
| AB-3-71 | R-N+-imidazole(Me)-N-(CH2)14 | R = CH3 (82%) | |
| AB-3-67 | R-N+-imidazole(Me)-N-(CH2)14 | R = CH2CH2OH (69%) | |
| AB-3-99 | R-N+-imidazole(Me)-N-(CH2)14 | R = CH2CHCH2 (80%) | |

TABLE A-continued

Exemplary NH-125 Analogues

| Compound number | Generic Formula | Definition of R (and % yield) | Structure |
|---|---|---|---|
| AB-3-102 | (imidazolium with Me at C2, R on one N, (CH2)14 chain on other N) | R = nBu (32%) | |
| AB-2-152 | | (31%) | (2-bromobenzyl imidazolium with Me at C2 and (CH2)14 chain) |
| AB-2-154 | (3-R-benzyl imidazolium with Me at C2 and (CH2)14 chain) | R = OCH3 (36%) | |
| AB-3-20 | (3-R-benzyl imidazolium with Me at C2 and (CH2)14 chain) | R = F (59%) | |
| AB-2-151 | (4-R-benzyl imidazolium with Me at C2 and (CH2)14 chain) | R = Br (51%) | |
| AB-3-19 | (4-R-benzyl imidazolium with Me at C2 and (CH2)14 chain) | R = tBu (52%) | |
| AB-3-23 | (4-R-benzyl imidazolium with Me at C2 and (CH2)14 chain) | R = iPr (71%) | |
| AB-3-16 | (3,5-di-R-benzyl imidazolium with Me at C2 and (CH2)14 chain) | R = Br (42%) | |

TABLE A-continued
Exemplary NH-125 Analogues
| Compound number | Generic Formula | Definition of R (and % yield) | Structure |
|---|---|---|---|
| AB-2-153 | 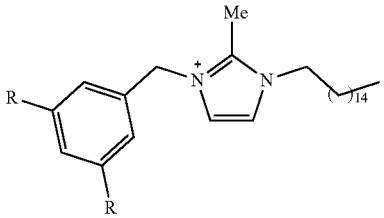 | R = CF$_3$ (37%) | |
| AB-3-17 | 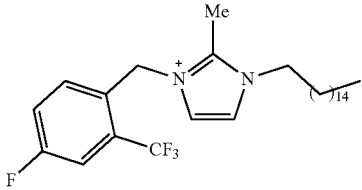 | (76%) | |
| AB-3-85 | 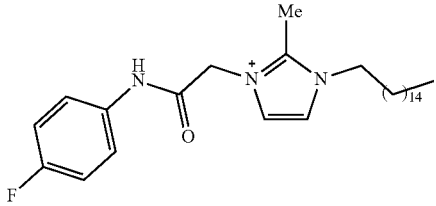 | (52%) | |
| AB-3-90 | 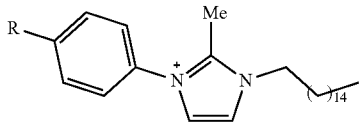 | R = H (86%) | |
| AB-3-113 | 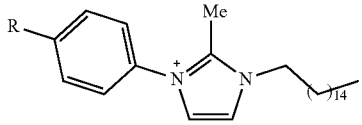 | R = OCH$_3$ (84%) | |
| AB-3-117 | 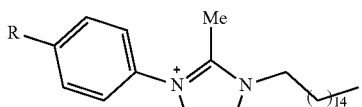 | R = NO$_2$ (88%) | |
| AB-3-170 | 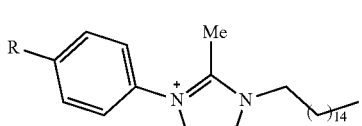 | R = CF$_3$ (51%) | |
| AB-3-173 | 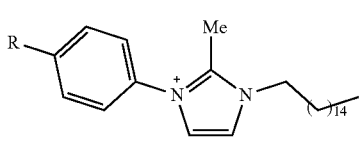 | R = OPh (60%) | |
| AB-3-175 | 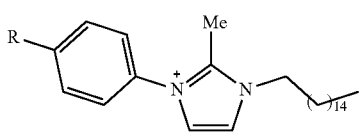 | R = Cl (48%) | |

TABLE A-continued

Exemplary NH-125 Analogues

| Compound number | Generic Formula | Definition of R (and % yield) | Structure |
|---|---|---|---|
| AB-3-180 | | R = OCF$_3$ (60%) | |
| AB-3-46 (64%) | | | |
| AB-3-29 | | R = H (56%) | |
| AB-3-31 | | R = OMe (31%) | |
| AB-3-33 | | R = F (33%) | |
| AB-3-35 | | (59%) | 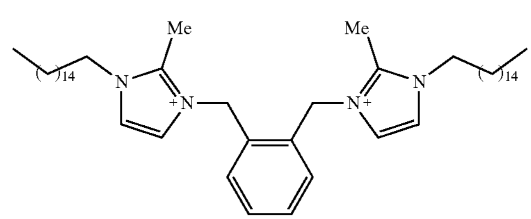 |
| AB-3-38 | | (72%) | 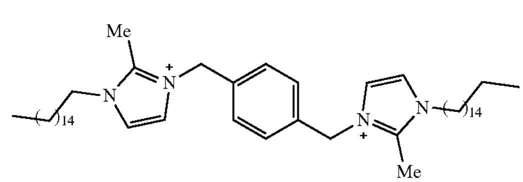 |

TABLE A-continued

Exemplary NH-125 Analogues

| Compound number | Generic Formula | Definition of R (and % yield) | Structure |
|---|---|---|---|
| AB-2-146 | | (86%) | 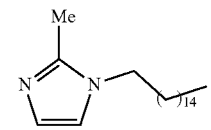 |

TABLE B

Exemplary Compounds

| Compound number | Structure |
|---|---|
| AB-3-91 (61%) | (61%) |
| AB-3-75 (73%) | 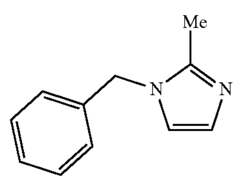 [SMILES: Cc1nccn1Cc1ccccc1] |
| AB-3-64 | 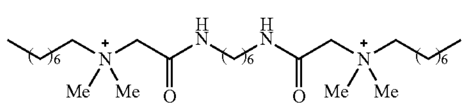 |

General Procedures for Biological Assays of Exemplary Compounds.

Reported biological data results from a minimum of three independent experiments. Bacterial strains used during these investigations include: methicillin-resistant *Staphylococcus aureus* (Clinical Isolate from Shands Hospital in Gainesville, Fla.: MRSA-2; ATCC strain: BAA-1707) methicillin-resistant *Staphylococcus epidermidis* (MRSE strain ATCC 35984), vancomycin-resistant *Enterococcus faecium* (VRE strain ATCC 700221), *Acinetobacter baumannii* (ATCC 1794), *Pseudomonas aeruginosa* (PAO1), *Klebsiella pneumonia* (ATCC 13883) and *Escherichia coli* clinical isolate (UAEC-1). All compounds were stored as DMSO stocks at room temperature in the absence of light for several months at a time without observing any loss in biological activity.

Minimum Inhibitory Concentration (MIC) Microdilution Assays.

The minimum inhibitory concentration (MIC) for each tested compound was determined by the broth microdilution method as recommended by the Clinical and Laboratory Standards Institute (CLSI). In a 96-well plate, eleven two-fold serial dilutions of each compound were made in a final volume of 100 µL Luria Broth. Each well was inoculated with ~$10^5$ bacterial cells at the initial time of incubation, prepared from a fresh log phase culture ($OD_{600}$ of 0.5 to 1.0 depending on bacterial strain). The MIC was defined as the lowest concentration of compound that prevented bacterial growth after incubating 16 to 18 hours at 37° C. (MIC values were supported by spectrophotometric readings at $OD_{600}$). DMSO served as our vehicle and negative control in each microdilution MIC assay. DMSO was serially diluted with a top concentration of 1% v/v.

Biofilm Eradication Assays (MBEC Determination; Calgary Biofilm Device Assays).

Biofilm eradication experiments were performed using the Calgary Biofilm Device to determine MBC/MBEC values for various compounds of interest (Innovotech, product code: 19111). The Calgary device (96-well plate with lid containing pegs to establish biofilms on) was inoculated with 125 µL of a mid-log phase culture diluted 1,000-fold in tryptic soy broth with 0.5% glucose (TSBG) to establish bacterial biofilms after incubation at 37° C. for 24 hours. The lid of the Calgary device was then removed, washed and transferred to another 96-well plate containing 2-fold serial dilutions of the test compounds (the "challenge plate"). The total volume of media with compound in each well in the challenge plate is 150 µL. The Calgary device was then incubated at 37° C. for 24 hours. The lid was then removed from the challenge plate and MBC/MBEC values were determined using different final assays. To determine MBC values, 20 µL of the challenge plate was transferred into a fresh 96-well plate containing 180 µL TSBG and incubated overnight at 37° C. The MBC values were determined as the concentration giving a lack of visible bacterial growth (i.e., turbidity). For determination of MBEC values, the Calgary device lid (with attached pegs/treated biofilms) was transferred to a new 96-well plate containing 150 µL of fresh TSBG media in each well and incubated for 24 hours at 37° C. to allow viable biofilms to grow and disperse resulting in turbidity after the incubation period. MBEC values were determined as the lowest test concentration that resulted in eradicated biofilm (i.e., wells that had no turbidity after final incubation period). In select experiments, pegs from the Calgary device were removed from lead biofilm eradicators after final incubation, sonicated for 30 minutes in PBS and plated out to determine biofilm cell killing of lead biofilm-eradicating agents (i.e., colony forming unit per milliliter, CFU/mL).

MRSA Persister Cell Kill Kinetics.

An overnight culture of MRSA BAA-1707 was diluted in fresh TSBG (1:13 to 1:20 fold) and allowed to grow with shaking. Once the culture reached stationary phase (4-6 hours), test compounds were added at a final test concentration of 50 µM. The cultures were incubated with shaking at 250 rpm and aliquots were removed and plated out at predetermined time points. Colony forming units (CFU) per milliliter data was recorded and plotted using Graphpad Prism 6.0.

Live/Dead Staining of MRSA Biofilms.

A mid-log culture of MRSA BAA-1707 was diluted 1:1000-fold and 500 μL was transferred to each compartment of a four-compartment CELLview dish (Greiner Bio-One 627871). The dish was then incubated for 24 hours at 37° C. to establish MRSA-1707 biofilms. After this time, the cultures were removed and the plate was washed with 0.9% saline. The dish was then treated with test compounds in fresh media at various concentrations. DMSO was used as a negative control in this assay. The dish was incubated with the test compound for 24 hours at 37° C. After this time, the cultures were removed and the dish was washed with 0.9% saline for 2 minutes. Saline was then removed and 500 μL of the stain (Live/Dead BacLight Viability Kit, Invitrogen) were added for 15 minutes and left in the dark. After this time, the stain was removed and the dish was washed twice with 0.9% saline. Then the dish was fixed with 500 μL 4% paraformaldehyde in PBS for 30 minutes. Images of remaining MRSA biofilms were then taken with a fluorescence microscope.

Hemolysis of Red Blood Cells.

Freshly drawn human red blood cells (hRBC) with ethylenediaminetetraacetic acid (EDTA) as an anticoagulant were washed with Tris-buffered saline (0.01M Tris-base, 0.155 M sodium chloride, pH 7.2) and centrifuged for 5 minutes at 3,500 rpm. The washing was repeated three times with the buffer. In a 96-well plate, test compounds were added to the buffer from DMSO stocks. Then 2% hRBCs (50 μL) in buffer were added to test compounds to give a final concentration of 200 μM. The plate was then incubated for 1 hour at 37° C. After incubation, the plate was centrifuged for 5 minutes at 3,500 rpm. Then 80 μL of the supernatant was transferred to another 96-well plate and the optical density (OD) was read at 405 nm. DMSO served as our negative control (0% hemolysis) while Triton X served as our positive control (100% hemolysis). The percent of hemolysis was calculated as ($OD_{405}$ of the compound–$OD_{405}$ DMSO)/($OD_{405}$ Triton X–$OD_{405}$ buffer). All reported data correspond to three independent experiments. Ten-point dose-response curves were generated in 96-well plates to determine 50% hemolysis ($HC_{50}$ values) of red blood cells.

Figure 2:
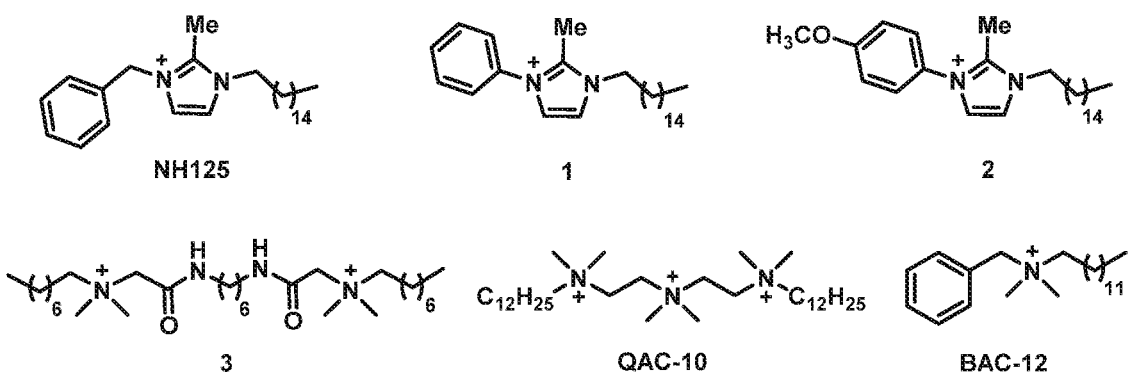
FIG. 2A. Structures of membrane-targeting agents investigated.
FIG. 2B. Synthesis of N-Arylated NH125 analogues 1 and 2.
Figure 2:
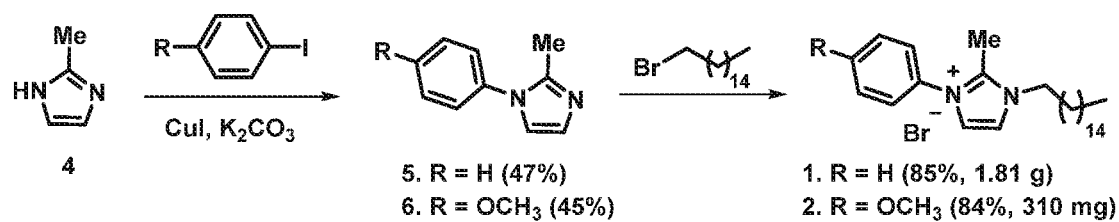

N-arylated NH 125 analogues 1 and 2 have been identified as performing well in view of NH 125 and other membrane-active agents (See FIG. 2A) in biofilm eradication assays against MRSA, methicillin-resistant *Staphylococcus epidermidis* (MRSE) and vancomycin-resistant *Enterococcus faecium* (VRE). In kill kinetic experiments against MRSA persister cells in stationary cultures, which have enriched persister cell populations, compounds 1 and 2 proved to be the most potent and rapid killing agents in our panel of membrane-targeting antibacterial agents. Compound 1 and 2 were identified from a library of diverse NH 125 analogues prepared and evaluated against a panel of pathogenic bacteria (a full paper detailing these findings will be reported in due course). The chemical synthesis of 1 and 2 involves a copper-catalyzed coupling reaction between iodobenzene, or 4-iodoanisole, and 2-methylimidazole 4 to yield N-arylated imidazoles 5 and 6, in 47% and 45% yields, respectively (FIG. 2B). Following the copper-catalyzed C—N coupling reactions, a final alkylation of the N-3-position with 1-bromohexadecane gives 1 in 85% yield (from 5) and 2 in 84% yield (from 6). This 2-step route was carried out to generate 1.81 grams of 1 and 310 milligrams of 2 on single runs to check the scalability of this route, which yields pure analogues without the use of chromatography.

Interest focused on evaluating a panel of chemically diverse membrane-targeting compounds for antibacterial, biofilm eradication, MRSA persister killing and red blood cell lysis (hemolysis) including: NH125, 1, 2, 3[33], QAC-10[16], BAC-12, and daptomycin. This small but diverse membrane-active panel was compiled for the following reasons: 1) BAC-12 is a commercial disinfectant with antibacterial properties, 2) QAC-10 and 3 are membrane-active quaternary ammonium cations (QAC)[16,33], and 3) daptomycin is a clinically used lipopeptide antibiotic known to depolarize bacterial membranes and eradicate *Staphylococcal* biofilms.[34]

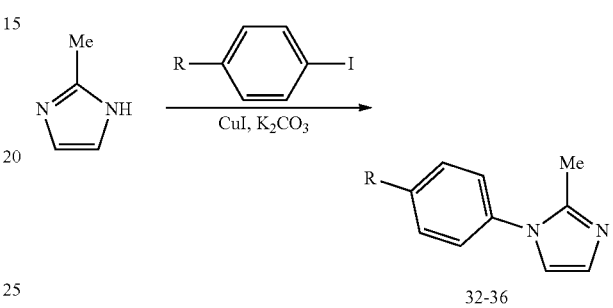

32-36

General Procedure for the N-arylation of 2-Methyl-1H-imidazole (Synthesis of 32-36): 1-Chloro-4-iodobenzene (726 mg, 3.04 mmol), copper(I) iodide (58 mg, 0.30 mmol) and anhydrous potassium carbonate (630 mg, 4.57 mmol) were sequentially added to a stirring solution of 2-methyl-1H-imidazole (250 mg, 3.04 mmol) in 5 mL anhydrous dimethyl sulfoxide in a glass tube under argon. The reaction tube was then sealed and stirred at 130° C. for 48 hours until the reaction was completed. The reaction mixture was then cooled to room temperature and transferred to a separatory funnel containing ethyl acetate (100 mL). The organic layer was then washed using water (3×30 mL) then brine (2×30 mL) before the organic layer was collected, dried with anhydrous sodium sulfate, filtered, and concentrated in vacuo. The crude product was then purified via flash column chromatography using hexanes:ethyl acetate (2:1 to 1:2) to elute pure 35 as a clear oil.

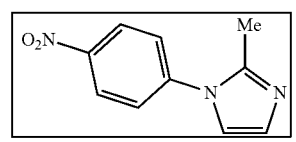

32

Yield: 45% yield; 285 mg of 32 was isolated as yellow solid. Note: 32 is a known compound. Our NMR spectra and melting point matched those previously reported for this compound.[1] MP: 142-143° C., lit. 140-141° C.[1]

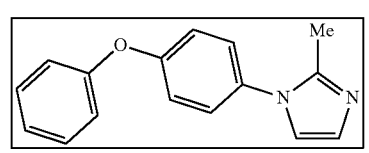

33

Yield: 40% yield; 240 mg of 33 was isolated as a clear oil. $^1$H NMR (400 MHz, CDCl$_3$): δ 7.41-7.36 (m, 2H), 7.24 (m, 1H), 7.22 (m, 1H), 7.18 (m, 1H), 7.09-7.05 (m, 4H), 7.02 (d, J=1.4 Hz, 1H), 6.98 (d, J=1.4 Hz, 1H), 2.35 (s, 3H). $^{13}$C NMR (100 MHz, CDCl$_3$): δ 157.6, 156.5, 145.1, 133.0, 130.2, 127.9, 127.2, 124.3, 121.0, 119.7, 119.1, 13.9. HRMS (ESI): calc. for C$_{16}$H$_{15}$N$_2$O [M+H]$^+$: 251.1179, found: 251.1168.

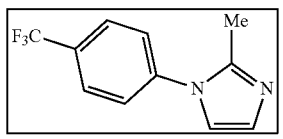

34

Yield: 38% yield; 210 mg of 34 was isolated as a clear oil. $^1$H NMR (400 MHz, CDCl$_3$): δ 7.73 (d, J=8.3 Hz, 2H), 7.41 (d, J=8.3 Hz, 2H), 7.15-6.88 (m, 2H), 2.36 (s, 3H). $^{13}$C NMR (100 MHz, CDCl$_3$): δ 144.9, 141.1, 130.4 (q, J=33.0 Hz), 128.4, 126.9 (q, J=3.7 Hz), 125.8, 123.7 (q, J=272.3 Hz), 120.6, 14.0. HRMS (ESI) m/z: calc. for C$_{11}$H$_{10}$F$_3$N$_2$[M+H$^+$]: 227.0791, found: 227.0784. Note: 34 is a known compound[2]; however, we could not locate NMR data following a literature search.

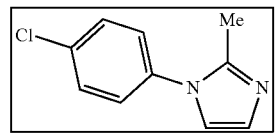

35

Yield: 45% yield; 260 mg of 35 was isolated. Note: 35 is a known compound (CAS No. 132026-81-4). Our NMR spectra match those previously reported for this compound.[3]

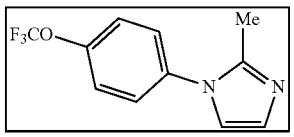

36

Yield: 36% yield; 160 mg of 36 was isolated as a clear oil. $^1$H NMR (400 MHz, CDCl$_3$): δ 7.32-7.28 (m, 4H), 7.00 (d, J=1.3 Hz, 1H), 6.96 (dd, J=1.4, 0.5 Hz, 1H), 2.33 (s, 3H). $^{13}$C NMR (100 MHz, CDCl$_3$): δ 148.7 (q, J=1.8 Hz), 144.8, 136.6, 128.2, 127.1, 122.1 (d, J=1.2 Hz), 120.7, 120.5 (q, J=258.1 Hz), 13.9. HRMS (ESI) m/z: calc. for C$_{11}$H$_{10}$F$_3$N$_2$O [M+H$^+$]: 243.0740, found: 243.0737.

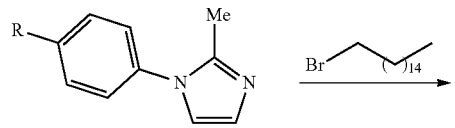

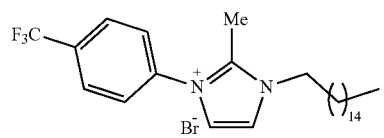

1-7

General Procedure for Alkylation Reactions to Generate Analogues 1-7:

1-Bromohexadecane (0.29 mL, 0.93 mmol) was added to a stirring solution of 1-(4-chlorophenyl)-2-methyl-1H-imidazole 35 (120 mg, 0.62 mmol) in 5 mL anhydrous acetonitrile in a glass tube at room temperature. The reaction mixture was then sealed and heated to 110° C. and allowed to stir for 24 hours. After this time, the reaction mixture was allowed to cool to room temperature before acetonitrile was evaporated in vacuo. The resulting crude product was then stirred in anhydrous ether under argon for 5 hours and resulting white precipitate, which was filtered under an argon environment. The resulting precipitate was washed with cold anhydrous ether and dried under vacuum to obtain 6 as a white solid (170 mg, 53%).

2

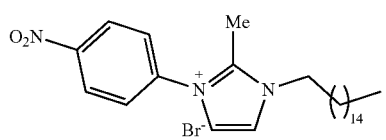

Figure 17:
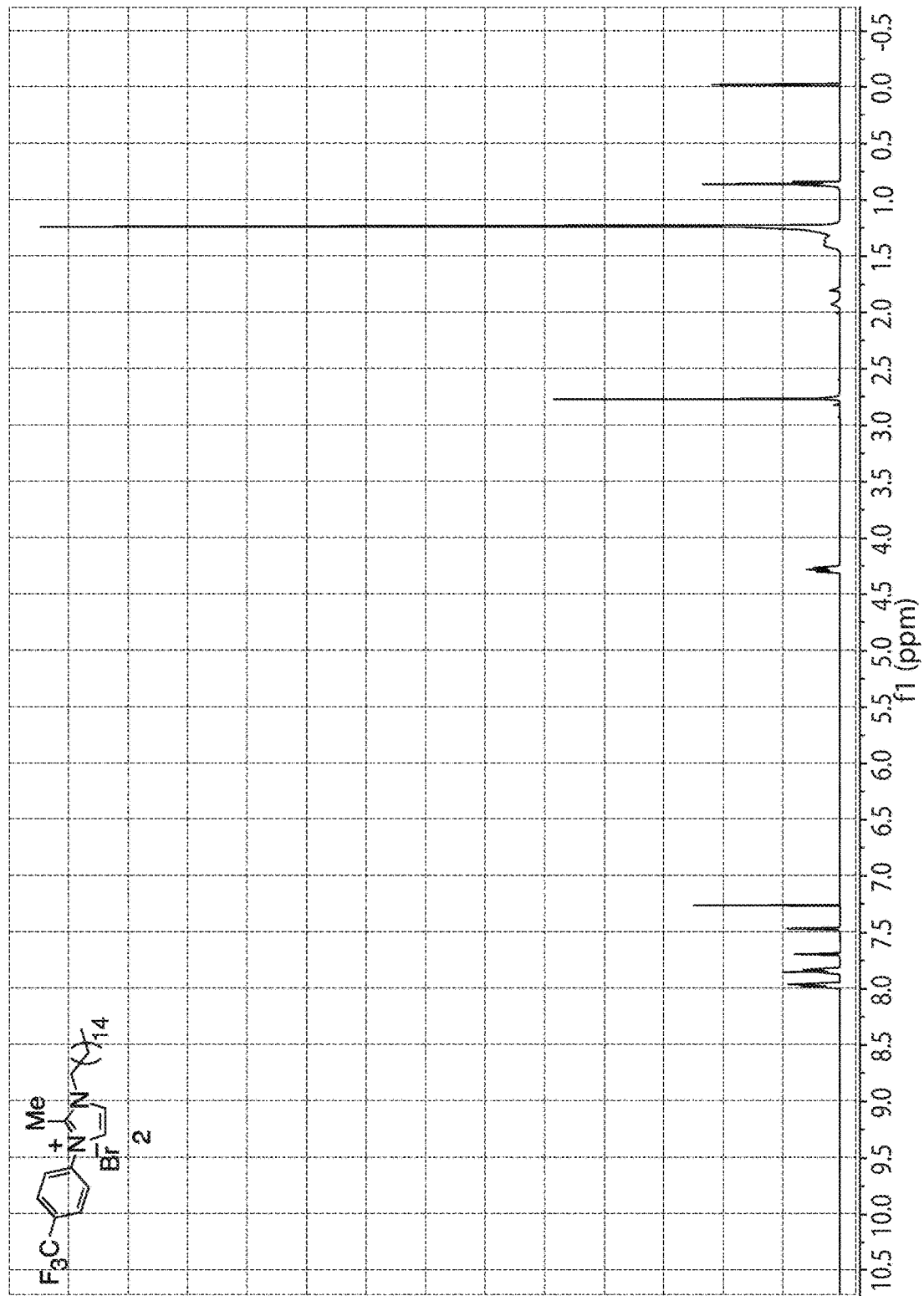
FIG. 17. NMR 1 for depicted compound 2.
Figure 18:
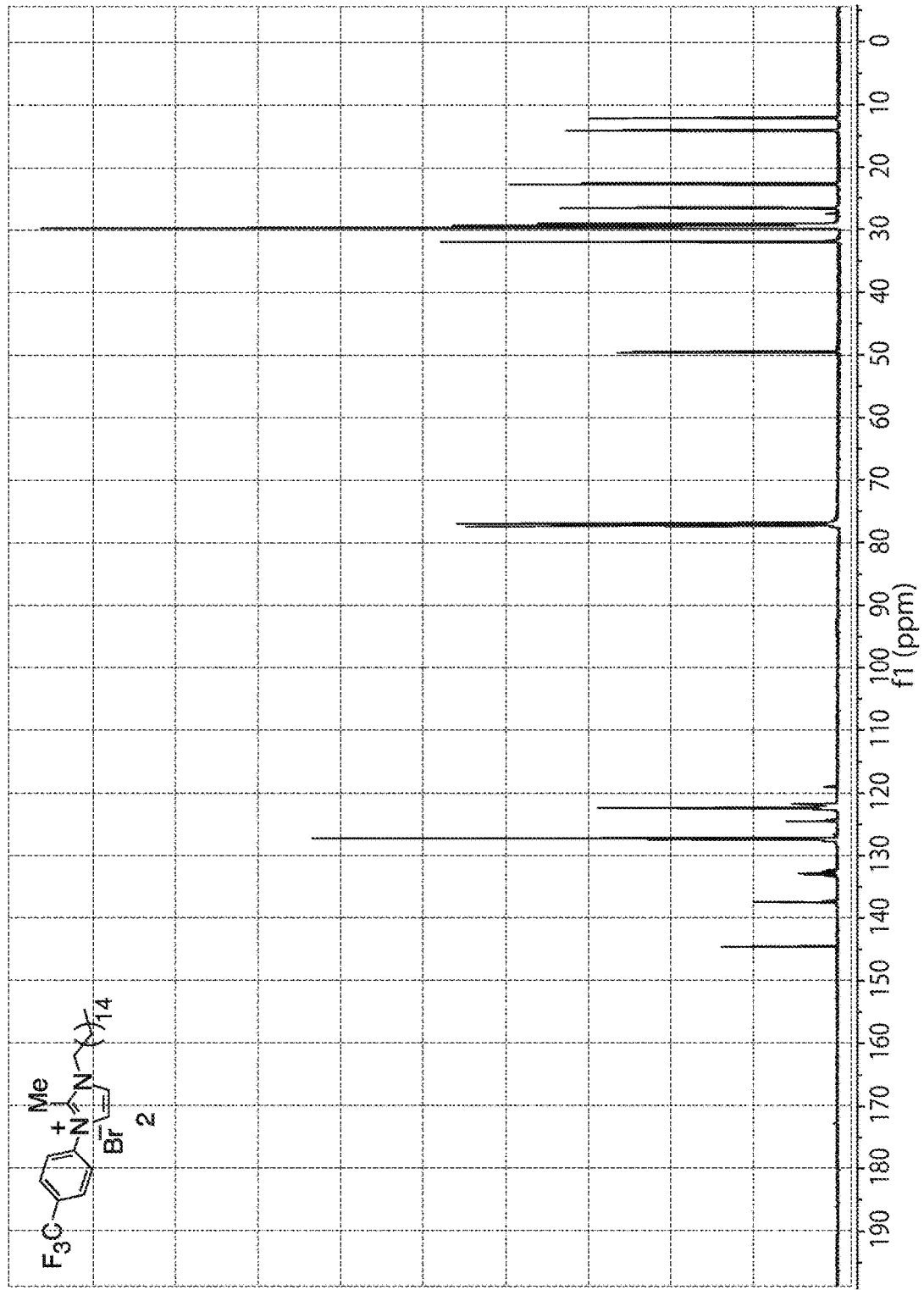
FIG. 18. NMR 2 for depicted compound 2.

Yield: 51% yield; 180 mg of 2 was isolated as a white solid. $^1$H NMR (400 MHz, CDCl$_3$): δ 7.97 (d, J=8.2 Hz, 2H), 7.84 (d, J=8.3 Hz, 2H), 7.70 (d, J=2.1 Hz, 1H), 7.47 (d, J=2.1 Hz, 1H), 4.29 (t, J=7.7 Hz, 2H), 2.77 (s, 3H), 1.98-1.88 (m, 2H), 1.41-1.12 (m, 26H), 0.86 (t, J=6.8 Hz, 3H). $^{13}$C NMR (100 MHz, CDCl3): δ 144.6, 137.4 (d, J=1.8 Hz), 132.9 (q, J=33.3 Hz), 127.5 (q, J=3.7 Hz), 127.3, 123.2 (q, J=272.9 Hz), 122.5, 122.3, 49.6, 31.9, 29.7, 29.7, 29.6, 29.6, 29.5, 29.4, 29.4, 29.4, 29.1, 26.6, 22.7, 14.1, 12.2. Note: 23 of the 25 $^{13}$C NMR signals could be found, multiple signals overlap at 29 ppm. HRMS (ESI) m/z: calc. for C$_{27}$H$_{42}$F$_3$N$_2$ [M$^+$]: 451.3295, found: 451.3303. MP: 78-79° C. See FIGS. 17 and 18.

3

Figure 19:
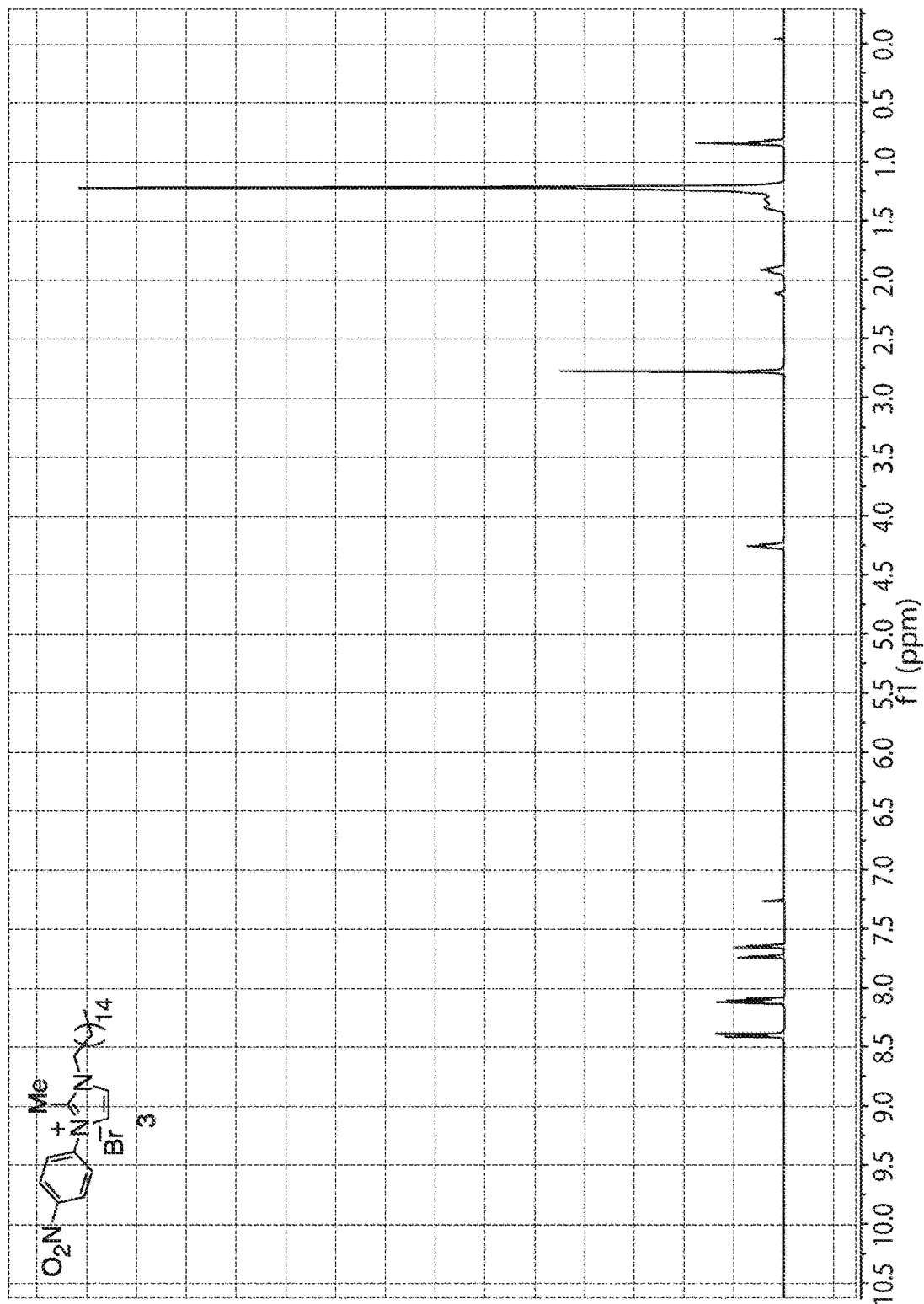
FIG. 19. NMR 3 for depicted compound 3.
Figure 20:
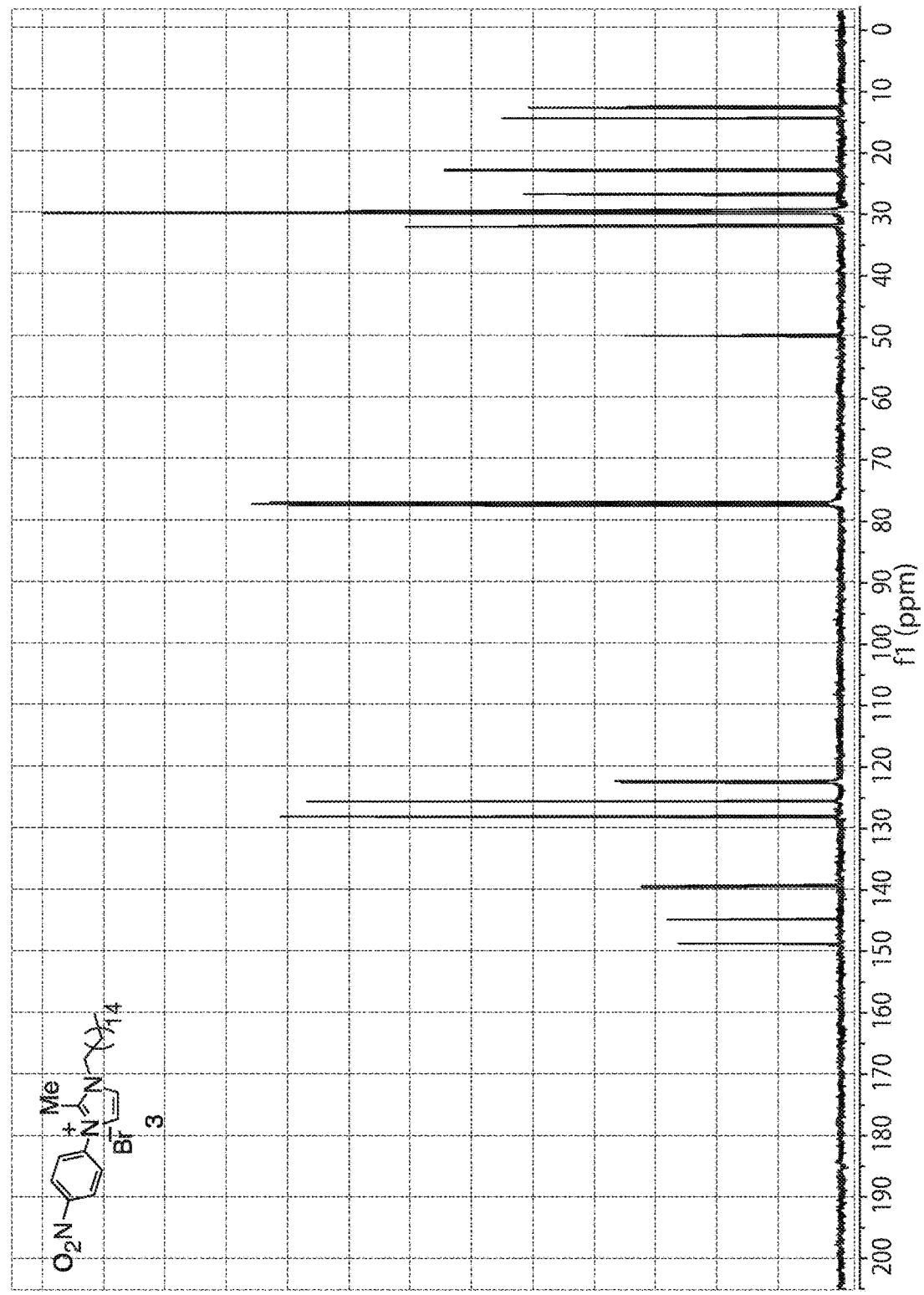
FIG. 20. NMR 4 for depicted compound 3.

Yield: 88% yield; 330 mg of 3 was isolated as a white solid. $^1$H NMR (400 MHz, CDCl$_3$): δ 8.39 (m, 2H), 8.10 (m, 2H), 7.73 (d, J=2.2 Hz, 1H), 7.65 (d, J=2.2 Hz, 1H), 4.25 (t, J=7.8 Hz, 2H), 2.78 (s, 3H), 1.92 (p, J=7.7 Hz, 2H), 1.49-1.14 (m, 26H), 0.84 (t, J=6.7 Hz, 3H). $^{13}$C NMR (100 MHz, CDCl$_3$): δ 148.9, 145.0, 139.4, 128.3, 125.7, 122.6, 122.4, 49.7, 32.0, 29.8, 29.8, 29.7, 29.7, 29.6, 29.5, 29.5, 29.2, 26.7, 22.8, 14.3, 12.5. Note: 21 of the 24 $^{13}$C NMR signals could be found, multiple signals overlap at 29 ppm. HRMS (ESI) m/z: calc. for C$_{26}$H$_{42}$N$_3$O$_2$[M$^+$]: 428.3272, found: 428.3256. MP: 87-88° C. See FIGS. 19 and 20.

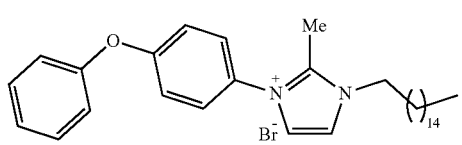

5

Figure 21:
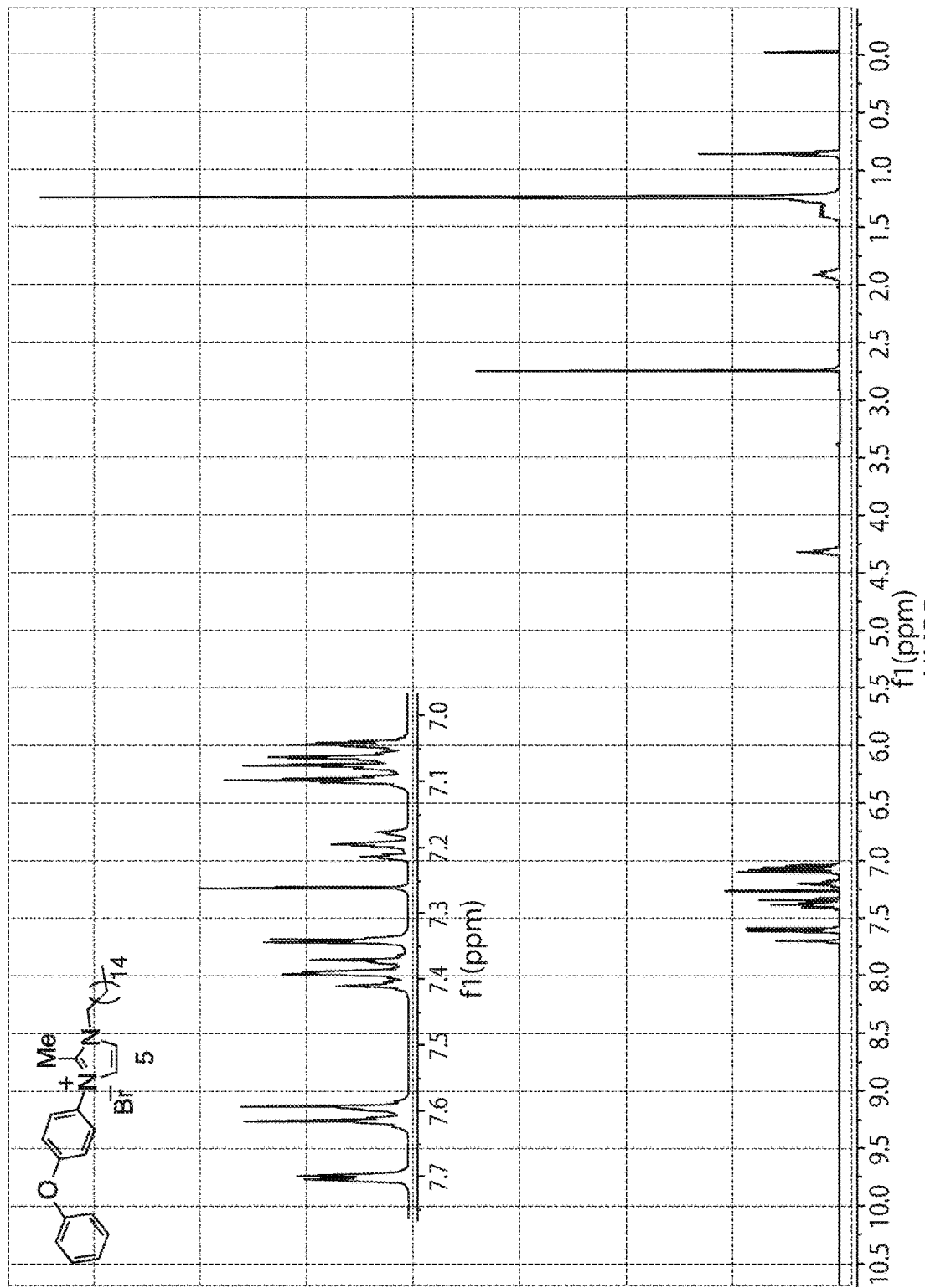
FIG. 21. NMR 5 for depicted compound 5.
Figure 22:
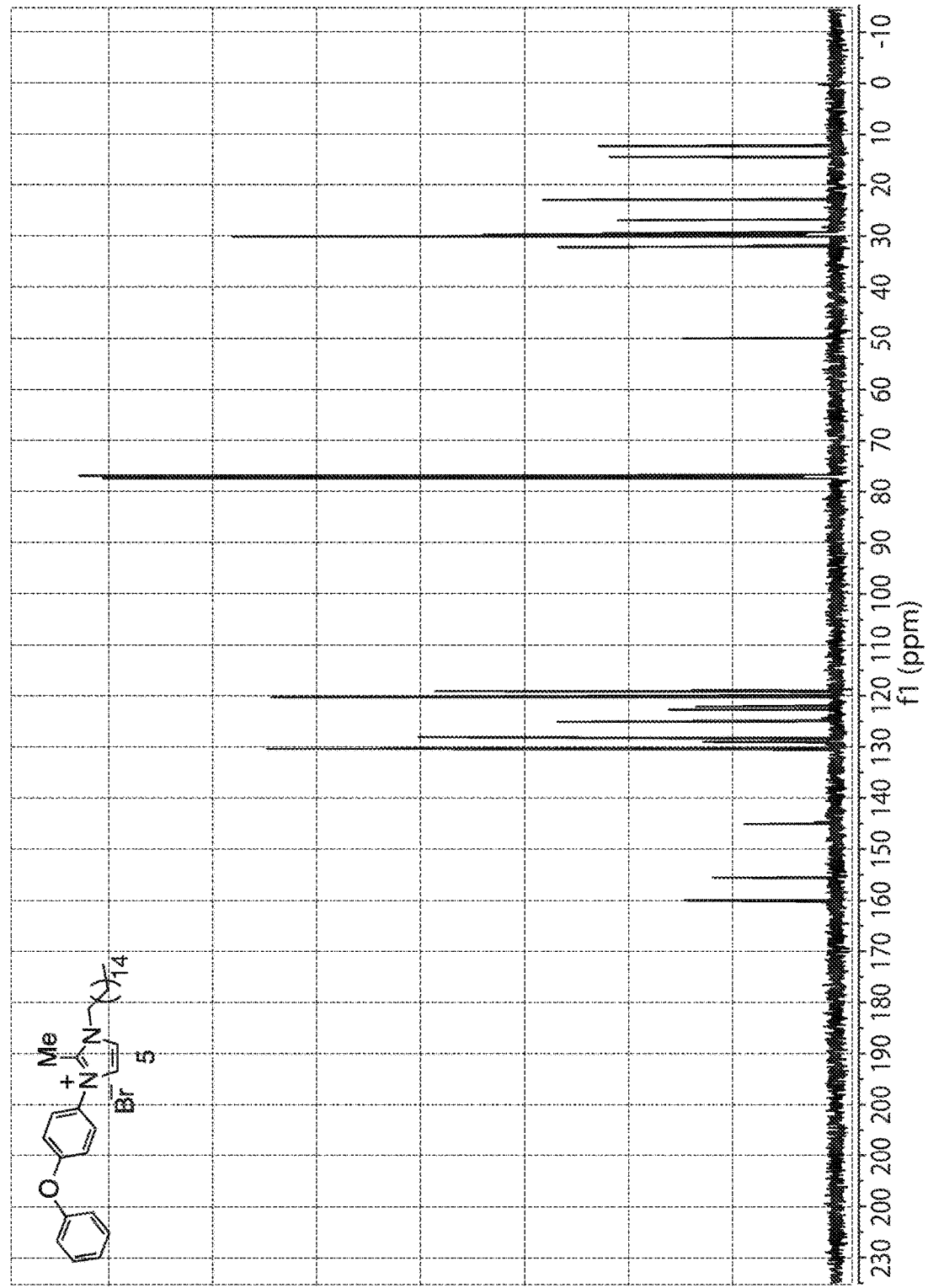
FIG. 22. NMR 6 for depicted compound 5.

Yield: 60% yield; 220 mg of 5 was isolated as a white solid. ¹H NMR (400 MHz, CDCl₃): δ 7.70 (d, J=2.1 Hz, 1H), 7.60 (m, 2H), 7.39 (m, 2H), 7.34 (d, J=2.1 Hz, 1H), 7.19 (tt, J=7.5 Hz, 1.1 Hz, 1H), 7.12-7.02 (m, 4H), 4.32 (t, J=7.5 Hz, 2H), 2.74 (s, 3H), 1.98-1.85 (m, 2H), 1.41-1.12 (m, 26H), 0.85 (t, J=7.0 Hz, 3H). ¹³C NMR (100 MHz, CDCl₃): δ 160.0, 155.5, 144.9, 130.4, 128.9, 128.1, 125.0, 122.6, 122.1, 120.2, 119.1, 49.7, 32.1, 29.9, 29.8, 29.8, 29.8, 29.7, 29.6, 29.6, 29.5, 29.3, 26.7, 22.9, 14.3, 12.2. Note: 26 of the 28 ¹³C NMR signals could be found, multiple signals overlap at 29 ppm. HRMS (ESI) m/z: calc. for $C_{32}H_{47}N_2O$ [M⁺]: 475.3683, found: 475.3686. MP: 66-67° C. See FIGS. 21 and 22.

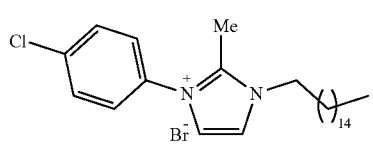

6

Figure 23:
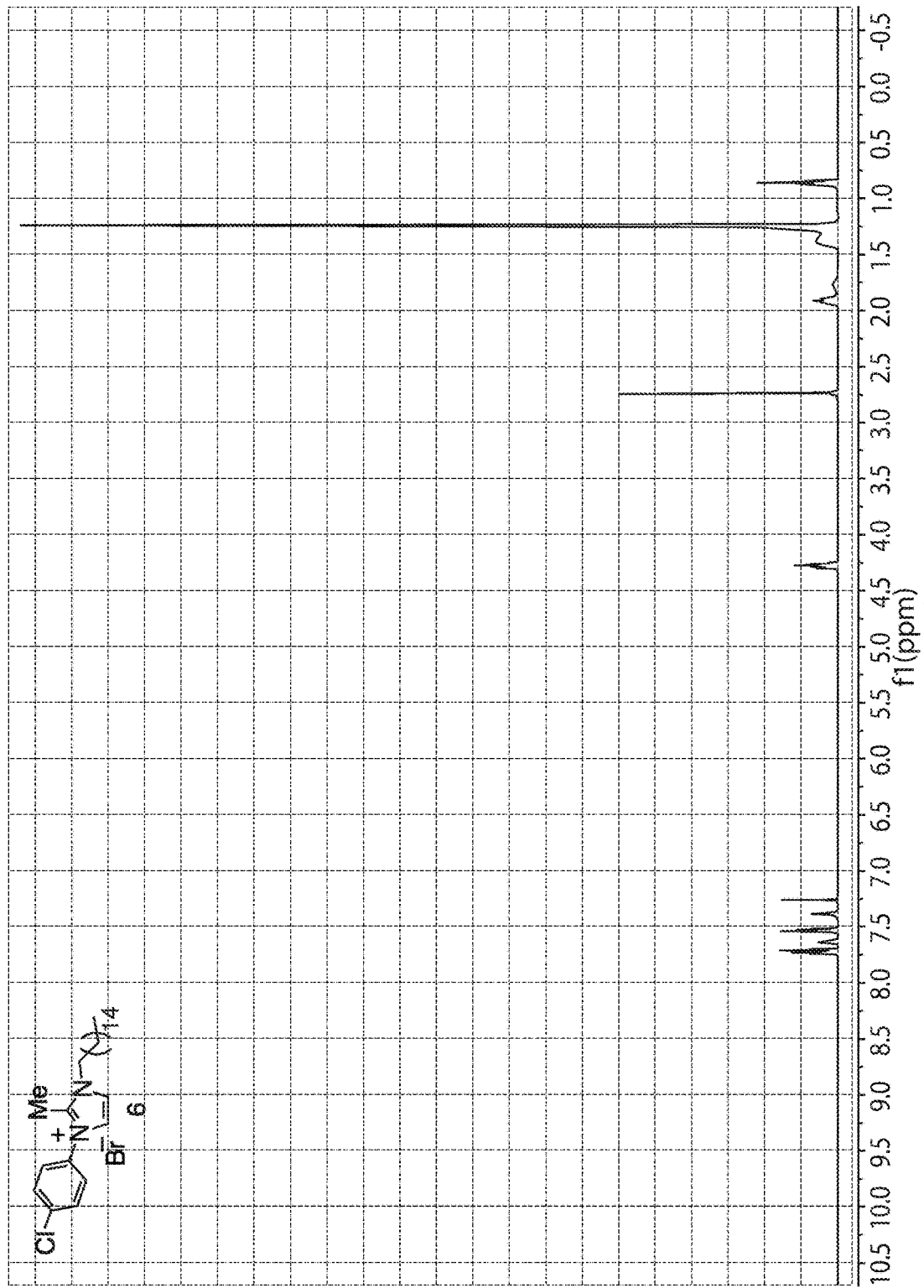
FIG. 23. NMR 7 for depicted compound 6.
Figure 24:
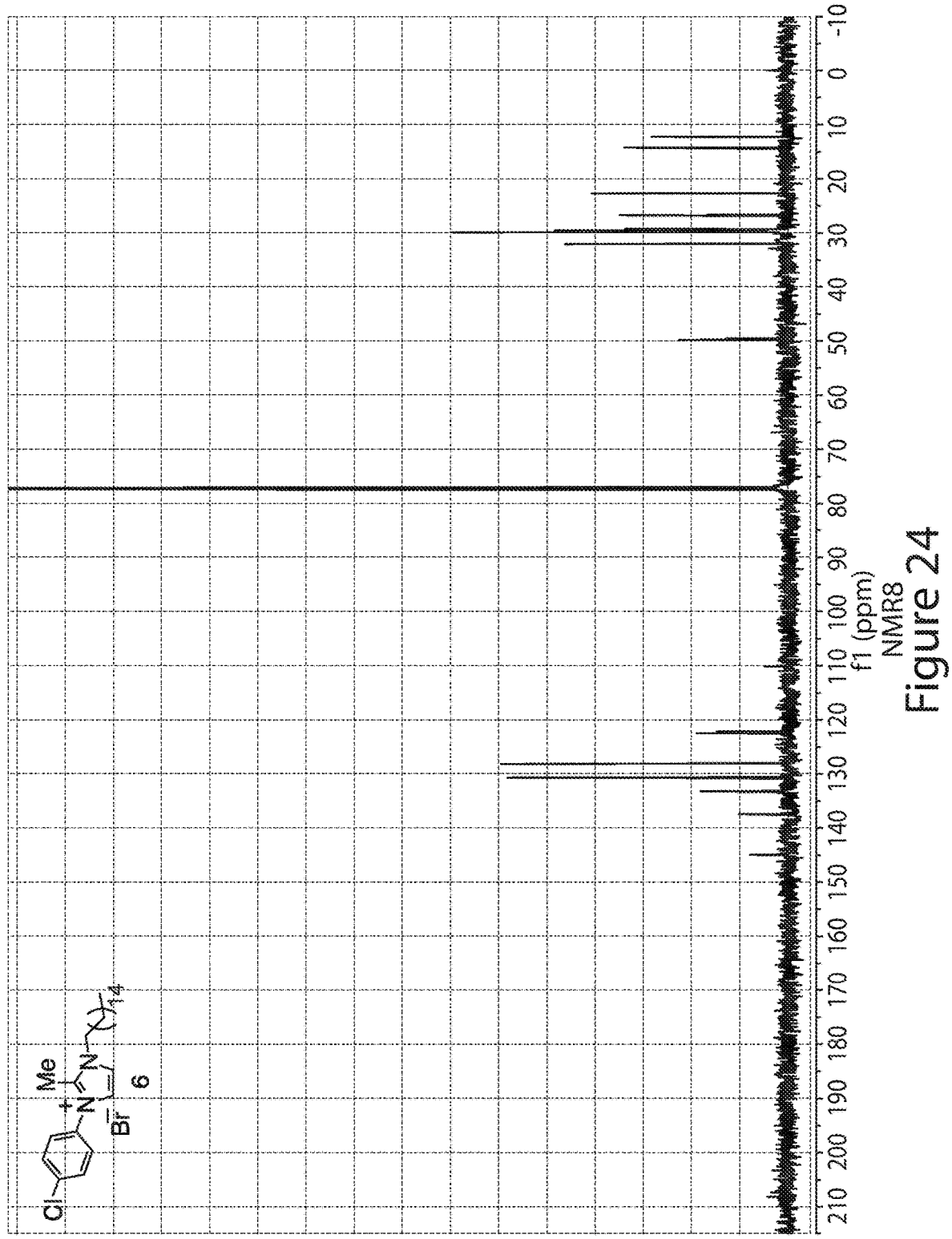
FIG. 24. NMR 8 for depicted compound 6.

Yield: 53% yield; 170 mg of 6 was isolated as a white solid. ¹H NMR (400 MHz, CDCl₃): δ 7.72 (d, J=8.6, Hz, 2H), 7.64 (m, 1H), 7.53 (d, J=8.7 Hz, 2H), 7.39 (m, 1H), 4.28 (t, J=7.5 Hz, 2H), 2.74 (s, 3H), 1.92 (p, J=7.8 Hz, 2H), 1.45-1.18 (m, 26H), 0.86 (t, J=6.7 Hz, 3H). ¹³C NMR (100 MHz, CDCl₃): δ 145.1, 137.4, 133.2, 130.7, 128.1, 122.4, 122.1, 49.8, 32.1, 29.9, 29.9, 29.9, 29.8, 29.8, 29.7, 29.6, 29.5, 29.5, 29.3, 26.8, 22.9, 14.3, 12.4. Note: 23 of the 24 ¹³C NMR signals could be found, likely due to signal overlap at 29 ppm. HRMS (ESI) m/z: calc. for $C_{26}H_{42}ClN_2$ [M⁺]: 417.3031, found: 417.3037. MP: 65-66° C. See FIGS. 23 and 24.

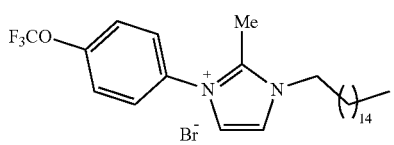

7

Figure 25:
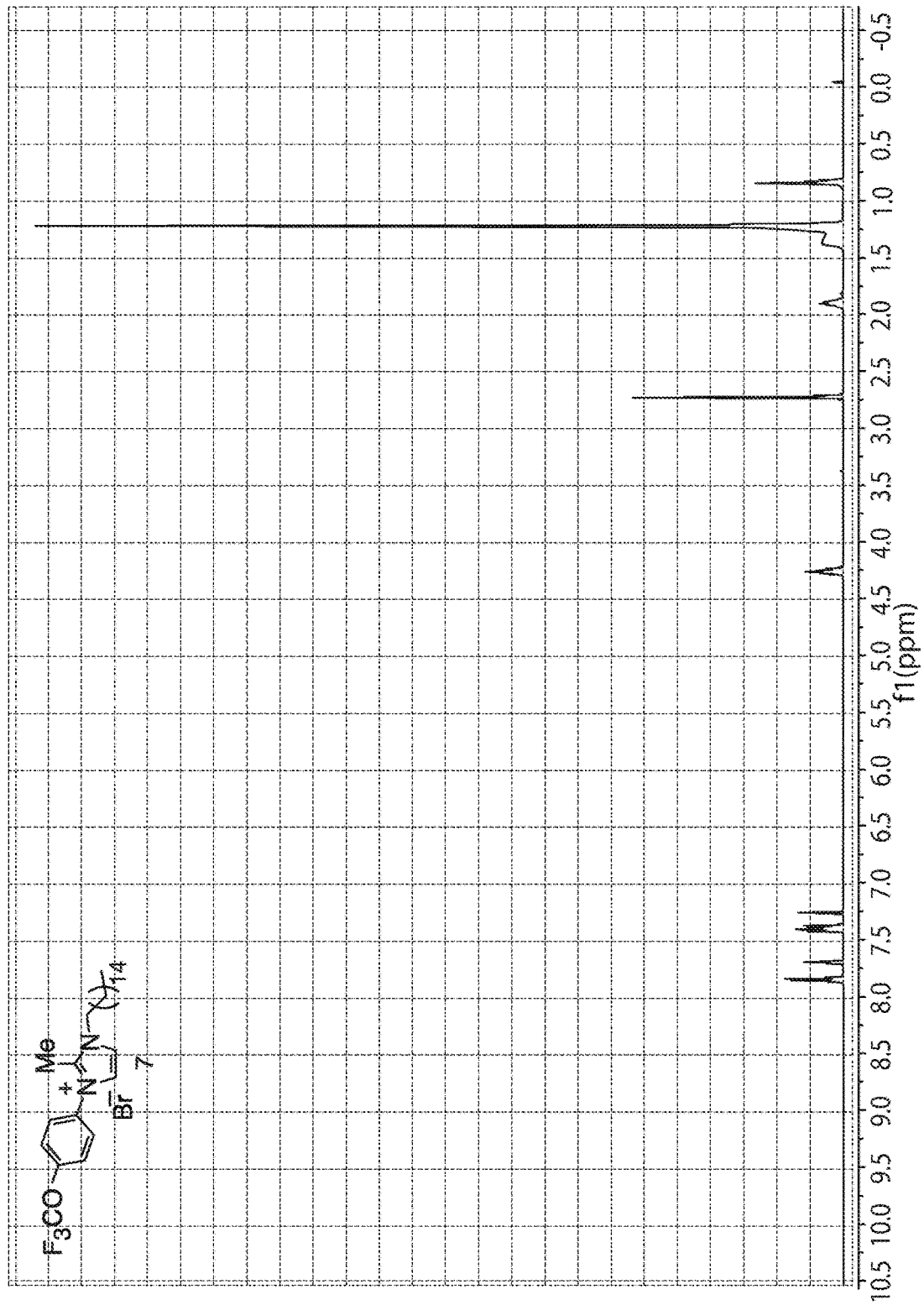
FIG. 25. NMR 9 for depicted compound 7.
Figure 26:
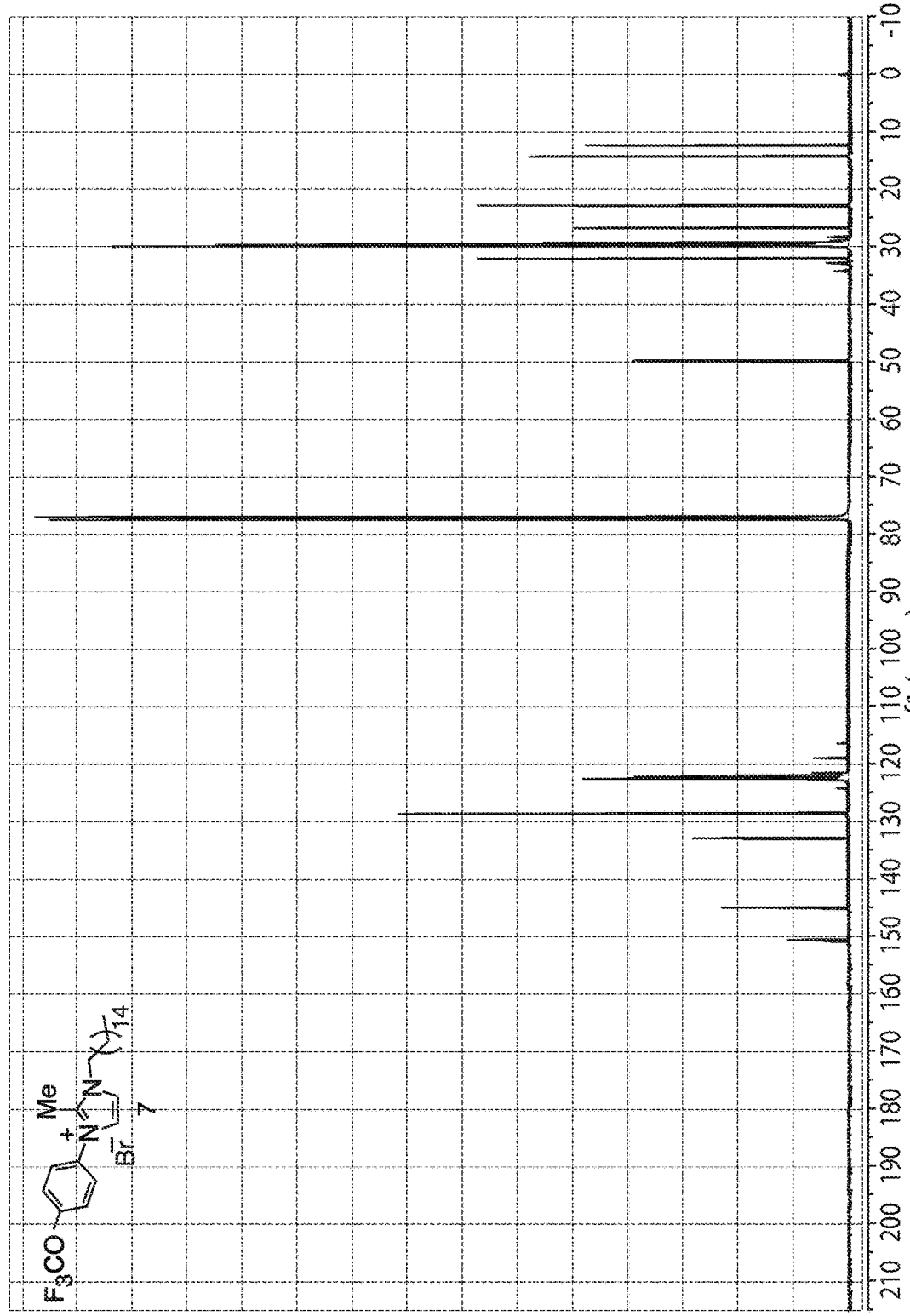
FIG. 26. NMR 10 for depicted compound 7.

Yield: 60% yield; 220 mg of 7 was isolated as a pale white solid. ¹H NMR (400 MHz, CDCl₃): δ 7.85 (d, J=8.8 Hz, 2H), 7.70 (d, J=2.1 Hz, 1H), 7.42 (d, J=2.1 Hz, 1H), 7.39 (d, J=8.5 Hz, 2H), 4.26 (t, J=7.7 Hz, 2H), 2.73 (s, 3H), 1.97-1.86 (m, 2H), 1.41-1.12 (m, 26H), 0.85 (t, J=6.7 Hz, 3H). ¹³C NMR (100 MHz, CDCl₃): δ 150.7 (q, J=1.9 Hz), 145.1, 132.9, 128.6, 122.5 (d, J=0.8 Hz), 122.5, 122.3, 120.4 (q, J=259.3 Hz), 49.7, 32.1, 29.8, 29.8, 29.8, 29.8, 29.7, 29.6, 29.5, 29.3, 26.7, 22.8, 14.3, 12.3. Note: 22 of the 25 ¹³C NMR signals could be found, multiple signals overlap at 29 ppm. HRMS (ESI) m/z: calc. for $C_{27}H_{42}F_3N_2O$ [M⁺]: 467.3244, found: 467.3240. MP: 42-43° C. See FIGS. 25 and 26.

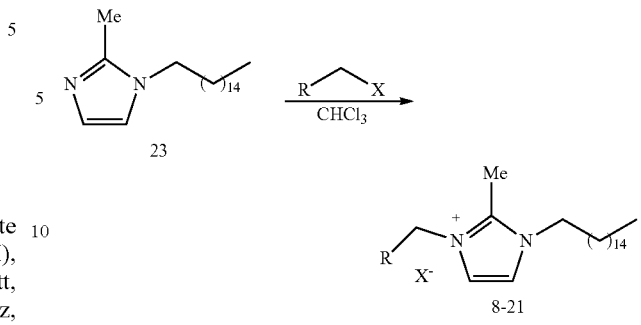

General Procedure for Alkylation of 23 to Generate Analogues 8-21:

3-Bromoprop-1-ene (42 μL, 0.49 mmol) was added to a stirring solution of 23 (100 mg, 0.33 mmol) in 5 mL anhydrous chloroform in a glass tube at room temperature. The reaction tube was then sealed and heated at 90° C. for 24 hours while the reaction occurred. Upon completion of the reaction, the solution was allowed to cool to room temperature and chloroform was then evaporated in vacuo. The crude product was then stirred in anhydrous ether under argon for 3 hours and the resulting white precipitate was filtered in an argon environment. The resulting precipitate was then washed with anhydrous ether and dried under vacuum to obtain pure 10 as a white solid (112 mg, 80%).

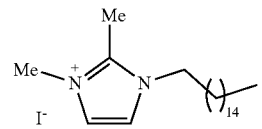

8

Figure 27:
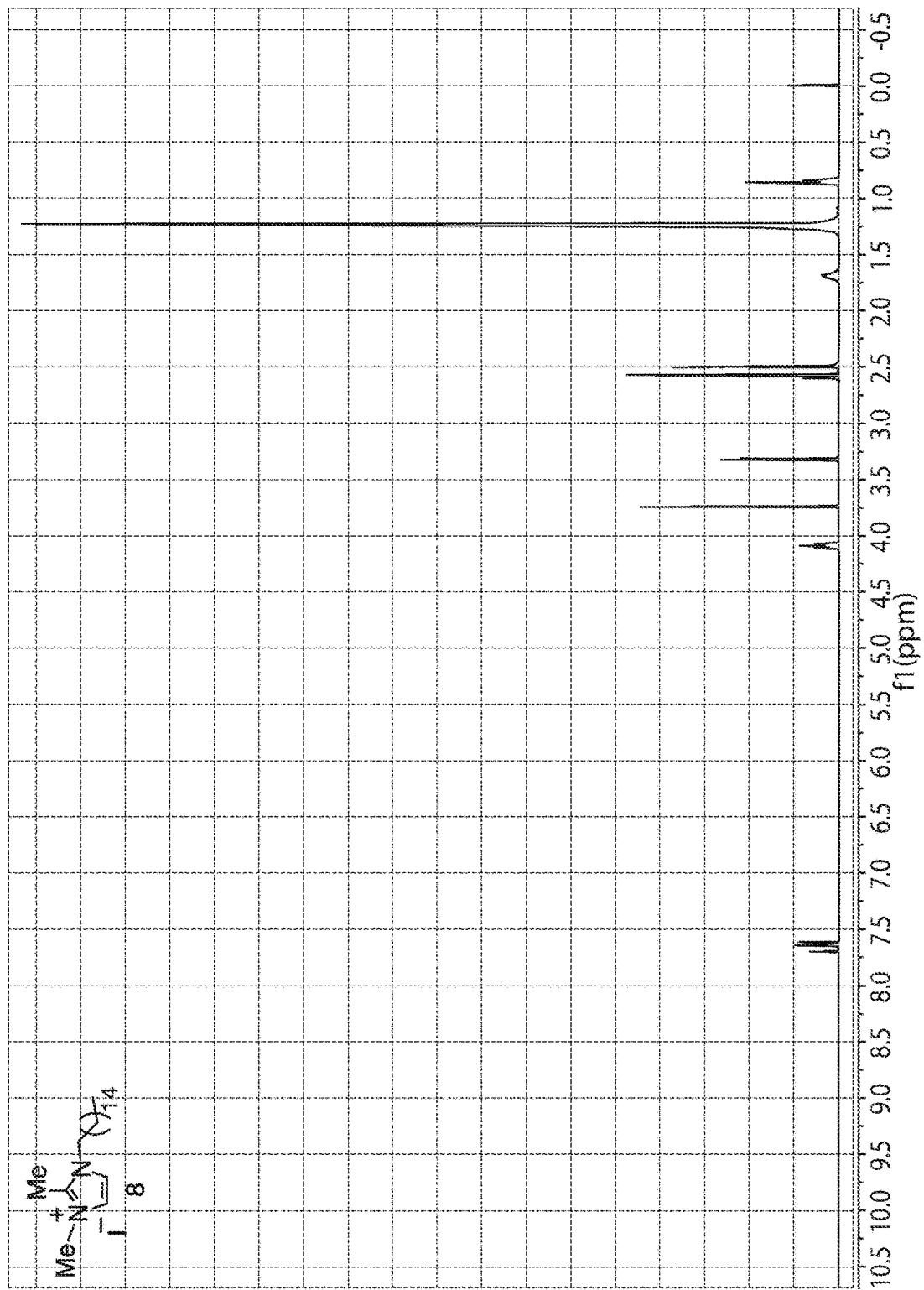
FIG. 27. NMR 11 for depicted compound 8.
Figure 28:
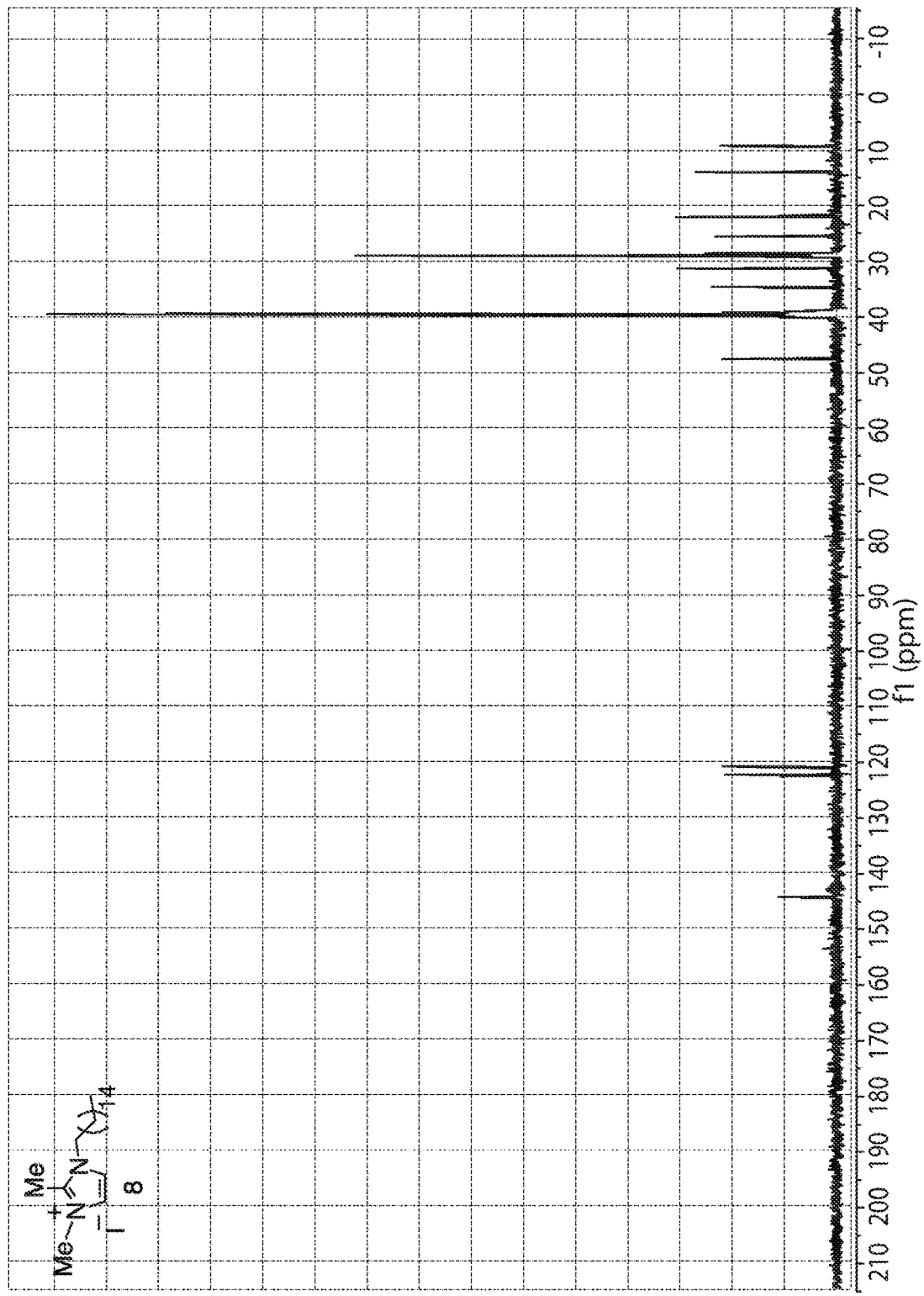
FIG. 28. NMR 12 for depicted compound 8.

Yield: 82% yield; 120 mg of 8 was isolated as a white solid. ¹H NMR (400 MHz, $d_6$-DMSO): δ 7.65 (d, J=2.1 Hz, 1H), 7.61 (d, J=2.1 Hz, 1H), 4.09 (dt, J=7.3, 2.5 Hz, 2H), 3.74 (s, 3H), 2.57 (s, 3H), 1.69 (p, J=7.1 Hz, 2H), 1.32-1.15 (m, 26H), 0.85 (t, J=7.1 Hz, 3H). ¹³C NMR (100 MHz, $d_6$-DMSO): δ 144.2, 122.3, 120.9, 47.5, 34.8, 31.3, 29.2, 29.1, 29.0, 29.0, 28.9, 28.7, 28.5, 25.6, 22.1, 14.0, 9.3. Note: 17 of the 21 ¹³C NMR signals could be found, multiple signals overlap at 29 ppm. HRMS (ESI) m/z: calc. for $C_{21}H_{41}N_2$ [M⁺]: 321.3264, found: 321.3258. MP: 72-73° C. See FIGS. 27 and 28.

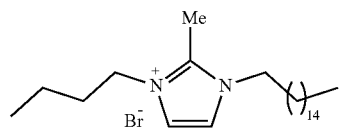

9

Figure 29:
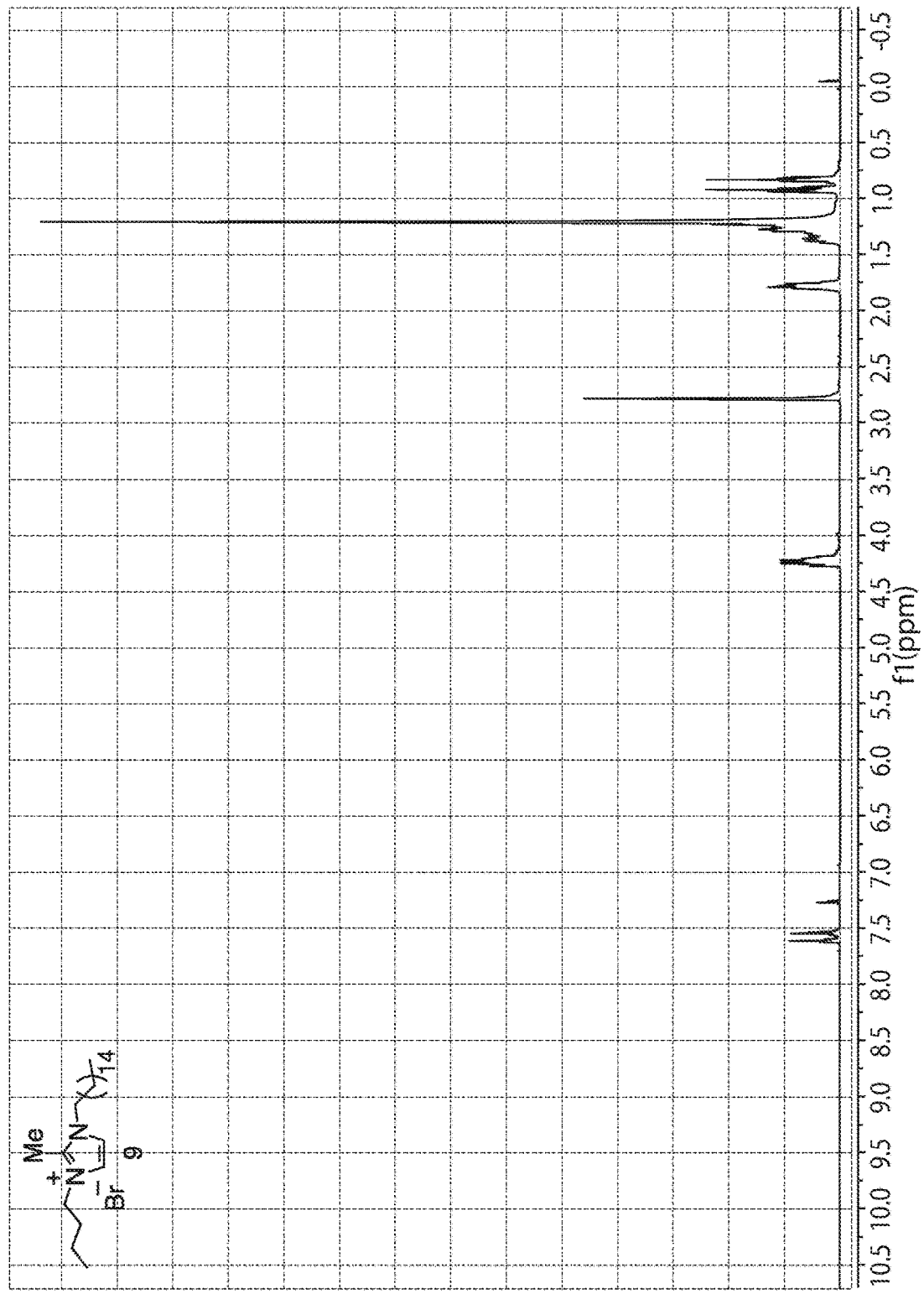
FIG. 29. NMR 13 for depicted compound 9.
Figure 30:
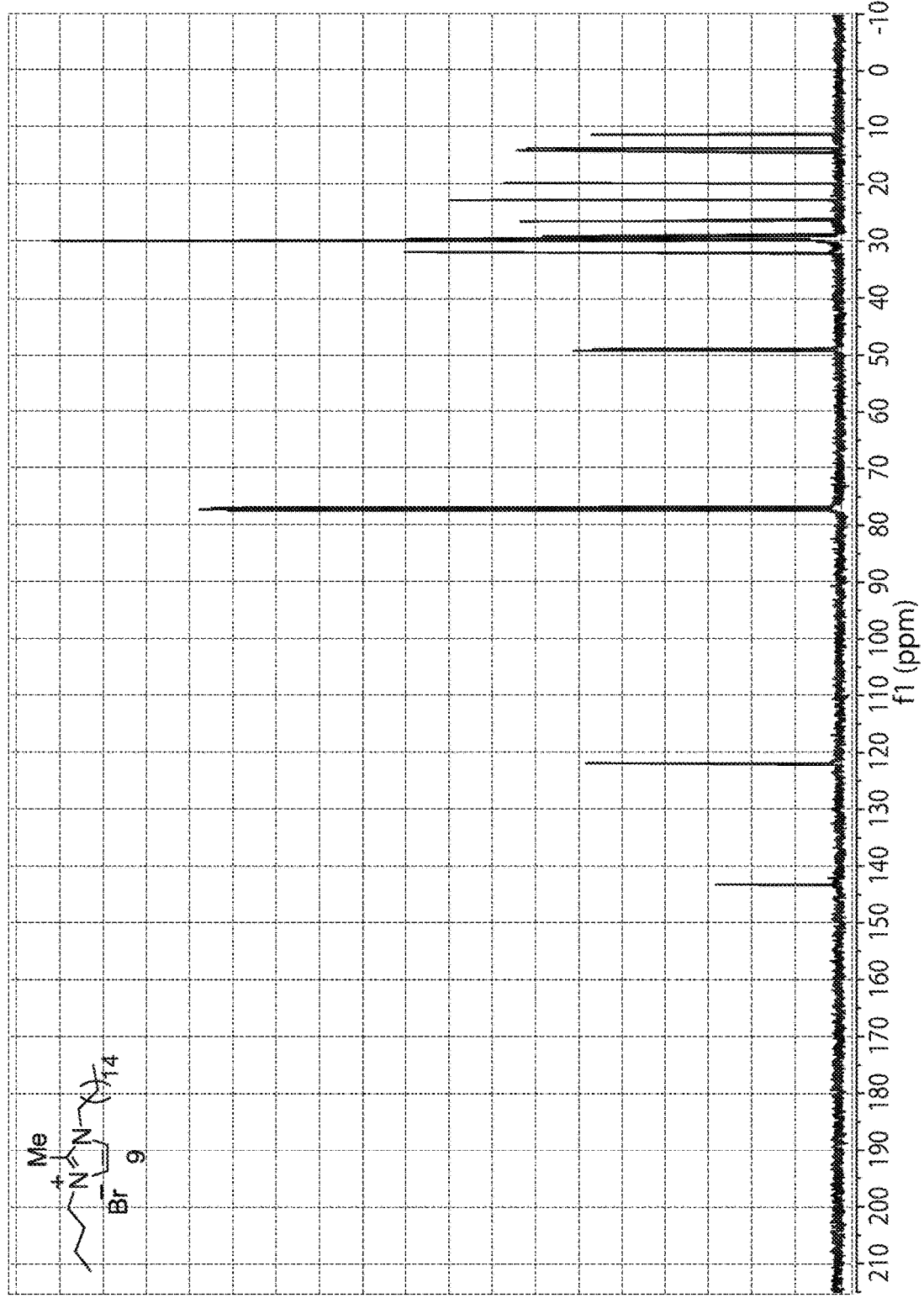
FIG. 30. NMR 14 for depicted compound 9.

Yield: 32% yield; 46 mg of 9 was isolated as a white solid. ¹H NMR (400 MHz, CDCl₃): δ 7.61 (d, J=2.1 Hz, 1H), 7.54 (d, J=2.1 Hz, 1H), 4.25 (t, J=7.4 Hz, 2H), 4.22 (t, J=7.5 Hz, 2H), 2.77 (s, 3H), 1.92-1.68 (m, 4H), 1.42-1.08 (m, 28H), 0.92 (t, J=7.3 Hz, 3H), 0.83 (t, J=6.7 Hz, 3H). ¹³C NMR (100 MHz, CDCl₃): δ 143.1, 121.9, 121.7, 49.2, 49.0, 32.0, 31.9, 30.0, 29.8, 29.8, 29.7, 29.6, 29.5, 29.5, 29.2, 26.5, 22.8, 19.7, 14.2, 13.7, 11.1. Note: 21 of the 24 ¹³C NMR signals could be found, multiple signals overlap at 29 ppm. HRMS (ESI) m/z: calc. for $C_{24}H_{47}N_2[M^+]$: 363.3734, found: 363.3745. MP: 68-69° C. See FIGS. 29 and 30.

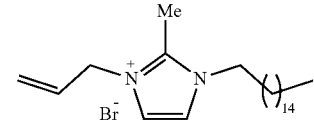

10

Figure 31:
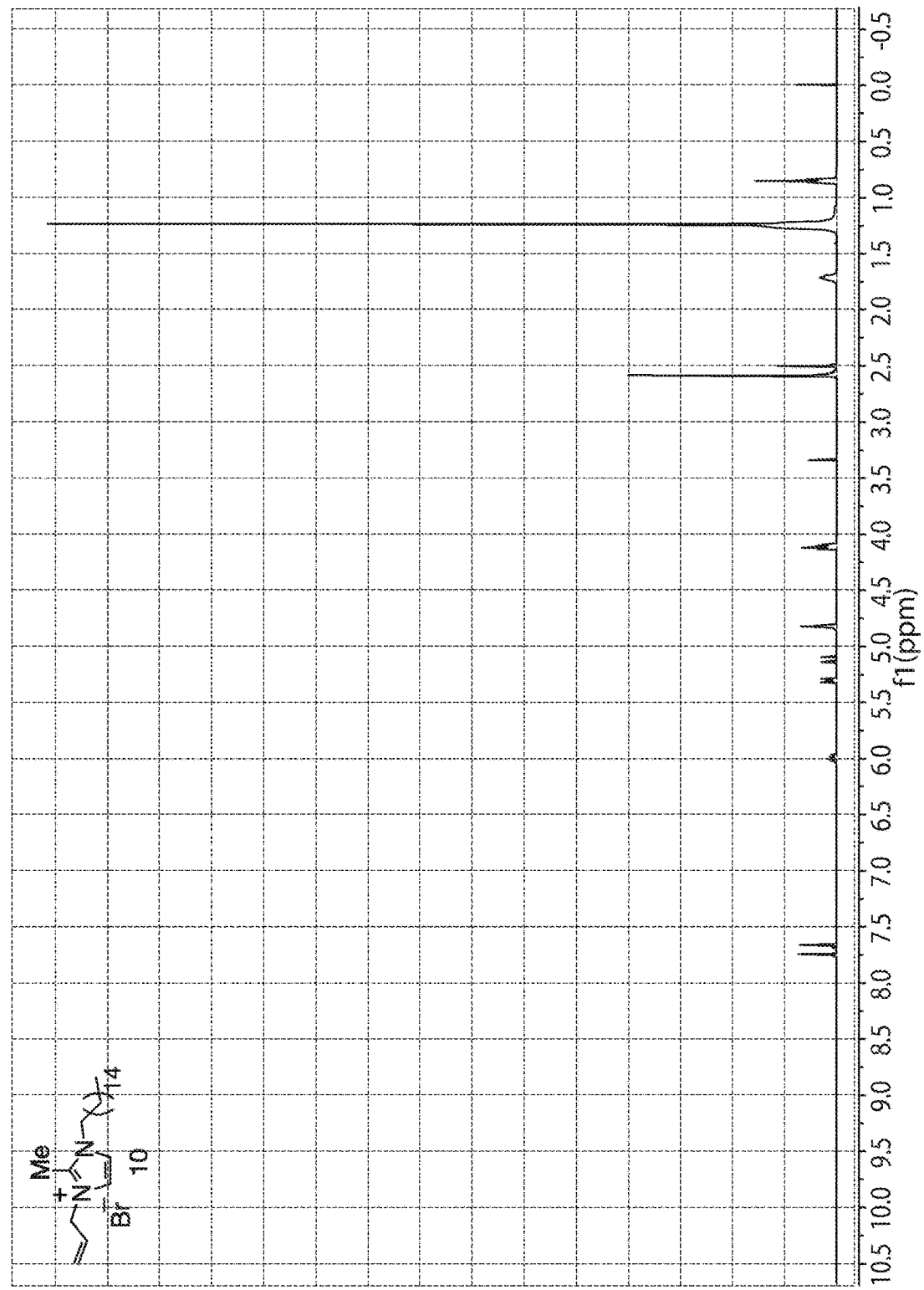
FIG. 31. NMR 15 for depicted compound 10.
Figure 32:
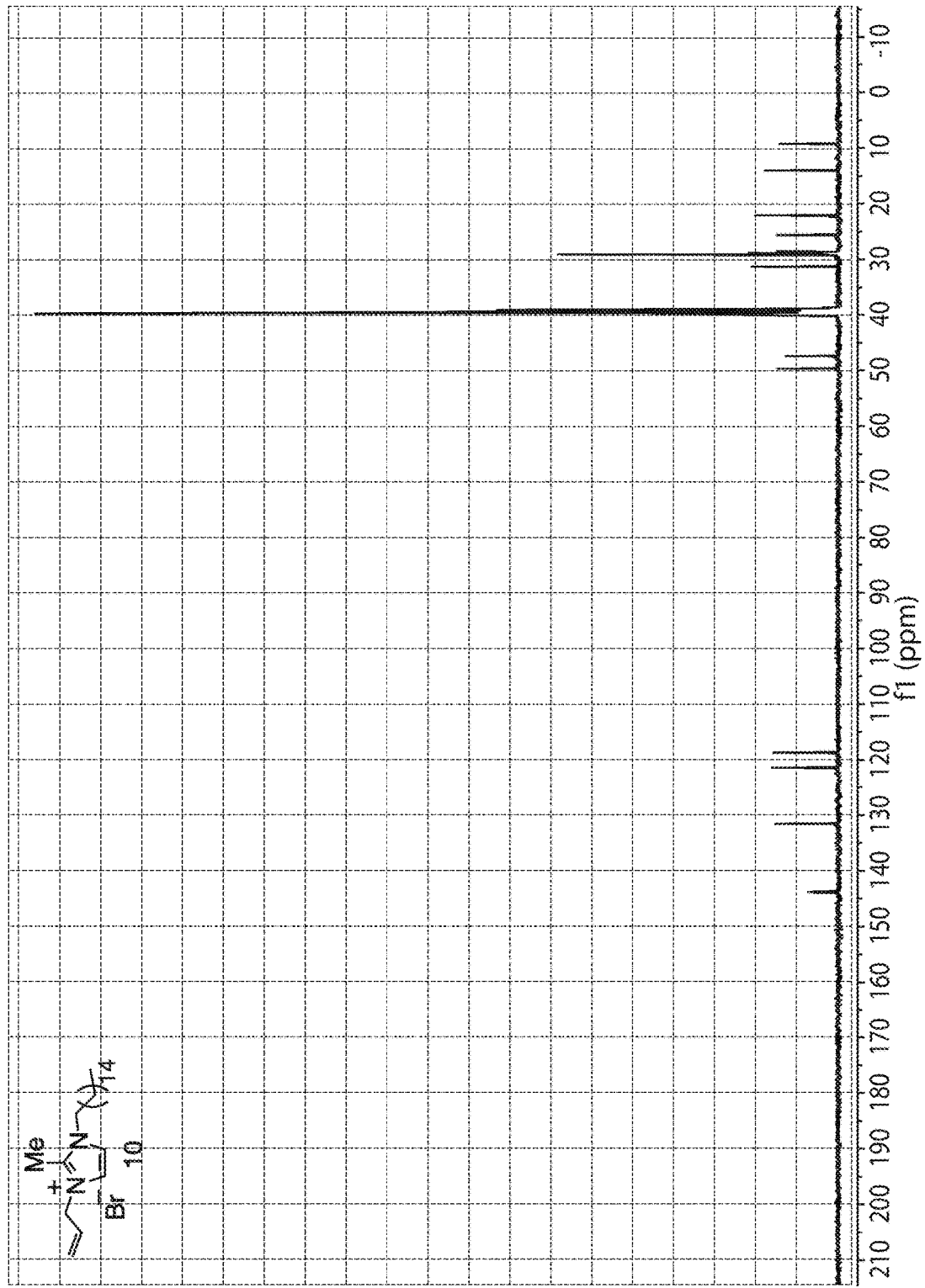
FIG. 32. NMR 16 for depicted compound 10.

Yield: 80% yield; 112 mg of 10 was isolated as a white solid. $^1$H NMR (400 MHz, $d_6$-DMSO): δ 7.74 (d, J=2.1 Hz, 1H), 7.66 (d, J=2.1 Hz, 1H), 6.03 (m, 1H), 5.30 (dd, J=10.3, 1.4 Hz, 1H), 5.11 (dd, J=17.2, 1.4 Hz, 1H), 4.82 (dt, J=5.5, 1.7 Hz, 2H), 4.11 (t, J=7.4 Hz, 2H), 2.58 (s, 3H), 1.71 (p, J=8.0 Hz, 2H), 1.32-1.16 (m, 26H), 0.85 (t, J=6.7 Hz, 3H). $^{13}$C NMR (100 MHz, $d_6$-DMSO): δ 144.0, 131.6, 121.5, 121.4, 118.8, 49.6, 47.6, 31.3, 29.1, 29.0, 29.0, 28.9, 28.7, 28.5, 25.6, 22.1, 14.0, 9.2. Note: 18 of the 23 $^{13}$C NMR signals could be found, multiple signals overlap at 29 ppm. HRMS (ESI) m/z: calc. for $C_{23}H_{43}N_2$ [$M^+$]: 347.3421, found: 347.3423. MP: 82-83° C. See FIGS. 31 and 32.

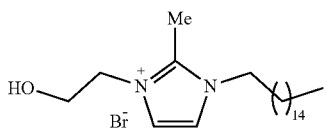

11

Figure 33:
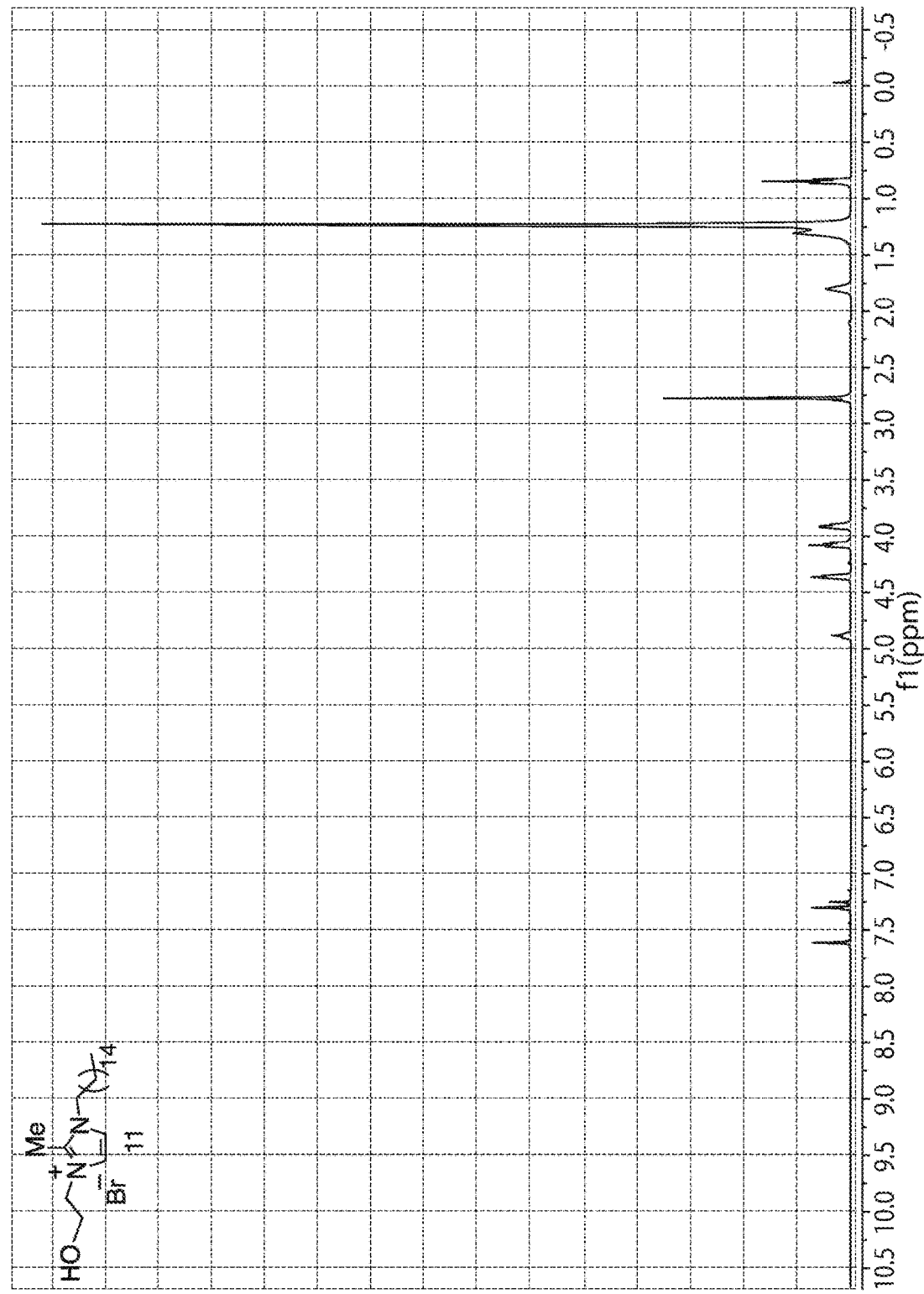
FIG. 33. NMR 17 for depicted compound 11.
Figure 34:
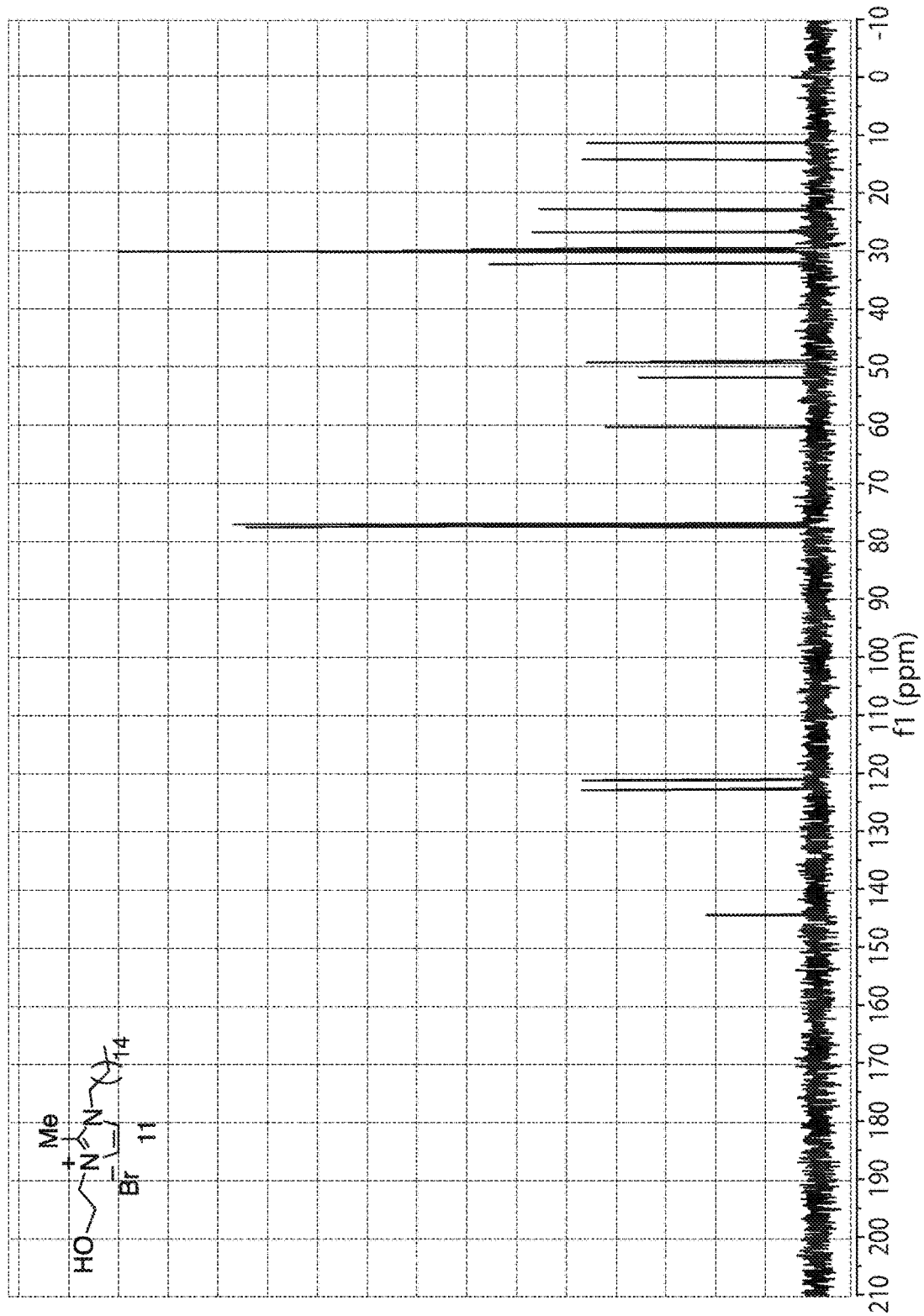
FIG. 34. NMR 18 for depicted compound 11.

Yield: 69% yield; 195 mg of 11 was isolated as a white solid. $^1$H NMR (400 MHz, CDCl$_3$): δ 7.62 (d, J=2.1 Hz, 1H), 7.31 (d, J=2.1 Hz, 1H), 4.89 (t, J=6.8 Hz, 1H), 4.37 (t, J=4.8 Hz, 2H), 4.08 (t, J=7.6 Hz, 2H), 3.91 (q, J=5.4 Hz, 2H), 2.77 (s, 3H), 1.81 (p, J=7.2 Hz, 2H), 1.43-1.13 (m, 26H), 0.85 (t, J=6.6 Hz, 3H). $^{13}$C NMR (100 MHz, CDCl$_3$): δ 144.3, 122.6, 121.0, 60.4, 51.8, 49.1, 32.1, 29.8, 29.8, 29.8, 29.7, 29.6, 29.5, 29.2, 26.6, 22.8, 14.3, 11.4. Note: 18 of the 22 $^{13}$C NMR signals could be found, multiple signals overlap at 29 ppm. HRMS (ESI) m/z: calc. for $C_{22}H_{43}N_2O$ [$M^+$]: 351.3370, found: 351.3380. MP: 58-59° C. See FIGS. 33 and 34.

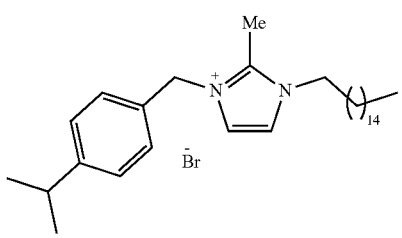

12

Figure 35:
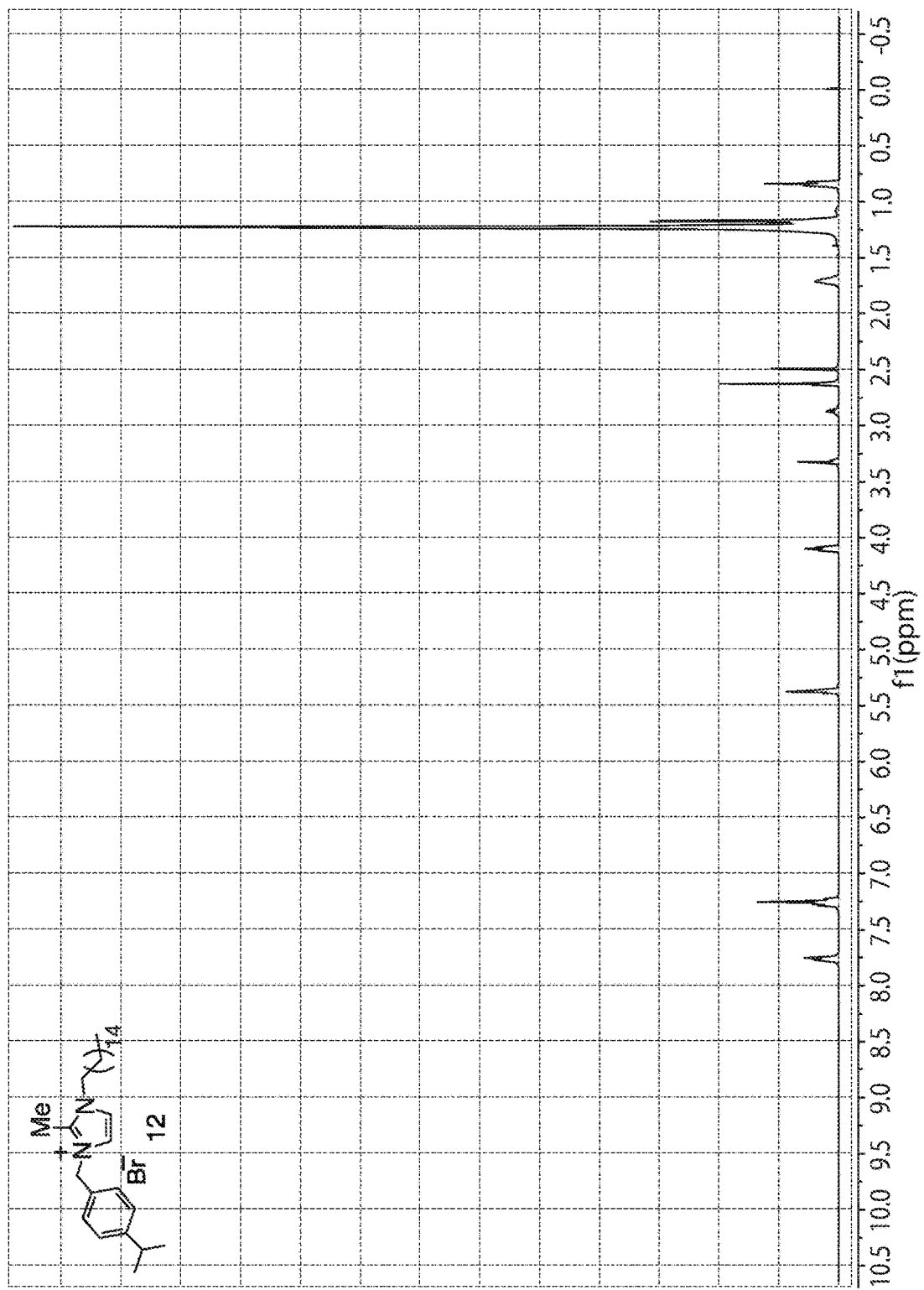
FIG. 35. NMR 19 for depicted compound 12.
Figure 36:
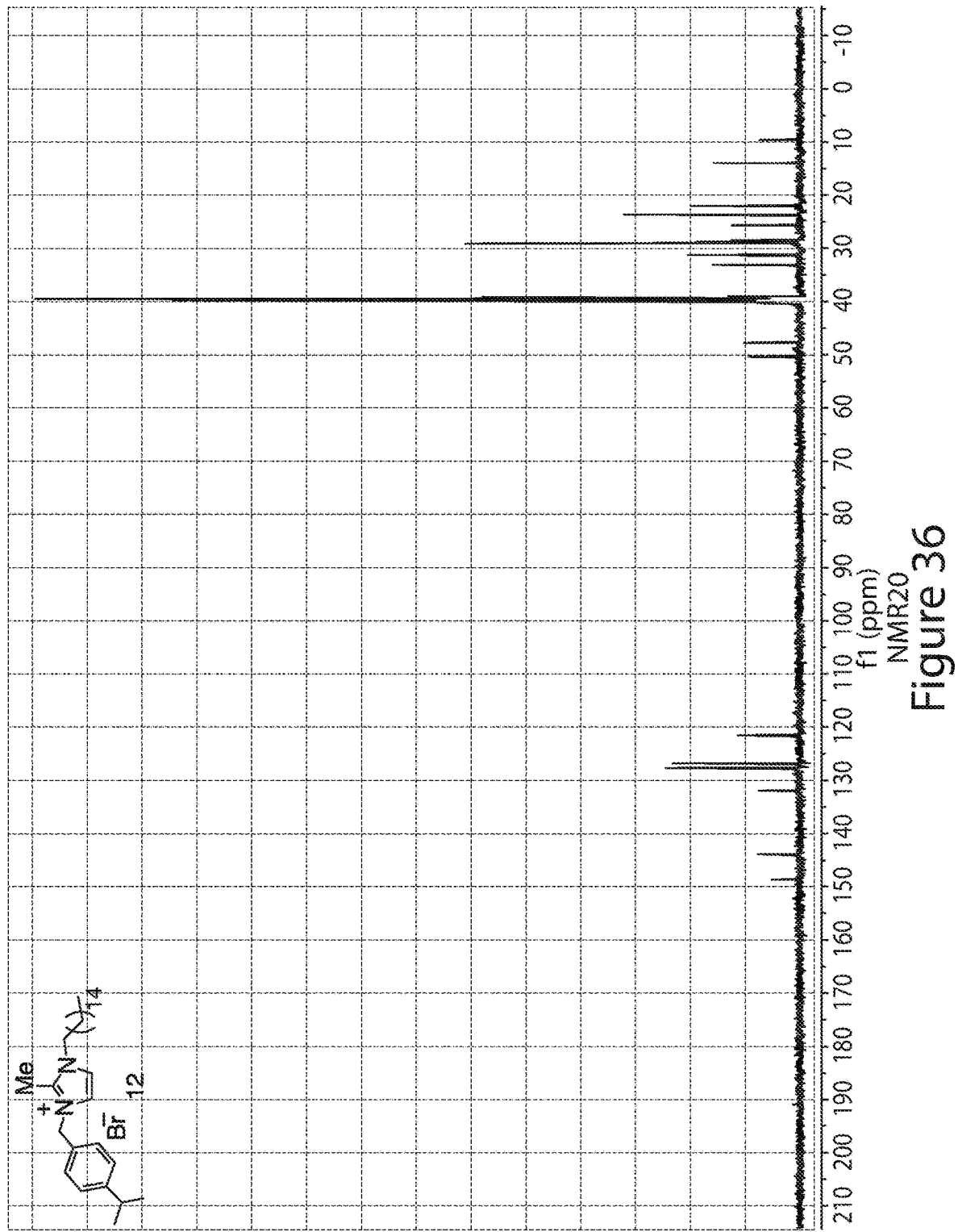
FIG. 36. NMR 20 for depicted compound 12.

Yield: 71% yield; 180 mg of 12 was isolated as a white solid. $^1$H NMR (400 MHz, $d_6$-DMSO): δ 7.81-7.72 (m, 2H), 7.31-7.21 (m, 4H), 5.37 (m, 2H), 4.11 (t, J=7.5 Hz, 2H), 2.88 (septet, J=7.0 Hz, 1H), 2.63 (s, 3H), 1.71 (p, J=7.4 Hz, 2H), 1.31-1.12 (m, 26H), 1.18 (d, J=6.9 Hz, 6H), 0.85 (t, J=6.6 Hz, 3H). $^{13}$C NMR (100 MHz, $d_6$-DMSO): δ 148.7, 143.9, 132.0, 127.8, 126.8, 121.6, 121.5, 50.4, 47.6, 33.1, 31.3, 29.0, 29.0, 28.9, 28.9, 28.8, 28.7, 28.4, 25.6, 23.7, 22.1, 13.9, 9.5. Note: 23 of the 27 $^{13}$C NMR signals could be found, multiple signals overlap at 29 ppm. HRMS (ESI) m/z: calc. for $C_{30}H_{51}N_2[M^+]$: 439.4047, found: 439.4051. MP: 72-73° C. See FIGS. 35 and 36.

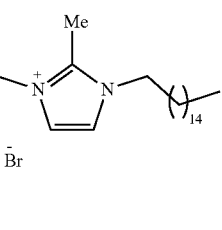

13

Figure 37:
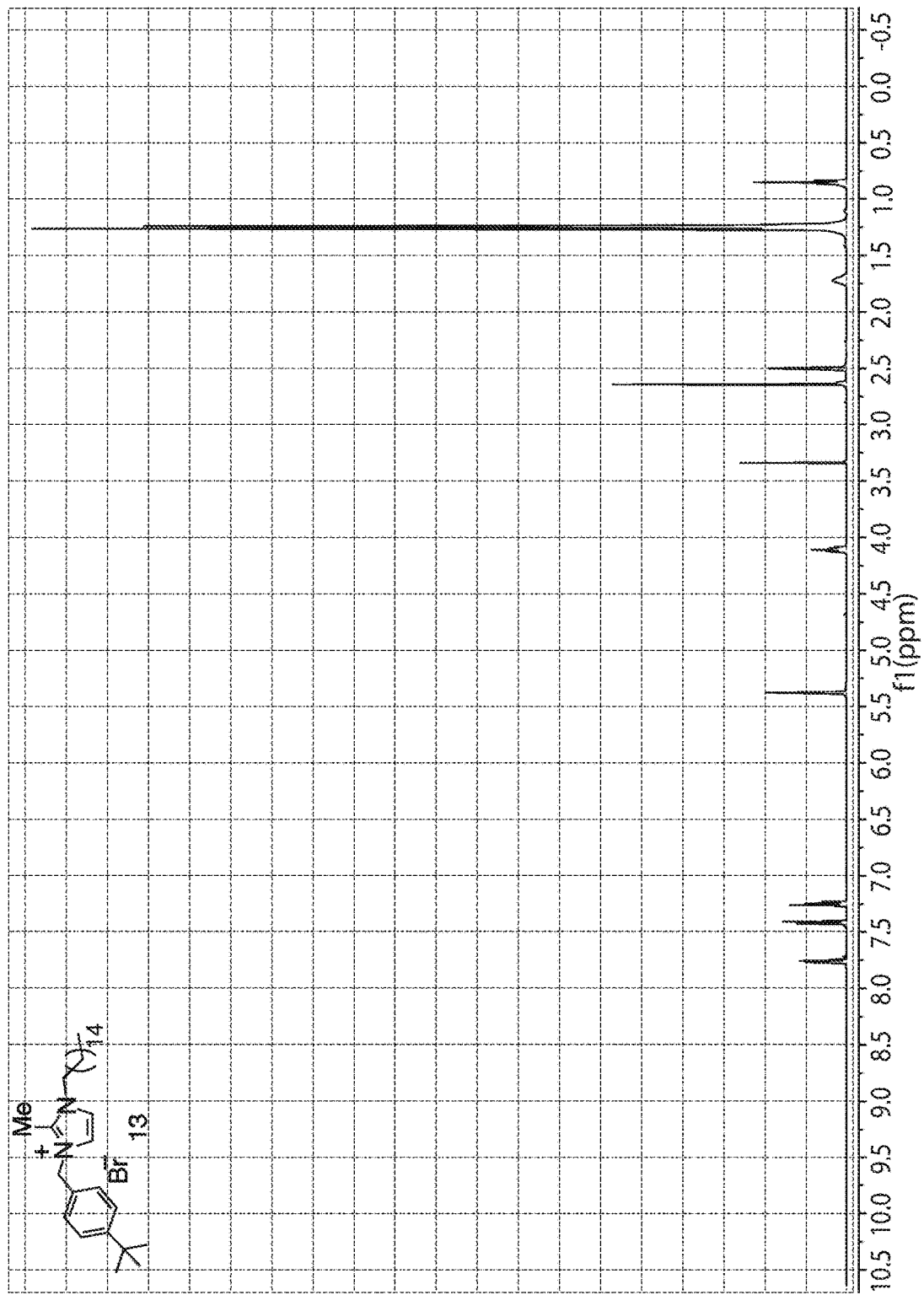
FIG. 37. NMR 21 for depicted compound 13.
Figure 38:
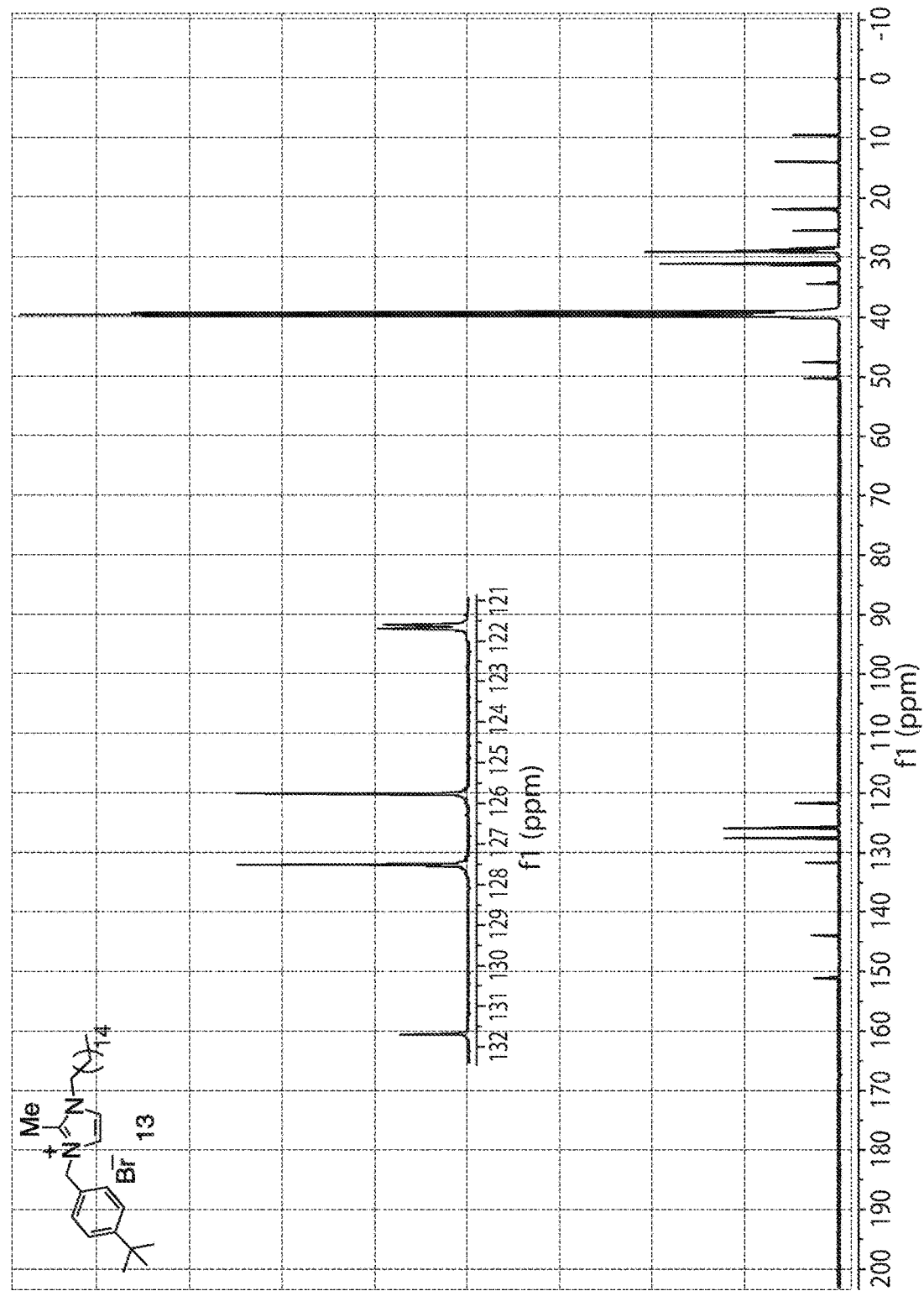
FIG. 38. NMR 22 for depicted compound 13.

Yield: 69% yield; 195 mg of 13 was isolated as a white solid. $^1$H NMR (400 MHz, $d_6$-DMSO): δ 7.77 (d, J=2.1 Hz, 1H), 7.75 (d, J=2.1 Hz, 1H), 7.42 (dt, J=8.4, 2.5, 2H), 7.25 (dt, J=8.3, 2.0 Hz, 2H), 5.38 (s, 2H), 4.10 (t, J=7.4 Hz, 2H), 2.63 (s, 3H), 1.76-1.66 (m, 2H), 1.26 (s, 9H), 1.26-1.18 (m, 26H), 0.85 (t, J=6.8 Hz, 3H). $^{13}$C NMR (100 MHz, $d_6$-DMSO): δ 151.0, 144.0, 131.7, 127.5, 125.7, 121.7, 121.6, 50.3, 47.6, 34.3, 31.3, 31.0, 29.1, 29.0, 29.0, 28.9, 28.9, 28.7, 28.5, 25.6, 22.1, 14.0, 9.5. Note: 23 of the 27 $^{13}$C NMR signals could be found, multiple signals overlap at 29 ppm. HRMS (ESI) m/z: calc. for $C_{31}H_{53}N_2[M^+]$: 453.4203, found: 453.4188. MP: 89-90° C. See FIGS. 37 and 38.

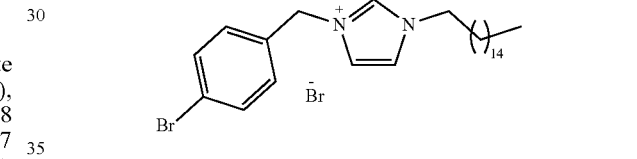

14

Figure 39:
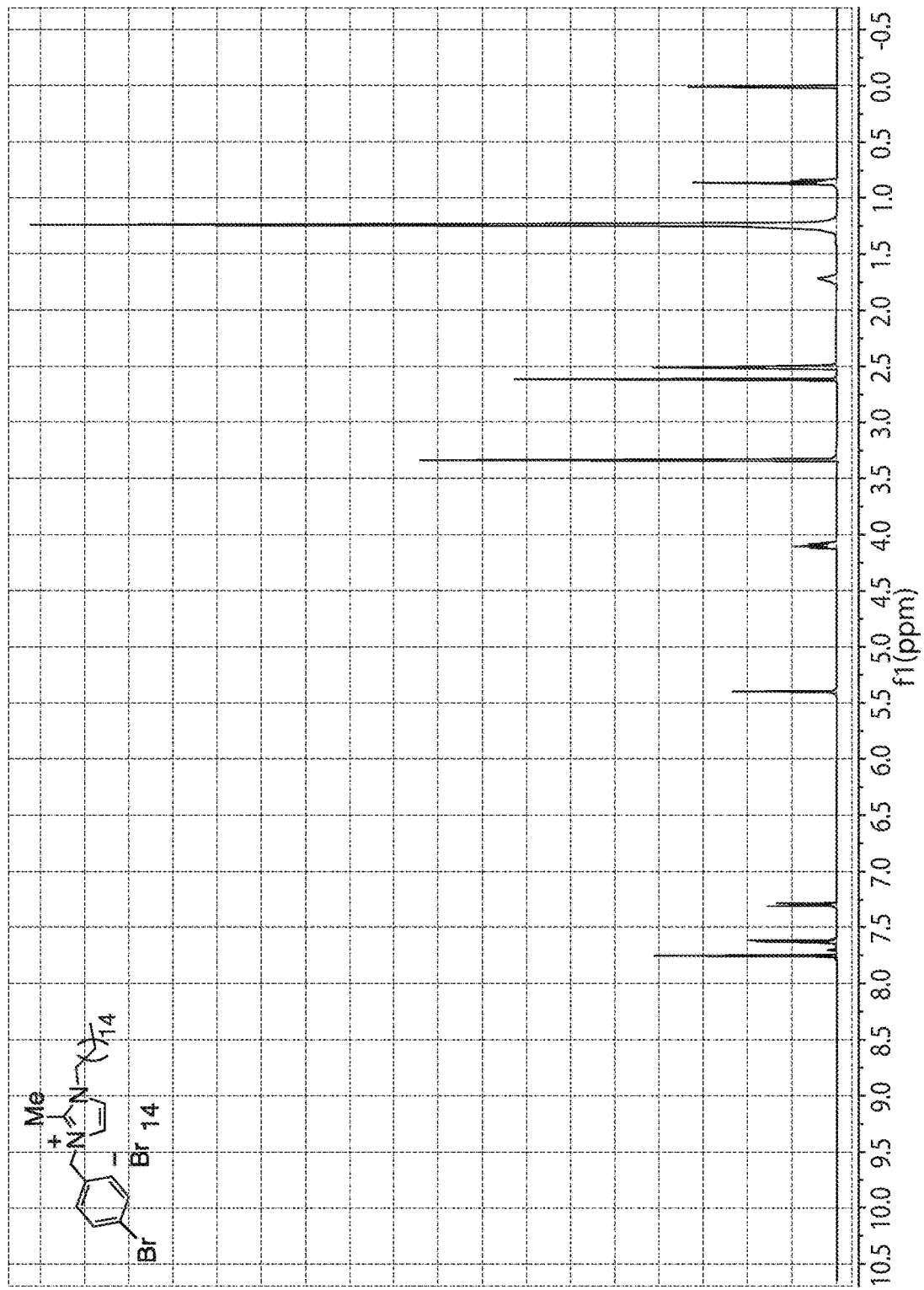
FIG. 39. NMR 23 for depicted compound 14.
Figure 40:
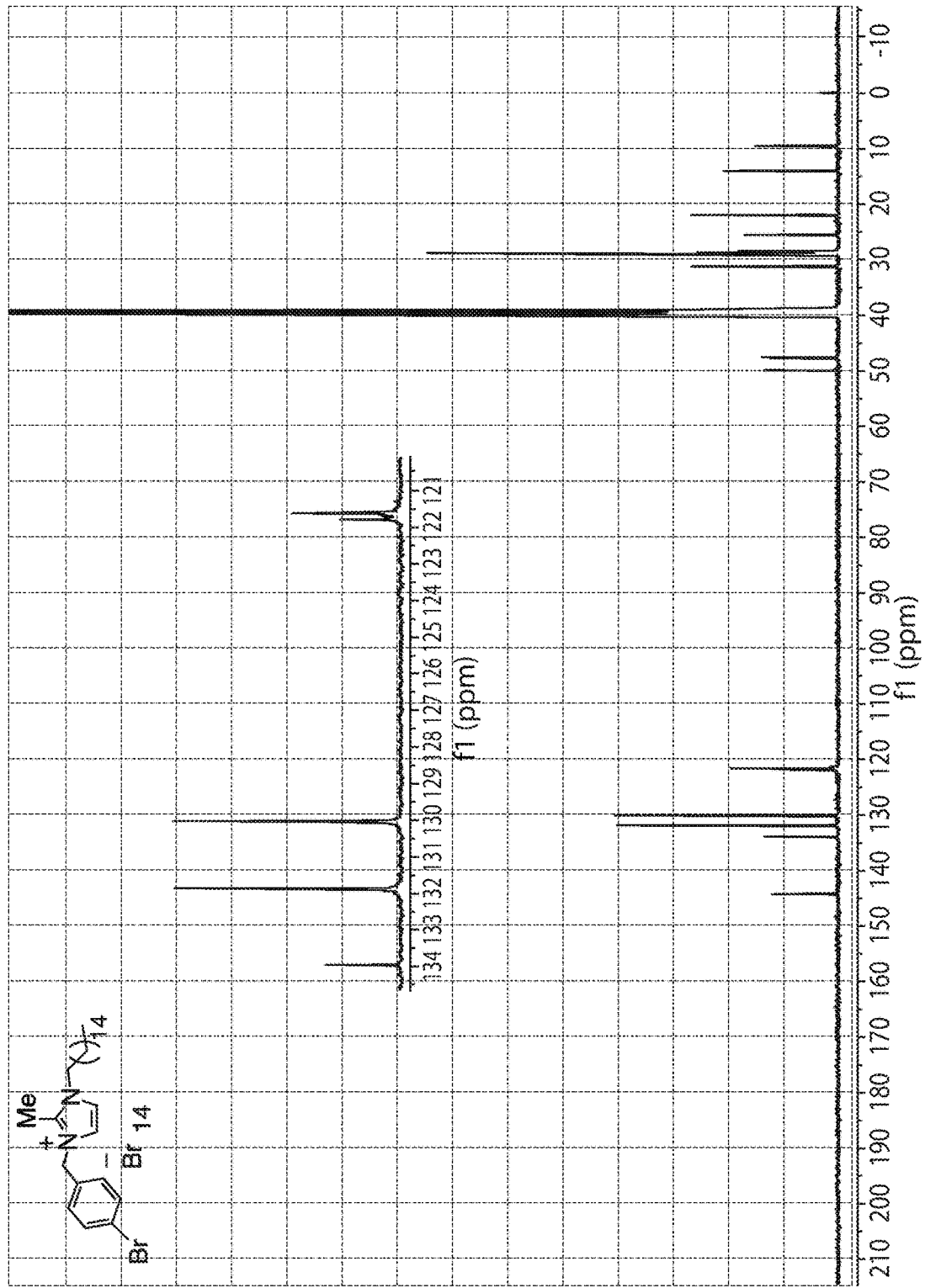
FIG. 40. NMR 24 for depicted compound 14.

Yield: 51% yield; 92 mg of 14 was isolated as a white solid. $^1$H NMR (400 MHz, $d_6$-DMSO): δ 7.73 (m, 2H), 7.62 (m, 2H), 7.29 (m, 2H), 5.39 (s, 2H), 4.09 (t, J=7.4 Hz, 2H), 2.61 (s, 3H), 1.71 (p, J=7.2 Hz, 2H), 1.33-1.16 (m, 26H), 0.85 (t, J=6.7 Hz, 3H). $^{13}$C NMR (100 MHz, $d_6$-DMSO): δ 144.2, 134.0, 131.9, 130.1, 121.8, 121.7, 121.6, 49.9, 47.7, 31.3, 29.1, 29.0, 28.9, 28.9, 28.9, 28.7, 28.5, 25.6, 22.1, 14.0, 9.5. Note: 21 of the 25 $^{13}$C NMR signals could be found, multiple signals overlap at 29 ppm. HRMS (ESI) m/z: calc. for $C_{27}H_{44}BrN_2$ [$M^+$]: 475.2682, found: 475.2690. MP: 66-67° C. See FIGS. 39 and 40.

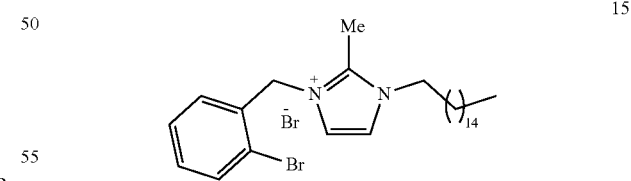

15

Figure 41:
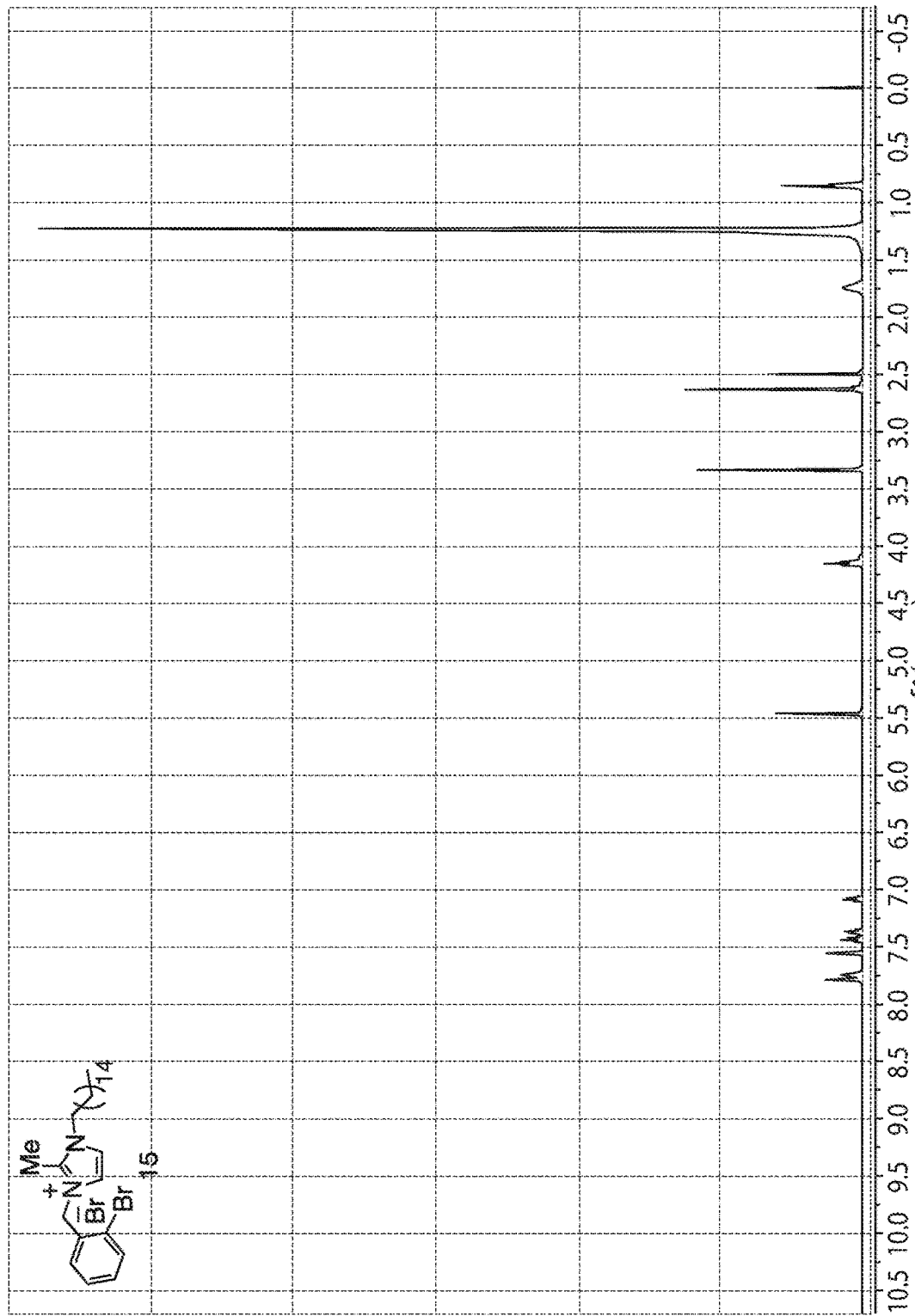
FIG. 41. NMR 25 for depicted compound 15.
Figure 42:
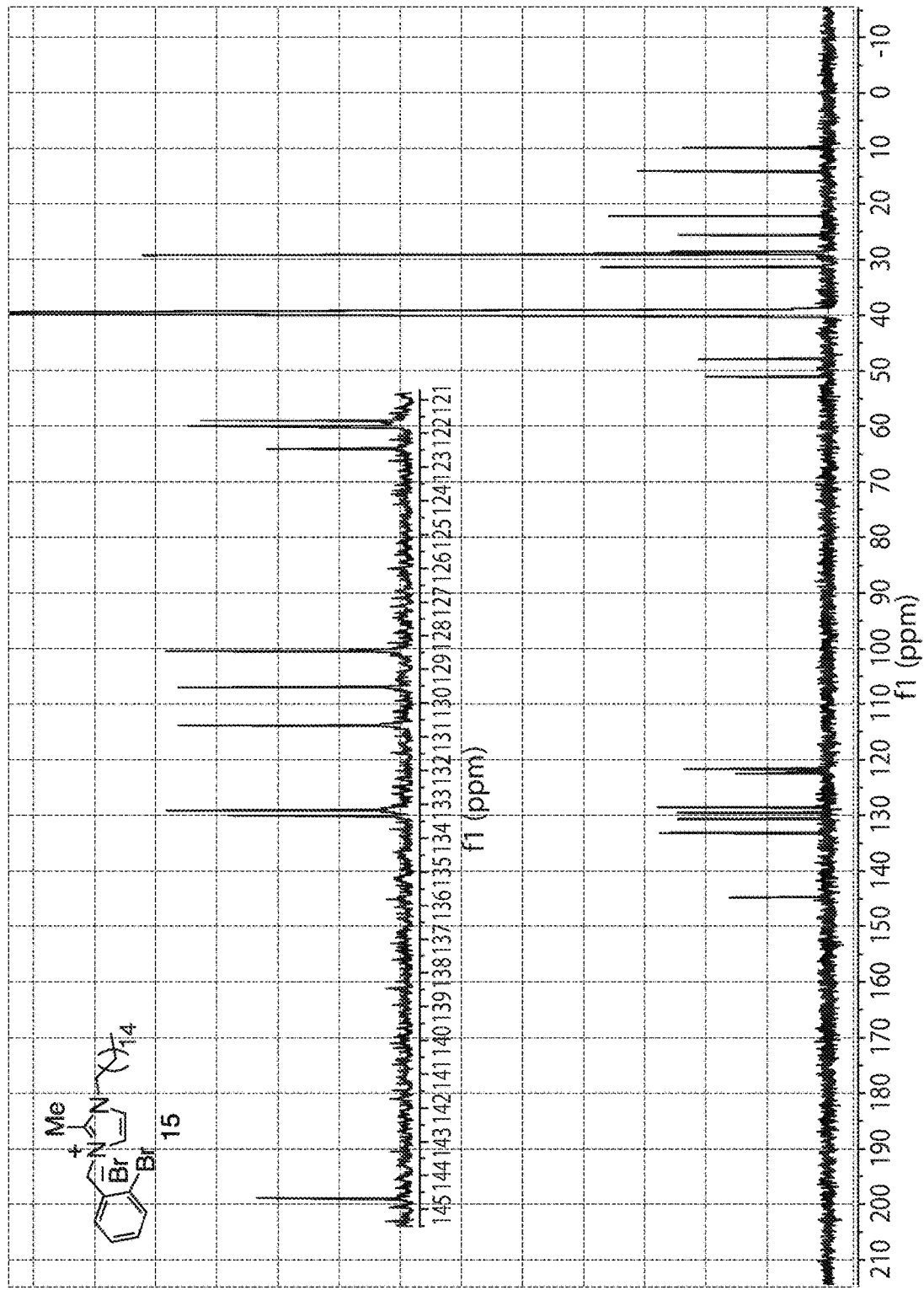
FIG. 42. NMR 26 for depicted compound 15.

Yield: 31% yield; 55 mg of 15 was isolated as a white solid. $^1$H NMR (400 MHz, $d_6$-DMSO): δ 7.78 (d, J=2.2 Hz, 1H), 7.74 (dd, J=7.9, 1.3 Hz, 1H), 7.56 (d, J=2.1 Hz, 1H), 7.44 (m, 1H), 7.36 (td, J=7.7, 1.7 Hz, 1H), 7.08 (dd, J=7.6, 1.7 Hz, 1H), 5.46 (s, 2H), 4.15 (t, J=7.3 Hz, 2H), 2.63 (s, 3H), 1.74 (p, J=7.4 Hz, 2H), 1.44-1.14 (m, 26H), 0.85 (t, J=6.5 Hz, 3H). $^{13}$C NMR (100 MHz, $d_6$-DMSO): δ 144.7, 133.3, 133.2, 130.7, 129.5, 128.5, 122.5, 121.8, 121.6, 51.0, 47.7, 31.3, 29.0, 28.9, 28.9, 28.7, 28.5, 25.6, 22.1, 14.0, 9.6. Note: 22 of the 27 $^{13}$C NMR signals could be found, multiple signals overlap at 29 ppm. HRMS (ESI) m/z: calc. for $C_{27}H_{44}BrN_2$ [M+]: 475.2682, found: 475.2705. MP: 64-65° C. See FIGS. 41 and 42.

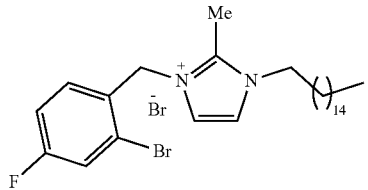

16

Figure 43:
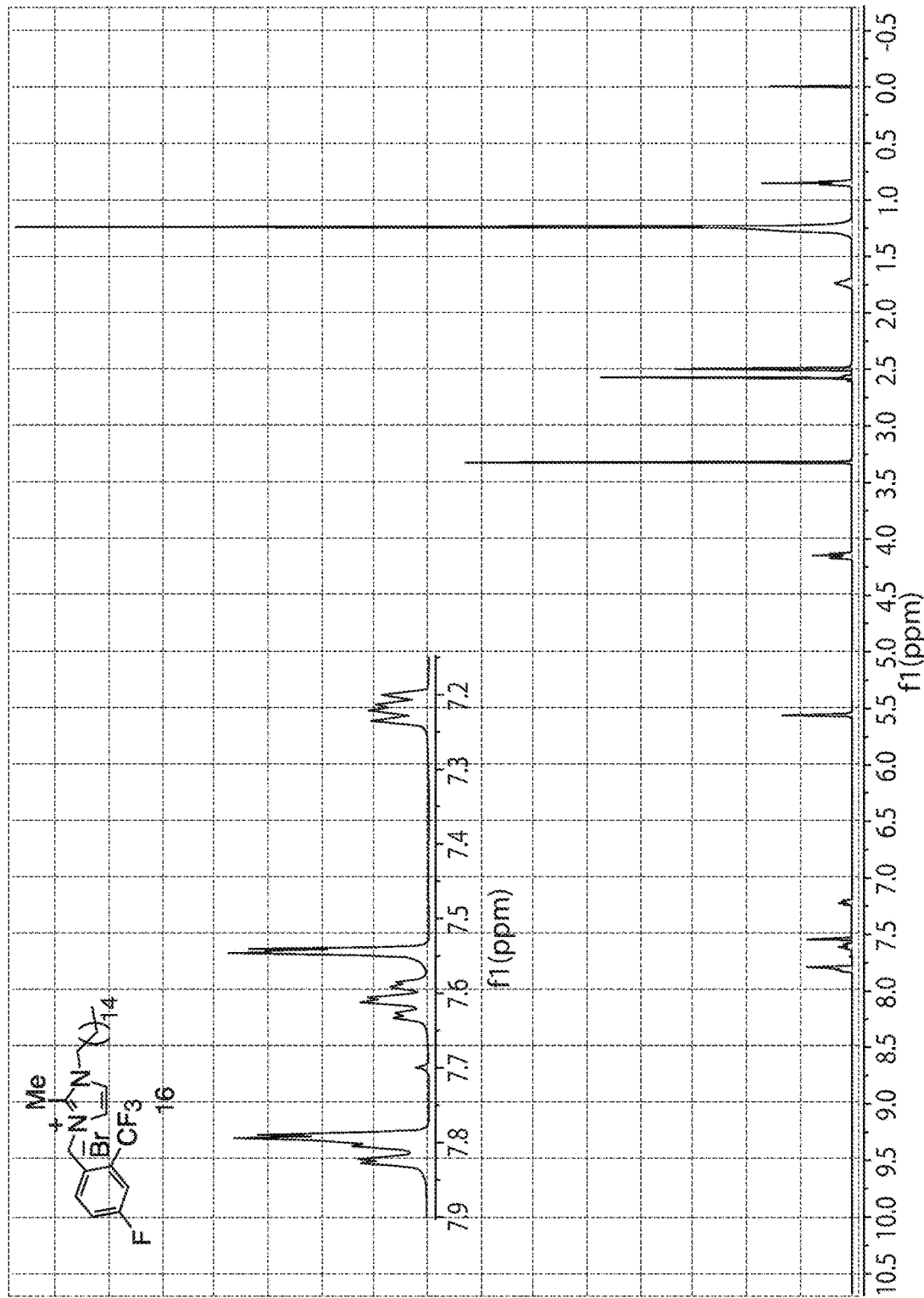
FIG. 43. NMR 27 for depicted compound 16.
Figure 44:
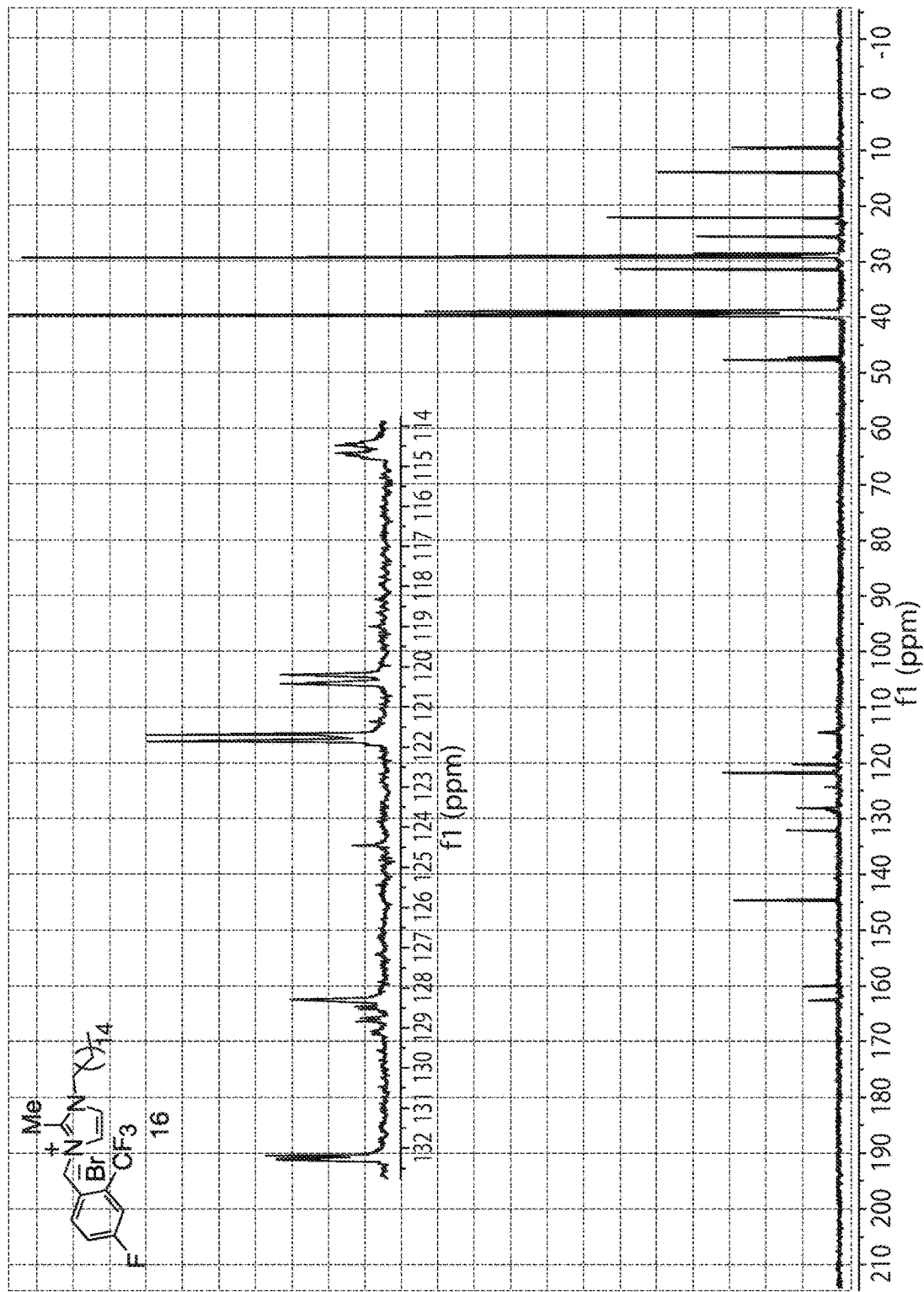
FIG. 44. NMR 28 for depicted compound 16.

Yield: 76% yield; 210 mg of 16 was isolated as a white solid. $^1$H NMR (400 MHz, $d_6$-DMSO): δ 7.82 (dd, J=4.2, 2.7 Hz, 1H), 7.79 (d, J=2.1 Hz, 1H), 7.61 (td, J=8.5, 2.8 Hz, 1H), 7.54 (d, J=2.1 Hz, 1H), 7.22 (dd, J=8.8, 5.3 Hz, 1H), 5.56 (s, 2H), 4.15 (t, J=7.3 Hz, 2H), 2.57 (s, 3H), 1.74 (p, J=7.3 Hz, 2H), 1.36-1.15 (m, 26H), 0.85 (t, J=6.8 Hz, 3H). $^{13}$C NMR (100 MHz, $d_6$-DMSO): δ 161.5 (d, J=248.1 Hz), 144.8, 132.3 (d, J=8.5 Hz), 128.8 (td, J=31.7, 7.9 Hz), 128.3, 124.5 (d, J=2.5 Hz), 121.8 (d, J=16.0 Hz), 120.3 (d, J=21.0 Hz), 120.2 (q, J=236.8 Hz), 114.6 (dq, J=25.7, 5.8 Hz), 47.8, 47.3, 31.3, 29.1, 29.1, 29.0, 28.9, 28.7, 28.5, 25.6, 22.1, 14.0, 9.6. Note: 23 of the 28 $^{13}$C NMR signals could be found, multiple signals overlap at 29 ppm. HRMS (ESI) m/z: calc. for $C_{28}H_{43}F_4N_2$ [M+]: 483.3357, found: 483.3355. MP: 49-50° C. See FIGS. 43 and 44.

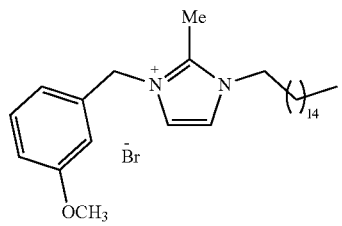

17

Figure 45:
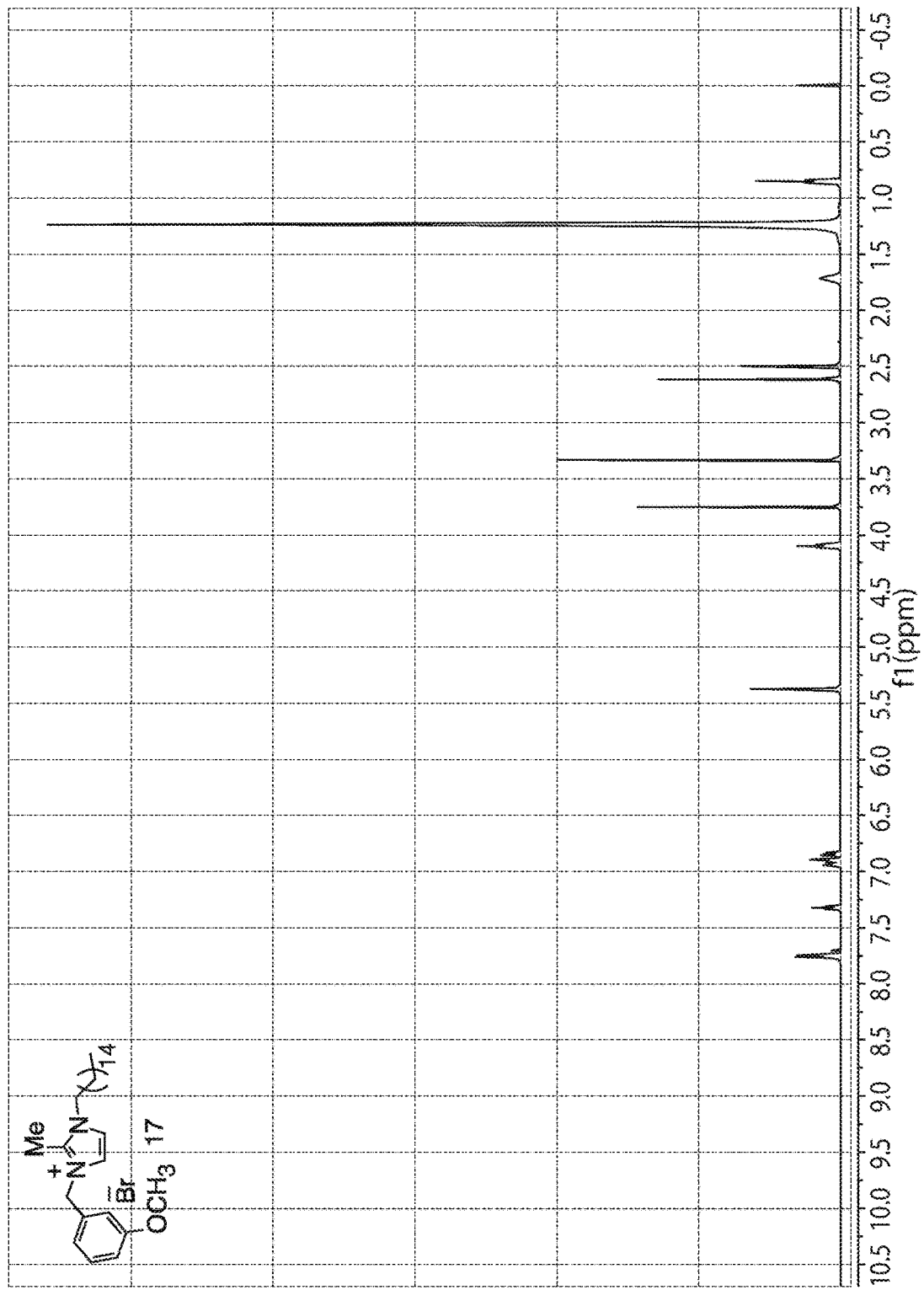
FIG. 45. NMR 29 for depicted compound 17.
Figure 46:
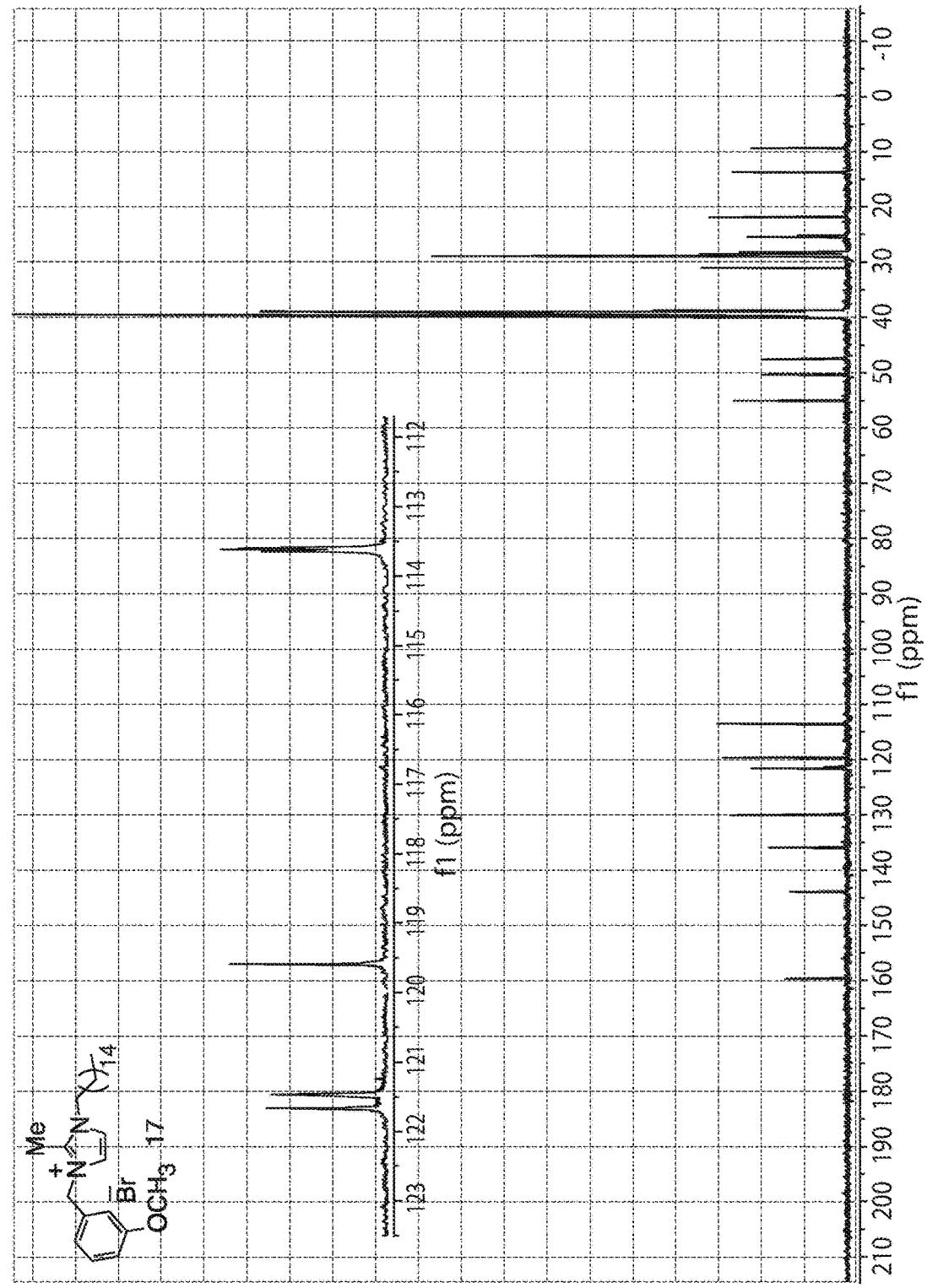
FIG. 46. NMR 30 for depicted compound 17.

Yield: 36% yield; 60 mg of 17 was isolated as a white solid. $^1$H NMR (400 MHz, $d_6$-DMSO): δ 7.79-7.73 (m, 2H), 7.33 (t, J=7.9 Hz, 1H), 6.94 (dd, J=8.2, 2.5 Hz, 1H), 6.90 (m, 1H), 6.85 (d, J=7.6 Hz, 1H), 5.37 (s, 2H), 4.10 (t, J=7.4 Hz, 2H), 3.75 (s, 3H), 2.62 (s, 3H), 1.72 (p, J=7.4 Hz, 2H), 1.34-1.14 (m, 26H), 0.85 (t, J=6.6 Hz, 3H). $^{13}$C NMR (100 MHz, $d_6$-DMSO): δ 159.6, 144.0, 135.9, 130.1, 121.7, 121.5, 119.6, 113.6, 113.6, 55.1, 50.5, 47.6, 31.2, 29.0, 28.9, 28.9, 28.8, 28.8, 28.6, 28.4, 25.6, 22.0, 13.9, 9.5. Note: 24 of the 28 $^{13}$C NMR signals could be found, multiple signals overlap at 29 ppm. HRMS (ESI) m/z: calc. for $C_{28}H_{47}N_2O$ [M+]: 427.3683, found: 427.3683. MP: 61-62° C. See FIGS. 45 and 46.

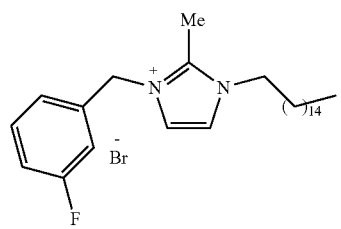

18

Figure 47:
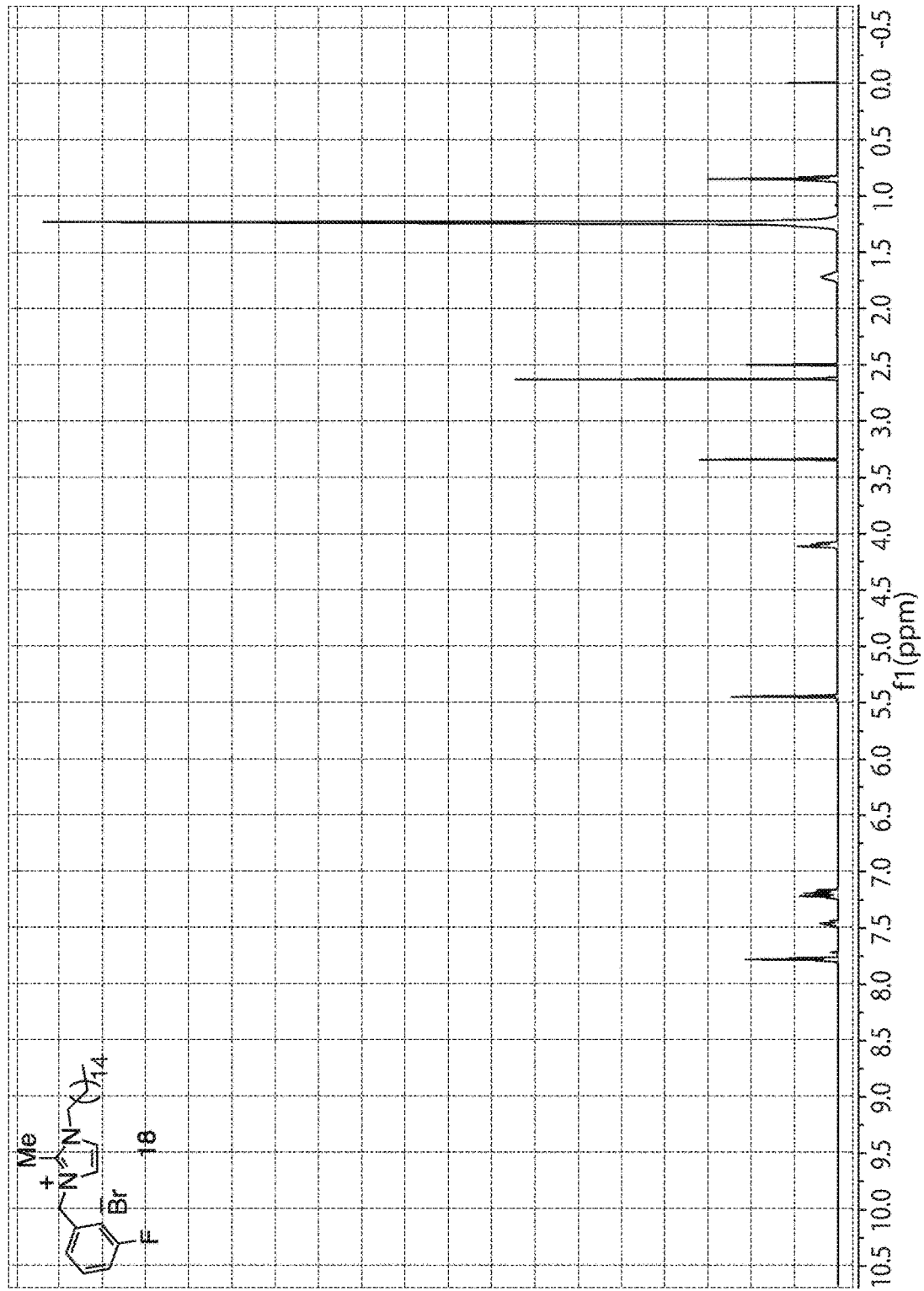
FIG. 47. NMR 31 for depicted compound 18.
Figure 48:
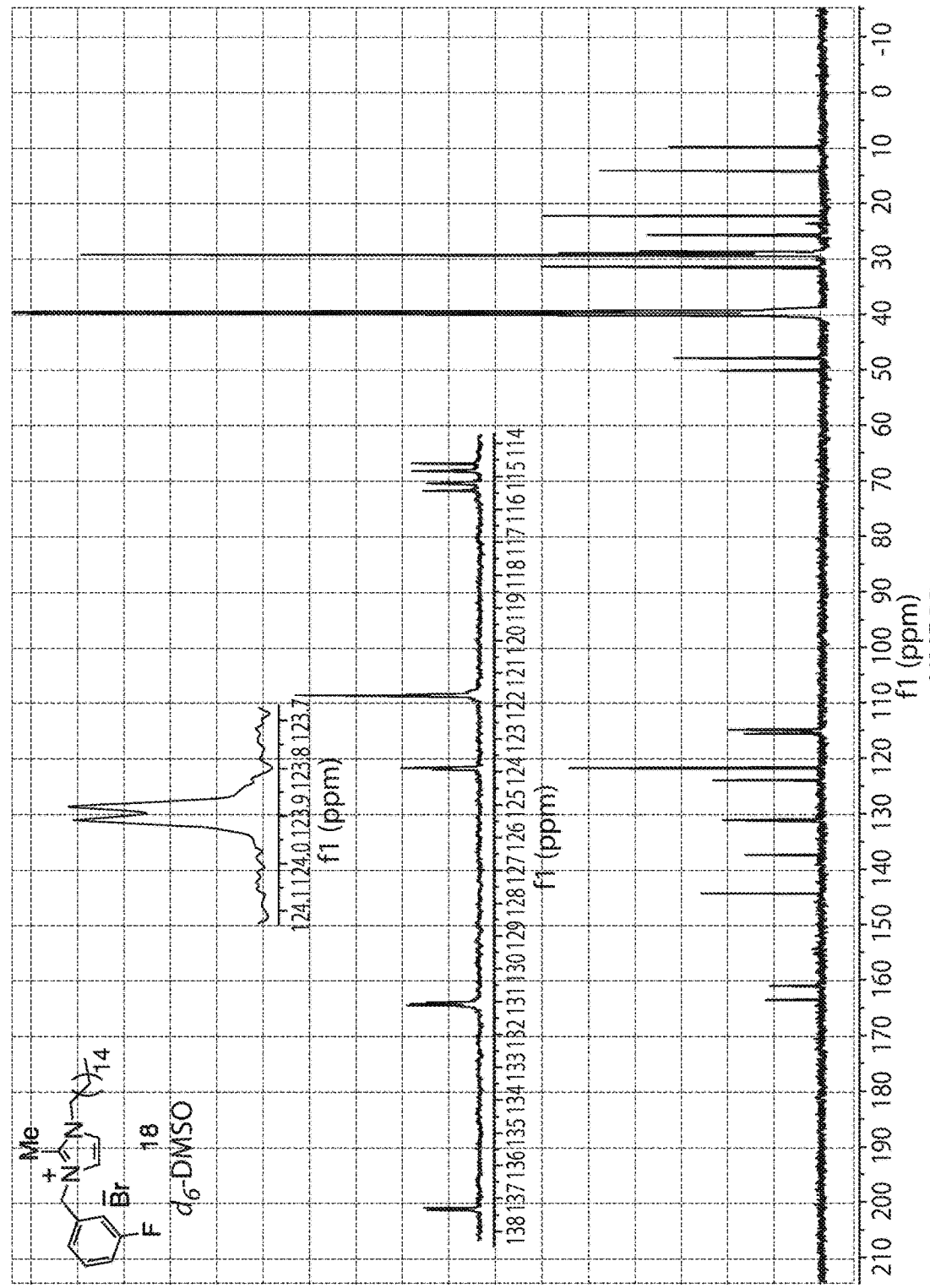
FIG. 48. NMR 32 for depicted compound 18.
Figure 49:
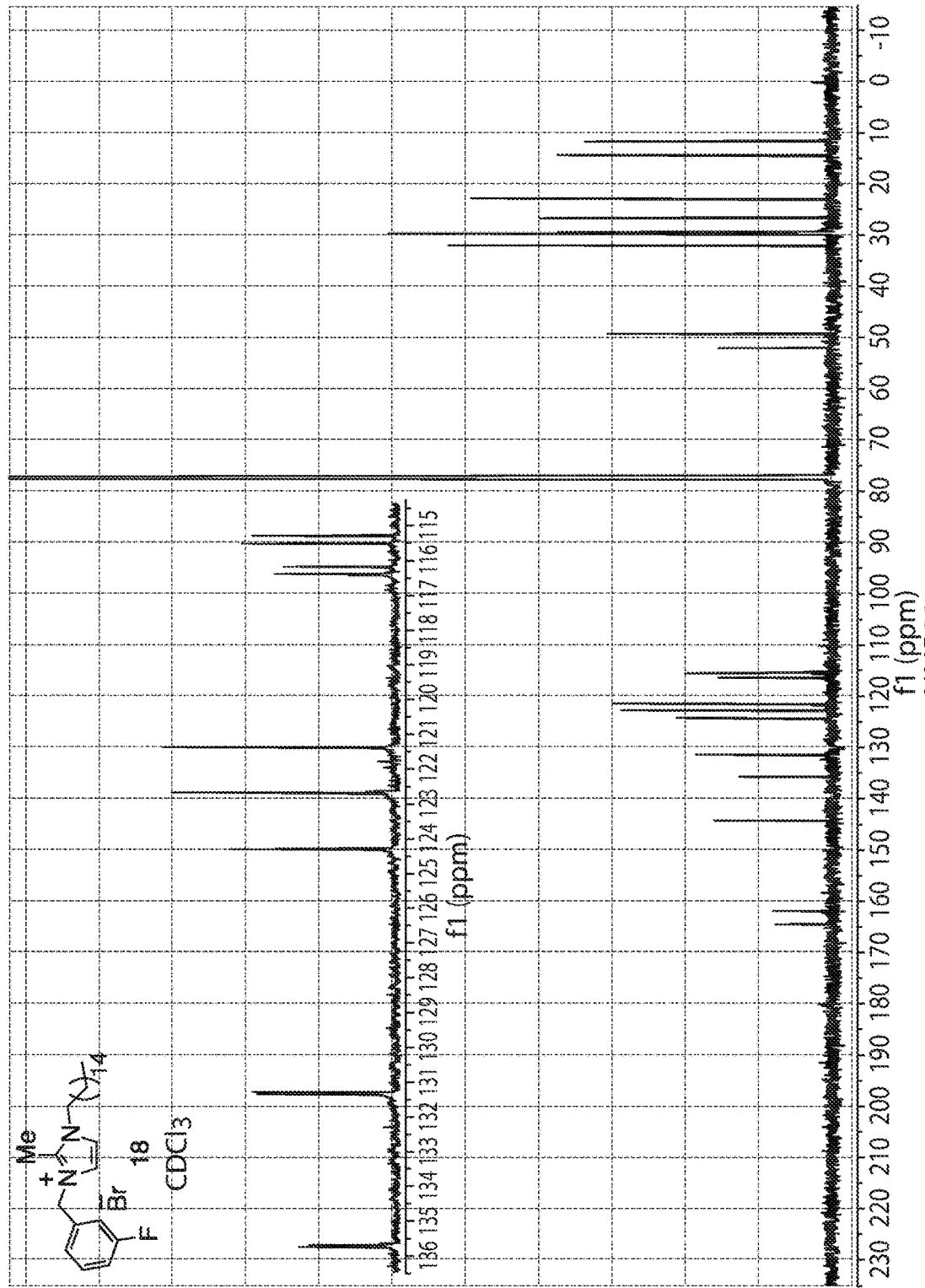
FIG. 49. NMR 33 for depicted compound 18.

Yield: 59% yield; 190 mg of 18 was isolated as a white solid. $^1$H NMR (400 MHz, $d_6$-DMSO): δ 7.78 (d, J=2.1 Hz, 1H), 7.77 (d, J=2.1 Hz, 1H), 7.50-7.11 (m, 4H), 5.44 (s, 2H), 4.10 (t, J=7.4 Hz, 2H), 2.63 (s, 3H), 1.72 (p, J=7.5 Hz, 2H), 1.32-1.17 (m, 26H), 0.83 (t, J=6.7 Hz, 3H). $^{13}$C NMR (100 MHz, $d_6$-DMSO): δ 162.3 (d, J=244.5 Hz), 144.3, 137.3 (d, J=7.6 Hz), 131.0 (d, J=8.3 Hz), 123.9 (d, J=2.9 Hz), 121.7, 115.4 (d, J=20.8 Hz), 114.8 (d, J=22.3 Hz), 49.9, 47.7, 31.3, 29.1, 29.0, 29.0, 28.9, 28.7, 28.5, 25.7, 22.1, 14.0, 9.6. Note: 21 of the 27 $^{13}$C NMR signals could be found, one aromatic signal missing and multiple signals overlap at 29 ppm. All $^{13}$C NMR signals were found in CDCl$_3$, which is reported below. $^{13}$C NMR (100 MHz, CDCl$_3$): δ 163.1 (d, J=248.5 Hz), 144.1, 135.7 (d, J=7.4 Hz), 131.3 (d, J=8.3 Hz), 124.3 (d, J=3.1 Hz), 122.7, 121.4, 116.3 (d, J=20.9 Hz), 115.4 (d, J=22.3 Hz), 52.0 (d, J=1.9 Hz), 49.2, 32.1, 30.0, 29.9, 29.9, 29.9, 29.8, 29.8, 29.8, 29.7, 29.5, 29.5, 29.2, 26.6, 22.9, 14.3, 11.6. HRMS (ESI) m/z: calc. for $C_{27}H_{44}FN_2$ [M+]: 415.3483, found: 415.3492. MP: 64-65° C. See FIGS. 47, 48, and 49.

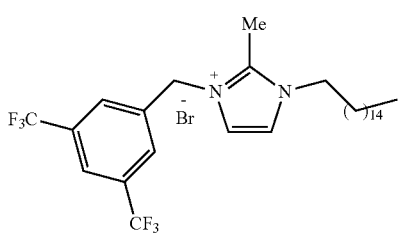

19

Figure 50:
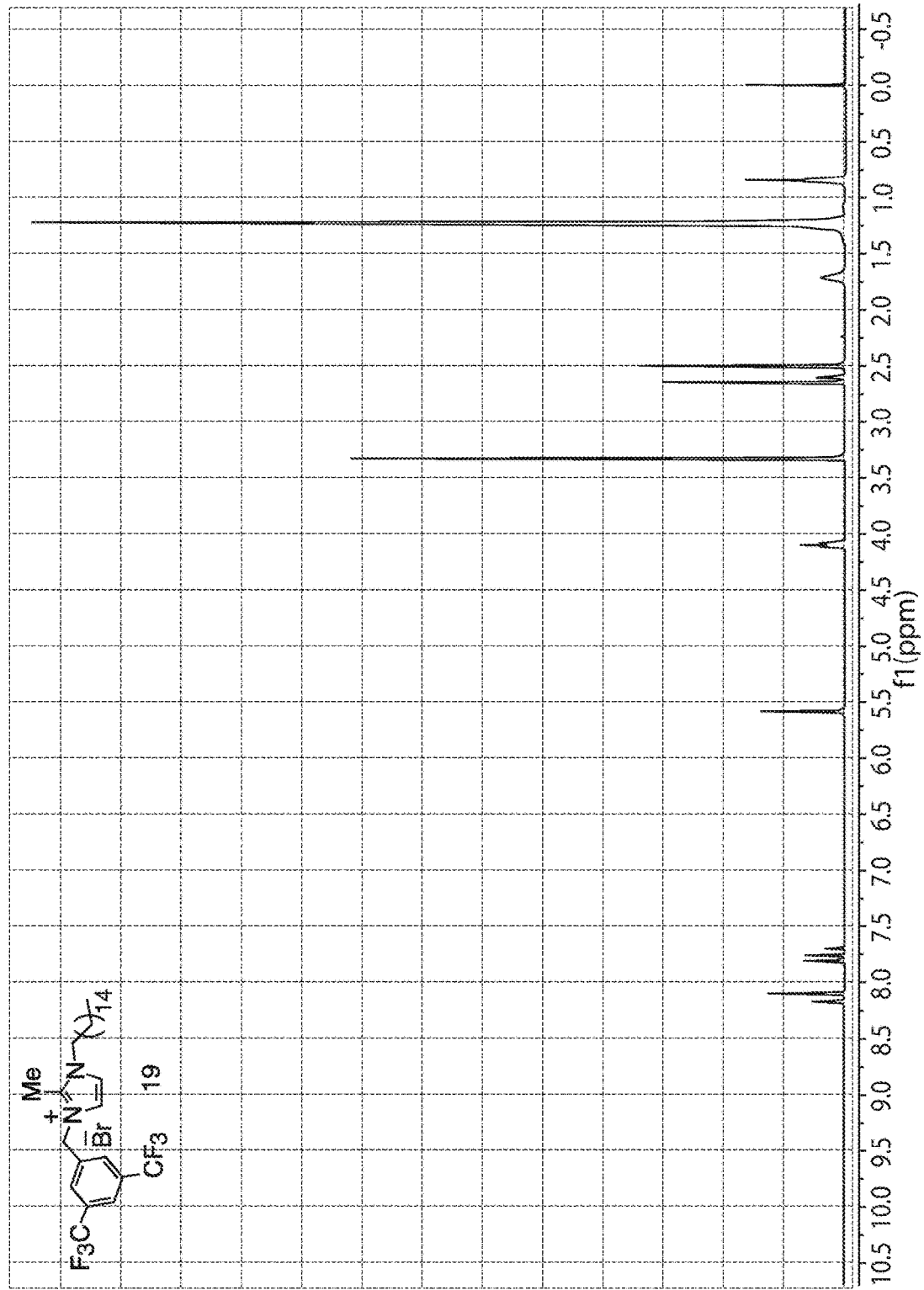
FIG. 50. NMR 34 for depicted compound 19.
Figure 51:
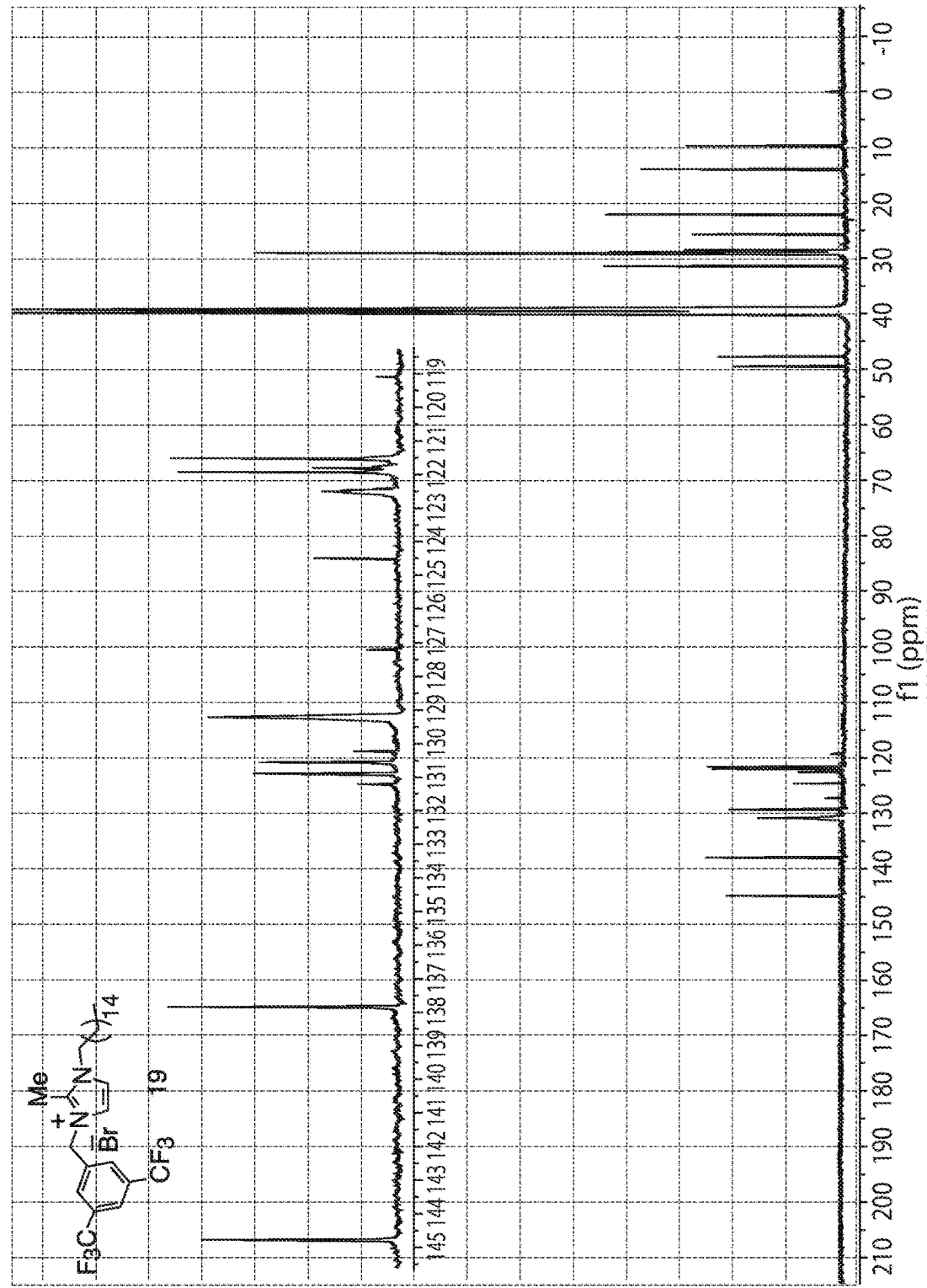
FIG. 51. NMR 35 for depicted compound 19.

Yield: 37% yield; 75 mg of 19 was isolated as a white solid. $^1$H NMR (400 MHz, $d_6$-DMSO): δ 8.17 (s, 1H), 8.10 (s, 2H), 7.81 (d, J=2.1 Hz, 1H), 7.76 (d, J=2.1 Hz, 1H), 5.58 (s, 2H), 4.10 (t, J=7.4 Hz, 2H), 2.65 (s, 3H), 1.72 (p, J=7.3 Hz, 2H), 1.32-1.18 (m, 26H), 0.85 (t, J=6.6 Hz, 3H). $^{13}$C NMR (100 MHz, $d_6$-DMSO): δ 144.8, 137.8, 130.7 (q, J=33.1 Hz), 129.2 (br m), 123.1 (q, J=272.9 Hz), 122.5 (septet, J=3.7 Hz), 121.9, 121.5, 49.4, 47.7, 31.3, 29.0, 29.0, 28.9, 28.9, 28.9, 28.7, 28.5, 25.6, 22.1, 14.0, 9.7. Note: 22 of the 26 $^{13}$C NMR signals could be found, multiple signals overlap at 29 ppm. HRMS (ESI) m/z: calc. for $C_{29}H_{43}F_6N_2$ [M+]: 533.3324, found: 533.3307. MP: 54-55° C. See FIGS. 50 and 51.

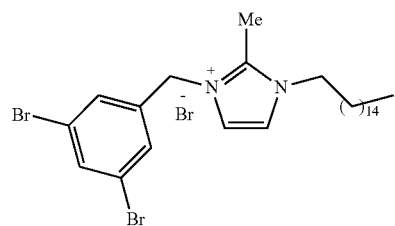

20

Figure 52:
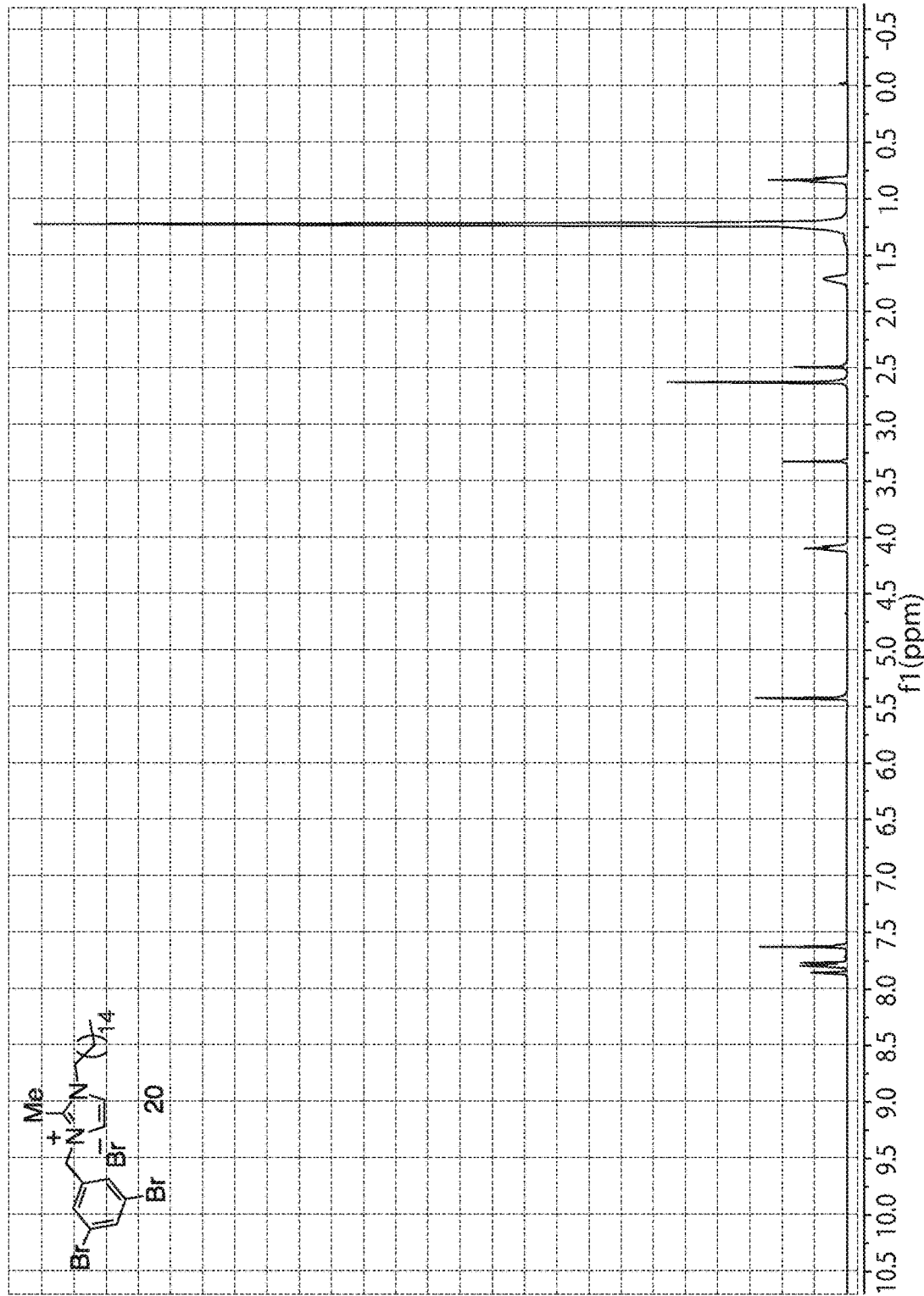
FIG. 52. NMR 36 for depicted compound 20.
Figure 53:
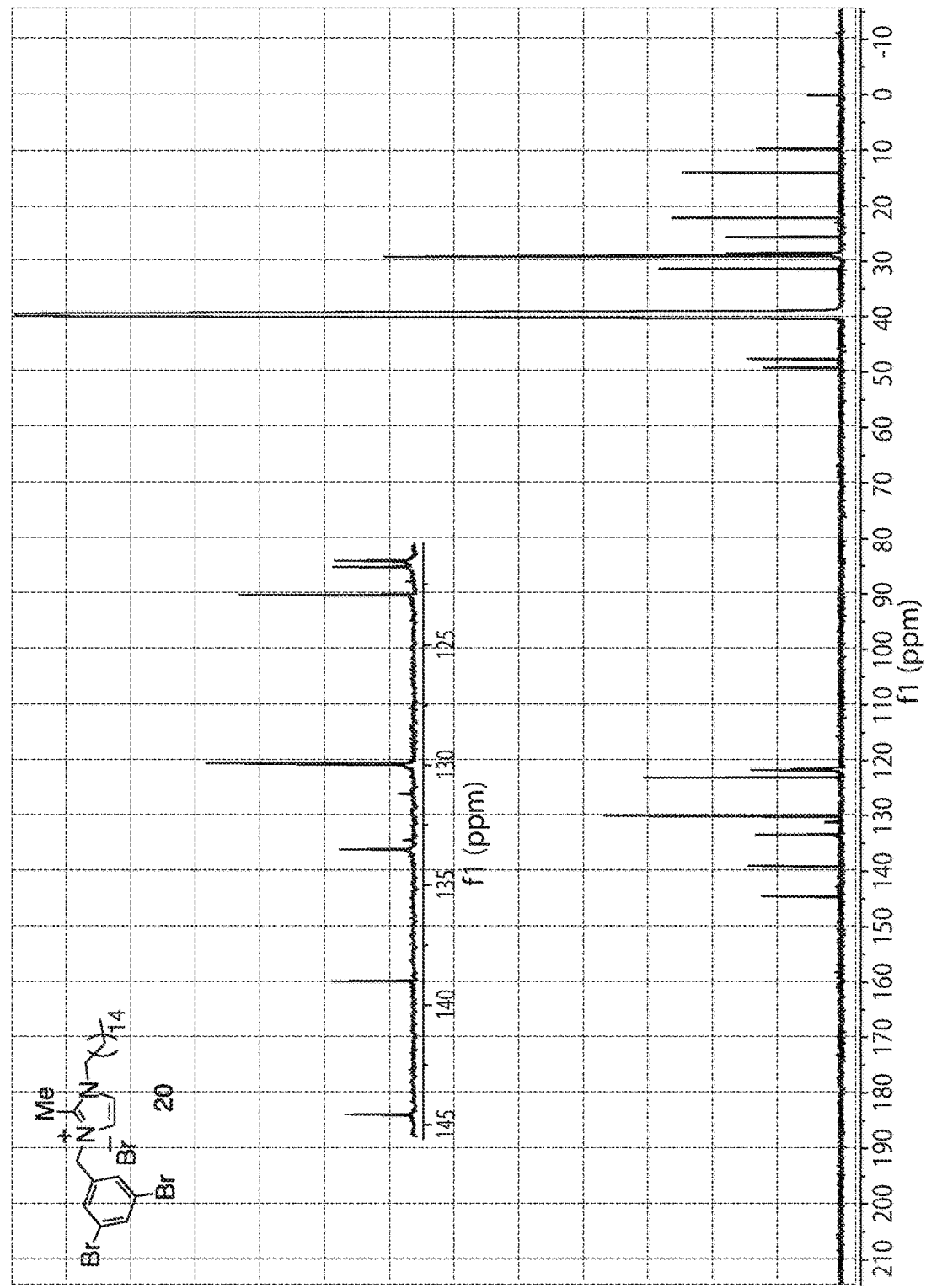
FIG. 53. NMR 37 for depicted compound 20.

Yield: 42% yield; 130 mg of 20 was isolated as a white solid. $^1$H NMR (400 MHz, $d_6$-DMSO): δ 7.86 (m, 1H), 7.80 (m, 1H), 7.77 (m, 1H), 7.63 (m, 2H), 5.43 (s, 2H), 4.10 (t, J=7.4 Hz, 2H), 2.64 (s, 3H), 1.72 (p, J=7.3 Hz, 2H), 1.47-1.09 (m, 26H), 0.85 (t, J=6.5 Hz, 3H). $^{13}$C NMR (100 MHz, $d_6$-DMSO): δ 144.6, 139.0, 133.5, 130.0, 122.9, 121.8, 121.5, 49.1, 47.7, 31.3, 29.1, 29.0, 29.0, 28.9, 28.9, 28.9, 28.7, 28.5, 25.6, 22.1, 14.0, 9.6. Note: 22 of the 25 $^{13}$C NMR signals could be found, multiple signals overlap at 29 ppm. HRMS (ESI) m/z: calc. for $C_{27}H_{43}Br_2N_2$ [M$^+$]: 553.1788, found: 553.1796. MP: 73-74° C. See FIGS. 52 and 53.

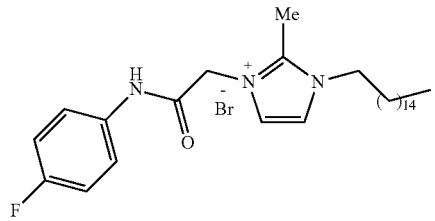

21

Figure 54:
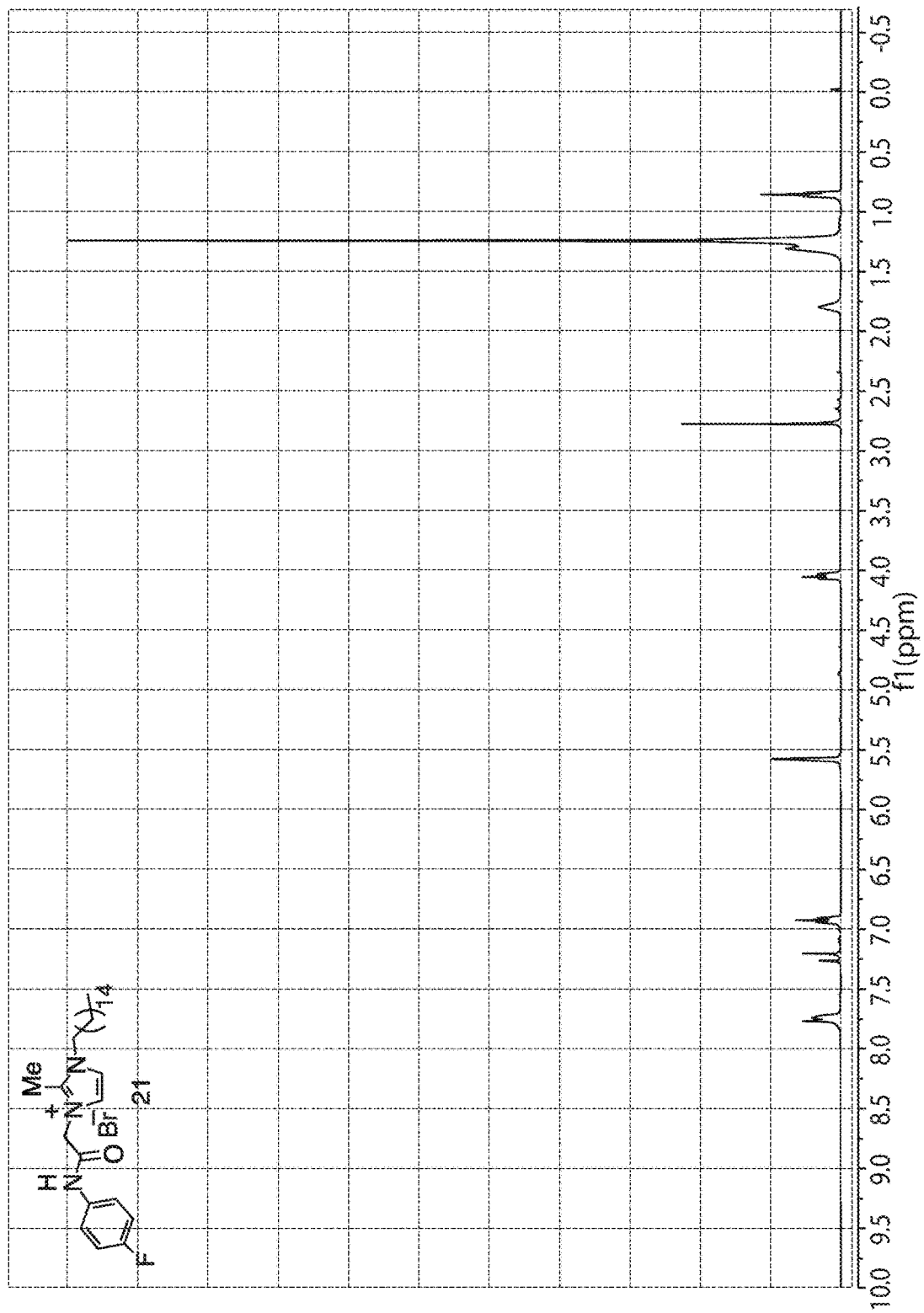
FIG. 54. NMR 38 for depicted compound 21.
Figure 55:
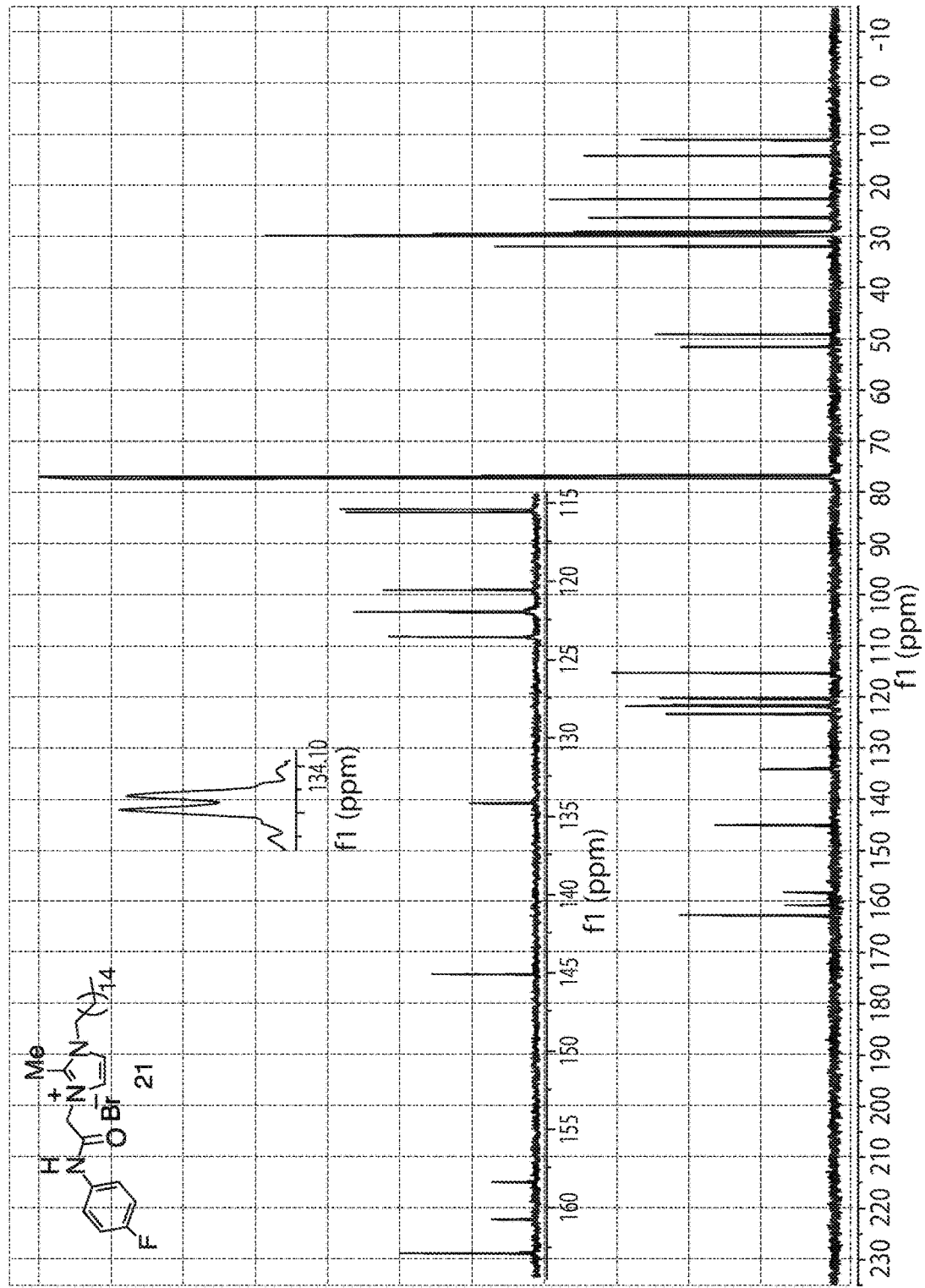
FIG. 55. NMR 39 for depicted compound 21.

Yield: 69% yield; 195 mg of 21 was isolated as a white solid. $^1$H NMR (400 MHz, CDCl$_3$): δ 7.77 (s, 1H), 7.77-7.70 (m, 2H), 7.20 (d, J=2.1 Hz, 1H), 6.97-6.87 (m, 2H), 5.57 (s, 2H), 4.05 (t, J=7.5 Hz, 2H), 2.77 (s, 3H), 1.80 (p, J=7.3 Hz, 2H), 1.40-1.17 (m, 26H), 0.86 (t, J=6.7 Hz, 3H). $^{13}$C NMR (100 MHz, CDCl$_3$): δ 162.9, 159.6 (d, J=243.5 Hz), 145.1, 134.2 (d, J=2.9 Hz), 123.5, 121.9 (d, J=7.8 Hz), 120.5, 115.5 (d, J=22.4 Hz), 51.8, 49.2, 32.1, 29.9, 29.9, 29.8, 29.8, 29.8, 29.7, 29.6, 29.5, 29.5, 29.1, 26.5, 22.8, 14.3, 11.2. Note: 25 of the 26 $^{13}$C NMR signals could be found, likely due to signal overlap at 29 ppm. HRMS (ESI) m/z: calc. for $C_{28}H_{45}FN_3O$ [M$^+$]: 458.3541, found: 458.3562. MP: 69-70° C. See FIGS. 54 and 55.

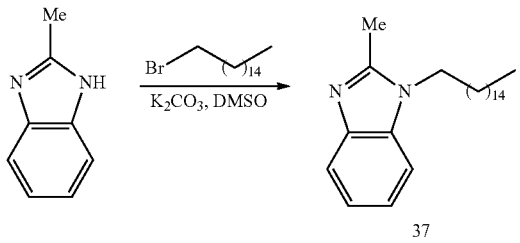

37

Synthesis of 37

1-Bromohexadecane (0.50 mL, 1.65 mmol) was added via syringe to a stirring solution of 2-methyl-1H-benzimidazole (1.08 g, 8.20 mmol) and potassium carbonate (230 mg, 1.65 mmol) in 10 mL anhydrous dimethyl sulfoxide (DMSO). The resulting reaction mixture was heated to 110° C. and allowed to stir for sixteen hours. After this time, the reaction mixture was transferred to a separatory funnel containing ethyl acetate (100 mL). The crude product was washed using water (3×30 mL), then brine (2×30 mL) before the organic layer was collected and dried with anhydrous sodium sulfate. The dried organic layer was then filtered and concentrated in vacuo to give crude product, which was purified via flash column chromatography using 1:1 hexanes:ethyl acetate to elute pure 37 as a clear oil which turned white semisolid upon standing (330 mg, 57%). Note: 37 is a known compound (CAS No. 405152-04-7). $^1$H NMR spectra match those previously reported.[4] We found the melting point for 37 to be 44-45° C.

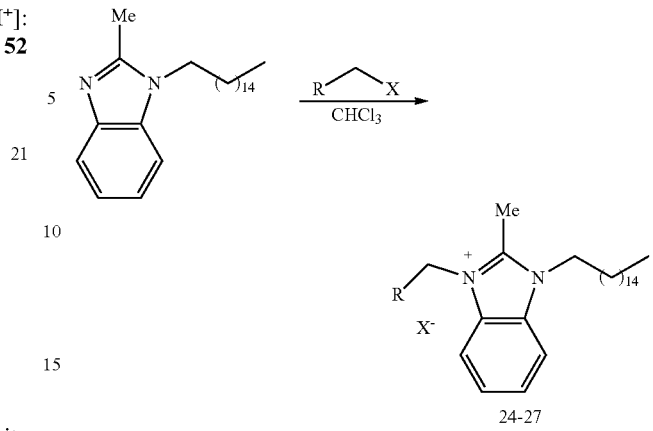

24-27

General Procedure for Alkylation of 1-Hexadecyl-2-Methyl-1H-Benzimidazole to Afford 24-27:

Benzyl bromide (42 μL, 0.35 mmol) was added to a stirring solution of 1-hexadecyl-2-methyl-1H-benzimidazole (105 mg, 0.46 mmol) in 5 mL anhydrous chloroform in a glass tube at room temperature. The tube was then sealed and the reaction was heated to 90° C. and allowed to stir for 24 hours. After this time, the reaction mixture was allowed to cool to room temperature and chloroform was evaporated in vacuo. The crude product was then stirred in anhydrous ether under argon for 5 hours and resulting white precipitate was filtered in an argon environment. The resulting precipitate was washed with anhydrous ether and dried under vacuum to obtain pure 25 as a white solid (82 mg, 56%).

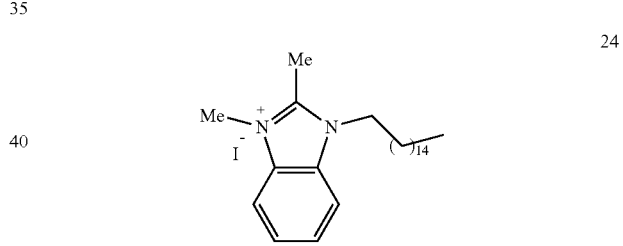

24

Figure 56:
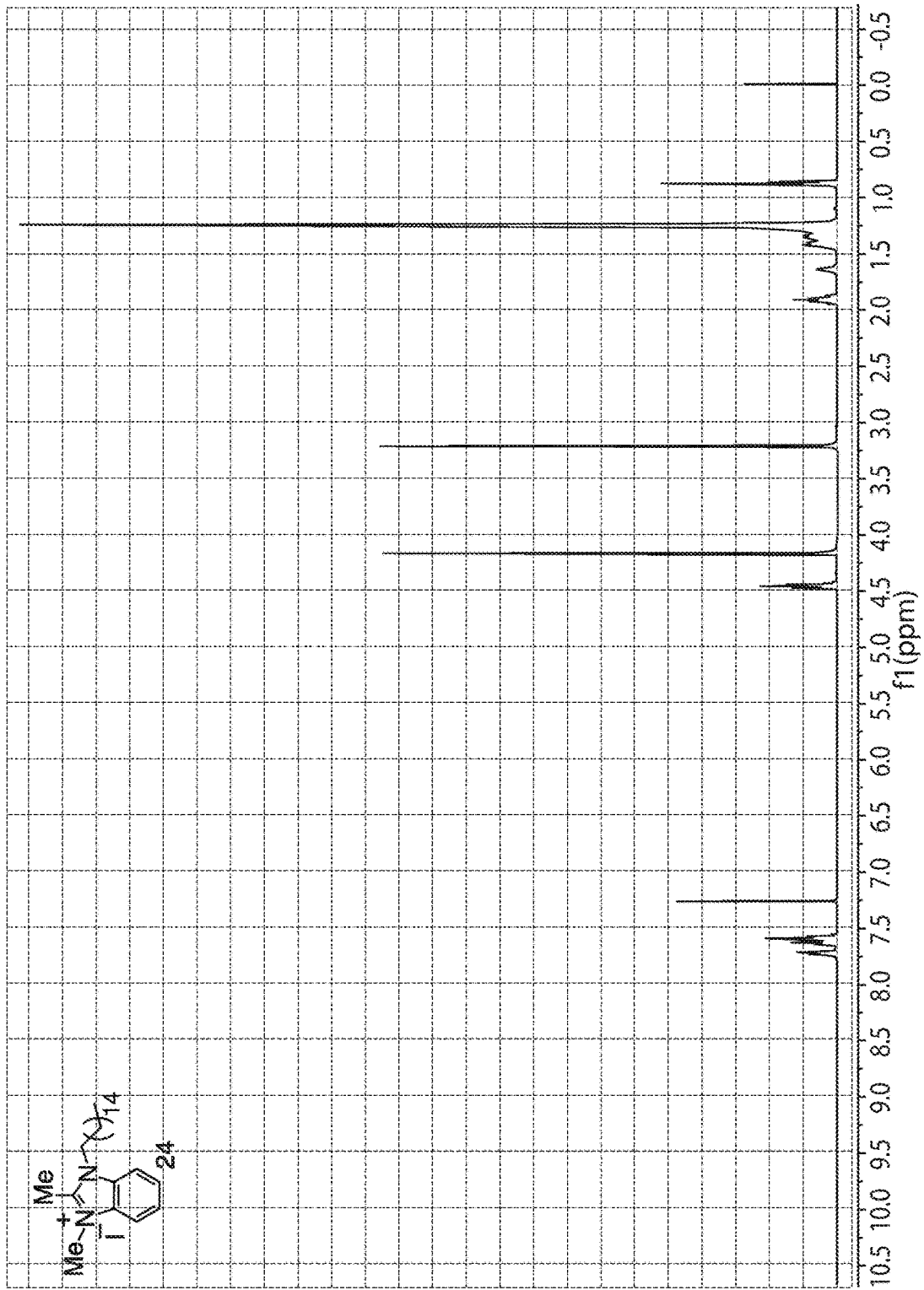
FIG. 56. NMR 40 for depicted compound 24.
Figure 57:
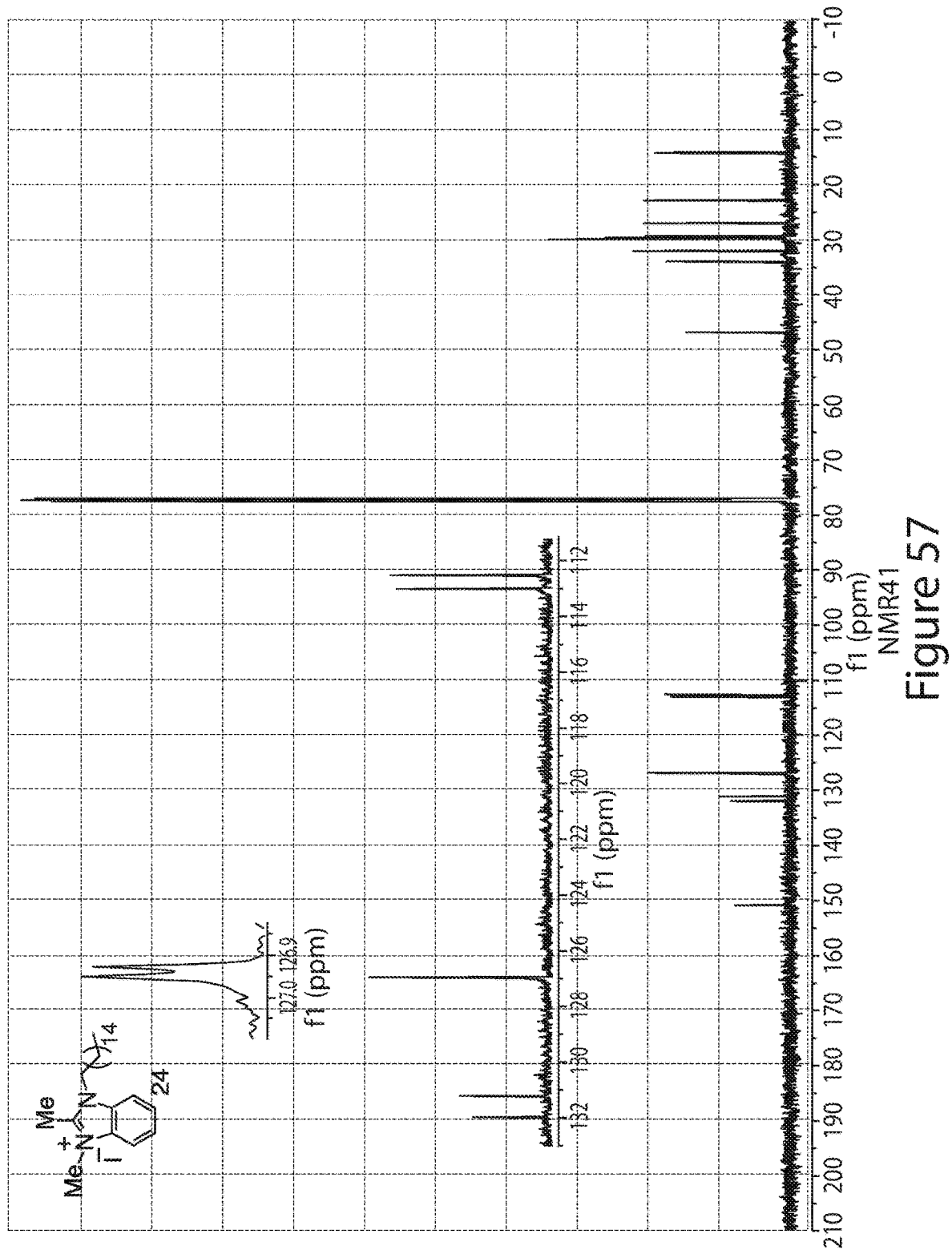
FIG. 57. NMR 41 for depicted compound 24.

Yield: 64% yield; 121 mg of 24 was isolated as a white solid. $^1$H NMR (400 MHz, CDCl$_3$): δ 7.75 (m, 1H), 7.67-7.55 (m, 3H), 4.45 (t, J=7.6 Hz, 2H), 4.17 (s, 3H), 3.21 (s, 3H), 1.91 (p, J=7.5 Hz, 2H), 1.48-1.15 (m, 26H), 0.87 (t, J=6.8 Hz, 3H). $^{13}$C NMR (100 MHz, CDCl$_3$): δ 151.0, 132.0, 131.2, 127.0, 126.9, 113.0, 112.5, 46.9, 33.9, 32.1, 29.9, 29.9, 29.9, 29.8, 29.8, 29.8, 29.7, 29.6, 29.5, 29.5, 29.3, 27.0, 22.9, 14.3, 14.1. HRMS (ESI) m/z: calc. for $C_{25}H_{43}N_2$ [M$^+$]: 371.3421, found: 371.3437. MP: 67-68° C. See FIGS. 56 and 57.

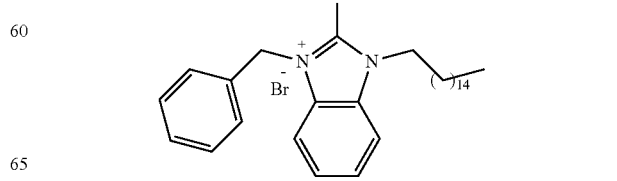

25

Figure 58:
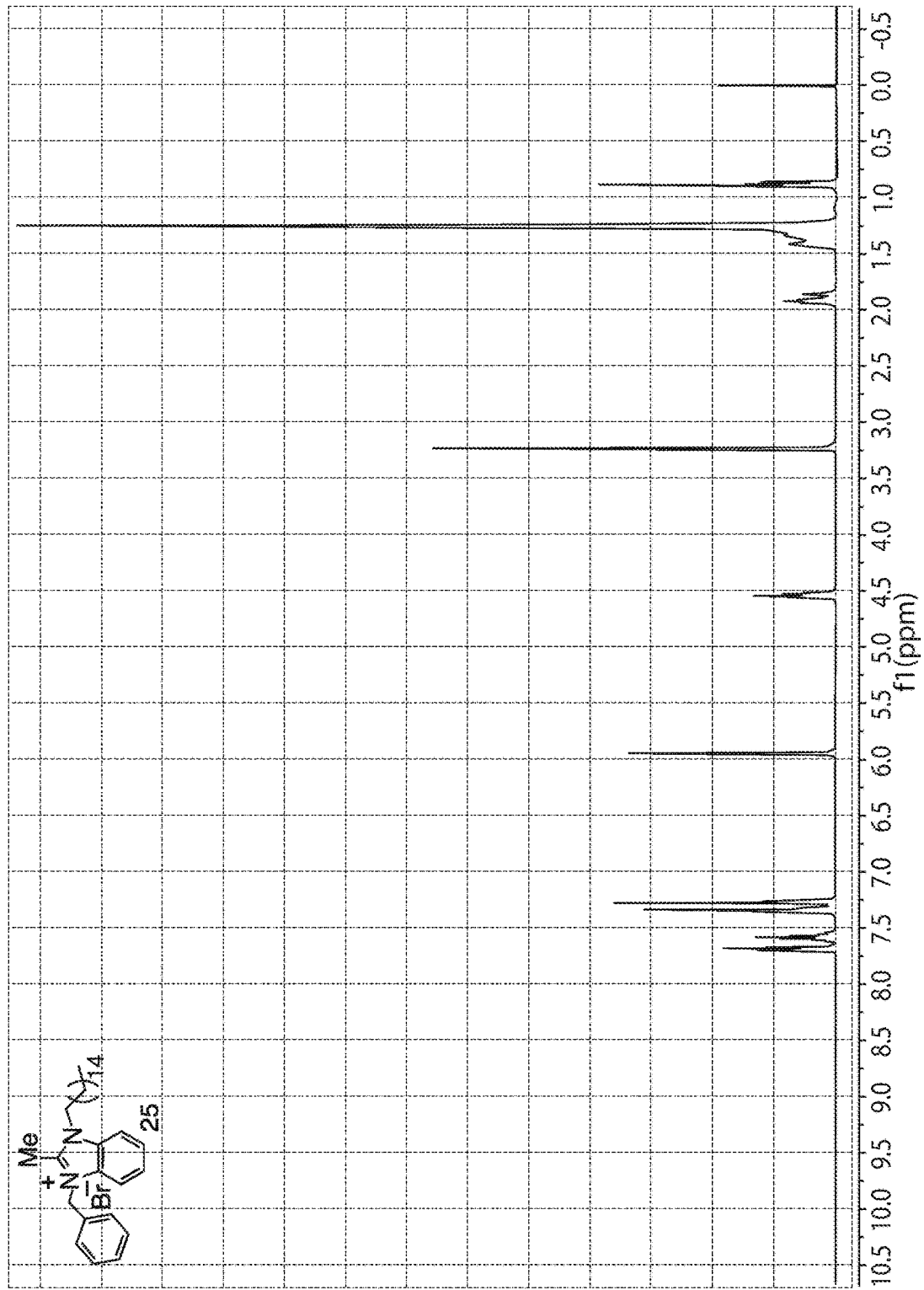
FIG. 58. NMR 42 for depicted compound 25.
Figure 59:
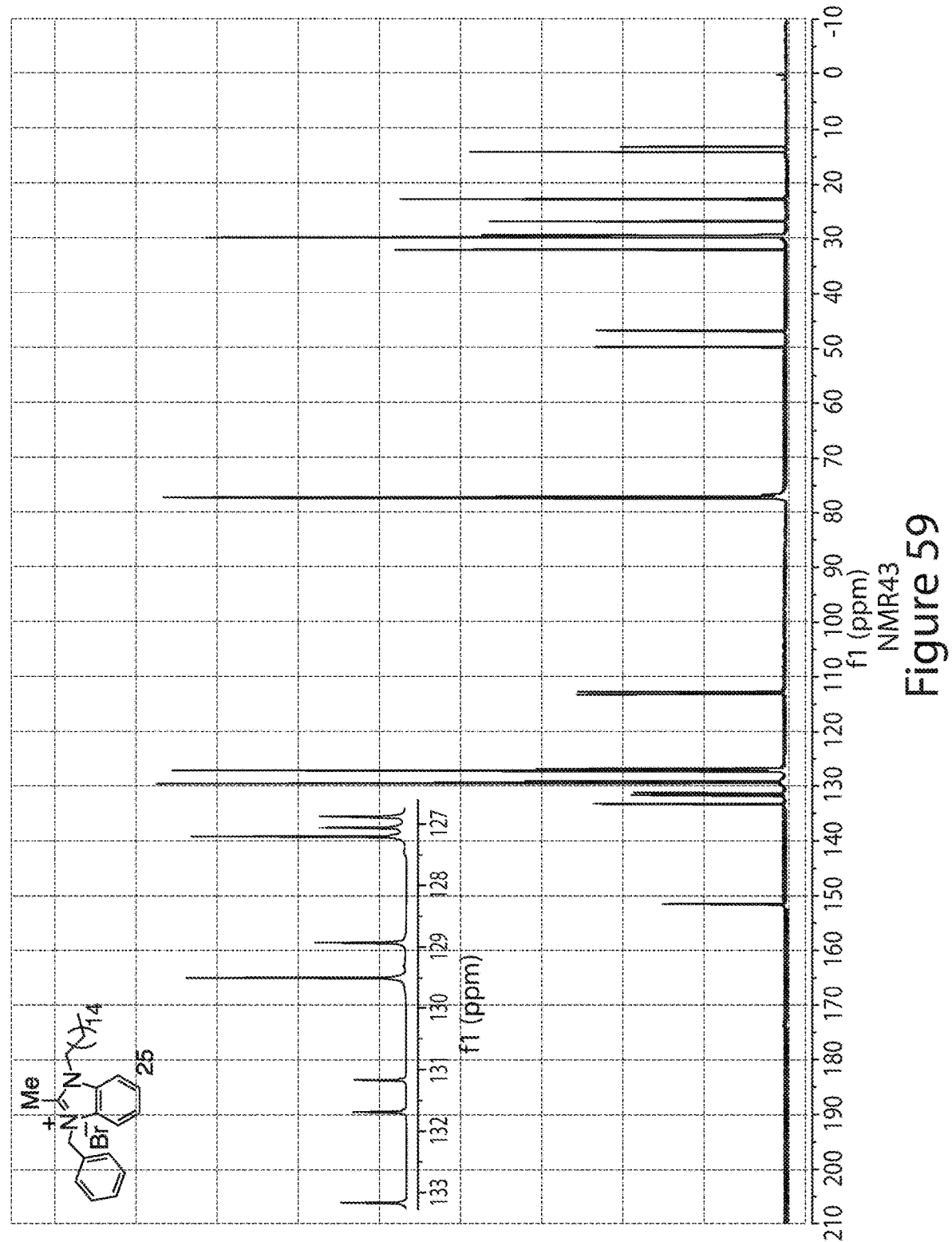
FIG. 59. NMR 43 for depicted compound 25.

Yield: 56% yield; 82 mg of 25 was isolated as a white solid. $^1$H NMR (400 MHz, CDCl$_3$): δ 7.70 (t, J=2.2 Hz, 1H), 7.68 (t, J=2.1 Hz, 1H), 7.63-7.53 (m, 2H), 7.40-7.31 (m, 3H), 7.30-7.24 (m, 2H), 5.95 (s, 2H), 4.54 (t, J=7.6 Hz, 2H), 3.23 (s, 3H), 1.92 (p, J=7.9 Hz, 2H), 1.47-1.18 (m, 26H), 0.88 (t, J=6.7 Hz, 3H). $^{13}$C NMR (100 MHz, CDCl$_3$): δ 151.5, 133.2, 131.7, 131.2, 129.5, 128.9, 127.2, 127.1, 126.9, 113.2, 112.8, 50.0, 46.8, 32.0, 29.8, 29.8, 29.8, 29.7, 29.7, 29.7, 29.6, 29.5, 29.4, 29.4, 29.2, 26.9, 22.8, 14.2, 13.3. HRMS (ESI) m/z: calc. for C$_{31}$H$_{47}$N$_2$[M$^+$]: 447.3734, found: 447.3747. MP: 72-73° C. See FIGS. 58 and 59.

26

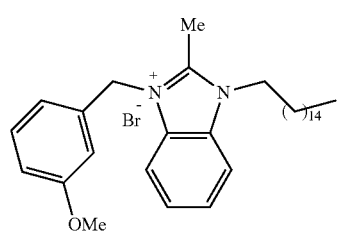

Figure 60:
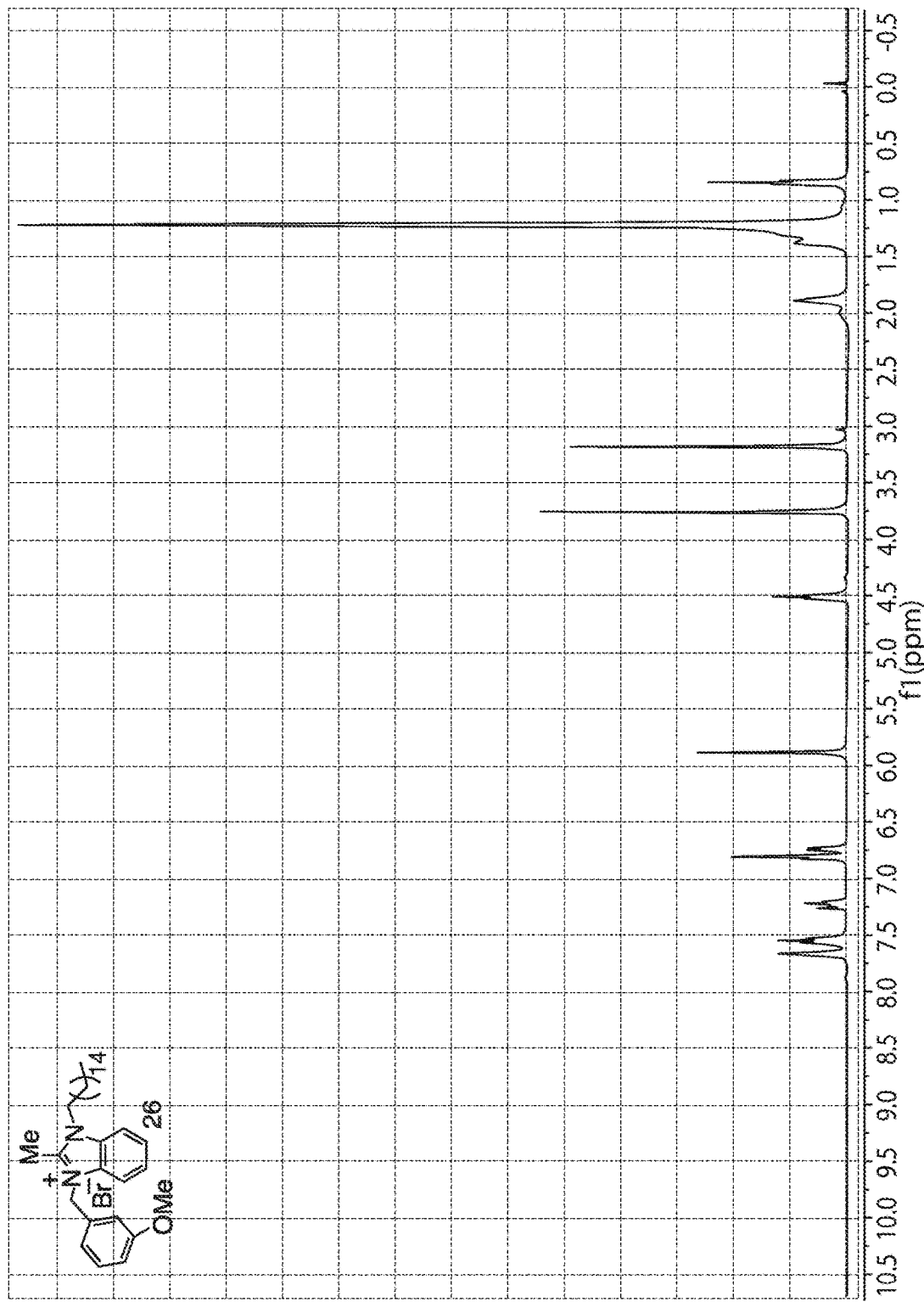
FIG. 60. NMR 44 for depicted compound 26.
Figure 61:
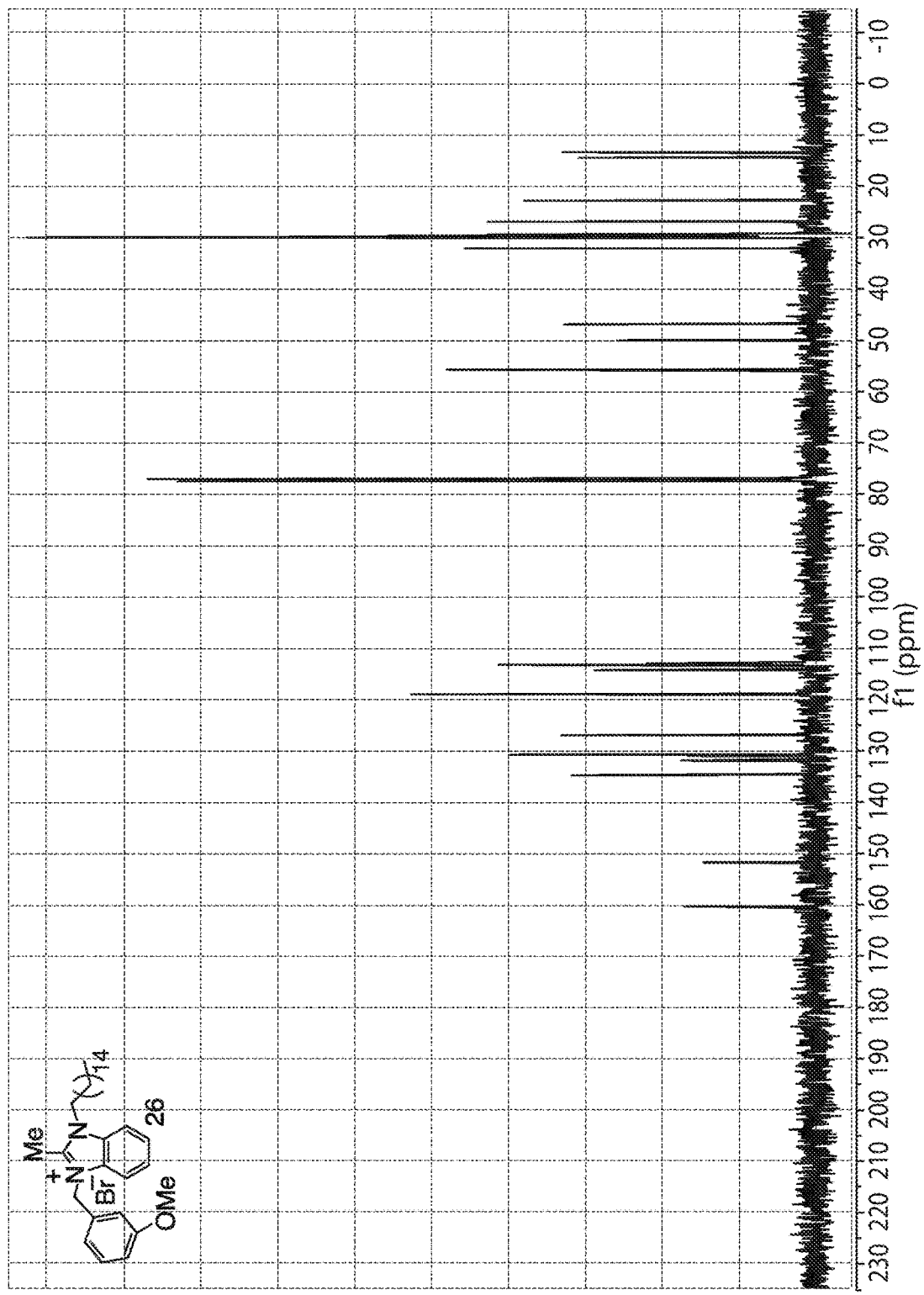
FIG. 61. NMR 45 for depicted compound 26.

Yield: 31% yield; 48 mg of 26 was isolated as a white solid. $^1$H NMR (400 MHz, CDCl$_3$): δ 7.71-7.62 (m, 2H), 7.60-7.49 (m, 2H), 7.22 (t, J=8.0 Hz, 1H), 6.81 (d, J=7.3 Hz, 1H), 6.80 (s, 1H), 6.74 (d, J=7.7 Hz, 1H), 5.88 (s, 2H), 4.51 (t, J=7.5 Hz, 2H), 3.75 (s, 3H), 3.18 (s, 3H), 1.88 (p, J=7.8 Hz, 2H), 1.45-1.10 (m, 26H), 0.84 (t, J=6.7 Hz, 3H). $^{13}$C NMR (100 MHz, CDCl$_3$): δ 160.4, 151.6, 134.7, 131.8, 131.2, 130.7, 127.1, 126.9, 119.0, 114.1, 113.2, 113.1, 112.7, 55.7, 49.8, 46.8, 32.0, 29.8, 29.8, 29.8, 29.8, 29.7, 29.6, 29.5, 29.5, 29.4, 29.3, 26.9, 22.8, 14.3, 13.2. Note: 31 of the 32 $^{13}$C NMR signals could be found, likely due to signal overlap at 29 ppm. HRMS (ESI) m/z: calc. for C$_{32}$H$_{49}$N$_2$O [M$^+$]: 477.3839, found: 477.3841. MP: 66-67° C. See FIGS. 60 and 61.

27

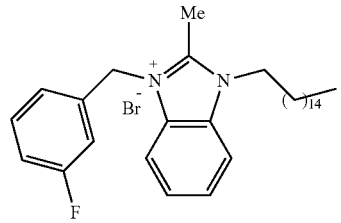

Figure 62:
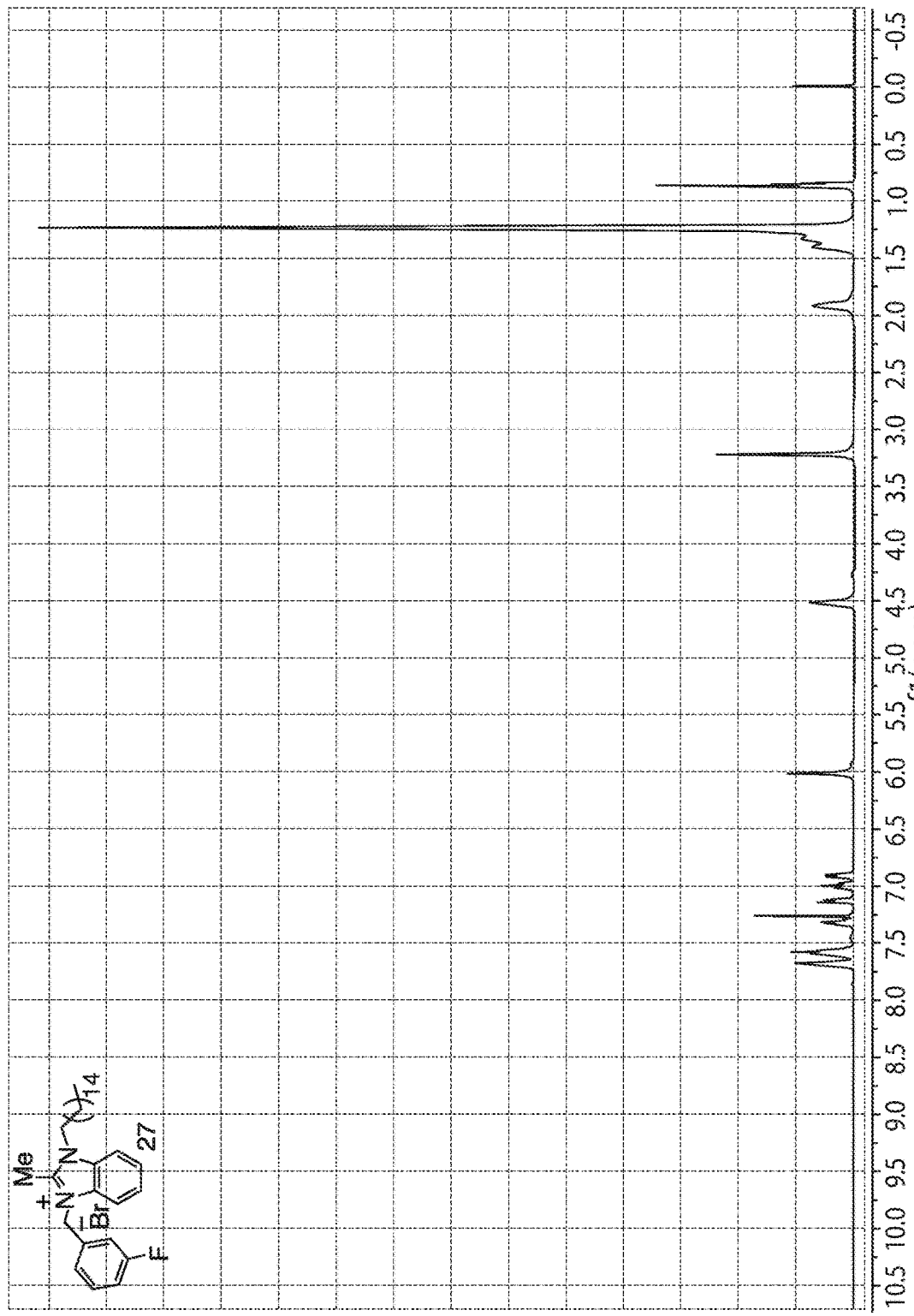
FIG. 62. NMR 46 for depicted compound 27.
Figure 63:
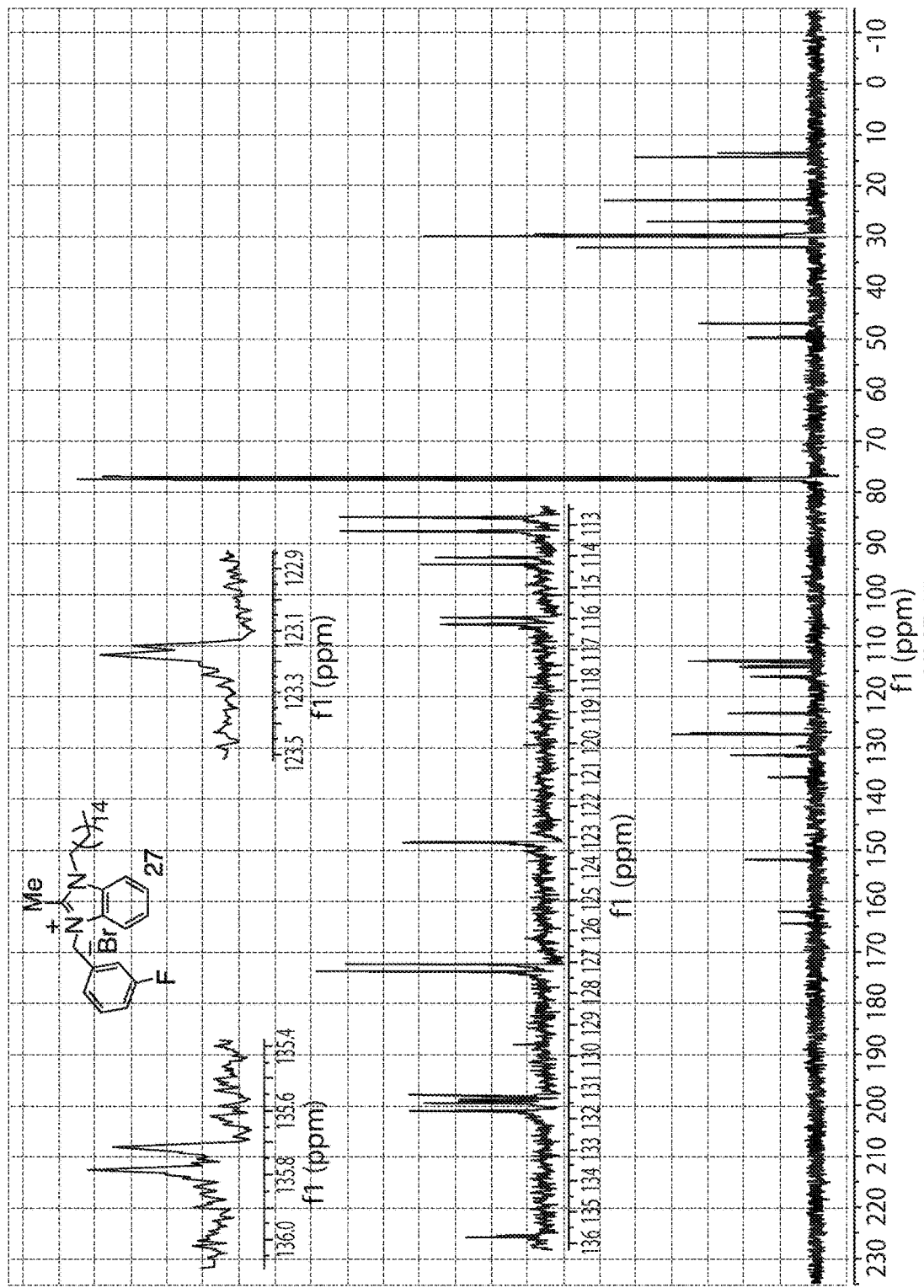
FIG. 63. NMR 47 for depicted compound 27.

Yield: 33% yield; 51 mg of 27 was isolated as a white solid. $^1$H NMR (400 MHz, CDCl$_3$): δ 7.73-7.64 (m, 2H), 7.63-7.52 (m, 2H), 7.32 (m, 1H), 7.13 (d, J=7.6 Hz, 1H), 7.00 (td, J=8.4, 2.3 Hz, 1H), 6.91 (d, J=8.8 Hz, 1H), 6.01 (s, 2H), 4.51 (t, J=6.8 Hz, 2H), 3.22 (s, 3H), 1.91 (p, J=6.8 Hz, 2H), 1.48-1.13 (m, 26H), 0.86 (t, J=6.6 Hz, 3H). $^{13}$C NMR (100 MHz, CDCl$_3$): δ 163.2 (d, J=248.6 Hz), 151.8, 135.8, 135.7, 131.5 (d, J=50.1 Hz), 131.4 (d, J=8.5 Hz), 127.3, 127.1, 123.2 (d, J=2.8 Hz), 116.1 (d, J=21.0 Hz), 114.3, 114.1, 113.0 (d, J=44.2 Hz), 49.6, 47.0, 32.1, 29.9, 29.9, 29.8, 29.8, 29.8, 29.7, 29.7, 29.5, 29.5, 29.5, 29.3, 27.0, 22.9, 14.3, 13.6. HRMS (ESI) m/z: calc. for C$_{31}$H$_{46}$FN$_2$ [M$^+$]: 465.3640, found: 465.3639. MP: 64-65° C. See FIGS. 62 and 63.

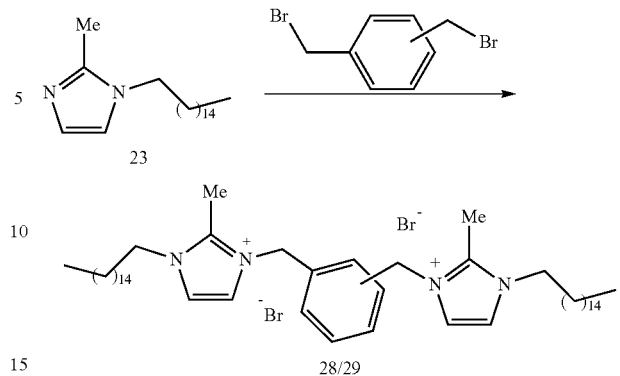

General Bis-Benzylation Procedure for the Synthesis of Dimeric Analogues 28 and 29:

1,4-Bis(bromomethyl)benzene (51 mg, 0.195 mmol) was added to a stirring solution of 23 (120 mg, 0.39 mmol) in 50 mL anhydrous chloroform in a reaction tube at room temperature. The reaction tube was then sealed and heated at 120° C. for 24 hours. After that time, the reaction mixture was allowed to cool to room temperature before chloroform was evaporated in vacuo. The crude product was stirred in anhydrous ether under argon for 5 hours and resulting white precipitate was filtered in an argon environment. The white precipitate was washed with anhydrous ether and dried under vacuum to obtain compound pure 28 as a white solid (76 mg, 44%).

28

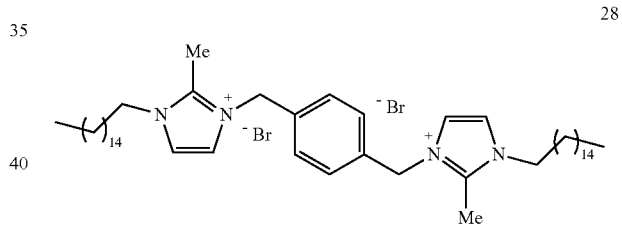

Figure 64:
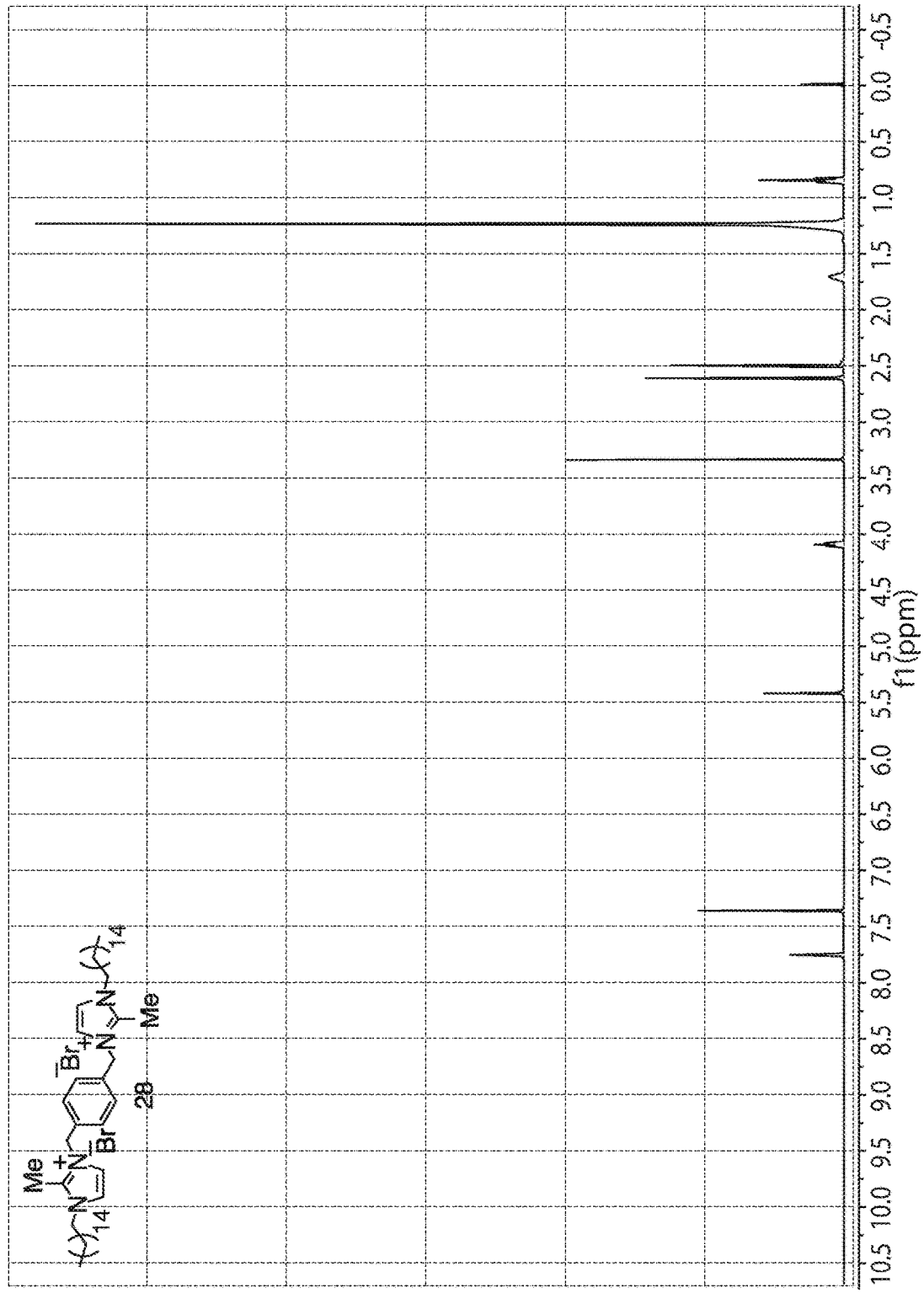
FIG. 64. NMR 48 for depicted compound 28.
Figure 65:
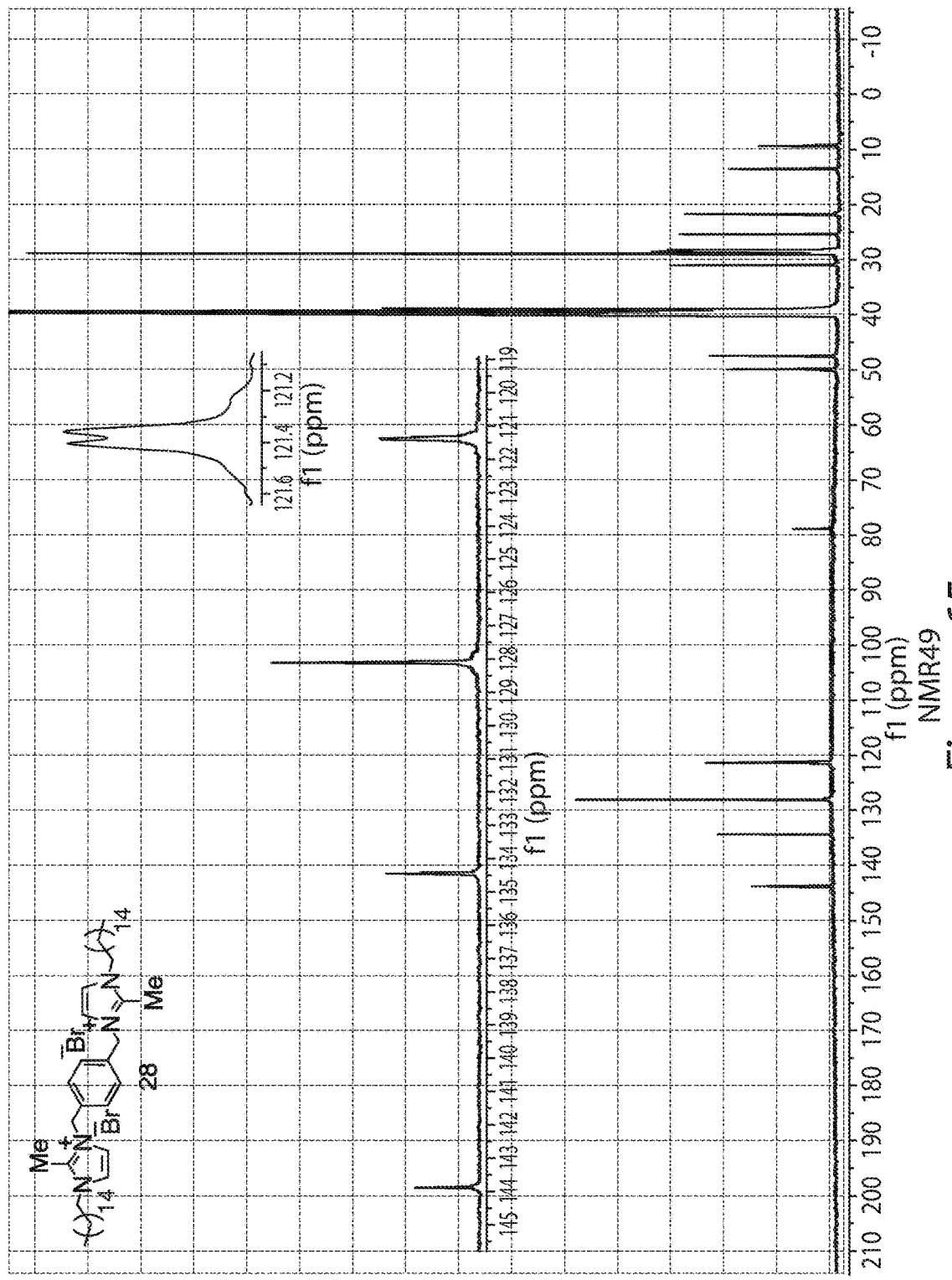
FIG. 65. NMR 49 for depicted compound 28.

Yield: 44% yield; 76 mg of 28 was isolated as a white solid. $^1$H NMR (400 MHz, d$_6$-DMSO): δ 7.75 (d, J=2.2 Hz, 2H), 7.74 (d, J=2.1 Hz, 2H), 7.35 (s, 4H), 5.42 (s, 4H), 4.09 (t, J=7.5 Hz, 4H), 2.61 (s, 6H), 1.71 (p, J=7.2 Hz, 4H), 1.33-1.16 (m, 52H), 0.85 (t, J=6.6 Hz, 6H). $^{13}$C NMR (100 MHz, d$_6$-DMSO): δ 143.9, 134.5, 128.1, 121.4, 121.4, 78.9, 50.1, 47.6, 30.9, 28.7, 28.6, 28.6, 28.5, 28.3, 28.1, 25.4, 21.7, 13.5, 9.3. Note: 19 of the 24 $^{13}$C NMR signals could be found, multiple signals overlap at 29 ppm. HRMS (ESI) m/z: calc. for C$_{48}$H$_{84}$N$_4$ [M$^{2+}$]: 358.3343, found: 358.3334. MP: 81-82° C. See FIGS. 64 and 65.

29

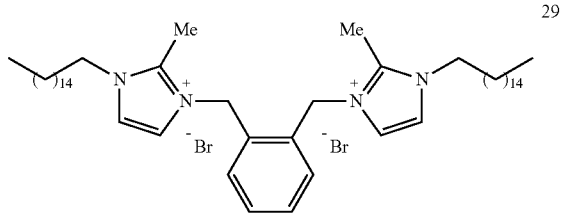

Figure 66:
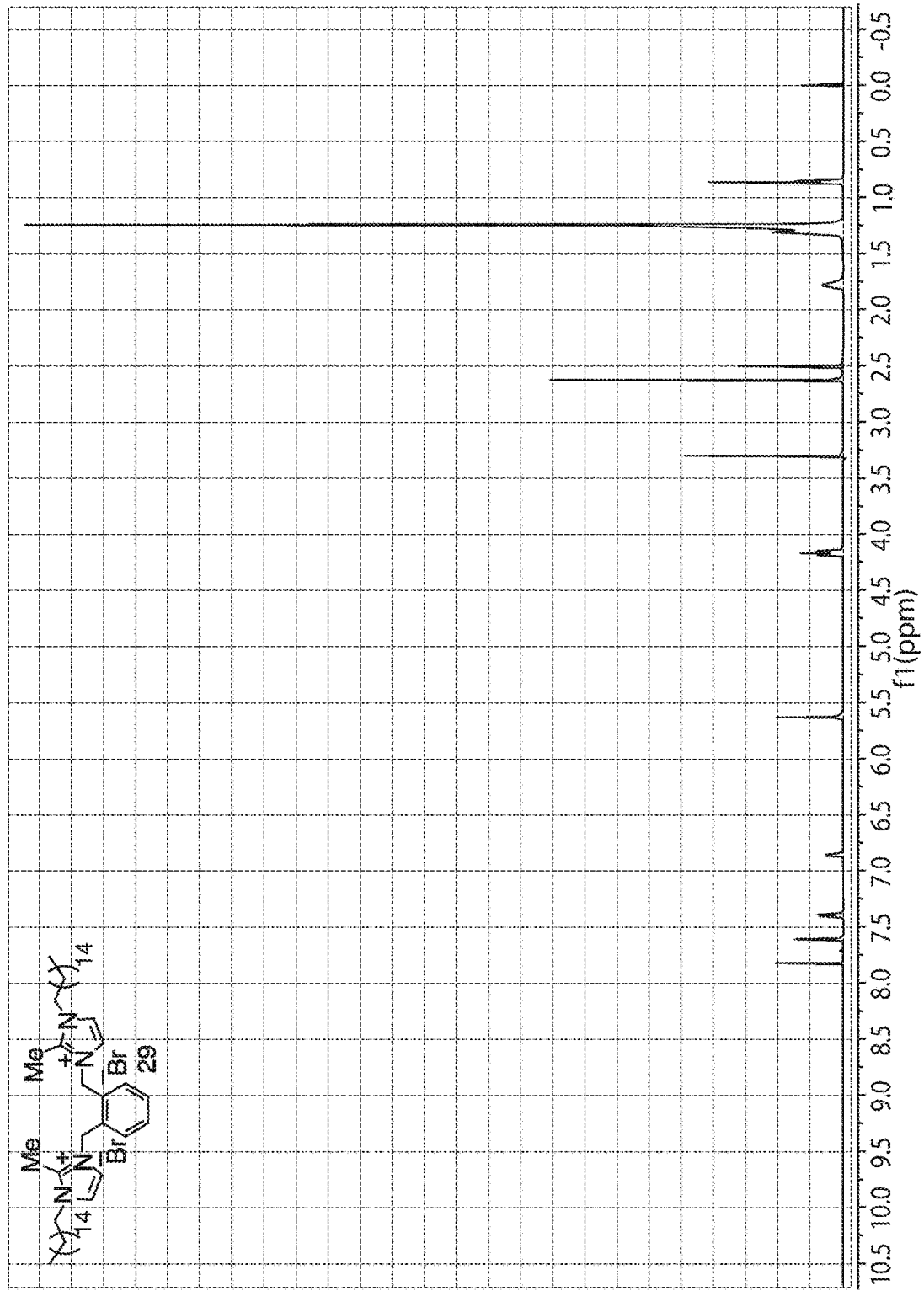
FIG. 66. NMR 50 for depicted compound 29.
Figure 67:
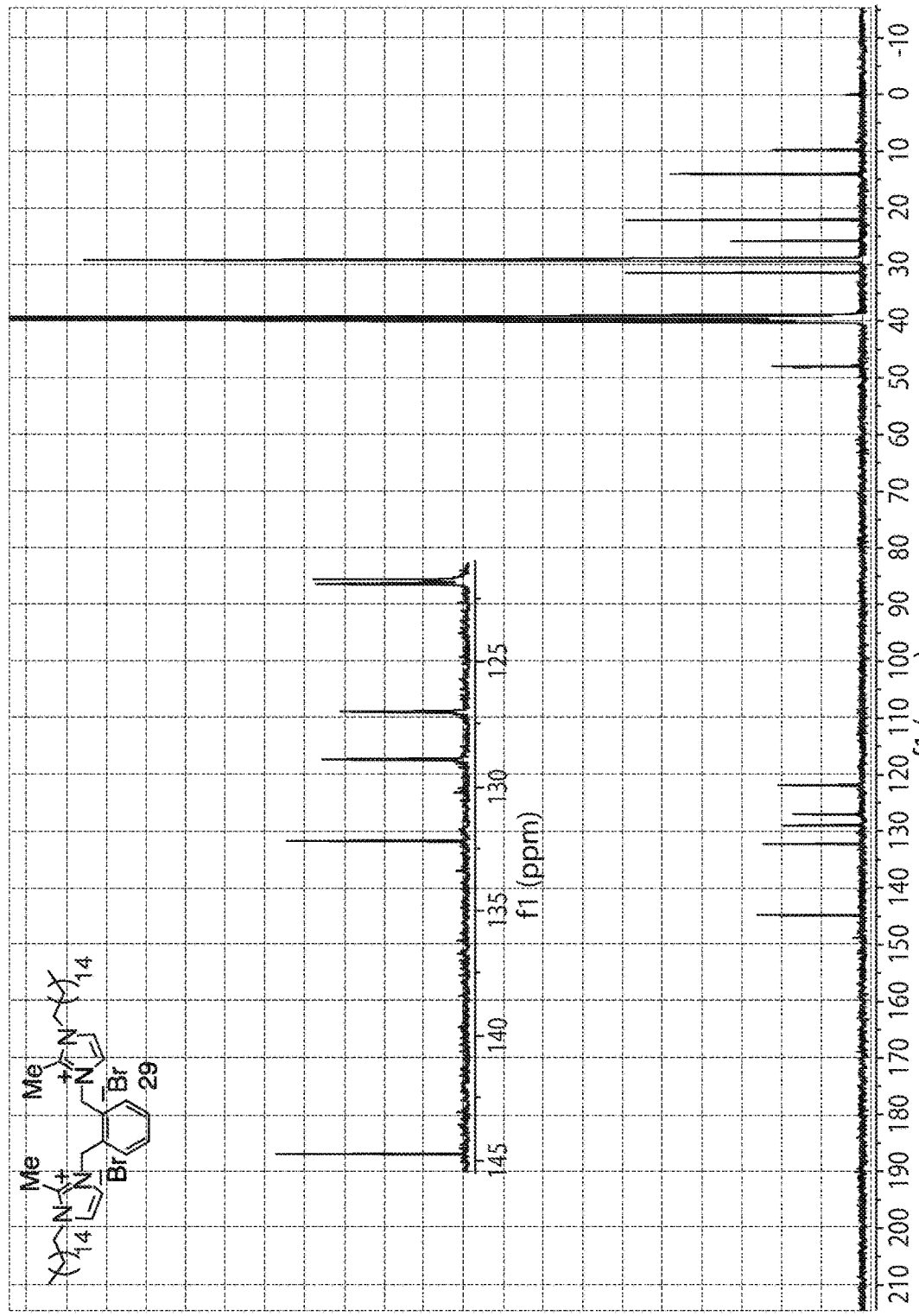
FIG. 67. NMR 51 for depicted compound 29.
Figure 68:
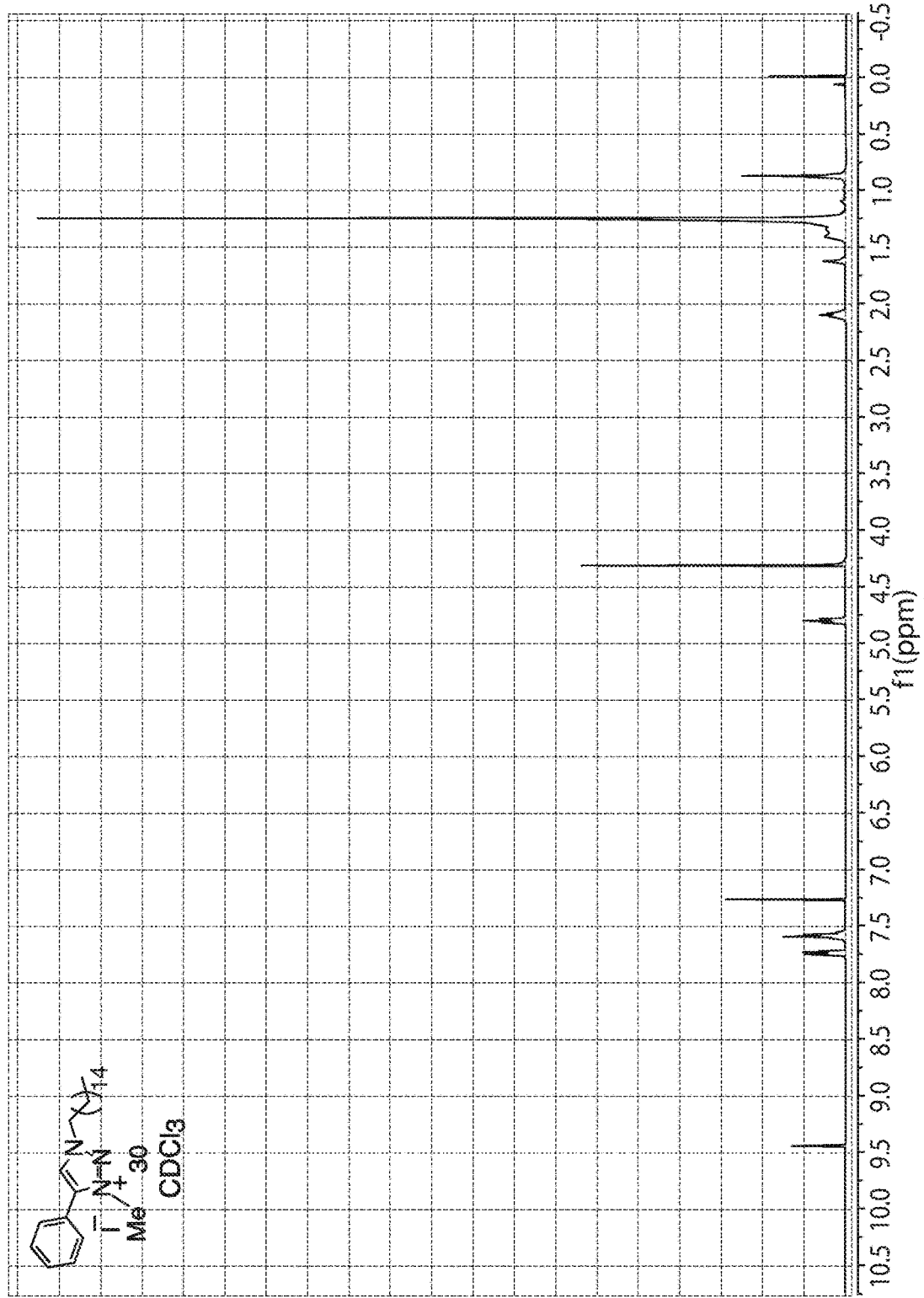
FIG. 68. NMR 52 for depicted compound 30.
Figure 69:
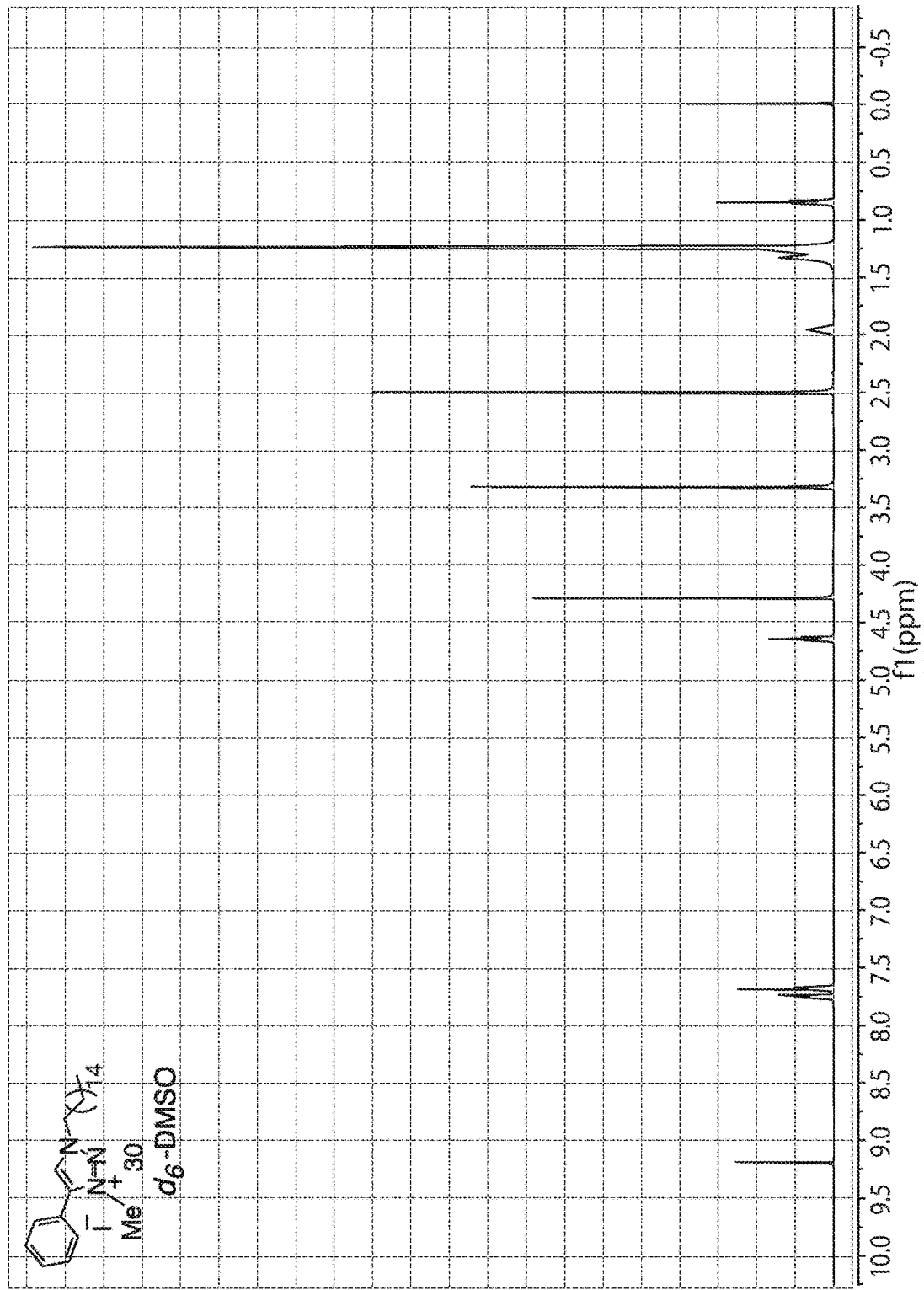
FIG. 69. NMR 53 for depicted compound 30.
Figure 70:
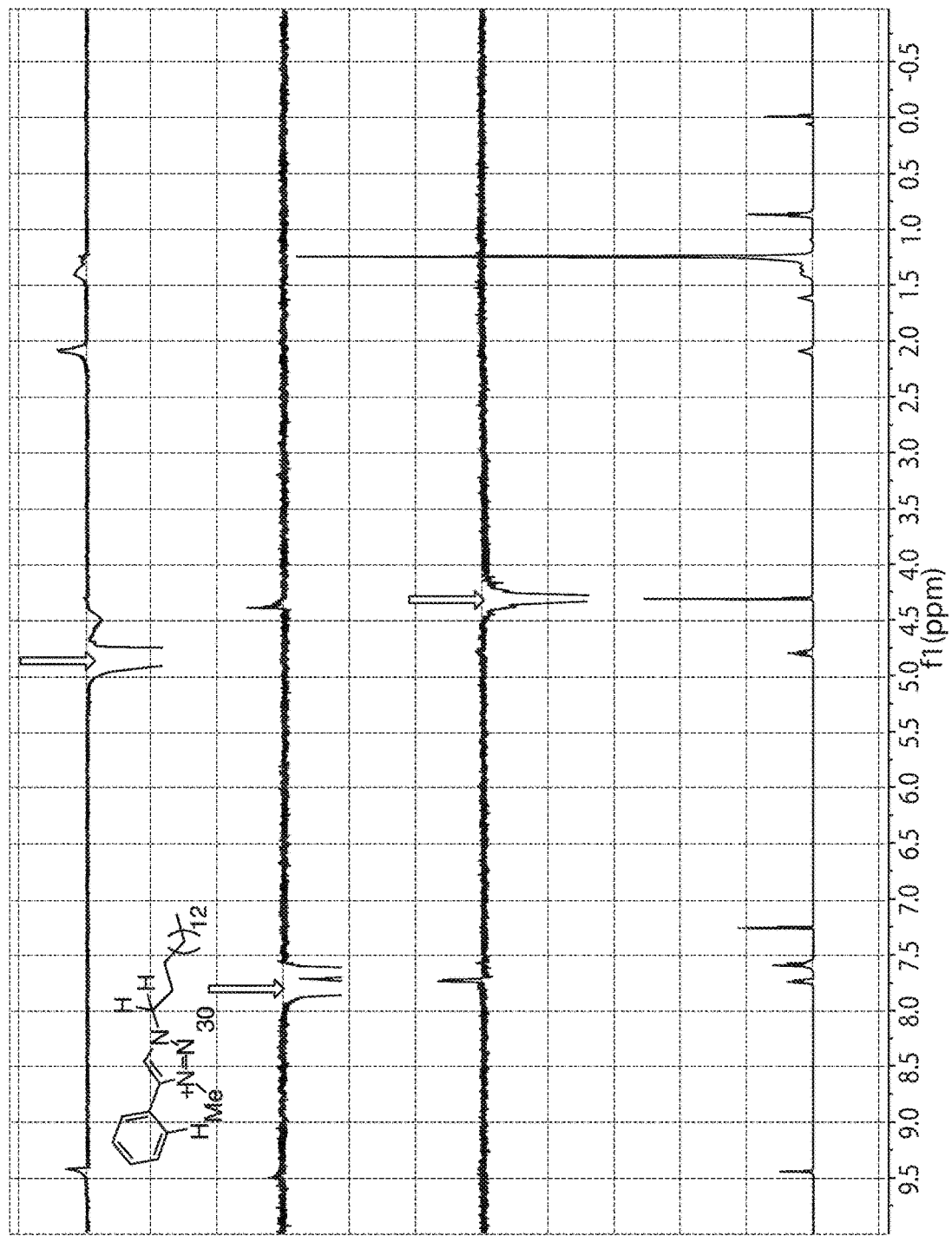
FIG. 70. NMR 54 for depicted compound 30.
Figure 71:
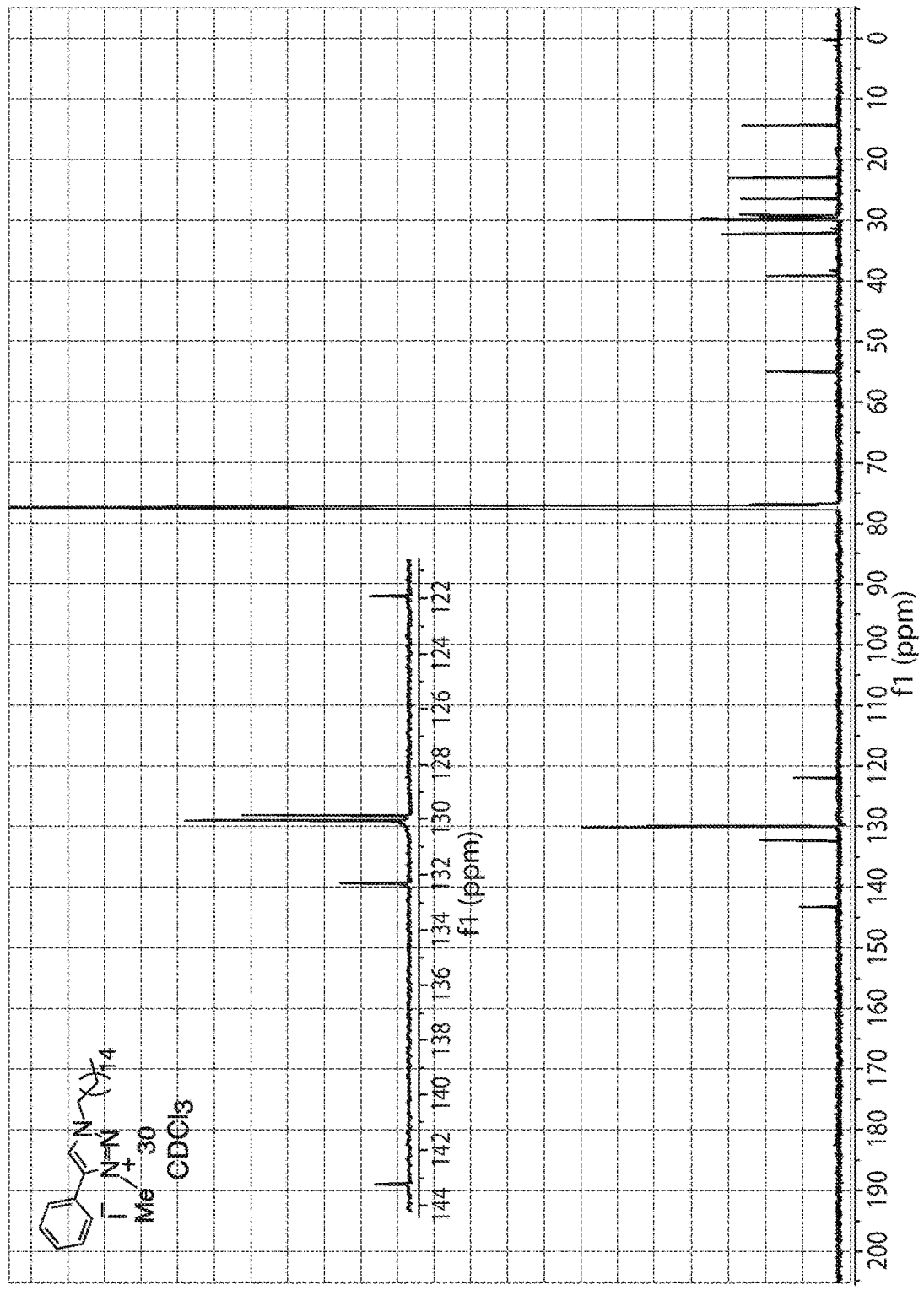
FIG. 71. NMR 55 for depicted compound 30.
Figure 72:
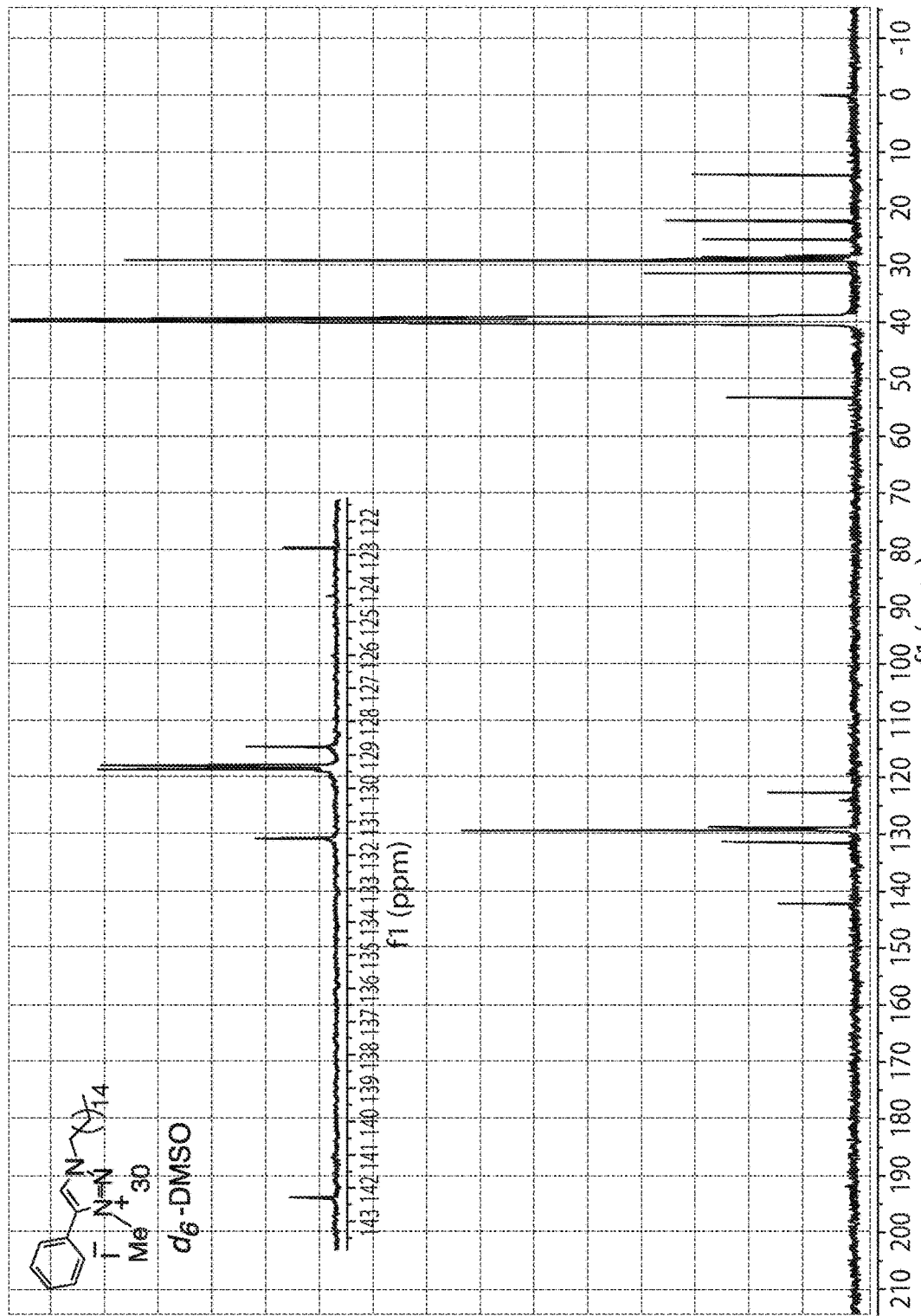
FIG. 72. NMR 56 for depicted compound 30.
Figure 73:
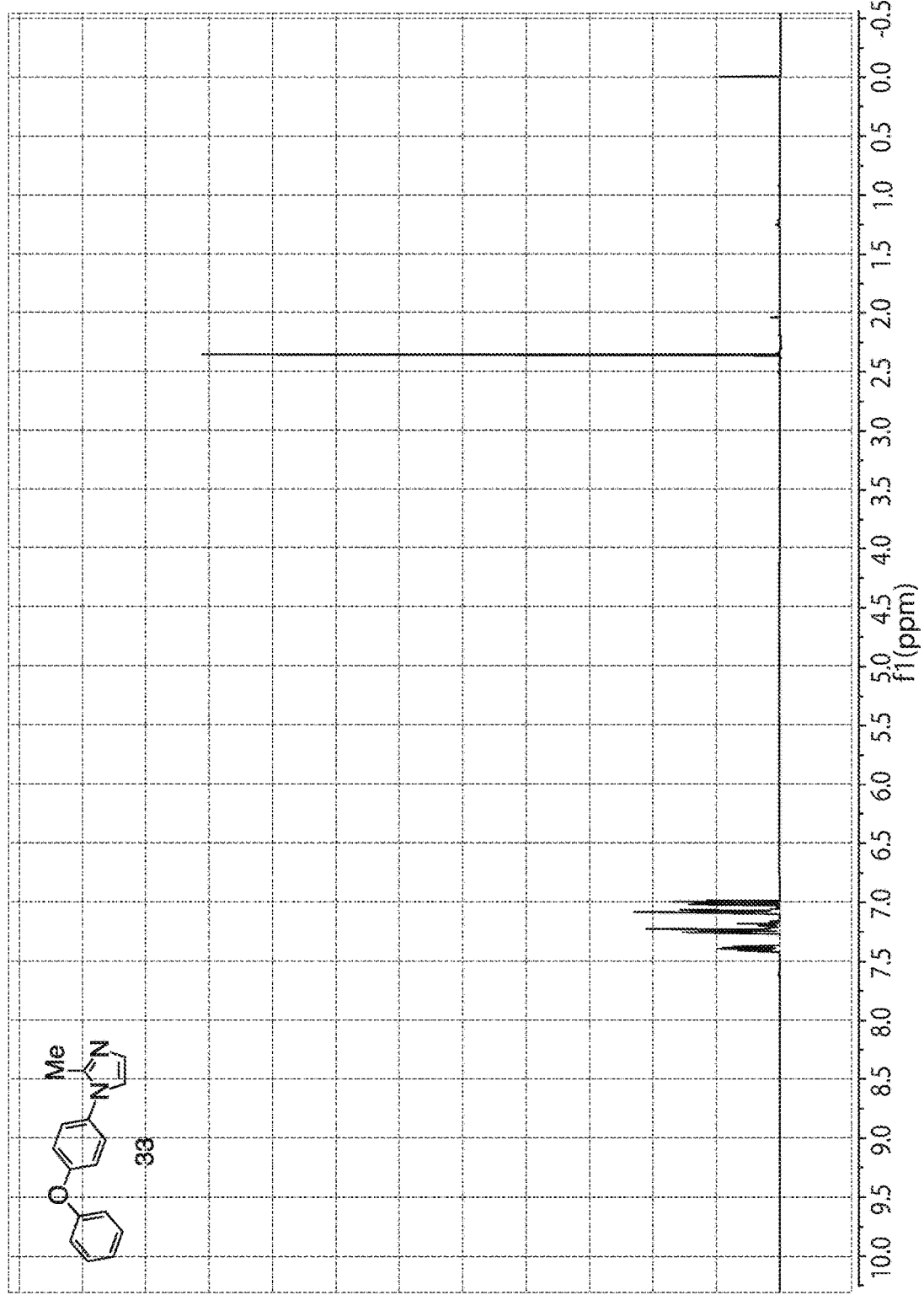
FIG. 73. NMR 57 for depicted compound 33.
Figure 74:
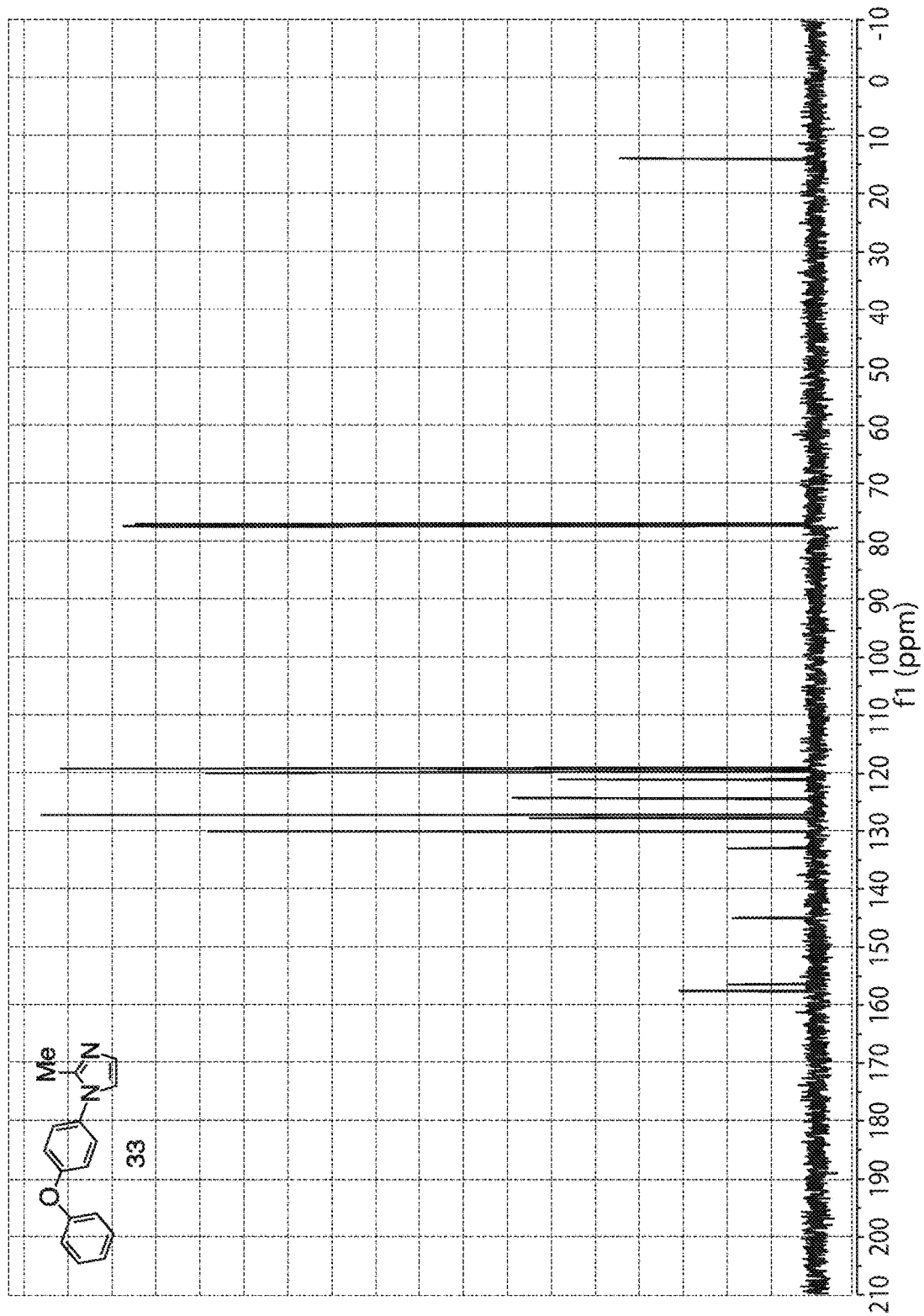
FIG. 74. NMR 58 for depicted compound 33.
Figure 75:
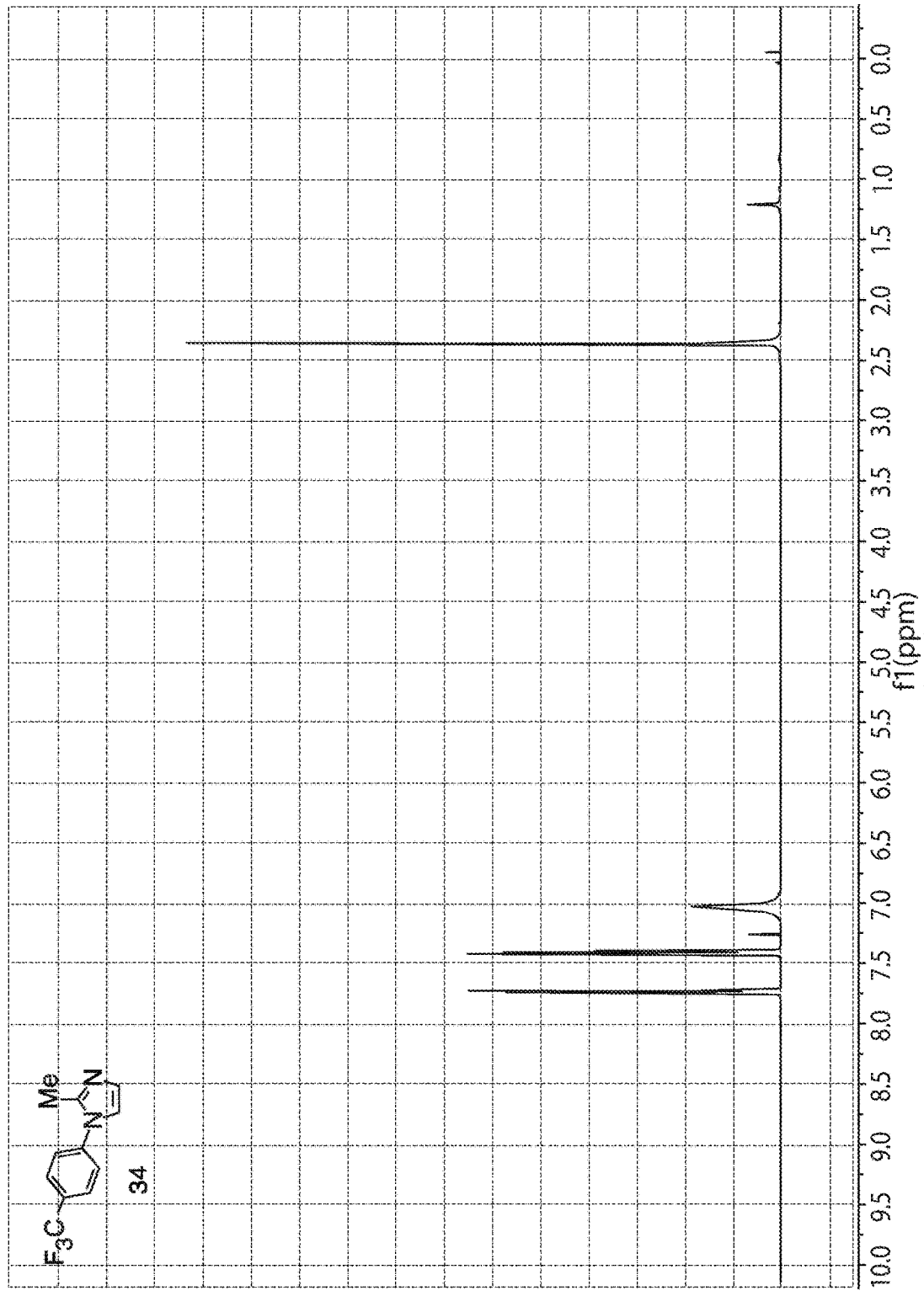
FIG. 75. NMR 59 for depicted compound 34.
Figure 76:
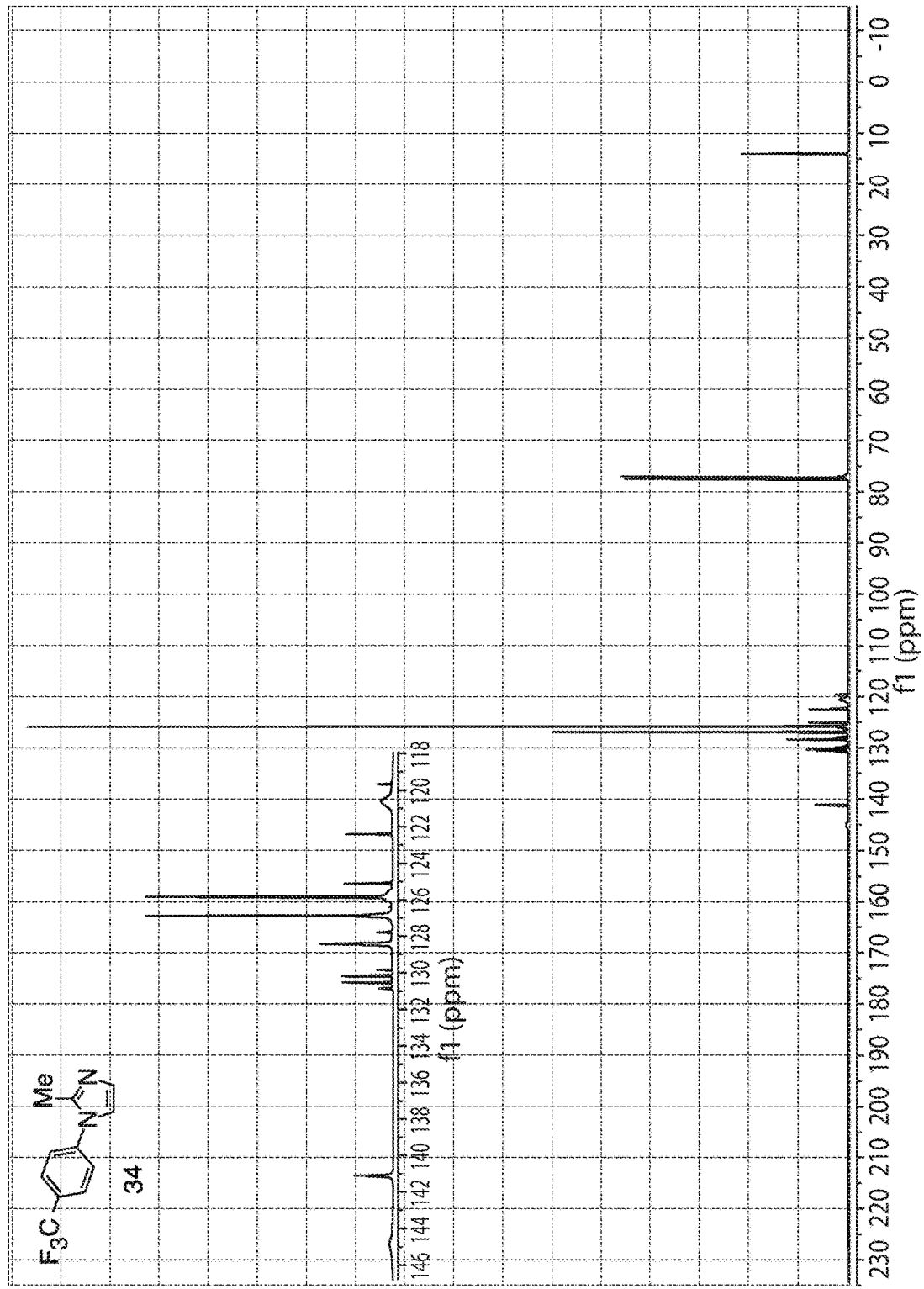
FIG. 76. NMR 60 for depicted compound 34.
Figure 77:
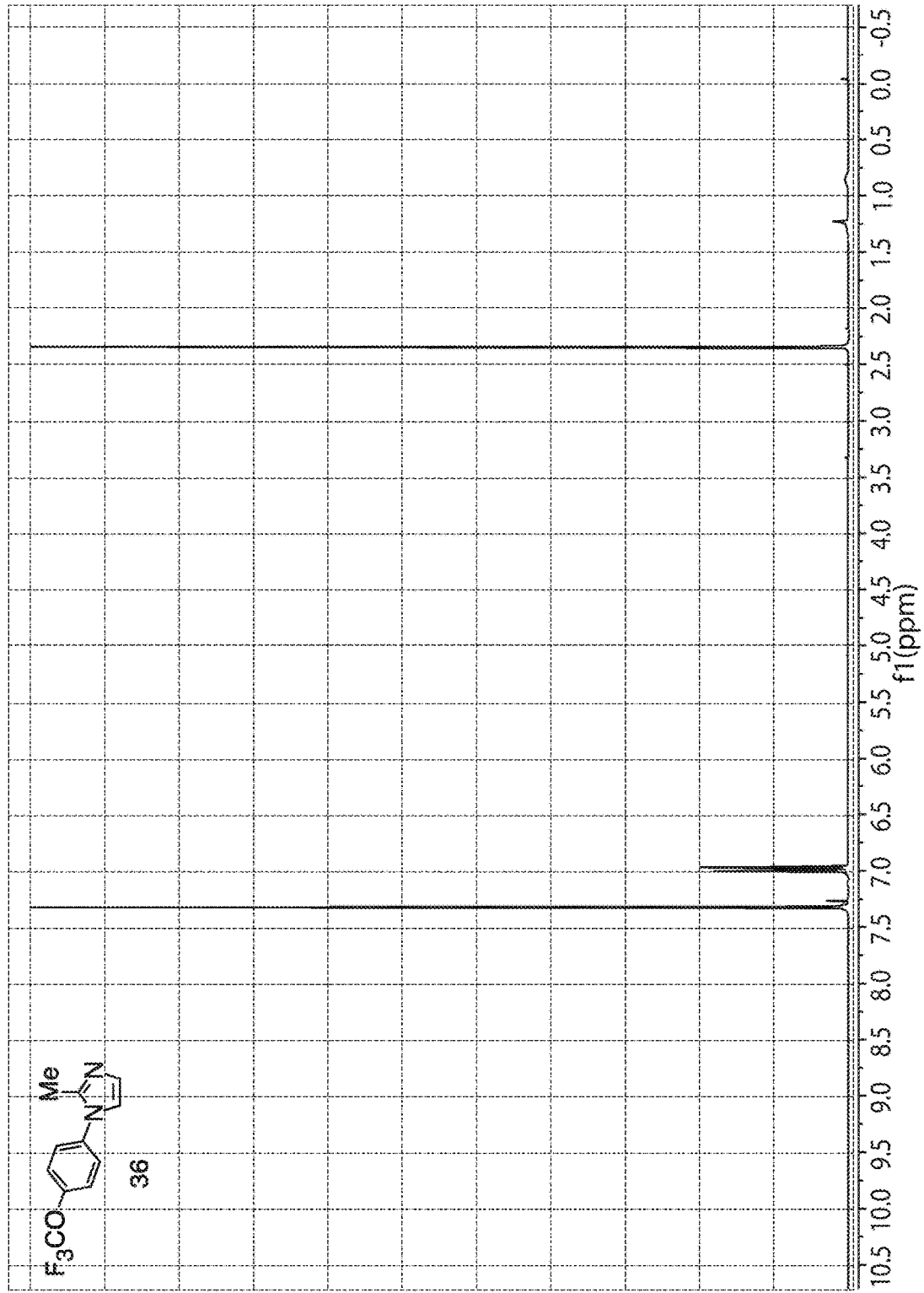
FIG. 77. NMR 61 for depicted compound 36.
Figure 78:
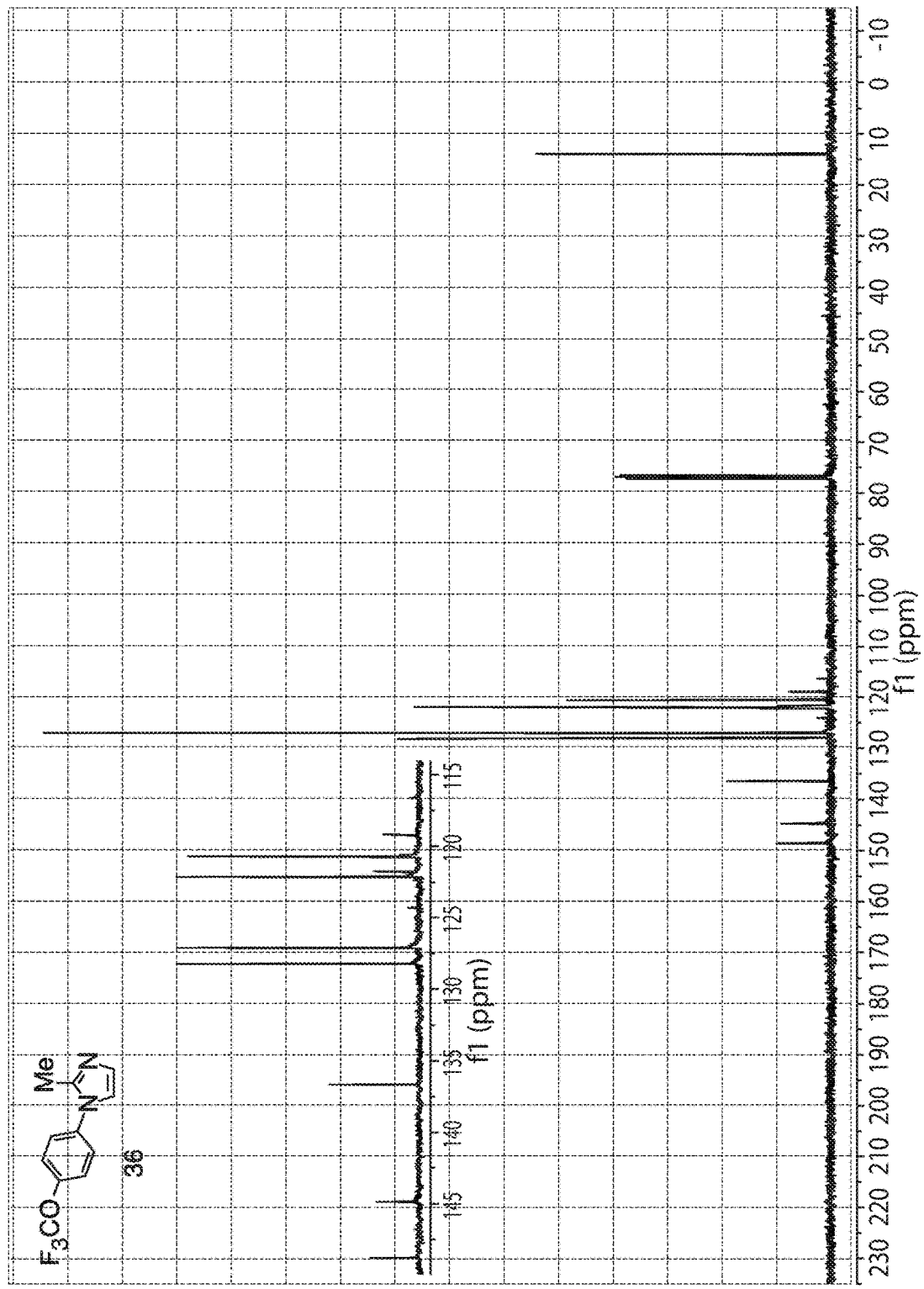
FIG. 78. NMR 62 for depicted compound 36.
Figure 79:
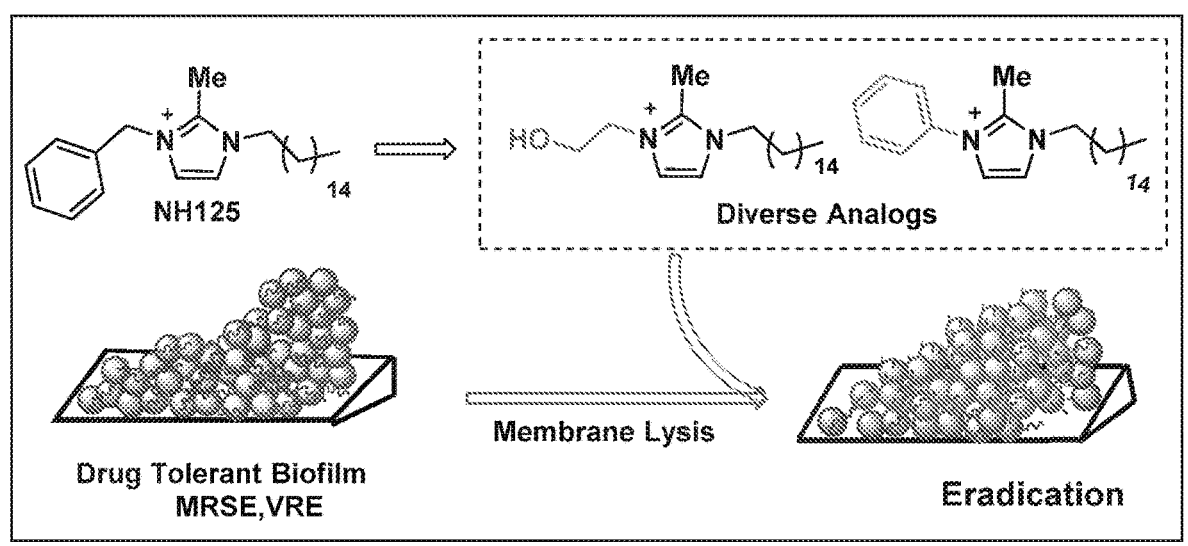
FIG. 79. Exemplary synthesis procedure for compound NH 125.

Yield: 72% yield; 123 mg of 29 was isolated as a white solid. $^1$H NMR (400 MHz, d$_6$-DMSO): δ 7.82 (d, J=2.1 Hz, 2H), 7.60 (d, J=1.8 Hz, 2H), 7.39 (m, 2H), 6.85 (m, 2H), 5.63 (s, 4H), 4.17 (t, J=7.4 Hz, 4H), 2.63 (s, 6H), 1.78 (p, J=7.2 Hz, 4H), 1.32-1.15 (m, 52H), 0.85 (t, J=6.6 Hz, 6H). $^{13}$C NMR (100 MHz, d$_6$-DMSO): δ 144.7, 132.2, 128.9, 127.0, 121.9, 121.7, 48.1, 47.8, 31.3, 29.1, 29.0, 29.0, 28.9, 28.7, 28.5, 25.7, 22.1, 14.0, 9.6. Note: 19 of the 24 $^{13}$C NMR signals could be found, multiple signals overlap at 29 ppm. HRMS (ESI) m/z: calc. for C$_{48}$H$_{84}$N$_4$[M$^{2+}$]: 358.3343, found: 358.3355. MP: 87-88° C. See FIGS. 66 and 67.

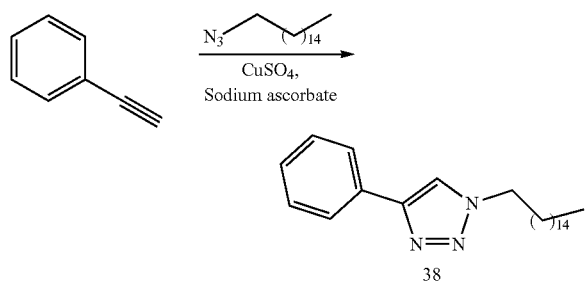

Click Reaction to Synthesize 38:

Phenyl acetylene (20 mg, 0.19 mmol) and 1-hexadecylazide (50 mg, 0.19 mmol) were sequentially added to a 9:1 mixture (10 mL) of tert-butanol and water containing copper sulfate (6 mg, 0.04 mmol) and sodium ascorbate (15 mg, 0.08 mmol). The solution was allowed to stir for 30 minutes before the reaction mixture was concentrated in vacuo. The crude reaction contents was transferred to a separatory funnel in ethyl acetate (100 mL), which was washed with water (3×30 mL), then brine (2×30 mL) before the organic layer was collected and dried with anhydrous sodium sulfate. The organic layer was then filtered, and concentrated in vacuo before being purified via flash column chromatography using hexanes:ethyl acetate (4:1 to 3:1) as an eluent to afford pure triazole 38 as a white solid (36 mg, 52%). Note: 38 is a known compound (CAS No. 1009089-53-5). Our NMR data matched those previously reported for this compound.[5]

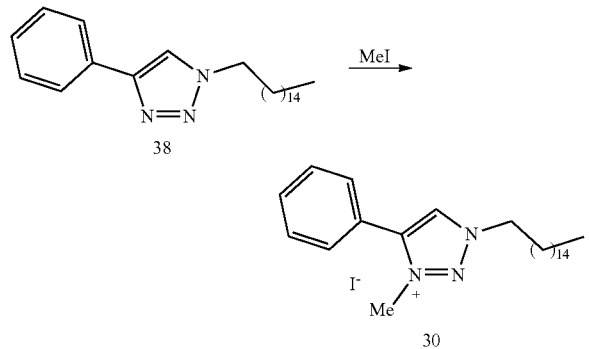

Methylation to Synthesize Agent 30

Iodomethane (0.18 mL, 0.12 mmol) was added to a stirring solution of 38 (30 mg, 0.81 mmol) in 5 mL anhydrous acetonitrile in a 10 mL glass tube at room temperature. The resulting mixture was sealed and heated at 110° C. and allowed to stir for 24 hours. After this time, the reaction mixture was allowed to cool to room temperature and acetonitrile was evaporated in vacuo. The crude product was stirred in anhydrous ether under argon for 5 hours and the resulting white precipitate was filtered under an argon environment. The filtered product was then washed with cold anhydrous ether and dried under vacuum to obtain pure 30 as a white solid (25 mg, 61%). Note: Due to a missing aromatic signal in the $^{13}$C NMR spectra in CDCl$_3$, NMR spectra were obtained in d$_6$-DMSO with corresponding tabulated data below. $^1$H NMR (400 MHz, CDCl$_3$): δ 9.44 (s, 1H), 7.78-7.71 (m, 2H), 7.64-7.54 (m, 3H), 4.80 (t, J=7.5 Hz, 2H), 4.31 (s, 3H), 2.10 (p, J=7.6 Hz, 2H), 1.47-1.17 (s, 26H), 0.87 (t, J=6.7 Hz, 3H). $^1$H NMR (400 MHz, d$_6$-DMSO): δ 9.19 (s, 1H), 7.78-7.73 (m, 2H), 7.70-7.65 (m, 3H), 4.64 (t, J=7.2 Hz, 2H), 4.29 (s, 3H), 1.96 (p, J=7.0 Hz, 2H), 1.44-1.17 (m, 26H), 0.85 (t, J=6.7 Hz, 3H). $^{13}$C NMR (100 MHz, CDCl$_3$): δ 143.2, 132.3, 130.0, 129.8, 121.9, 55.0, 39.2, 32.1, 29.9, 29.9, 29.8, 29.7, 29.7, 29.6, 29.6, 29.1, 26.5, 22.9, 14.3. Note: Missing one $^{13}$C signal from aromatic region, which was found in d$_6$-DMSO. 19 of the 22 $^{13}$C NMR signals could be found, several signals buried at 29 ppm. $^{13}$C NMR (100 MHz, d$_6$-DMSO): δ 142.3, 131.5, 129.4, 129.3, 128.7, 122.7, 53.2, 31.3, 29.1, 29.0, 29.0, 29.0, 28.8, 28.7, 28.6, 28.3, 25.4, 22.1, 14.0. Note: 19 of the 22 $^{13}$C NMR signals could be found, several signals buried at 29 ppm. HRMS (ESI) m/z: calc. for C$_{25}$H$_{42}$N$_3$[M$^+$]: 384.3373, found: 384.3382. See FIGS. 68 to 72. NMR for compounds 33, 34, and 36 can be found in FIGS. 73 to 78.

Example 2. Biological Assays of Exemplary Compounds

Bacterial strains used during these investigations include: methicillin-resistant *Staphylococcus aureus* (Clinical Isolate from Shands Hospital in Gainesville, Fla.: MRSA-2; ATCC strain: BAA-1707) methicillin-resistant *Staphylococcus epidermidis* (MRSE strain ATCC 35984), vancomycin-resistant *Enterococcus faecium* (VRE strain ATCC 700221), *Acinetobacter baumannii* (ATCC 1794), *Pseudomonas aeruginosa* (PAO1), *Klebsiella pneumonia* (ATCC 13883) and *Escherichia coli* clinical isolate (UAEC-1). Other bacterial strains used include methicillin-sensitive *Staphylococcus aureus* ATCC 29213, methicillin-resistant *Staphylococcus aureus* ATCC MRSA BAA-44 and MRSA BAA-1707, Clinical Isolates of *S. aureus*, including MRSA strains, from Shands Hospital, Gainesville, Fla.: MRSA-1, MRSA-2, SA-129, SA-138, SA-147, SA-156, methicillin-resistant *Staphylococcus epidermidis* (MRSE, ATCC 35984), vancomycin-resistant *Enterococcus faecium* (VRE, ATCC 700221), *Pseudomonas aeruginosa* (PAO1), multi-drug resistant *Acinetobacter baumannii* (ATCC 1794), *Klebsiella pneumoniae* (ATCC 13883) and *Escherichia coli* (UAEC-1; clinical isolate, University of Arkansas for Medical Sciences). All compounds were stored as DMSO stocks at room temperature in the absence of light for several months at a time without observing any loss in biological activity. To ensure compound integrity of our DMSO stock solutions, we did not subject DMSO stocks of our test compounds to freeze-thaw cycles.

This panel of membrane-active agents was initially tested against methicillin-resistant *Staphylococcus aureus* (MRSA) isolates (MRSA-2, clinical isolate from Shands Hospital, Gainesville, Fla.; MRSA BAA-1707, a multidrug resistant strain purchased from ATCC), methicillin-resistant *Staphylococcus epidermidis* (MRSE), vancomycin-resistant *Enterococcus faecium* (VRE), multidrug-resistant *Acineto-* bacter baumannii, Pseudomonas aeruginosa, Klebsiella pneumoniae and Escherichia coli (UAEC-1, clinical isolate) for antibacterial activity in minimum inhibitory concentration (MIC) assays (Table 1). Compounds 1 and 2 demonstrated very potent antibacterial activities against two MRSA strains (MIC=1.56-3.13 µM) in this panel edging out NH125 (MIC=2.35-4.69 µM), QAC-10 (MIC=3.13-4.69 µM), daptomycin (MIC=3.13-4.69 µM) and BAC-12 (MIC=6.25 µM). Compound 3 has reduced antibacterial activities against these MRSA strains (MIC=12.5-25 µM) in these assays. Similar activity trends were observed against MRSE and VRE; however, daptomycin reported a significantly higher MIC against VRE (MIC=125 µM). Analogues 1 and 2 reported more potent antibacterial activities against K. pneumoniae and E. coli (MIC=6.25 µM) among the panel with moderate activities against multidrug-resistant A. baumannii (MIC=12.5 µM for 1; 18.8 µM for 2). Only QAC-10 reported more potent antibacterial activities against A. baumannii in this panel (MIC=6.25 µM) and was found to be the only membrane-active compound to demonstrate antibacterial activity against P. aeruginosa (MIC=9.38 µM; all other compounds on this panel reported MIC values >100 µM). As expected, daptomycin was inactive (MIC >100 µM) against all gram-negative pathogens. Following antibacterial assays, this panel was tested in hemolysis assays to determine hemolytic activities ($HC_{50}$ values; the concentration at which 50% of red blood cells are lysed) and found that 1, 2, QAC-10 and NH125 demonstrate potent hemolytic activities, correlating with their antibacterial activities. Analogue 3, BAC-12 and daptomycin reported $HC_{50}$ values >100 µM (highest concentration tested).

Tables 1, 1A, and 1B below show antibacterial activity and hemolysis results for exemplary compounds.

TABLE 1

Summary of antibacterial activity and hemolysis results. All values are reported in µM.

| Compound | MRSA-2 | MRSA BAA-1707 | MRSE 35984 | VRE 700221 | A. baumannii 1794 | PAO1 | K. pneumoniae 13883 | UAEC-1 | RBC $HC_{50}$ |
|---|---|---|---|---|---|---|---|---|---|
| NH125 | 4.69[a] | 2.35[a] | 4.69 | 3.13 | 37.5[a] | >100 | 18.8[a] | 18.8[a] | 12.3 |
| 1 | 3.13 | 1.56 | 1.17[a] | 3.13 | 12.5 | >100 | 6.25 | 6.25 | 7.84 |
| 2 | 3.13 | 3.13 | 2.35[a] | 1.56 | 18.8[a] | >100 | 6.25 | 6.25 | 13.4 |
| 3 | 25 | 12.5 | 9.38[a] | 50 | >100 | >100 | 100 | 25 | >100 |
| QAC-10 | 3.13 | 4.69[a] | 2.35[a] | 2.35[a] | 6.25 | 9.38[a] | 25 | 12.5 | 7.92 |
| BAC-12 | 6.25 | 6.25 | 3.13 | 25 | 75[a] | >100 | 75[a] | 50 | >100 |
| Daptomycin | 4.69[a] | 3.13 | 3.13 | 125 | >100 | >100 | >100 | >100 | >100 |

Notes:
[a]Midpoint value for a 2-fold range in independent experiments.
All MIC and $HC_{50}$ values were obtained from a minimum of three independent experiments. MRSA BAA-1707, MRSE 35984, VRE 700221, A. Baumannii 1794, K. pneumoniae 13883 were purchased from ATCC. MRSA-2 and UAEC-1 are clinical isolates.

TABLE 1A

Antibacterial Activity and Hemolysis of Exemplary Compounds

| Compound | MRSA-2 | S. epidermidis MRSE 35984 | E. faecium VRE 700221 | A. baumannii 1794 | PAO1 | HC50 |
|---|---|---|---|---|---|---|
| AB-2-147/NH125 | 4.69[a] | 4.69[a] | 3.13 | 37.5[a] | >100 | 35.6 |
| AB-2-151 | 6.25 | 6.25 | 4.69[a] | >100* | >100 | |
| AB-2-152 | 3.13 | 3.13 | 2.35[a] | >100* | >100 | |
| AB-2-153 | 12.5 | 12..5 | 9.38[a] | >100 | >100 | |
| AB-2-154 | 1.56 | 2.35[a] | 1.56 | >100* | >100 | |
| AB-3-16 | 37.5 | 12.5 | 6.25 | >100 | >100 | |
| AB-3-17 | 3.13 | 3.13 | 1.56 | >100 | >100 | 10.7 |
| AB-3-19 | 12.5 | 9.38[a] | 4.69[a] | >100 | >100 | |
| AB-3-20 | 2.35[a] | 1.17[a] | 1.56 | 25 | >100 | 16.7 |
| AB-3-23 | 6.25 | 2.35[a] | 3.13 | >100 | >100 | |
| AB-3-71 | 1.17[a] | 1.17[a] | 2.35[a] | 12.5 | >100 | 13.0 |
| AB-3-29 | 3.13 | 3.13 | 1.56 | >100 | >100 | 10.4 |
| AB-3-31 | 3.13 | 6.25 | 1.56 | >100 | >100 | |
| AB-3-33 | 6.25 | 9.38[a] | 3.13 | >100 | >100 | |
| AB-3-35 | >100 | >100 | >100 | >100 | >100 | 34.5 |
| AB-3-38 | >100 | >100 | >100 | >100 | >100 | |
| AB-3-46 | 3.13 | 4.69[a] | 2.35[a] | 37.5 | >100 | |
| AB-3-67 | 1.56 | 0.59[a] | 1.56 | 6.25 | >100 | 6.8 |
| AB-3-85 | 6.25 | >100 | 6.25 | >100 | >100 | 46.3 |
| AB-3-90 | 3.13 | 1.17[a] | 3.13 | 12.5 | >100 | 11.4 |
| AB-3-91 | 3.13 | 1.56 | 3.13 | 12.5 | >100 | 12.6 |
| AB-3-99 | 2.35[a] | 0.78 | 2.35[a] | 9.38[a] | >100 | |
| AB-3-102 | 2.35[a] | 1.17[a] | 1.17[a] | 12.5 | >100 | |
| AB-3-113 | 3.13 | 2.35[a] | 1.56 | 18.75[a] | >100 | 13.4 |
| AB-3-117 | 6.25 | 3.13 | 2.35[a] | 25 | >100 | 14.2 |
| QAC-10 | 3.13 | 2.35[a] | 2.35[a] | 6.25 | 9.38[a] | 7.92 |
| AB-3-64/JH-2d | 25 | 9.38[a] | 50 | >100 | >100 | >100 |
| AB-2-146 | 6.25 | 3.13 | 2.35[a] | >100 | >100 | |
| AB-3-75 | >100 | >100 | >100 | >100 | >100 | |

TABLE 1B

Antibacterial Activity and Hemolysis of Exemplary Compounds, Showing Minimum inhibitory concentration (MIC) against (Clinical isolates). (Concentrations are reported in µM).

| Compound | S. aureus 29213 | MRSA-2 | MRSA-1 | SA-129 | SA-147 | SA-138 | SA-156 | MRSA BAA-44 | MRSA BAA-1707 |
|---|---|---|---|---|---|---|---|---|---|
| AG-3-101 | 1.56 | 1.17$^a$ | 1.56 | 1.56 | 1.56 | 1.56 | 1.56 | 1.17$^a$ | 0.78 |
| AB-2-147 | 4.69$^a$ | 3.13 | 6.25 | 4.69$^a$ | 4.69$^a$ | 6.25 | 6.25 | 4.69$^a$ | 2.35$^a$ |
| AB-2-154 | 3.13 | 2.35$^a$ | 4.69$^a$ | 3.13 | 2.35$^a$ | 3.13 | 2.35$^a$ | 2.35$^a$ | 1.56 |
| AB-3-20 | 4.69$^a$ | 2.35$^a$ | 3.13 | 3.13 | 2.35$^a$ | 3.13 | 3.13 | 2.35$^a$ | 1.56 |
| AB-3-71 | 1.56 | 1.56 | 1.56 | 1.56 | 1.17$^a$ | 2.35$^a$ | 1.56 | 1.56 | 0.39 |
| AB-3-67 | 1.17$^a$ | 0.78 | 1.17$^a$ | 1.56 | 1.17$^a$ | 1.56 | 1.56 | 1.56 | 0.39 |
| AB-3-29 | 12.5 | 12.5 | 12.5 | 3.13 | 6.25 | 6.25 | 12.5 | 12.5 | 12.5 |
| AB-3-90 | 2.35$^a$ | 2.35$^a$ | 2.35$^a$ | 1.56 | 1.17$^a$ | 1.56 | 2.35$^a$ | 2.35 | 1.56 |
| AB-3-91 | 3.13 | 6.25 | 4.69$^a$ | 1.56 | 1.56 | 2.35$^a$ | 2.35$^s$ | 4.69$^a$ | 3.13 |
| AB-3-102 | 2.35$^a$ | 2.35$^a$ | 1.56 | 1.56 | 1.17$^a$ | 1.17$^a$ | 2.35$^s$ | 2.35$^a$ | 2.35$^a$ |
| AB-3-113 | 2.35$^a$ | 4.69$^a$ | 3.13 | 1.56 | 1.56 | 1.56 | 2.35$^s$ | 3.13 | 3.13 |
| AB-3-170 | 3.13 | 3.13 | | | | | | | 4.69$^a$ |
| AB-3-173 | 4.69$^a$ | 4.69$^a$ | | | | | | | 4.69$^a$ |
| AB-3-175 | 3.13 | 3.13 | | | | | | | 3.13 |
| AB-3-180 | 2.35$^a$ | 3.13 | | | | | | | 4.69$^a$ |
| QAC-10 | 4.69$^a$ | 2.35$^a$ | 3.13 | 2.35$^a$ | 3.13 | 2.35$^a$ | 2.35$^a$ | 2.35$^a$ | 1.56 |

Notes:
$^a$Midpoint value for a 3-fold range in independent experiments. All MIC values and haemolysis data were obtained from at least three independent experiments.

Figure 3A:
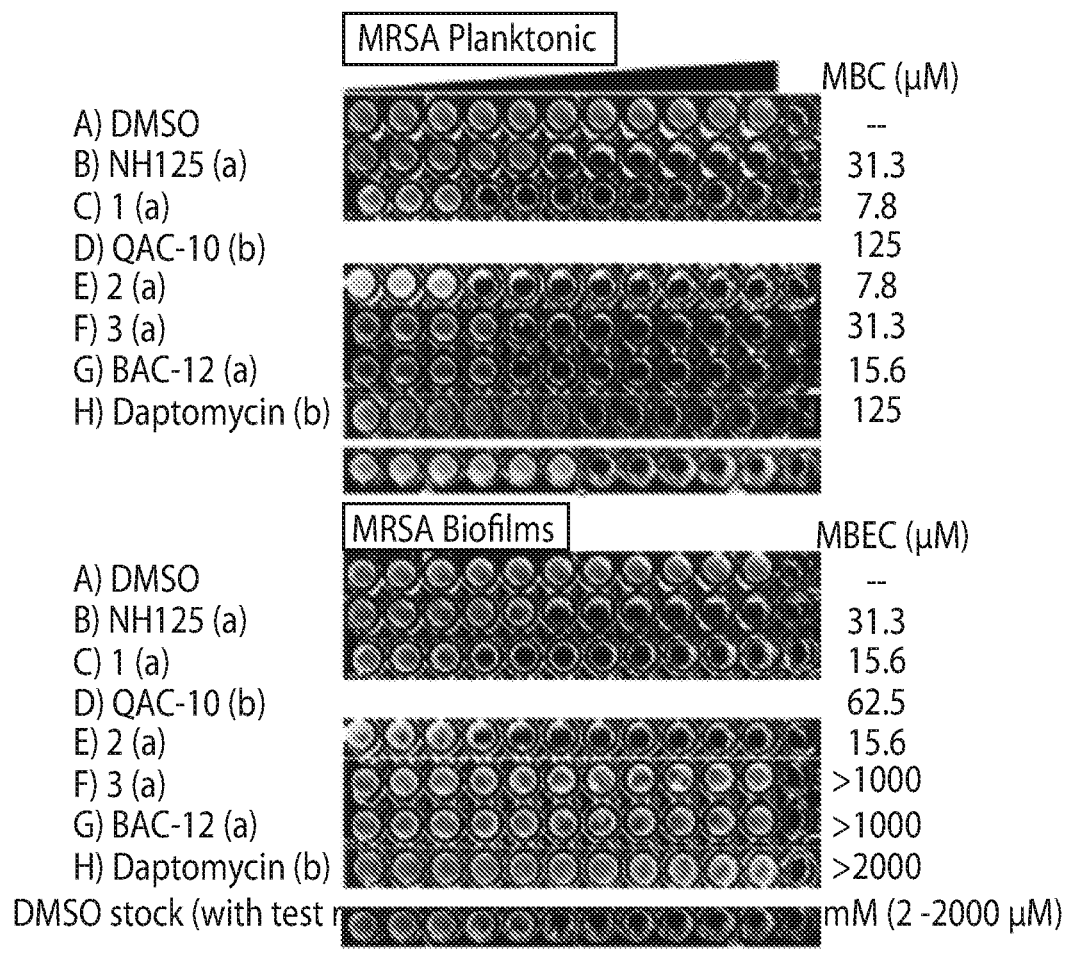
FIG. 3A. Image of Calgary Biofilm Device (CBD) assay of exemplary compounds (NH125, 1, 2, 3, QAC-10, BAC-12, and daptomycin) tested against MRSA BAA-1707.

Then, attention was turned to biofilm eradication assays using the Calgary Biofilm Device[7,15,35] and tested our panel of membrane-active compounds against MRSA BAA-1707, MRSE ATCC 35984 and VRE ATCC 700221 (Table 2). Using a Calgary Biofilm Device, bacterial biofilms are established on pegs suspended to the bottom of a 96-well plate lid. Following biofilm establishment on lid pegs, lids are then transferred to new 96-well plates containing serial dilutions of test compound and allowed to incubate. After compound treatment, 96-well plate lids with pegs are once again transferred to 96-well plates containing fresh media. During this final phase of the assay, viable biofilms will grow and disperse planktonic cells into the media where they will grow and give a turbid well result. Conversely, wells that have no growth are a result of pegs that had eradicated bacterial biofilms. The lowest concentration at which no turbidity is observed is the minimum biofilm eradication concentration (MBEC). Using the Calgary Biofilm Device, both minimum biofilm eradication concentrations and minimum bactericidal concentrations (MBC) for planktonic bacterial can be determined using one assay from a single bacterial culture (FIG. 3A). Effective biofilm-eradicating agents typically have MBEC:MBC ratios of 1-3 for biofilm:planktonic killing.[7,15]

Tables 2 and 2A below show biofilm eradication from Calgary Biofilm Device (CBD) assays for exemplary compounds.

TABLE 2

Summary of biofilm eradication from CBD assays. All values are reported in µM.

| Compound | MRSA BAA-1707 MIC | MRSA BAA-1707 MBC/MBEC | MRSE 35984 MIC | MRSE 35984 MBC/MBEC | VRE 700221 MIC | VRE 700221 MBC/MBEC |
|---|---|---|---|---|---|---|
| NH125 | 2.35$^a$ | 23.5$^a$/46.9$^a$ | 4.69$^a$ | 15.6/5.9$^a$ | 3.13 | 59$^a$/11.7$^a$ |
| 1 | 1.56 | 11.7$^a$/23.5$^a$ | 1.17$^a$ | 5.9$^a$/11.7$^a$ | 3.13 | 4.69$^a$/2.35$^a$ |
| 2 | 3.13 | 78$^b$/11.7$^a$ | 2.35$^a$ | 5.9$^a$/5.9$^a$ | 1.56 | 3.0$^a$/5.9$^a$ |
| 3 | 12.5 | 62.5/>1000 | 9.38$^a$ | 5.9$^a$/7.8 | 50 | 46.9$^a$/46.9$^a$ |
| QAC-10 | 4.69$^a$ | 93.8$^a$/93.8$^a$ | 2.35$^a$ | 31.3/31.3 | 2.35$^a$ | 3.0$^a$/3.0$^a$ |
| BAC-12 | 6.25 | 15.6/>1000 | 3.13 | 11.7$^a$/>2000 | 25 | 31.3/23.5$^a$ |
| Daptomycin | 3.13 | 125/>2000 | 3.13 | 31.3/>2000 | 125 | 375$^a$/93.8$^a$ |

Notes:
$^a$Midpoint value for a 2-fold range in independent experiments. All MIC, MBC, MBEC values were obtained from a minimum of three independent experiments.

TABLE 2A

Summary of biofilm eradication activities for exemplary NH125 analogues and controls. All concentrations are reported in µM.

| Compound | MRSA-2 MIC | MRSA-2 MBC/MBEC | MRSA BAA-1707 MIC | MRSA BAA-1707 MBC/MBEC | MRSE 35984 MIC | MRSE 35984 MBC/MBEC | VRE MIC | VRE MBC/MBEC |
|---|---|---|---|---|---|---|---|---|
| AB-2-147 | 4.69$^a$ | 62.5$^b$/46.9$^a$ | 2.35$^a$ | 23.5$^a$/46.9$^a$ | 4.69$^a$ | 15.6/5.85$^a$ | 3.13 | 5.85$^a$/11.7$^a$ |

TABLE 2A-continued

Summary of biofilm eradication activities for exemplary NH125 analogues and controls. All concentrations are reported in µM.

| Compound | MRSA-2 MIC | MRSA-2 MBC/MBEC | MRSA BAA-1707 MIC | MRSA BAA-1707 MBC/MBEC | MRSE 35984 MIC | MRSE 35984 MBC/MBEC | VRE MIC | VRE MBC/MBEC |
|---|---|---|---|---|---|---|---|---|
| AB-3-20 | 2.35$^a$ | 93.8$^a$/93.8$^a$ | 1.56 | — | 1.17$^a$ | 11.7$^a$/11.7$^a$ | 1.56 | 5.85$^a$/11.7$^a$ |
| AB-3-71 | 1.17$^a$ | 11.7$^a$/23.5$^a$ | 0.39 | 11.7$^a$/31.3 | 1.17$^a$ | 3.0$^a$/3.0$^a$ | 2.35$^a$ | 3.9/3.9 |
| AB-3-67 | 1.56 | 11.7$^a$/31.3 | 0.39 | 23.5$^a$/46.9$^a$ | 0.59$^a$ | 3.9/3.9 | 1.56 | 3.0$^a$/3.9 |
| AB-3-17 | 3.13 | 62.5/62.5 | 4.69$^a$ | 62.5$^b$/93.8$^a$ | 3.13 | 23.5$^a$/23.5$^a$ | 1.56 | 2.0/3.0$^a$ |
| AB-3-29 | 3.13 | 250/188$^a$ | 9.38$^a$ | — | 3.13 | — | 1.56 | — |
| AB-3-91 | 3.13 | 31.3$^b$/31.3 | 3.13 | 11.7$^a$/23.5$^a$ | 1.56 | — | 3.13 | — |
| AB-3-85 | 6.25 | 375$^a$/>1000 | 25 | — | >100 | — | 6.25 | — |
| AB-3-90 | 3.13 | 11.7$^a$/15.6 | 1.56 | 11.7$^a$/23.5$^a$ | 1.17$^a$ | 5.85$^a$/11.7$^a$ | 3.13 | 4.69$^a$/3.0$^a$ |
| AB-3-113 | 3.13 | 11.7$^a$/15.6 | 3.13 | 7.8$^b$/11.7$^a$ | 2.35$^a$ | 5.85$^a$/5.85$^a$ | 1.56 | 3.0$^a$/5.85$^a$ |
| AB-3-117 | 6.25 | 15.6$^b$/31.3 | 3.13 | — | 3.13 | — | 2.35$^a$ | — |
| AB-3-64 | 25 | 31.3$^b$/>1000 | 12.5 | 62.5/>1000 | 9.38$^a$ | 5.85$^a$/7.8 | 50 | 46.9$^a$/46.9$^a$ |
| QAC-10 | 2.35$^a$ | 31.3$^b$/125 | 4.69$^a$ | 93.8$^a$/93.8$^a$ | 2.35$^a$ | 31.3/31.3 | | 3.0$^a$/3.0$^a$ |

Figure 3B:
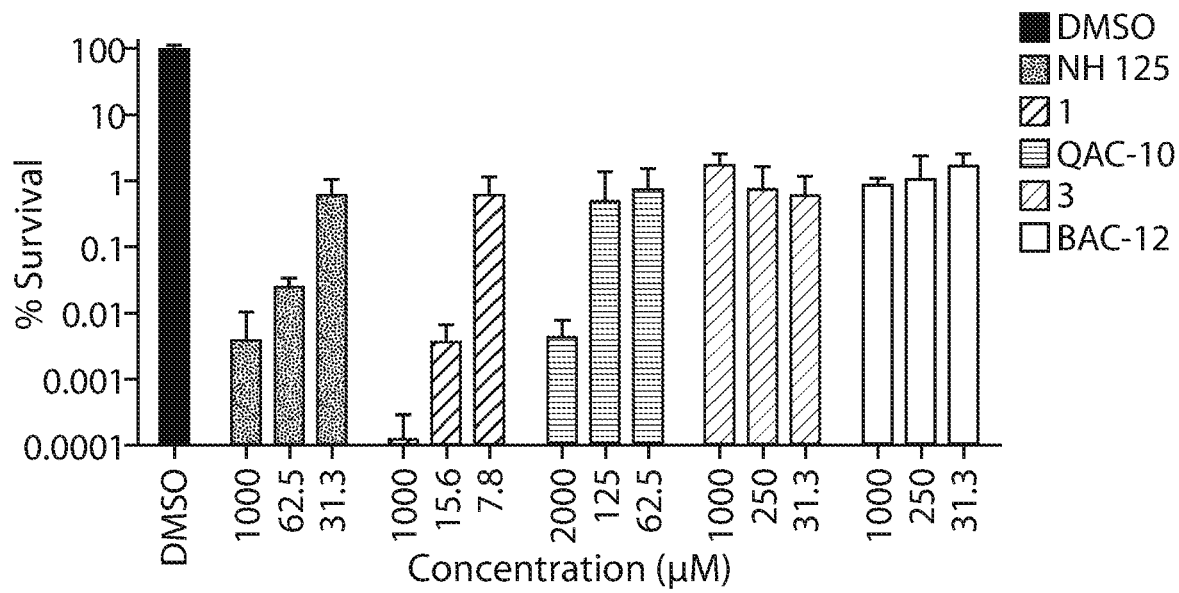
FIG. 3B. Viable MRSA BAA-1707 biofilm cells from colony counts of CBD pegs.
Figure 4:
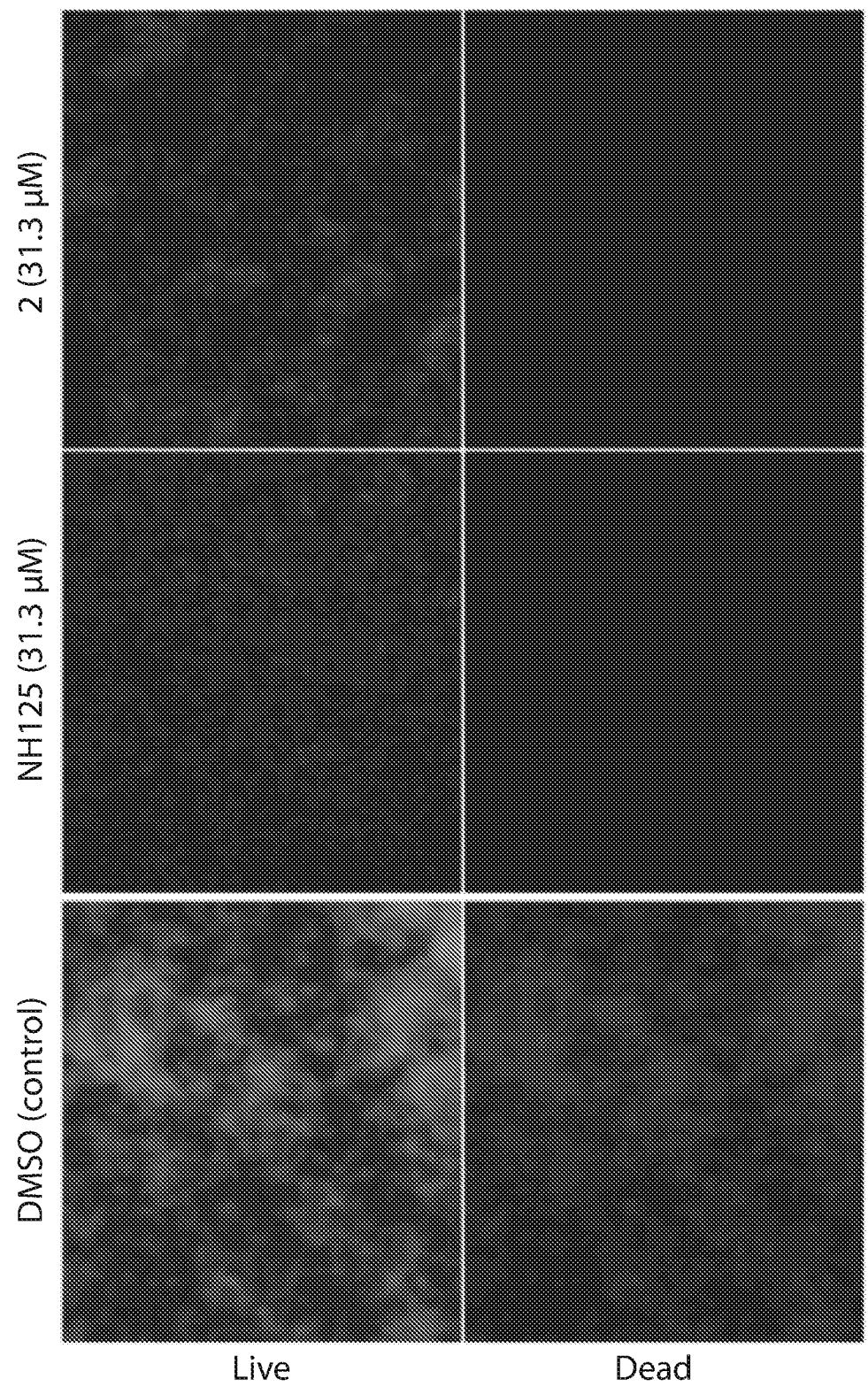
FIG. 4. Live/Dead stain of MRSA BAA-1707 biofilms 24 hours after treatment with vehicle (DMSO), NH125, and 2. Fluorescence images show potent clearance of MRSA biofilms for NH 125 and 2.

Notes:
$^a$Midpoint value for a 3-fold range in independent experiments. (—) means not tested. All MIC values were obtained from at least three independent experiments Analogues 1 and 2 were very potent analogues against MRSA BAA-1707 biofilms and reported minimum biofilm eradication concentration (MBEC) values of 23.5 µM and 11.7 µM, respectively (Table 2). The biofilm-killing activities of 1 and 2 were 2- to 4-fold more potent than NH125 (MBEC=46.9 µM) and 4- to 8-fold more potent than QAC-10 (MBEC=93.8 µM) against MRSA BAA-1707 (FIG. 3A). Interestingly, 3, BAC-12 and daptomycin all reported MBECs >1,000 µM, despite reporting MBC values of 15.6-125 µM against planktonic cells in the same assays. When viable biofilm cell counts were assessed using the Calgary Biofilm Device, the entire panel reduced MRSA BAA-1707 2-logs at sub-MBEC values (FIG. 3B). NH-125 and 1 showed a clear dose-response in these assays while 1 reduced viable MRSA BAA-1707 biofilm cells by >4-logs at 15.6 µM (MBEC=23.5 µM), which was a more dramatic biofilm killing effect than NH-125 at 62.5 (MBEC=46.9 µM; 3 to 4-log reduction of viable biofilm cells). Live/Dead staining of MRSA BAA-1707 biofilms treated with NH-125 and 2 show that these analogues have an effective clearance of established biofilms at 31.3 µM (FIG. 4).

The Calgary Biofilm Device (CBD) assay can be used to determine the planktonic and biofilm killing effects of antibacterial agents from a single bacterial culture. FIG. 3A shows a CBD assay image against MRSA BAA-1707. FIG. 3B shows the viable MRSA BAA-1707 biofilm cells from colony counts of CBD pegs.

A similar trend in biofilm eradication was observed against MRSE ATCC 35984 although N-arylated NH 125 analogues 1 and 2 did not demonstrate improvements in potencies against MRSE biofilms compared to NH125 (MBECs 5.9-11.7 µM). Interestingly, 3 and QAC-10 demonstrated potent biofilm eradication activities against MRSE biofilms with MBEC values of 7.8 µM and 31.3 µM, respectively. Against VRE biofilms, 1 and QAC-10 proved to be the most potent reporting MBEC values of 2.35 µM (>4-fold more potent than NH-125) and 3.0 µM, respectively. See FIG. 4.

Example 3. Evaluation of Exemplary Compounds in Kinetic Killing Experiments

Figure 5:
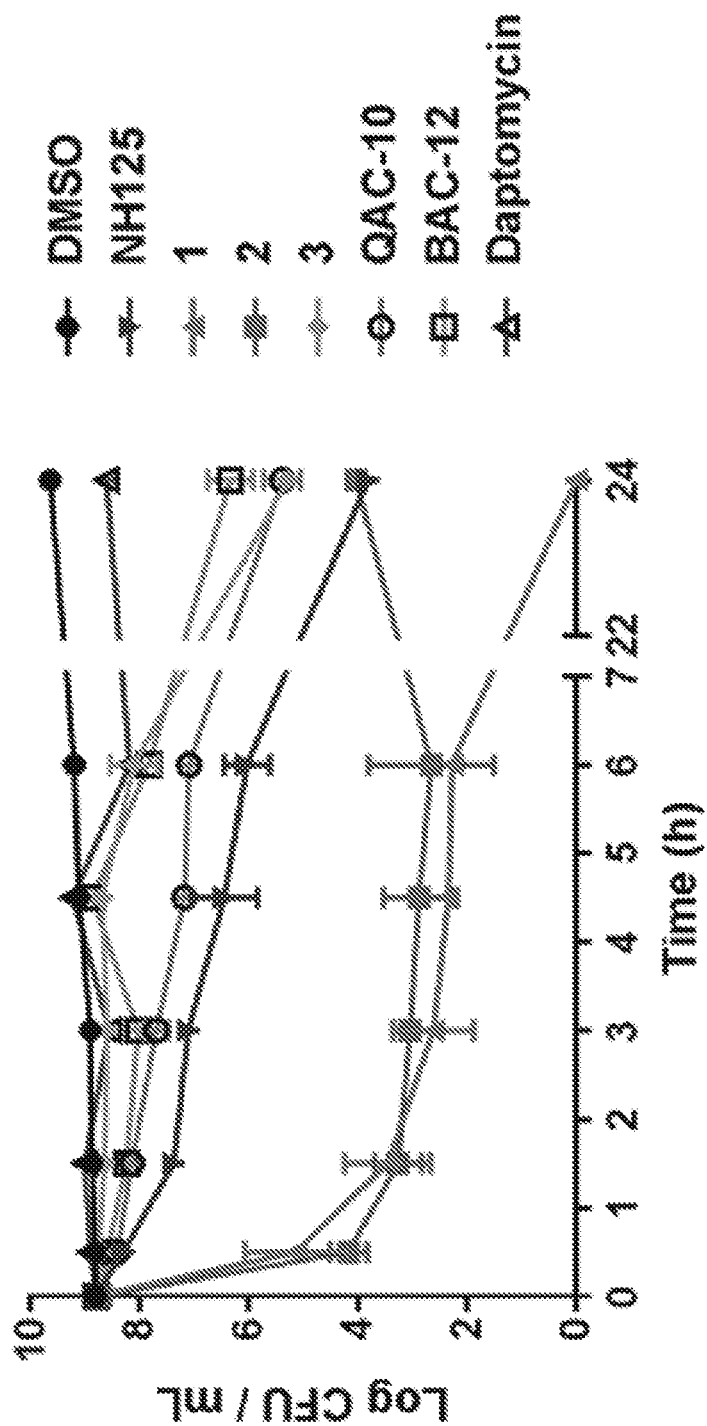
FIG. 5. Experimental results for the killing kinetics of MRSA BAA-1707 stationary cultures, which are highly populated with persister cells. All compounds were tested at 50 μM from three independent experiments.
Figure 6A:
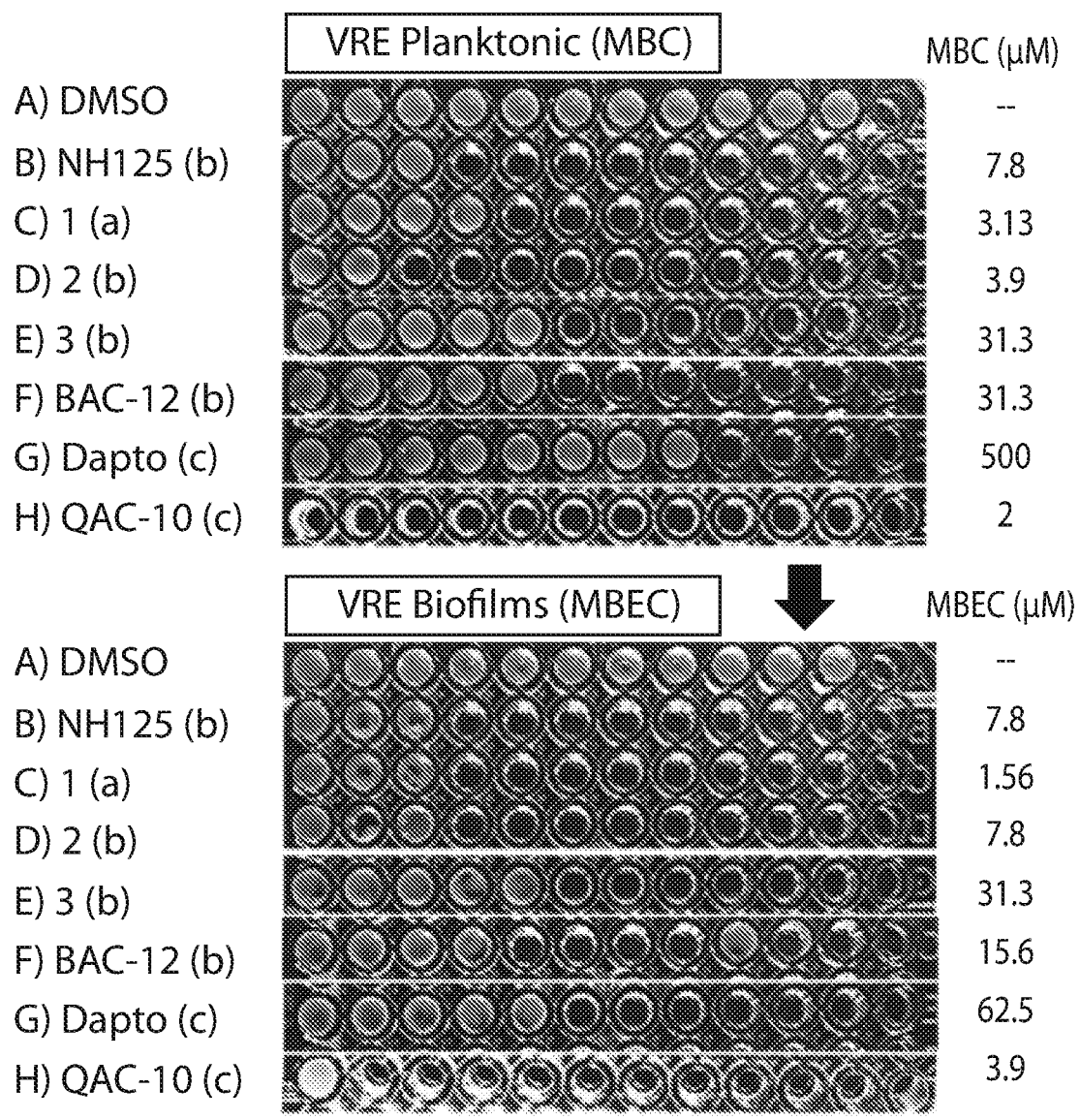
FIG. 6A. Image of Calgary Biofilm Device (CBD) Assay with Membrane-Active Panel of exemplary compounds (NH125, 1, 2, 3, QAC-10, BAC-12, and daptomycin ("dapto")) tested against VRE Biofilms (compound concentration increases left to right; 2-fold serial dilutions used to test compounds).
Figure 6B:
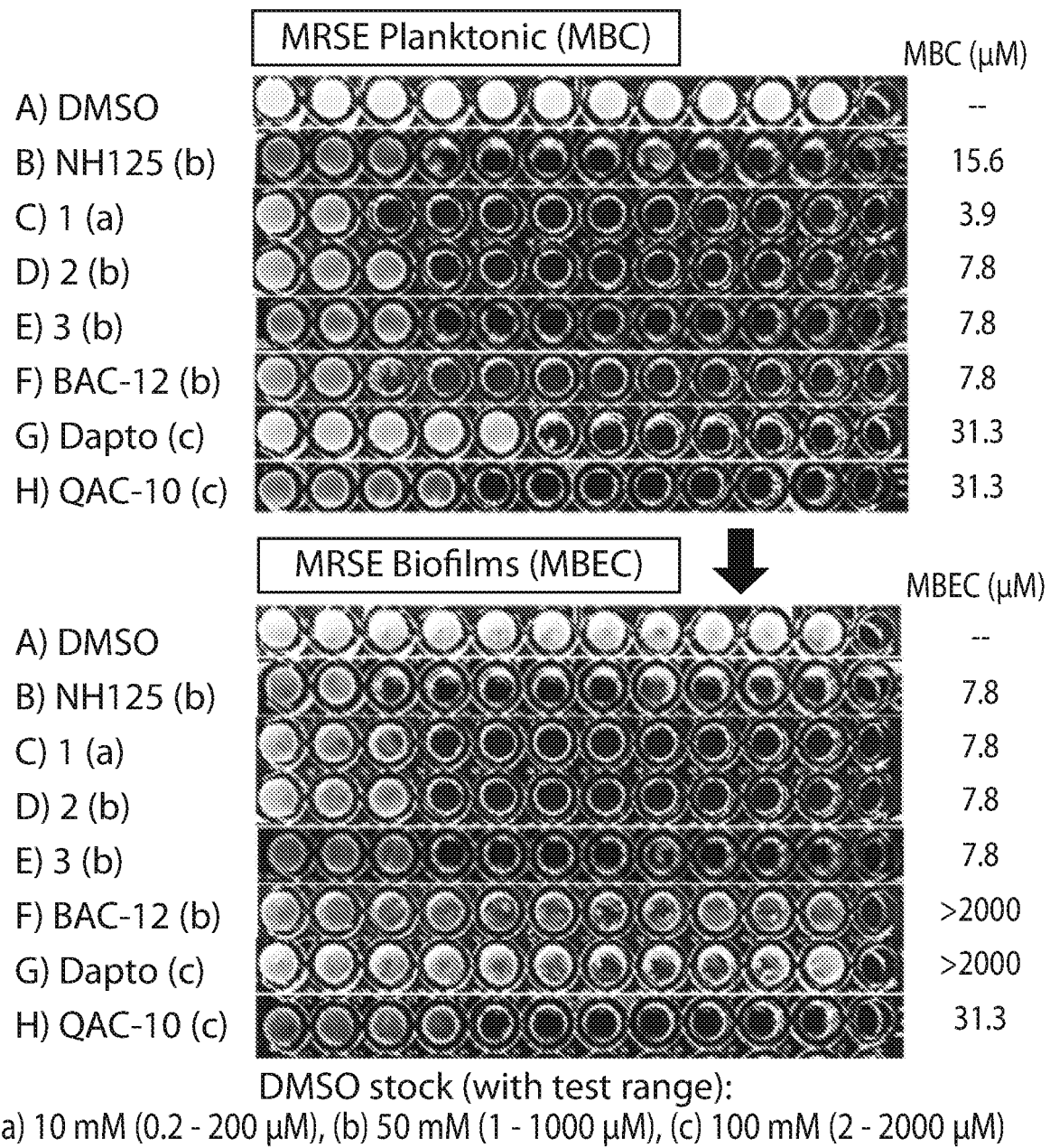
FIG. 6B. Image of Calgary Biofilm Device (CBD) Assay with Membrane-Active Panel of exemplary compounds (NH125, 1, 2, 3, QAC-10, BAC-12, and daptomycin ("dapto")) tested against VRE Biofilms (compound concentration increases left to right; 2-fold serial dilutions used to test compounds).
Figure 7A:
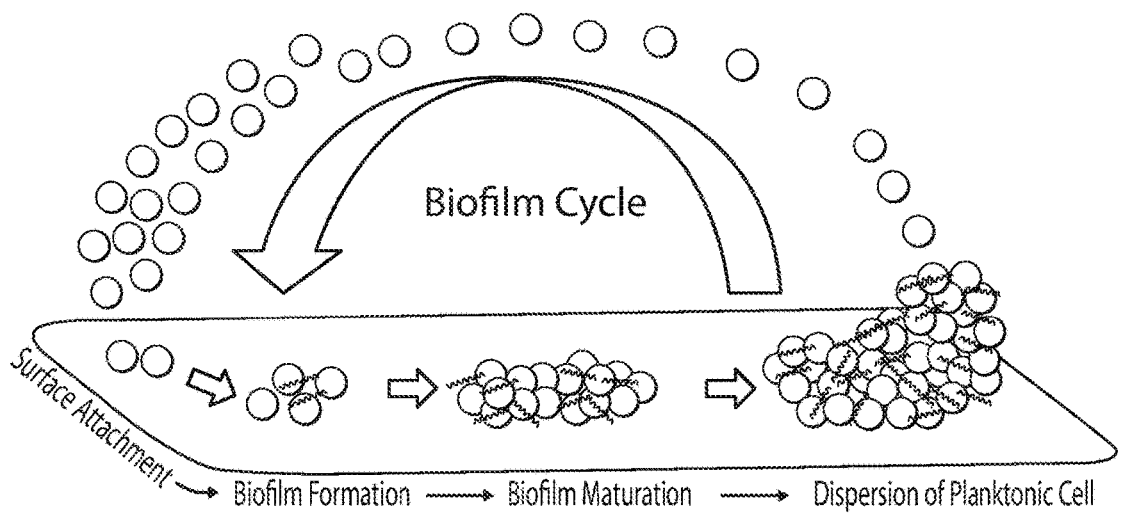
FIG. 7A. Biofilm cycle.
Figure 7B:
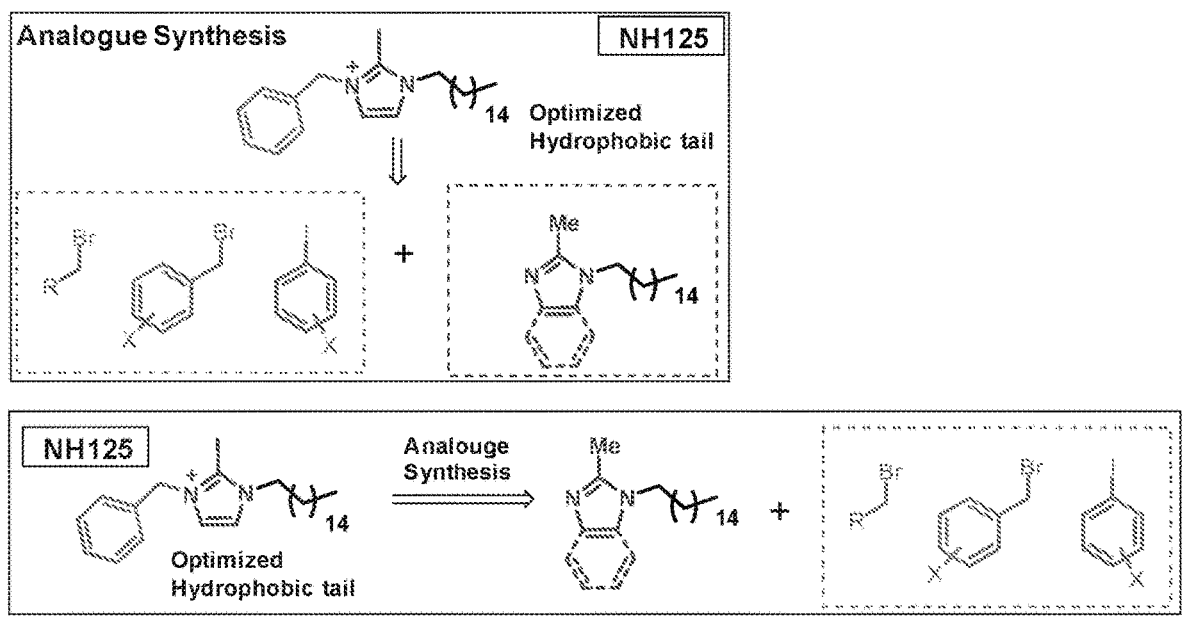
FIG. 7B. Synthetic scheme for analogs of NH 125.
Figure 8:
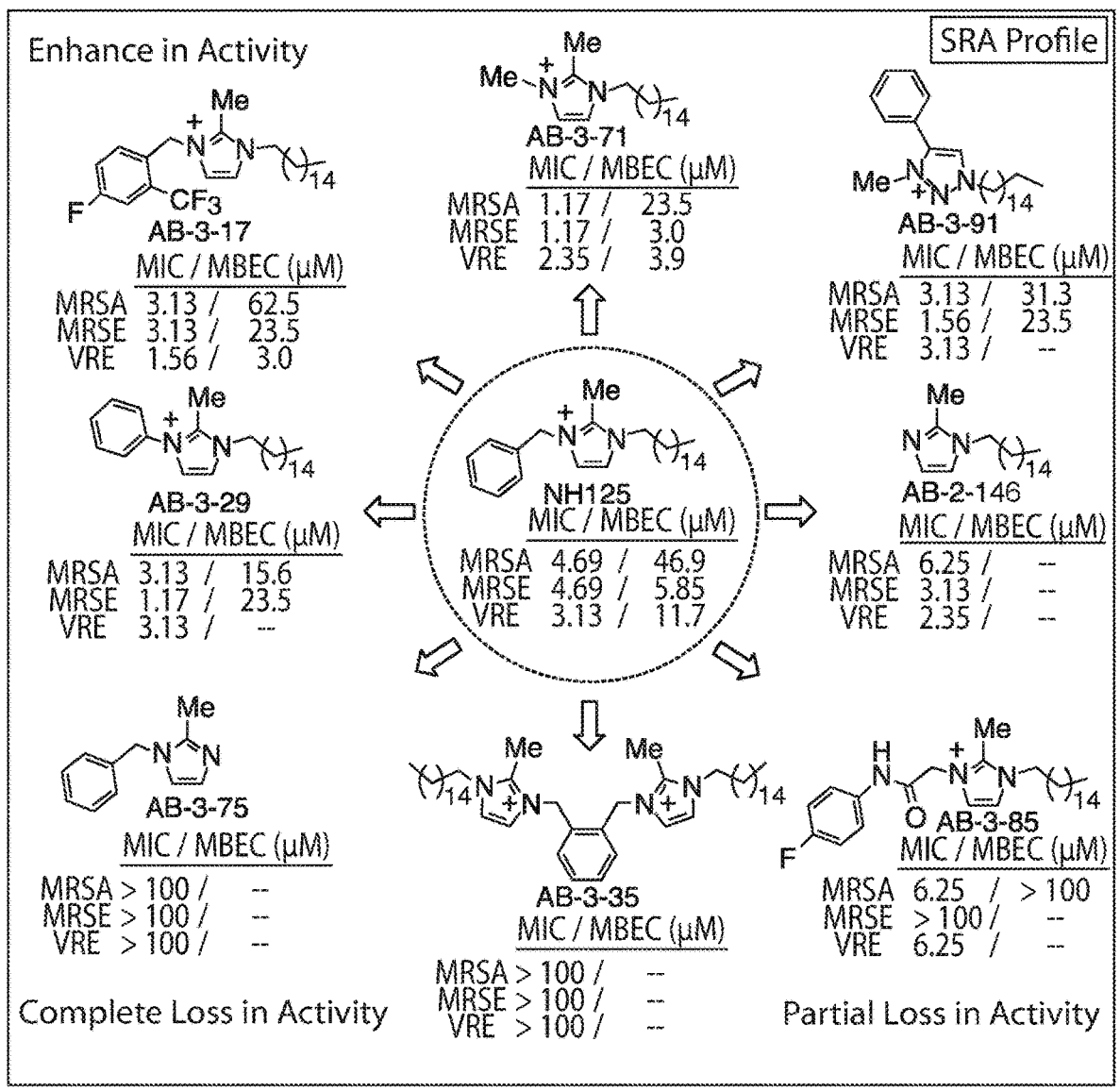
FIG. 8. Structure-activity relationship profile for exemplary compounds and analogs of compound NH 125.

The panel of membrane-active compounds was also evaluated head-to-head at 50 µM against MRSA BAA-1707 stationary cultures in kinetic killing experiments. Stationary cultures of S. aureus have elevated populations of metabolically dormant persister cells[36,37] and using this experiment, we could get multiple early time points to see if 1 and 2 were rapid killers of MRSA persister cells. The entire panel reduced the number of viable stationary cultures after 24 hours; however, 1 and 2 were the only compounds to elicit a rapid killing effect of 4-logs (99.99% killing of stationary cells) in 30 minutes and >5-logs after 90 minutes. The remaining compounds on the panel, showed very little activity at 30 minutes and only NH 125 showed ~1-log reduction of stationary MRSA cells after 90 minutes. The rapid killing of stationary MRSA cultures with 1 and 2 was sustained for 6 hours and no viable MRSA cells could be found at 24 hours upon treatment with 1 whereas there was a slight recovery of MRSA cultures after 24 hours with 2. See FIG. 5.

Two new N-arylated NH 125 analogues 1 and 2, designed from NH 125, demonstrate broad-spectrum antibacterial activities against multiple pathogenic bacteria, including drug-resistant strains. Compounds 1 and 2 demonstrate potent hemolysis activity, similar to quaternary ammonium cationic agents (e.g., QAC-10), and eradicate MRSA, MRSE and VRE biofilms with the most potent activity in a panel of diverse membrane-active agents. Interestingly, 1 and 2 were found to be rapid killers of MRSA persister cells in stationary cultures. N-Arylated NH 125 analogues are promising agents for the development of new disinfectants and antiseptics to effectively eradicate bacteria, biofilms and persister cells.

Example 4. Evaluation of Exemplary Compounds in Bacterial and Fungal Minimum Inhibitory Concentration (MIC) Assays, and Kinetic Killing Experiments Bacterial Minimum Inhibitory Concentration (MIC) Susceptibility Assay (in 96-Well Plate)

The minimum inhibitory concentration (MIC) for each compound was determined by the broth microdilution method as recommended by the Clinical and Laboratory Standards Institute (CLSI).[6] In a 96-well plate, eleven two-fold serial dilutions of each compound were made in a final volume of 100 µL Luria Broth. Each well was inoculated with ~$10^5$ bacterial cells at the initial time of incubation, prepared from a fresh log phase culture ($OD_{600}$ of 0.5 to 1.0 depending on bacterial strain). The MIC was defined as the lowest concentration of test compound that prevented bacterial growth after incubating 16 to 18 hours at 37° C. The concentration range tested for each compound during this study was 0.10 to 100 µM. DMSO served as our vehicle and negative control in each microdilution MIC assay. DMSO was serially diluted with a top concentration of 1% v/v. All MIC values were obtained from a minimum of three independent experiments.

Figure 9:
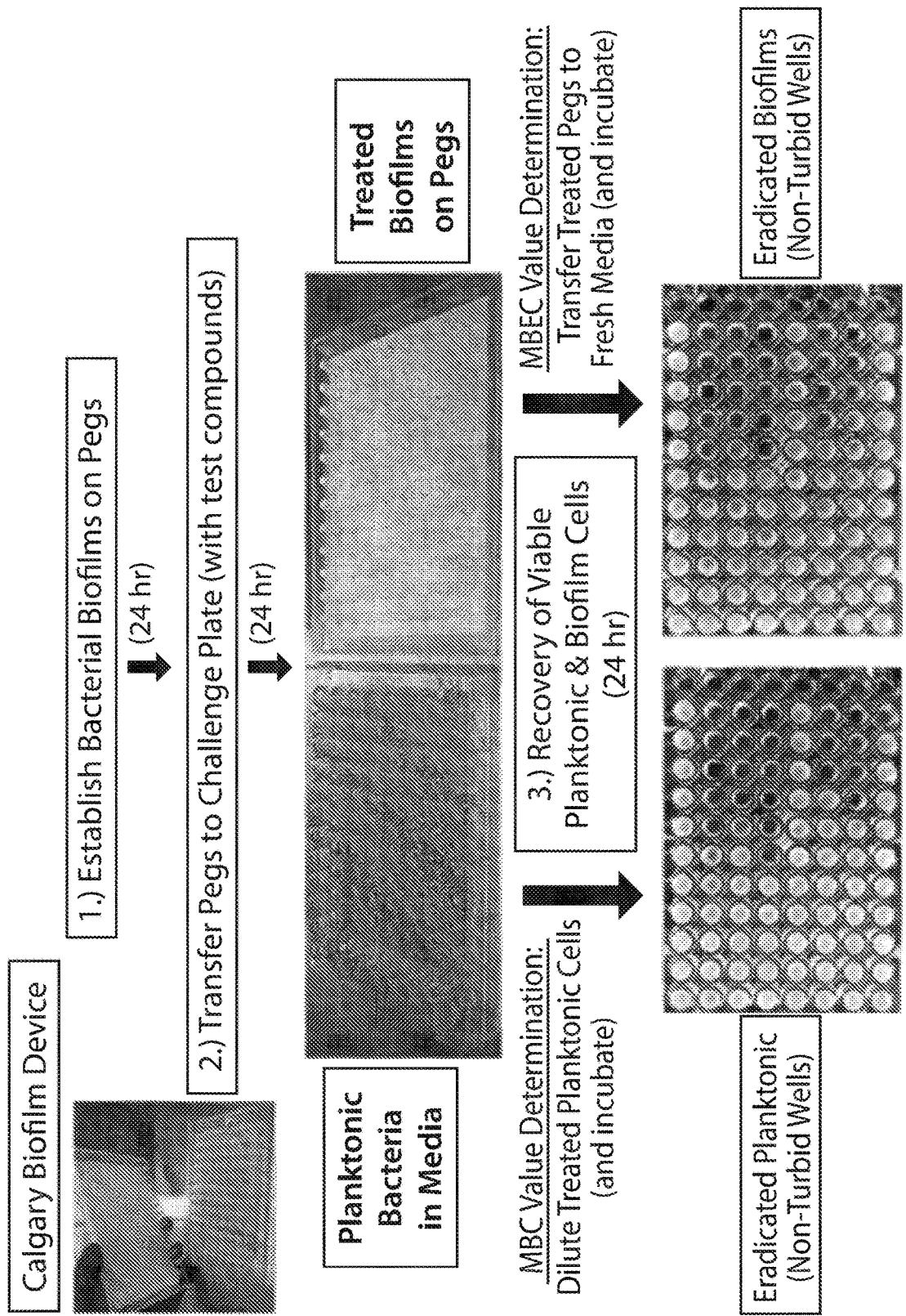
FIG. 9. Determination of minimum bactericidal concentrations (MBC) and minimum biofilm eradication concentrations (MBEC) using the Calgary Biofilm Device.
Figure 10:
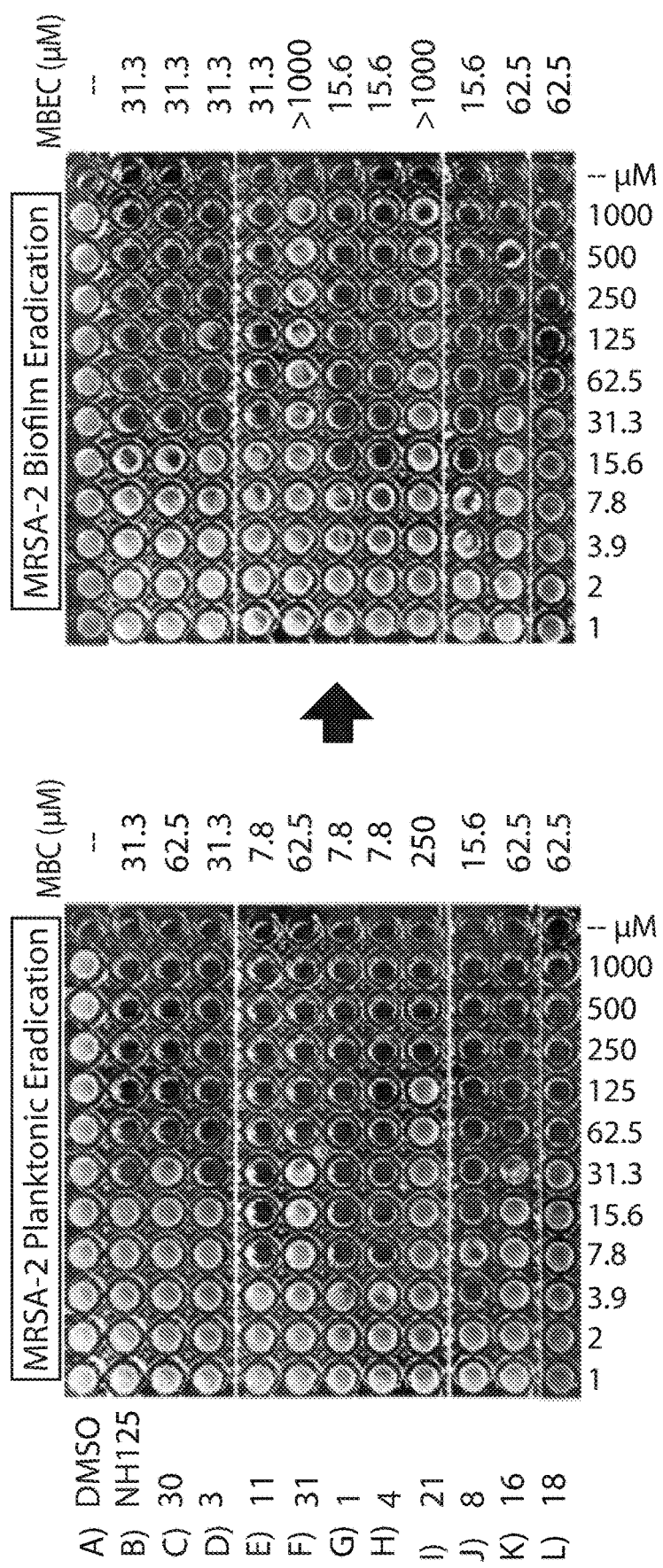
FIG. 10. MRSA-2 biofilm eradication (CBD assay).
Figure 11:
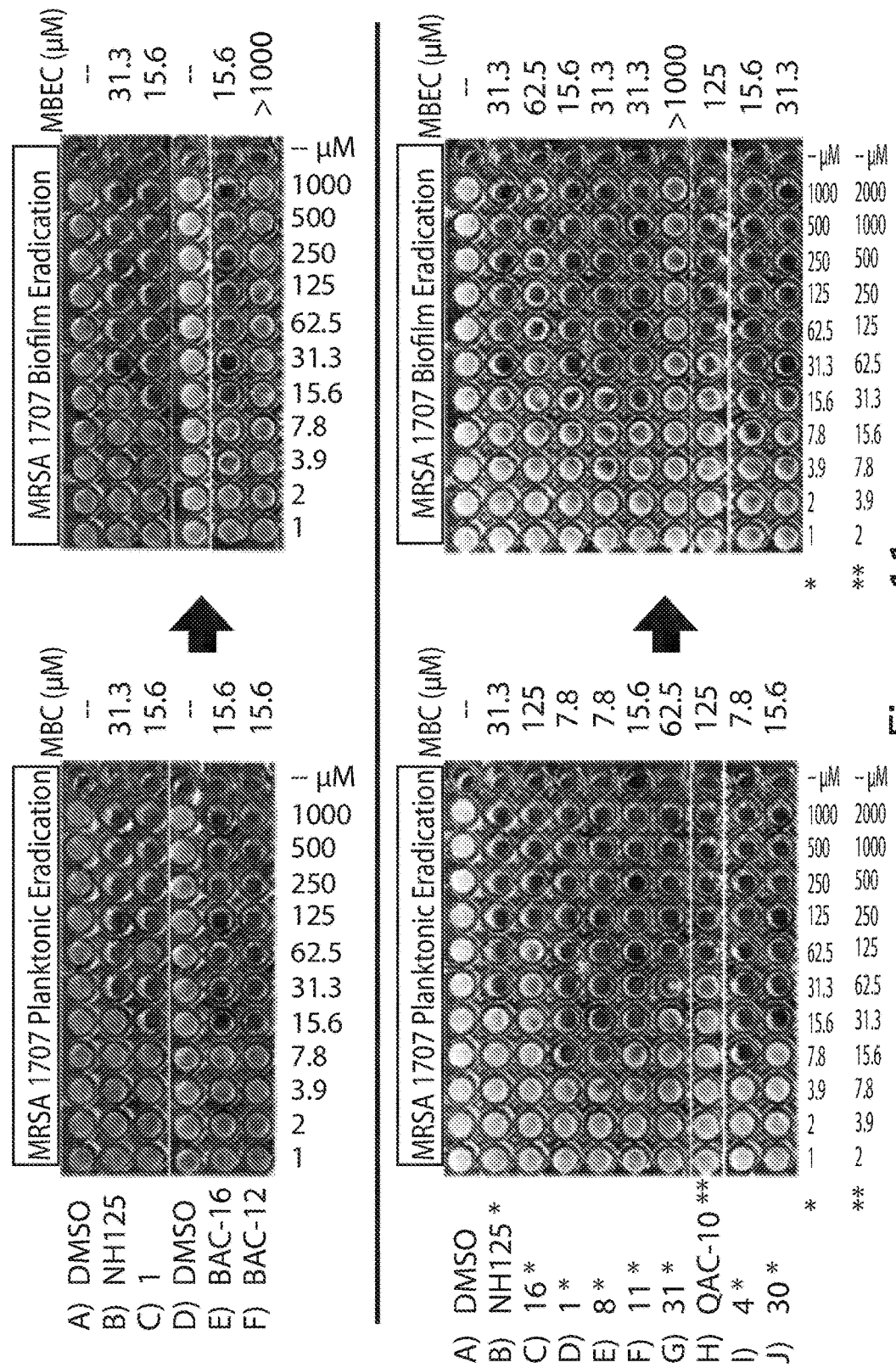
FIG. 11. MRSA BAA-1707 biofilm eradication (CBD assay).
Figure 12:
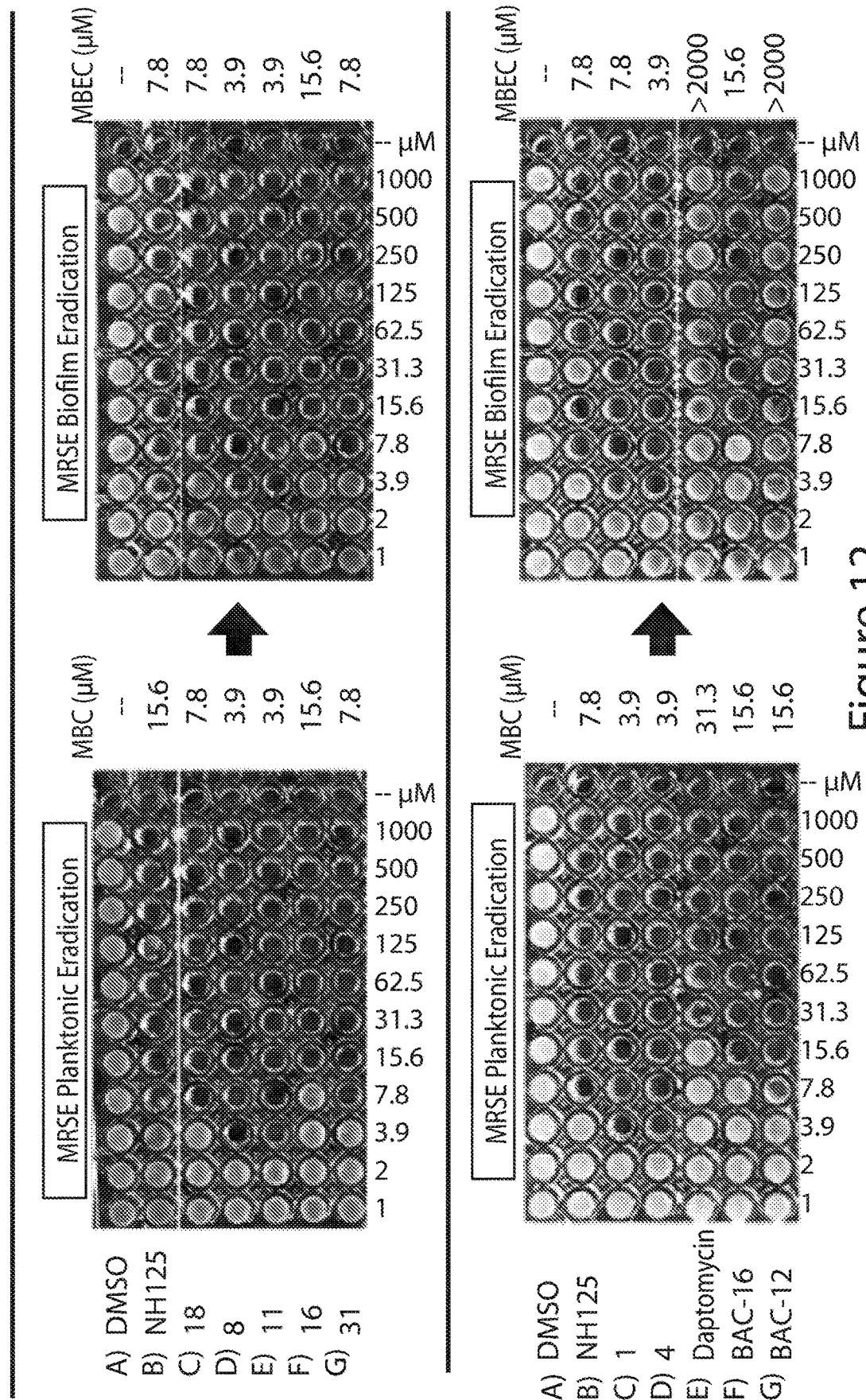
FIG. 12. *S. epidermidis* (MRSE 35984) biofilm eradication (CBD assay).
Figure 13:
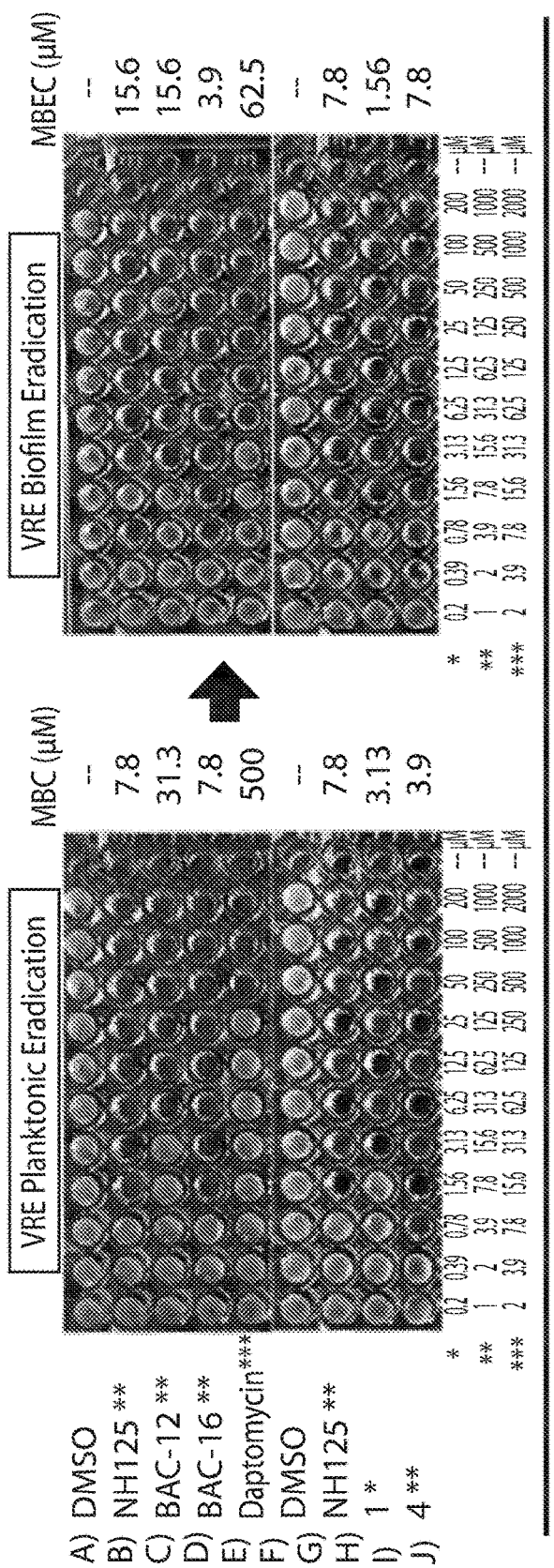
FIG. 13. *E. faecium* (VRE 100221) biofilm eradication (CBD assay).
Figure 13:
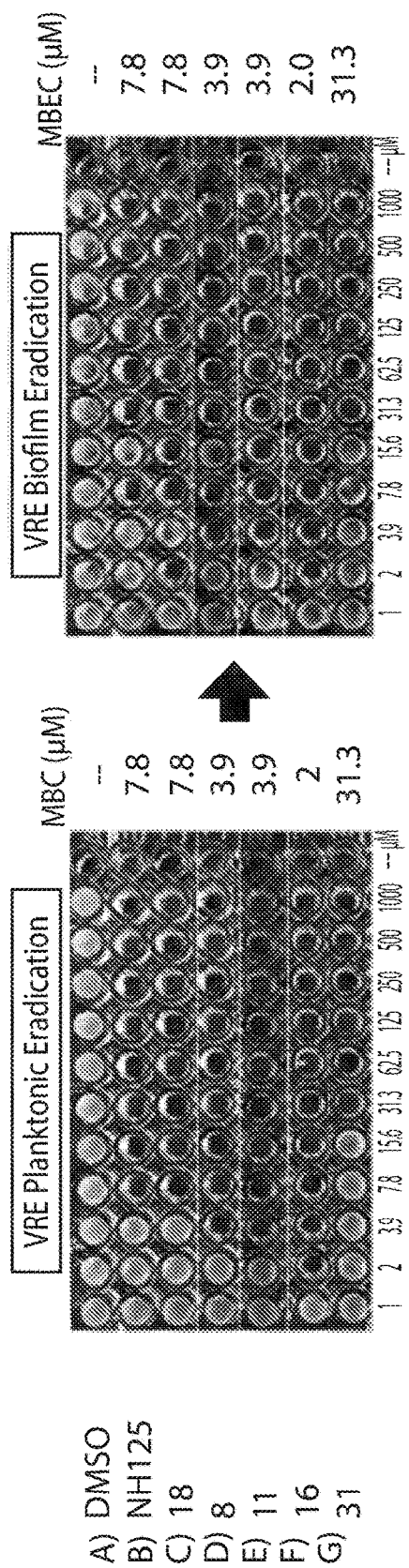
Figure 14:
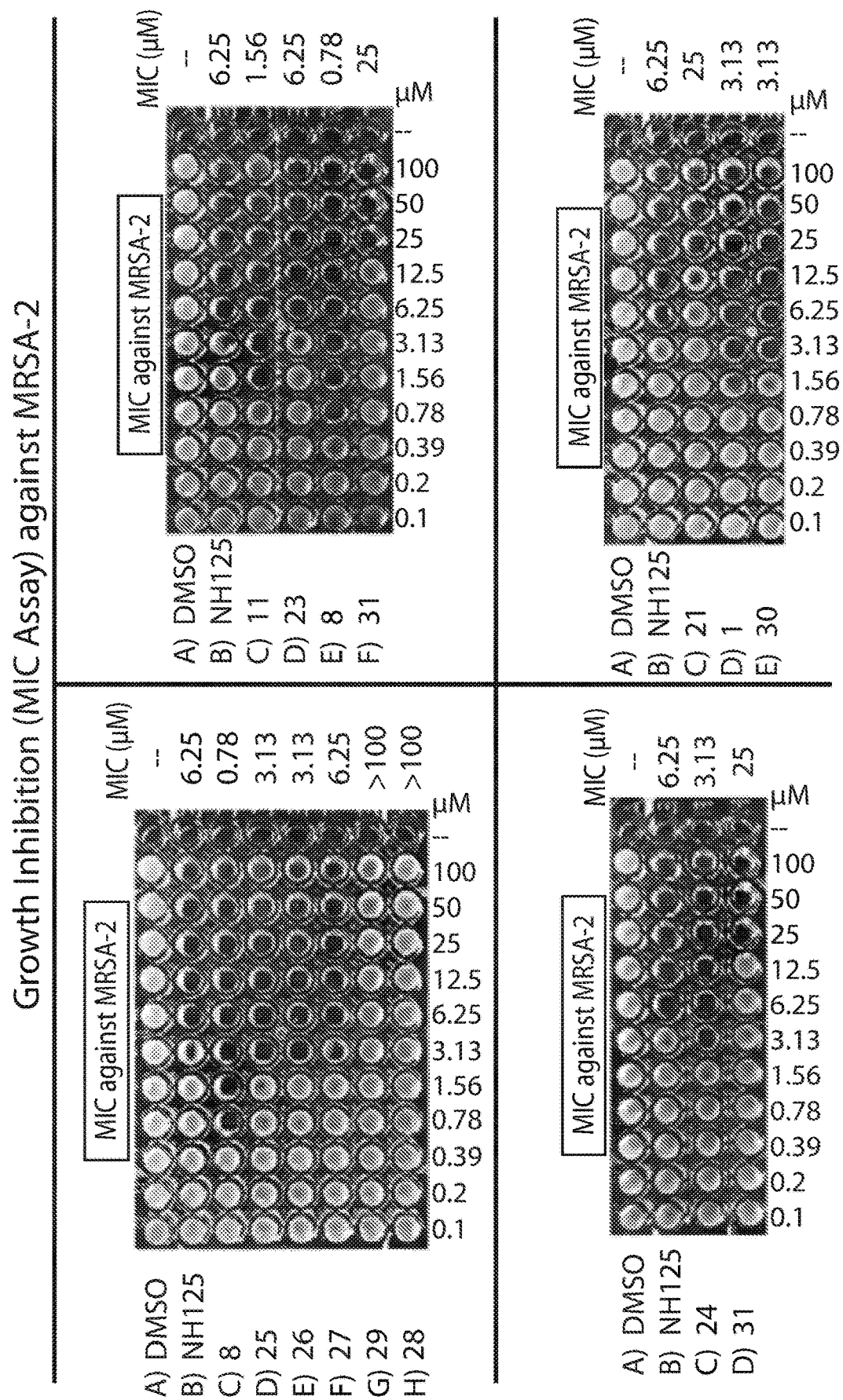
FIG. 14. Growth inhibition (MIC assay) against MRSA-2.
Figure 15:
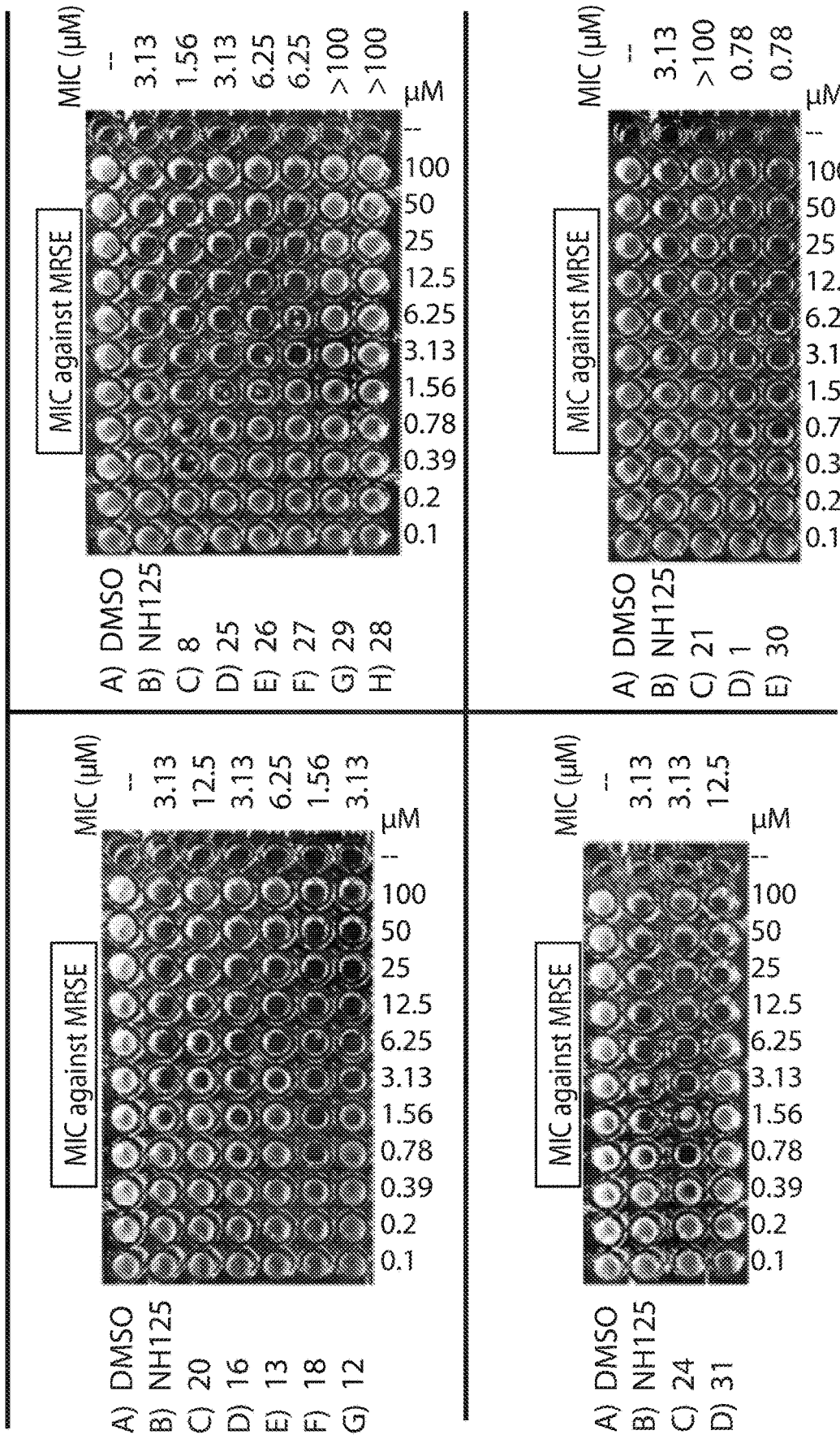
FIG. 15. Growth inhibition (MIC assay) against MRSE 35984.
Figure 16:
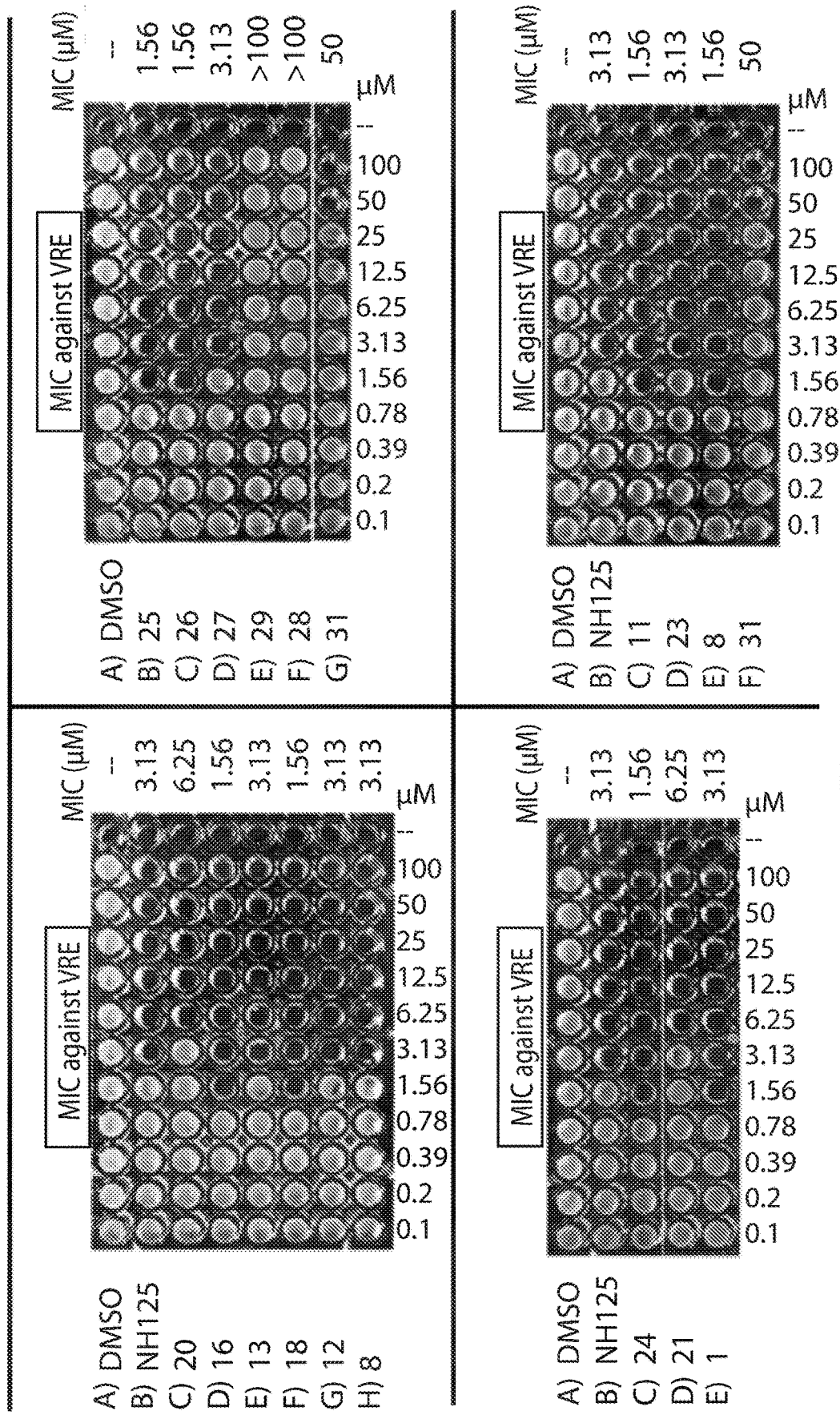
FIG. 16. Growth inhibition (MIC assay) against VRE 700221.

Fungal Minimum Inhibition Concentrations (MICs) were determined using standard microdilution methods according to the Clinical and Laboratory Standards Institute document M27-A3. Procedures are shown in FIG. 9. The test compound concentration ranged from 0.01 to 100 µM. Amphotericin B (AmB) and itraconazole (ITC) (Fisher Scientific) were included as positive controls. DMSO, the vehicle control, was used at ≤1% v/v for these experiments. The fungal M27-A3 standard MIC assay protocol requires the following inoculum preparation protocol: The organisms were cultured onto PDA medium at 35° C. The inoculum is prepared by picking five colonies from 24-hour old culture of *Candida* spp. or 48-hour old culture of *C. neoformans*. The inoculum was suspended in 5 ml of sterile water, the resulting suspension was vortexed for 15 seconds and the cell density adjusted (by adding more sterile water) to an $OD_{530}$=0.30, which yields a suspension of $1×10^6$ to $5×10^6$ cells per mL. The suspension was diluted 50 times and then 20 times using RPMI 1640 medium to obtain the two times test inoculum ($1×10^3$ to $5×10^3$ cells per mL). The following steps are the same with the standard bacterial MIC protocol using 96-well plates. NOTE: RPMI 1640 medium was used in the fungal MIC assay (for both cell inoculum and compound dilution). Assays are shown in FIGS. 10 to 16.

Table 4 provides a summary of antibacterial (MIC), antifungal (MIC) and haemolysis (HC50) studies with NH 125, analogues and other membrane-active antimicrobials

TABLE 3

Summary of antibacterial (MIC) assay for select compounds against a panel of *S. aureus* strains, including several clinical/MRSA isolates. All concentrations are reported as micromolar (µM).

| Compound | *S. aureus* 29213 | MRSA-2 | MRSA-1 | SA-129 | SA-147 | SA-138 | SA-156 | MRSA BAA-44 | MRSA BAA-1707 |
|---|---|---|---|---|---|---|---|---|---|
| NH125 | 4.69[a] | 3.13 | 6.25 | 4.69[a] | 4.69[a] | 6.25 | 6.25 | 4.69[a] | 2.35[a] |
| 1 | 2.35[a] | 3.13 | 2.35[a] | 1.56 | 1.17[a] | 1.56 | 2.35[a] | 2.35 | 1.56 |
| 2 | 3.13 | 3.13 | — | — | — | — | — | — | 4.69[a] |
| 4 | 2.35[a] | 4.69[a] | 3.13 | 1.56 | 1.56 | 1.56 | 2.35[a] | 3.13 | 3.13 |
| 5 | 4.69[a] | 4.69[a] | — | — | — | — | — | — | 4.69[a] |
| 6 | 3.13 | 3.13 | — | — | — | — | — | — | 3.13 |
| 7 | 2.35[a] | 3.13 | — | — | — | — | — | — | 4.69[a] |
| 8 | 1.56 | 1.17[a] | 1.56 | 1.56 | 1.17[a] | 2.35[a] | 1.56 | 1.56 | 0.39 |
| 9 | 2.35[a] | 2.35[a] | 1.56 | 1.56 | 1.17[a] | 1.17[a] | 2.35[a] | 2.35[a] | 2.35[a] |
| 11 | 1.17[a] | 1.17[a] | 1.17[a] | 1.56 | 1.17[a] | 1.56 | 1.56 | 1.56 | 0.39 |
| 17 | 3.13 | 2.35[a] | 4.69[a] | 3.13 | 2.35[a] | 3.13 | 2.35[a] | 2.35[a] | 1.56 |
| 18 | 4.69[a] | 2.35[a] | 3.13 | 3.13 | 2.35[a] | 3.13 | 3.13 | 2.35[a] | 1.56 |
| 25 | 12.5 | 3.13 | 12.5 | 3.13 | 6.25 | 12.5 | 12.5 | 12.5 | 12.5 |
| 30 | 3.13 | 6.25 | 4.69[a] | 1.56 | 1.56 | 2.35[a] | 2.35[a] | 4.69[a] | 3.13 |
| QAC-10 | 4.69[a] | 3.13 | 4.69[a] | 2.35[a] | 3.13 | 2.35[a] | 2.35[a] | 2.35[a] | 1.56 |

Note:
[a]Represents midpoint of a two-fold range in MIC assays. All MICs were obtained from a minimum of three independent experiments.

Fungal Minimum Inhibitory Concentration (MIC) Susceptibility Assay (in 96-Well Plate)

and controls. All MIC and HC50 values are recorded in micromolar (JIM) concentrations.

TABLE 4

Antibacterial (MIC), antifungal (MIC) and haemolysis (HC50) studies with Exemplary Compounds

| Agent | MRSA-2 | MRSA 1707 | MRSE 35984 | VRE 700221 | *A. bau.* 1794 | PAO1 | UAEC-1 | *K. pneu.* 13883 | *C. albicans* SC5314 | *C. neof* 66031 | RBC HC50 |
|---|---|---|---|---|---|---|---|---|---|---|---|
| NH125 | 4.69a | 2.35a | 4.69a | 3.13 | 37.5a | >100 | 18.8a | 18.8a | 3.13 | 3.13 | 12.3 |
| 1 | 3.13 | 1.56 | 1.17a | 3.13 | 12.5 | >100 | 6.25 | 6.25 | 3.13 | 6.25 | 7.8 |
| 2 | 3.13 | 4.69a | 1.56 | 1.56 | 18.8a | >100 | 12.5 | 12.5 | — | — | — |
| 3 | 6.25 | 3.13 | 3.13 | 2.35a | 25 | >100 | 12.5 | 50 | 3.13 | 6.25 | 14.2 |

TABLE 4-continued

Antibacterial (MIC), antifungal (MIC) and haemolysis (HC50) studies with Exemplary Compounds

| Agent | MRSA-2 | MRSA 1707 | MRSE 35984 | VRE 700221 | A. bau. 1794 | PAO1 | UAEC-1 | K. pneu. 13883 | C. albicans SC5314 | C. neof 66031 | RBC HC50 |
|---|---|---|---|---|---|---|---|---|---|---|---|
| 4 | 4.69a | 3.13 | 2.35a | 1.56 | 18.8a | >100 | 6.25 | 6.25 | 3.13 | 3.13 | 13.4 |
| 5 | 4.69a | 4.69a | — | — | 37.5a | >100 | — | — | — | — | — |
| 6 | 3.13 | 3.13 | 1.17a | 1.56 | 12.5 | >100 | 6.25 | 6.25 | — | — | — |
| 7 | 3.13 | 4.69a | — | — | 18.8a | >100 | — | — | — | — | — |
| 8 | 1.17a | 0.39 | 1.17a | 2.35a | 12.5 | >100 | 12.5 | 12.5 | 3.13 | 6.25 | 13.0 |
| 9 | 2.35a | 2.35a | 1.17a | 1.17a | 12.5 | >100 | — | — | — | — | — |
| 10 | 2.35a | — | 0.78 | 2.35a | 9.38a | >100 | — | — | — | — | — |
| 11 | 1.17a | 0.39 | 0.59a | 1.56 | 6.25 | >100 | 12.5 | 18.8a | 3.13 | 6.25 | 6.8 |
| 12 | 6.25 | — | 2.35a | 3.13 | >100 | >100 | — | — | — | — | — |
| 13 | 12.5 | — | 9.38a | 4.69a | >100 | >100 | — | — | — | — | — |
| 14 | 6.25 | — | 6.25 | 4.69a | >100 | >100 | — | — | — | — | — |
| 15 | 3.13 | — | 3.13 | 2.35a | >100 | >100 | — | — | — | — | — |
| 16 | 3.13 | 4.69a | 3.13 | 1.56 | >100 | >100 | — | — | — | — | 10.7 |
| 17 | 2.35a | 1.56 | 2.35a | 1.56 | >100 | >100 | — | — | — | — | — |
| 18 | 2.35a | 1.56 | 1.17a | 1.56 | 25 | >100 | — | — | — | — | 16.7 |
| 19 | 12.5 | — | 12.5 | 9.38a | >100 | >100 | — | — | — | — | — |
| 20 | 37.5 | — | 12.5 | 6.25 | >100 | >100 | — | — | — | — | — |
| 21 | 25 | 25 | >100 | 6.25 | >100 | >100 | — | — | — | — | 46.3 |
| 22 | >100 | — | >100 | >100 | >100 | >100 | — | — | — | — | — |
| 23 | 6.25 | — | 3.13 | 2.35a | >100 | >100 | — | — | — | — | — |
| 24 | 3.13 | — | 4.69a | 2.35a | 37.5a | >100 | — | — | — | — | — |
| 25 | 3.13 | 9.38a | 3.13 | 1.56 | >100 | >100 | — | — | — | — | 10.4 |
| 26 | 3.13 | — | 6.25 | 1.56 | >100 | >100 | — | — | — | — | — |
| 27 | 6.25 | — | 9.38a | 3.13 | >100 | >100 | — | — | — | — | — |
| 28 | >100 | >100 | >100 | >100 | >100 | >100 | >100 | >100 | 50 | 25 | — |
| 29 | >100 | >100 | >100 | >100 | >100 | >100 | >100 | >100 | — | — | 34.5 |
| 30 | 3.13 | 3.13 | 1.56 | 3.13 | 12.5 | >100 | — | — | — | — | 12.6 |
| 31 | 25 | 12.5 | 9.38a | 50 | >100 | >100 | 25 | 100 | — | — | >100 |
| BAC-12 | 6.25 | 6.25 | 3.13 | 25 | 75a | >100 | 50 | 75a | — | — | >100 |
| BAC-16 | 1.56 | 1.56 | 1.56 | 3.13 | 6.25 | >100 | 6.25 | 9.38a | 3.13 | 6.25 | 21.8 |
| QAC-10 | 3.13 | 4.69a | 2.35a | 2.35a | 6.25 | 9.38a | 12.5 | 25 | — | — | 7.9 |
| Dapto. | 4.69a | 3.13 | 3.13 | 125 | >100 | >100 | >100 | >100 | — | — | >100 |
| Amp. B | — | — | — | — | — | — | — | — | 0.78 | 0.1 | — |

Note:
[a] corresponds to a midpoint of a 2-fold range in values. Dapto. = Daptomycin. Amp. B = Amphotericin B. A. bau. = A. baumannii; K. pneu. = K. pneumoniae; C. neof. = C. neoformans; UAEC-1 = E. coli (clinical isolate). RBC = red blood cells. MIC = minimum inhibitory concentration (antibacterial activity). HC50 = concentration required to lyse 50% of red blood cells (haemolysis assays). All values are the result of a minimum of three independent experiments.

Minimum Fungicidal Concentration (MFC) Assay

For determination of minimum fungicidal concentrations (MFC), fungal cells from MIC assays are centrifuged, re-suspended in fresh RPMI 1640 medium, and then plated onto PDA or YPD agar plates. The plates were incubated at 35° C. Colonies were counted after 24 hours for Candida spp. and 48 hours for C. neoformans. The minimum fungicidal concentration (MFC) was defined as the lowest concentration of test compound that killed 99.9% of fungal cells compared to the DMSO control.

MTT Assay to Determine Minimum Biofilm Eradication Concentration (MBEC) in Fungal Strains Mature biofilms of C. albicans SC5314 and C. neoformans ATCC 66031 were formed in Corning 96-well flat-bottom plates using MT as previously described.[8] These organisms were cultured onto PDA or YPD agar medium at 37° C. One colony was picked from a 24-hour old culture of Candida spp. or 48-hour old culture of C. neoformans and added to YPD liquid medium for inoculation and cultured at 37° C. overnight. Cells were then washed with PBS (Phosphate-buffered saline (10 mM potassium phosphate, 150 mM NaCl, pH 7.0)) and standardized to $OD_{600}$=1.0. Microtiter wells were then treated with 50% FCS (Fetal calf serum) in PBS for at least 30 min at room temperature (FCS pre-treatment is not absolutely required for Candida spp.). The FCS was aspirated and microtiter wells were rinsed once with 200 μL PBS before 100 μL of the cell suspension was added to each microtiter well. The plate was then incubated statically at 37° C. for 2 hours. Non-adherent cells were then removed by aspiration and microtiter wells were washed with PBS twice to remove loosely associated cells. Biofilm growth was initiated by addition of 200 μL YNB supplemented with 0.5% w/v glucose to each well and subsequently incubated at 37° C. for 48 hours for Candida spp. or 72 hours for C. neoformans.

Biofilm Susceptibility was Measured Using Following Method:

The resulting cell culture was aspirated and wells were rinsed once with 200 μL PBS. Controls and compounds were diluted in YNB medium (200 μL) were added to microtiter wells. The plates were incubated at 37° C. for an additional 48 hours.

Biofilm Viability was Detected Using MTT Assay as Follows:

Following incubation, the culture was aspirated and wells are rinsed twice with 200 μL PBS before 100 μL of MTT (0.5 mg/mL dissolved in PBS containing 1% glucose) was added to each microtiter well. The plate was then incubated at 37° C. for 30 min, or longer, until dark blue/black crystals formation could be observed (usually 2 hours at most). The MTT reaction was terminated by aspiration of the solution. The crystals were then solubilized by adding 100 μL of 40% acetic acid to the microtiter wells. Killing efficacies were monitored by eye or quantitatively measured using a plate reader (absorbance at 550 nm). MBEC values were determined as the lowest compound concentration leading to 90% eradicated biofilm. All MBEC values using the MTT assay were recorded from at least three independent experiments.

See Table 2B. Table 2B below shows biofilm eradication assays for exemplary compounds.

TABLE 2B

Summary of biofilm eradication activities for exemplary compounds

| | C. albicans SC5314 | | | C. neoformans 66031 | |
|---|---|---|---|---|---|
| | MIC | MBC | MBEC | MIC | MBC |
| AB-3-67 | 3.13 | 6.25 | 7.82 | 1.56 | 3.13 |
| 16-BAC | 3.13 | 6.25 | 15.63 | 3.12 | 6.25 |
| AB-3-117 | 3.13 | 6.25 | 15.63 | 1.56 | 6.25 |
| AB-3-113 | 3.13 | 6.25 | 7.82 | 1.56 | 3.13 |
| AB-3-71 | 3.13 | 6.25 | 15.63 | 1.56 | 6.25 |
| AB-3-90 | 3.13 | 6.25 | 15.63 | 3.13 | 6.25 |
| AB-2-147 | 6.25 | 6.25 | 62.5 | 3.13 | 6.25 |
| AB-3-38 | 50 | >500 | 250 | 12.5 | 25 |

MRSA Persister Cell Kill Kinetics (Killing of Stationary Cultures)

An overnight culture of MRSA BAA-1707 was diluted in fresh TSBG (1:13 to 1:20 fold) and allowed to grow with shaking. Once the culture reached stationary phase (4-6 hours), test compounds were added at a final test concentration of 50 µM. The cultures were incubated with shaking at 250 rpm and aliquots were removed and plated out at different time points. Colony forming units (CFU) per milliliter data was recorded and plotted using Graphpad Prism 6.0.

Haemolysis Assay

Freshly drawn human red blood cells (hRBC with ethylenediaminetetraacetic acid (EDTA) as an anticoagulant) were washed with Tris-buffered saline (0.01M Tris-base, 0.155 M sodium chloride (NaCl), pH 7.2) and centrifuged for 5 minutes at 3500 rpm. The washing was repeated three times with the buffer. In 96-well plate, the test compounds were added to the buffer. Then 50 µL of 2% of hRBCs in the buffer were added to the test plate to make the final concentrations ranging from 0.2 to 200 µM of each test compound. The plate was then incubated for 1 hour at 37° C. After incubation, the plate was centrifuged for 5 minutes at 3500 rpm and then 80 µL of the supernatant was transferred to another 96-well plate and the Optical Density (OD) was read at 405 nm. DMSO served as our negative control (0% haemolysis) and Triton X served as our positive control (100% haemolysis). The $HC_{50}$ (concentration of test compound required to lyse red blood cells by 50%) was calculated by plotting the dose-response curve (not shown) with Graphpad Prism 6.0. All data were obtained from three independent haemolysis experiments.

REFERENCES

1. R. M. Donlan, J. W. Costerton, *Clin. Microbiol. Rev.* 2002, 15, 167-193.
2. L. Hall-Stoodley, J. W. Costerton, P. Stoodley, *Nat. Rev. Microbiol.* 2004, 2, 95-108.
3. K. Lewis, *Nat. Rev. Microbiol.* 2007, 5, 48-56.
4. R. Wolcott, S. Dowd, *Plast. Reconstr. Surg.* 2011, 127, Suppl 1: 28S-35S.
5. T. K. Wood, *Biotechnol. Bioengineer.* 2016, 113, 476-483.
6. J. D. Bryers, *Biotechnol. Bioeng.* 2008, 100, 1-18.
7. A. T. Garrison, Y. Abouelhassan, V. M. Norwood IV, D. Kallifidas, F. Bai, M. T. Nguyen, M. Rolfe, G. M. Burch, S. Jin, H. Luesch, R. W. Huigens III, *J. Med. Chem.* 2016, 59, 3808-3825.
8. C. N. Street, A. Gibbs, *Corros. Sci.* 2010, 52, 1447-1452.
9. C. U. Schwermer, G. Lavik, R. M. M. Abed, B. Dunsmore, T. G. Ferdelman, P. Stoodley, A. Gieseke, D. de Beer, *Appl. Environ. Microbiol.* 2008, 74, 2841-2851.
10. T. Danhorn, C. Fuqua, *Annu. Rev. Microbiol.* 2007, 61, 401-422.
11. L. S. Muranaka, M. A. Takita, J. C. Olivato, L. T. Kishi, A. A. de Souza, *J. Bacteriol.* 2012, 194, 4561-4569.
12. M. H. Fletcher, M. C. Jennings, W. M. Wuest, *Tetrahedron* 2014, 70, 6373-6383.
13. R. J. Worthington, J. J. Richards, C. Melander, *Org. Biomol. Chem.* 2012, 10, 7457-7474.
14. M. B. Miller, B. L. Bassler, *Annu. Rev. Microbiol.* 2001, 55, 165-199.
15. A. Basak, Y. Abouelhassan, V. M. Norwood IV, F. Bai, M. Nguyen, S. Jin, R. W. Huigens III, *Chem. Eur. J.* 2016, 22, 9181-9189.
16. M. C. Jennings, L. C. Ator, T. J. Paniak, K. P. C. Minbiole, W. M. Wuest, *ChemBioChem* 2014, 15, 2211-2215.
17. K. A. Brogden, *Nat. Rev. Microbiol.* 2015, 3, 238-250.
18. M. C. Jennings, B. A. Buttaro, K. P. C. Minbiole, W. M. Wuest, *ACS Infect. Dis.* 2015, 1, 304-309.
19. Y. J. Gordon, E. G. Romanowski, *Curr. Eye Res.* 2005, 30, 505-515.
20. T. Böttcher, I. Kolodkin-Gal, R. Kolter, R. Losick, J. Clardy, *J. Am. Chem. Soc.* 2013, 135, 2927-2930.
21. R. Joseph, A. Naugolny, M. Feldman, I. M. Herzog, M. Fridman, Y. Cohen, *J. Am. Chem. Soc.* 2016, 138, 754-757.
22. I. M. Herzog, K. D. Green, Y. Berkov-Zrihen, M. Feldman, R. R. Vidavski, A. Eldar-Boock, R. Satchi-Fainaro, A. Eldar, S. Garneau-Tsodikova, M. Fridman, *Angew. Chem. Int. Ed.* 2012, 51, 5652-5656.
23. G. Guchhait, A. Altieri, B. Gorityala, X. Yang, B. Findlay, G. G. Zhanel, N. Mookherjee, F. Schweizer, *Angew. Chem. Int. Ed.* 2015, 54, 6278-6282.
24. G. McDonnell, A. D. Russell, *Clin. Microbiol. Rev.* 1999, 12, 147-179.
25. A. C. Abreu, R. R. Tavares, A. Borges, F. Mergulhão, M. Simões, *J. Antimicrob. Chemother.* 2013, 68, 2718-2732.
26. W. Kim, A. L. Conery, R. Rajamuthiah, B. B. Fuchs, F. M. Ausubel, E. Mylonakis, *PLoS One* 2015, 10, 15p.
27. W. Kim, N. Fricke, A. L. Conery, B. B. Fuchs, R. Rajamuthiah, E. Jayamani, P. M. Vlahovska, F. M. Ausubel, E. Mylonakis, *Future Med. Chem.* 2016, 8, 257-269.
28. S. Arora, J. M. Yang, R. Utsumi, T. Okamoto, T. Kitayama, W. N. Hait, *Mol. Pharmacol.* 2004, 66, 460-467.
29. L. Liu, P. Huang, Z. Wang, N. Chen, C. Tang, Z. Lin, P. Peng, *BMC Cancer* 2016,16, 813-820.
30. A. E. Autry, M. Adachi, E. Nosyreva, E. S. Na, M. F. Los, P. Cheng, E. T. Kavalali, L. M. Monteggia, *Nature* 2011, 475, 91-95.
31. C. L. Bender, Q. Yang, L. Sun, S. J. Liu, *Neuropharmacol.* 2016, 101, 531-537.
32. L. A. T. Asri, M. Crismaru, S. Roest, Y. Chen, O. Ivashenko, P. Rudolf, J. C. Tiller, H. C. van der Mei, T. J. A. Loontjens, H. J. Busscher, *Adv. Funct. Mater.* 2014, 24, 346-355.
33. J. Hoque, M. M. Konai, S. Samaddar, S. Gonuguntala, G. B. Manjunath, C. Ghosh, J. Haldar, *Chem. Commun.* 2015, 51, 13670-13673.
34. S. Roveta, A. Marchese, G. C. Schito, *Int. J. Antimicrob. Agents* 2008, 31, 321-328.

35. J. J. Harrison, C. A. Stremick, R. J. Turner, N. D. Allan, M. E. Olson, H. Ceri, *Nat. Protoc.* 2010, 5, 1236-1254.
36. I. Keren, N. Kaldalu, A. Spoering, Y. Wang, K. Lewis, *FEMS Microbiol.* 2004, 230, 13-18.
37. S. Lechner, K. Lewis, R. Bertram, *J. Mol. Microbiol. Biotechnol.* 2012, 22, 235-244.
38. *J. Org. Chem.,* 2009, 74, 1971-1976.
39. *Syn. Commun.,* 2012, 42, 114-121.
40. *Adv. Synth. Catal.,* 2016, 358, 597-609.
41. *Polymer Degrad. Stability,* 2007, 92, 1753-1762.
42. *Bioorg. Med. Chem. Lett.,* 2016, 26, 1029-1038
43. *Catal. Sci. Technol.,* 2011, 1, 1512-1525.
44. Clinical and Laboratory Standards Institute. 2009. *Methods for dilution antimicrobial susceptibility tests for bacteria that grow aerobically; approved standard,* 8th edition (M7-M8), Clinical and Laboratory Standard, Wayne, Pa.
45. *Angew. Chem. Int. Ed.,* 2015, 54, 14819-14823.
46. *Methods Mol. Biol.,* 2016, 1356, 183-197.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (I'):

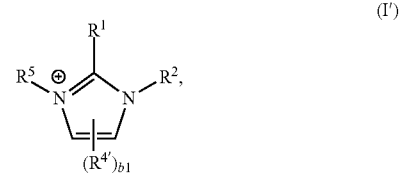

or a pharmaceutically acceptable salt, solvate, hydrate, tautomer, or stereoisomer thereof, wherein:
$R^1$ is $C_1$-$C_6$ alkyl;
$R^2$ is optionally substituted $C_5$-$C_{24}$ alkyl;

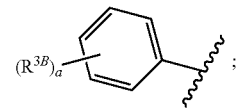

$R^5$ is of the formula:
wherein a is 1, 2, 3, 4, or 5;
each instance of $R^{3B}$ is independently —CN, —SCN, —$NO_2$, —$N_3$, optionally substituted alkyl, optionally substituted acyl, optionally substituted alkenyl, optionally substituted alkynyl, —$OR^{a1}$, —$N(R^{b1})_2$, or —$SR^{a1}$;
each instance of $R^{a1}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; and
each instance of $R^{b1}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^{b1}$ are joined together with the intervening atoms to form optionally substituted heterocyclyl or optionally substituted heteroaryl;

each instance of $R^{4'}$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted acyl, sulfonyl, —OR$^a$, —N(R$^b$)$_2$, or —SR$^a$, or optionally two instances of $R^{4'}$ are joined together with the intervening atoms to form optionally substituted aryl;

each instance of $R^a$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

each instance of $R^b$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^b$ are joined together with the intervening atoms to form optionally substituted heterocyclyl or optionally substituted heteroaryl; and b1 is 0, 1, or 2.

2. The compound of claim 1, wherein the compound is of Formula (I):

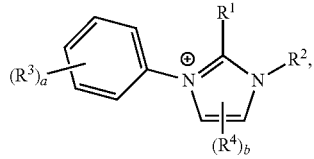

(I)

or a pharmaceutically acceptable salt, solvate, hydrate, tautomer, or stereoisomer thereof, wherein:

$R^1$ is $C_1$-$C_6$ alkyl;

$R^2$ is optionally substituted $C_5$-$C_{24}$ alkyl;

each instance of $R^{3B}$ is independently —CN, —SCN, —NO$_2$, —N$_3$, optionally substituted alkyl, optionally substituted acyl, optionally substituted alkenyl, optionally substituted alkynyl, —OR$^{a1}$, —N(R$^{b1}$)$_2$, or —SR$^{a1}$;

each instance of $R^4$ is independently hydrogen, halogen, —CN, —SCN, —NO$_2$, —N$_3$, optionally substituted alkyl, optionally substituted acyl, optionally substituted alkenyl, optionally substituted alkynyl, optionally substituted carbocyclyl, optionally substituted heterocyclyl, optionally substituted aryl, optionally substituted heteroaryl, optionally substituted acyl, sulfonyl, —OR$^a$, —N(R$^b$)$_2$, or —SR$^a$;

each instance of $R^{a1}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom; and each instance of $R^{b1}$ is independently hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^{b1}$ are joined together with the intervening atoms to form optionally substituted heterocyclyl or optionally substituted heteroaryl;

a is 1, 2, 3, 4, or 5; and b is 0, 1, or 2.

3. The compound of claim 1, wherein the compound is of formula:

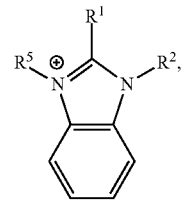

or a pharmaceutically acceptable salt, solvate, hydrate, tautomer, or stereoisomer thereof.

4. The compound of claim 1, or a pharmaceutically acceptable salt, solvate, hydrate, tautomer, or stereoisomer thereof, wherein $R^2$ is optionally substituted $C_{12}$-$C_{16}$ alkyl.

5. The compound of claim 1, or a pharmaceutically acceptable salt, solvate, hydrate, tautomer, or stereoisomer thereof, wherein $R^5$ is of formula

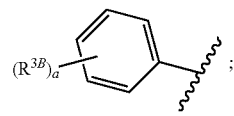

and a is 1 or 2;

each instance of $R^{3B}$ is independently —CN, —NO$_2$, optionally substituted alkyl, optionally substituted acyl, optionally substituted alkenyl, optionally substituted alkynyl, —OR$^{a1}$, or —N(R$^{b1}$)$_2$.

6. The compound of claim 1, or a pharmaceutically acceptable salt, solvate, hydrate, tautomer, or stereoisomer thereof, wherein at least one instance of $R^{3B}$ is —OR$^{a1}$, wherein $R^{a1}$ is optionally substituted $C_1$-$C_6$ alkyl or optionally substituted aryl.

7. The compound of claim 1, or a pharmaceutically acceptable salt, solvate, hydrate, tautomer, or stereoisomer thereof, wherein b1 is 0.

8. The compound of claim 1, wherein the compound is of formula:

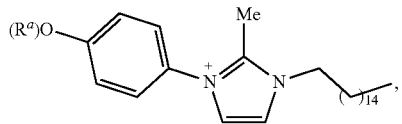

-continued

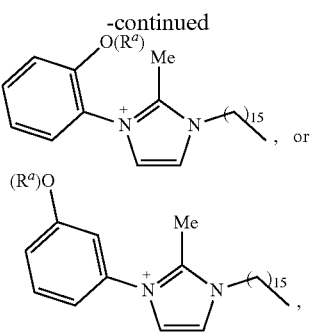

, or or a pharmaceutically acceptable salt, solvate, hydrate, tautomer, or stereoisomer thereof.

9. The compound of claim 1, wherein the compound is of formula:

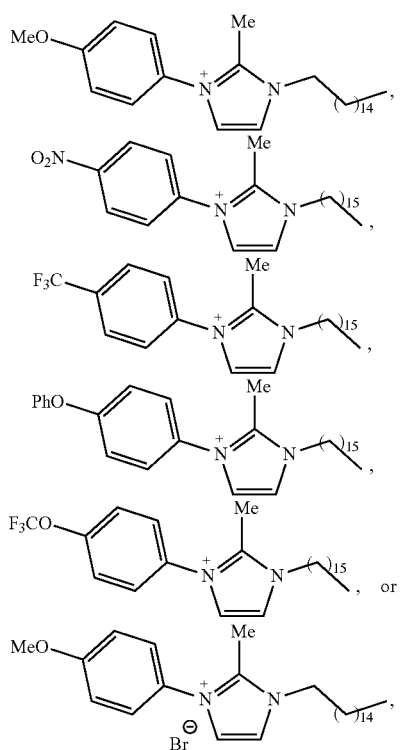

or a pharmaceutically acceptable salt, solvate, hydrate, tautomer, or stereoisomer thereof.

10. The compound of claim 1, or a pharmaceutically acceptable salt, solvate, hydrate, tautomer, or stereoisomer thereof, wherein $R^5$ is of formula

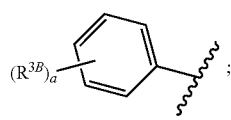

and at least one instance of $R^{3B}$ is —OMe, —NO$_2$, —CF$_3$, —OPh, or —OCF$_3$.

11. The compound of claim 1, or a pharmaceutically acceptable salt, solvate, hydrate, tautomer, or stereoisomer thereof, wherein $R^1$ is methyl.

12. A compound of formula:

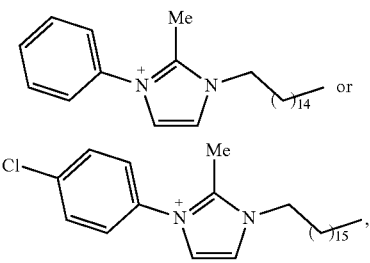

or a pharmaceutically acceptable salt, solvate, hydrate, tautomer, or stereoisomer thereof.

13. The compound of claim 1, or a pharmaceutically acceptable salt, solvate, hydrate, tautomer, or stereoisomer thereof, wherein $R^5$ is of formula

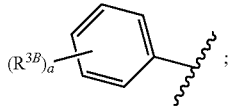

at least one instance of $R^{3B}$ is halogen, optionally substituted alkyl, optionally substituted acyl, optionally substituted alkenyl, optionally substituted alkynyl, —OR$^{a1}$, —N(R$^{b1}$)$_2$, —CN, or —NO$_2$;

each instance of $R^{a1}$ is independently hydrogen, optionally substituted acyl, optionally substituted alkyl, optionally substituted alkenyl, optionally substituted alkynyl, or optionally substituted aryl; and each instance of $R^{b1}$ is independently hydrogen, optionally substituted acyl, optionally substituted alkyl, optionally substituted alkenyl, or optionally substituted alkynyl.

14. The compound of claim 1, or a pharmaceutically acceptable salt, solvate, hydrate, tautomer, or stereoisomer thereof, wherein $R^5$ is

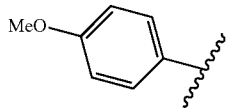

15. The compound of claim 1, or a pharmaceutically acceptable salt, solvate, hydrate, tautomer, or stereoisomer thereof, wherein $R^5$ is

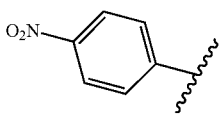

16. The compound of claim 1, or a pharmaceutically acceptable salt, solvate, hydrate, tautomer, or stereoisomer thereof, wherein $R^5$ is

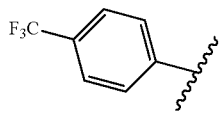

17. The compound of claim 1, or a pharmaceutically acceptable salt, solvate, hydrate, tautomer, or stereoisomer thereof, wherein R⁵ is

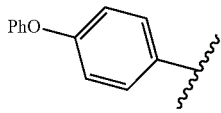

18. The compound of claim 1, or a pharmaceutically acceptable salt, solvate, hydrate, tautomer, or stereoisomer thereof, wherein R⁵ is

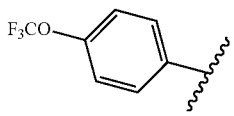

19. The compound of claim 1, or a pharmaceutically acceptable salt, solvate, hydrate, tautomer, or stereoisomer thereof, wherein R² is an optionally substituted $C_{16}$ alkyl.

20. The compound of claim 1, or a pharmaceutically acceptable salt, solvate, hydrate, tautomer, or stereoisomer thereof, wherein R² is unsubstituted $C_{16}$ alkyl.

21. The compound of claim 1, or a pharmaceutically acceptable salt, solvate, hydrate, tautomer, or stereoisomer thereof, wherein the compound is of the formula:

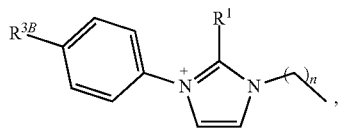

wherein n is 11, 12, 13, 14, or 15.

22. The compound of claim 1, or a pharmaceutically acceptable salt or tautomer thereof.

23. The compound of claim 9, or a pharmaceutically acceptable salt or tautomer thereof.

24. A method of treating an infectious disease in a subject in need thereof, the method comprising administering to the subject an effective amount of a compound of claim 1, or a pharmaceutically acceptable salt, solvate, hydrate, tautomer, or stereoisomer thereof.

25. The method of claim 24, wherein the subject is a human.

26. The method of claim 24, wherein the infectious disease is a cystic fibrosis infection, foreign body infection, or urinary tract infection.

27. The method of claim 24, wherein the infectious disease is a bacterial infection.

28. The method of claim 27, wherein the bacterial infection is an infetion with a Gram-positive bacterium.

29. The method of claim 27, wherein the bacterial infection is an infection with a Gram-negative bacterium.

30. The method of claim 28, wherein the Gram-positive bacterium is selected from the group consisting of *Staphylococcus* spp, *Streptococcus* spp, *Micrococcus* spp, *Peptococcus* spp, *Peptostreptococcus* spp, *Enterococcus* spp, *Bacillus* spp, *Clostridium* spp, *Lactobacillus* spp, *Listeria* spp, *Erysipelothrix* spp, *Propionibacterium* spp, *Eubacterium* spp,*Corynebacterium* spp, *Capnocytophaga* spp, *Bifidobacterium* spp, and *Gardnerella* spp.

31. The method of claim 28, wherein the Gram-positive bacterium is methicillin resistant *Staphylococcus aureus* (MRSA), methicillin-resistant *Staphylococcus epidermidis* (MRSE), or vancomycin resistant *Enterococcus faecium* (VRE).

32. The method of claim 29, wherein the Gram-negative bacterium is selected from the group consisting of *Escherichia coli, Citrobacter* spp, *Enterobacter* spp, *Klebsiella* spp, *Proteus* spp, *Serratia* spp, *Shigella* spp, *Salmonella* spp, *Morganella morganii, Providencia* spp, *Edwardsiella* spp, *Erwinia* spp, *Hafnia* spp, *Yersinia* spp, *Acinetobacter* spp, *Vibrio* spp, *Aeromonas* spp, *Pseudomonas* spp, *Haemophilus* spp, *Pasteurella* spp, *Campylobacter* spp, *Helicobacter* spp, *Branhamella catarrhalis, Moraxella* spp, *Neisseria* spp, *Veillonella parvula, Fusobacterium* spp, *Bacteroides* spp, *Actinobacillus actinomycetemcomitans, Aggregatibacter actinomycetemcomitans, Agrobacterium* spp, *Porphyromonas* spp, *Prevotella* spp, *Ruminobacter* spp, *Roseburia* spp, *Caulobacter crescentus, Francisella* spp, *Borrelia* spp, *Treponema pallidum, Brucella* spp, and *Rickettsia*.

33. The compound of claim 12, or a pharmaceutically acceptable salt or tautomer thereof.

34. A pharmaceutical composition comprising a compound of claim 1, or a pharmaceutically acceptable salt, solvate, hydrate, tautomer, or stereoisomer thereof, and optionally a pharmaceutically acceptable excipient.

35. A pharmaceutical composition comprising a compound of claim 12, or a pharmaceutically acceptable salt, solvate, hydrate, tautomer, or stereoisomer thereof, and optionally a pharmaceutically acceptable excipient.

36. The method of claim 24, wherein the compound is of formula:

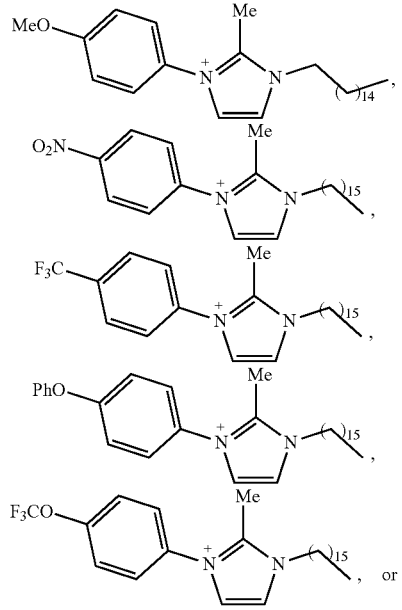

-continued

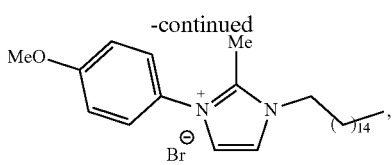

or a pharmaceutically acceptable salt, solvate, hydrate, tautomer, or stereoisomer thereof.

37. A method of treating an infectious disease in a subject in need thereof, the method comprising administering to the subject an effective amount of a compound of claim 12, or a pharmaceutically acceptable salt, solvate, hydrate, tautomer, or stereoisomer thereof.

38. A method for killing a microorganism, the method comprising administering to the subject an effective amount of a compound of claim 1, or a pharmaceutically acceptable salt, solvate, hydrate, tautomer, or stereoisomer thereof.

39. A method for killing a microorganism, the method comprising administering to the subject an effective amount of a compound of claim 12, or a pharmaceutically acceptable salt, solvate, hydrate, tautomer, or stereoisomer thereof.

40. A method for treating or eradicating bacterial biofilm, or preventing biofilm formation, the method comprising administering to the subject an effective amount of a compound of claim 1, or a pharmaceutically acceptable salt, solvate, hydrate, tautomer, or stereoisomer thereof.

41. A method for treating or eradicating bacterial biofilm, or preventing biofilm formation, the method comprising administering to the subject an effective amount of a compound of claim 12, or a pharmaceutically acceptable salt, solvate, hydrate, tautomer, or stereoisomer thereof.

42. A method for killing or eradicating persister cells, the method comprising administering to the subject an effective amount of a compound of claim 1, or a pharmaceutically acceptable salt, solvate, hydrate, tautomer, or stereoisomer thereof.

43. A method for killing or eradicating persister cells, the method comprising administering to the subject an effective amount of a compound of claim 12, or a pharmaceutically acceptable salt, solvate, hydrate, tautomer, or stereoisomer thereof.

44. A method for sterilizing a surface, the method comprising contacting the surface with an effective amount of a compound of claim 1, or a pharmaceutically acceptable salt, solvate, hydrate, tautomer, or stereoisomer thereof.

45. A method for sterilizing a surface, the method comprising contacting the surface with an effective amount of a compound of claim 12, or a pharmaceutically acceptable salt, solvate, hydrate, tautomer, or stereoisomer thereof.

\* \* \* \* \*

UNITED STATES PATENT AND TRADEMARK OFFICE
CERTIFICATE OF CORRECTION

PATENT NO. : 11,419,335 B2
APPLICATION NO. : 16/467461
DATED : August 23, 2022
INVENTOR(S) : Robert William Huigens, III et al.

Page 1 of 1

It is certified that error appears in the above-identified patent and that said Letters Patent is hereby corrected as shown below:

In the Claims

In Claim 2, Column 119, Lines 36-43, the formula: " 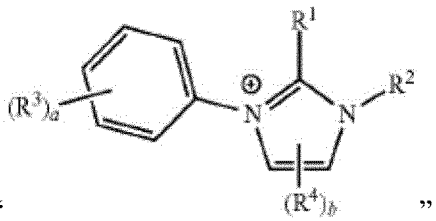 "

Should be replaced with the formula: -- 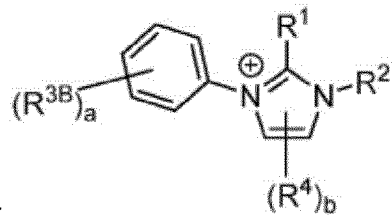 --.

In Claim 12, Column 122, Lines 9-13, the formula: " 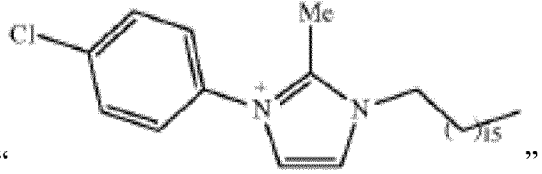 "

Should be replaced with the formula: -- 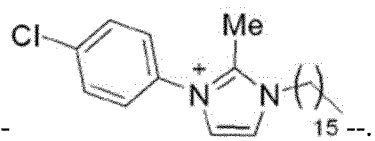 --.

In Claim 28, Column 123, Line 65, the text: "infetion"
Should be replaced with: --infection--.

Signed and Sealed this
Twenty-seventh Day of December, 2022

*Katherine Kelly Vidal*

Katherine Kelly Vidal
*Director of the United States Patent and Trademark Office*